(12) United States Patent
Hutchinson et al.

(10) Patent No.: US 12,268,668 B2
(45) Date of Patent: *Apr. 8, 2025

(54) AUTOTAXIN INHIBITOR COMPOUNDS

(71) Applicant: Sabre Therapeutics LLC, South San Francisco, CA (US)

(72) Inventors: John Howard Hutchinson, San Diego, CA (US); David Lonergan, San Diego, CA (US)

(73) Assignee: Sabre Therapeutics LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/481,141

(22) Filed: Oct. 4, 2023

(65) Prior Publication Data

US 2024/0189281 A1 Jun. 13, 2024

Related U.S. Application Data

(60) Continuation of application No. 17/662,403, filed on May 6, 2022, now Pat. No. 11,779,568, which is a continuation of application No. 16/874,073, filed on May 14, 2020, now Pat. No. 11,344,533, which is a continuation of application No. 15/970,337, filed on May 3, 2018, now Pat. No. 10,688,081, which is a continuation of application No. 15/261,659, filed on Sep. 9, 2016, now Pat. No. 9,999,615, which is a continuation of application No. 15/060,398, filed on Mar. 3, 2016, now Pat. No. 9,468,628, which is a division of application No. 14/926,877, filed on Oct. 29, 2015, now Pat. No. 9,334,261, which is a continuation of application No. PCT/US2014/066706, filed on Nov. 20, 2014.

(60) Provisional application No. 62/038,121, filed on Aug. 15, 2014, provisional application No. 61/907,965, filed on Nov. 22, 2013.

(51) Int. Cl.
| | |
|---|---|
| *A61K 31/4155* | (2006.01) |
| *A61K 9/00* | (2006.01) |
| *A61K 9/06* | (2006.01) |
| *A61K 9/08* | (2006.01) |
| *A61K 9/20* | (2006.01) |
| *A61K 9/48* | (2006.01) |
| *A61K 31/4439* | (2006.01) |
| *A61K 45/06* | (2006.01) |
| *C07D 401/04* | (2006.01) |
| *C07D 401/14* | (2006.01) |
| *C07D 403/04* | (2006.01) |
| *C07D 405/14* | (2006.01) |
| *C07D 493/10* | (2006.01) |

(52) U.S. Cl.
CPC ........ *A61K 31/4155* (2013.01); *A61K 9/0014* (2013.01); *A61K 9/0019* (2013.01); *A61K 9/0053* (2013.01); *A61K 9/06* (2013.01); *A61K 9/08* (2013.01); *A61K 9/20* (2013.01); *A61K 9/48* (2013.01); *A61K 31/4439* (2013.01); *A61K 45/06* (2013.01); *C07D 401/04* (2013.01); *C07D 401/14* (2013.01); *C07D 403/04* (2013.01); *C07D 405/14* (2013.01); *C07D 493/10* (2013.01)

(58) Field of Classification Search
CPC . A61K 31/4155; C07D 401/04; C07D 401/14
See application file for complete search history.

(56) References Cited

U.S. PATENT DOCUMENTS

| | | |
|---|---|---|
| 5,186,522 A | 2/1993 | Spencer |
| 5,210,574 A | 5/1993 | Kita |
| 5,538,444 A | 7/1996 | Strand et al. |
| 5,564,676 A | 10/1996 | Goloff et al. |
| 5,564,949 A | 10/1996 | Wellinsky |
| 5,711,925 A | 1/1998 | Noda et al. |
| 5,761,473 A | 6/1998 | Kahle et al. |
| 6,143,757 A | 11/2000 | Daugan et al. |
| 6,890,933 B1 | 5/2005 | Feng et al. |
| 7,060,697 B2 | 6/2006 | Marsilje et al. |
| 7,839,888 B2 | 11/2010 | Jung et al. |
| 7,905,958 B2 | 3/2011 | Sasaki et al. |
| 7,921,385 B2 | 4/2011 | Abrams et al. |
| 8,022,239 B2 | 9/2011 | Parrill-Baker et al. |
| 8,268,891 B1 | 9/2012 | Parrill-Baker et al. |
| 8,329,907 B2 | 12/2012 | Schultz et al. |
| 8,343,934 B2 | 1/2013 | Parrill-Baker et al. |

(Continued)

FOREIGN PATENT DOCUMENTS

| | | |
|---|---|---|
| CL | 2016001118 A1 | 12/2016 |
| CL | 2016001079 A1 | 1/2017 |

(Continued)

OTHER PUBLICATIONS

Albers et al. Boronic acid-based inhibitor of autotaxin reveals rapid turnover of LPA in the circulation. PNAS USA 107:7257-7262 (2010).
Albers et al. Chemical evolution of autotaxin inhibitors. Chem. Rev. 112:2593-2603 (2012).
Albers et al. Discovery and optimization of boronic acid based inhibitors of autotaxin. J. Med. Chem. 53:4958-4967 (2010).
Albers et al. Structure-based design of novel boronic acid-based inhibitors of autotaxin. J. Med. Chem. 54:4619-4626 (2011).
Aljammal et al. Serum Autotaxin Correlates with Insulin Resistance and Features of the Metolic syndrom in Humans. Poster and Abstract (3 pgs.) (Jun. 2014).
American Diabetes Association. Diagnosis and Classification of Diabetes Mellitus. Diabetes Care 37(Supp. 1): S81-S90 (2014).
American Diabetes Association. Standards of Medical care in Diabetes. Diabetes Care 37(Supp. 1): S14-S80 (2014).

(Continued)

*Primary Examiner* — Kamal A Saeed

(74) *Attorney, Agent, or Firm* — Knobbe, Martens, Olson & Bear, LLP

(57) ABSTRACT

Described herein are compounds that are autotaxin inhibitors, methods of making such compounds, pharmaceutical compositions and medicaments comprising such compounds, and methods of using such compounds in the treatment of conditions, diseases, or disorders associated with autotaxin activity.

18 Claims, No Drawings

(56) References Cited

U.S. PATENT DOCUMENTS

| | | | |
|---|---|---|---|
| 8,378,100 B2 | 2/2013 | Lynch et al. | |
| 8,497,371 B2 | 7/2013 | Parrill-Baker et al. | |
| 8,530,650 B2 | 9/2013 | Schiemann et al. | |
| 8,552,001 B2 | 10/2013 | Schiemann et al. | |
| 8,557,824 B2 | 10/2013 | Schiemann et al. | |
| 8,673,882 B2 | 3/2014 | Gupte et al. | |
| 8,841,324 B2 | 9/2014 | Staehle | |
| 9,000,025 B2 | 4/2015 | Roppe et al. | |
| 9,051,320 B1 | 6/2015 | Evans | |
| 9,334,261 B2 | 5/2016 | Hutchinson et al. | |
| 9,468,628 B2 | 10/2016 | Hutchinson et al. | |
| 9,758,485 B2 | 9/2017 | Hallenbach et al. | |
| 9,926,318 B2 | 3/2018 | Hutchinson et al. | |
| 9,999,615 B2 | 6/2018 | Hutchinson et al. | |
| 10,632,104 B2* | 4/2020 | Bain | A61K 9/0019 |
| 10,688,081 B2 | 6/2020 | Hutchinson et al. | |
| 11,344,533 B2 | 5/2022 | Hutchinson et al. | |
| 11,779,568 B2 | 10/2023 | Hutchinson et al. | |
| 2005/0004156 A1 | 1/2005 | Feng et al. | |
| 2005/0267108 A1 | 12/2005 | Hsieh et al. | |
| 2006/0270634 A1 | 11/2006 | Miller et al. | |
| 2008/0167356 A1 | 7/2008 | Caldwell et al. | |
| 2010/0016258 A1 | 1/2010 | Lynch et al. | |
| 2010/0136650 A1 | 6/2010 | Parrill-Baker et al. | |
| 2010/0222341 A1 | 9/2010 | Schiemann et al. | |
| 2010/0240676 A1 | 9/2010 | Schiemann et al. | |
| 2010/0249132 A1 | 9/2010 | Schultz et al. | |
| 2010/0267037 A1 | 10/2010 | Westbrook et al. | |
| 2011/0110886 A1 | 5/2011 | Braddock | |
| 2011/0160148 A1 | 6/2011 | Parrill-Baker et al. | |
| 2011/0230471 A1 | 9/2011 | Staehle et al. | |
| 2011/0237583 A1 | 9/2011 | Schiemann et al. | |
| 2012/0015959 A1 | 1/2012 | Staehle et al. | |
| 2012/0015976 A1 | 1/2012 | Schultz et al. | |
| 2012/0059016 A1 | 3/2012 | Schiemann et al. | |
| 2012/0100592 A1 | 4/2012 | Parrill-Baker et al. | |
| 2012/0115852 A1 | 5/2012 | Schultz et al. | |
| 2012/0190650 A1 | 7/2012 | Gupte et al. | |
| 2012/0202827 A1 | 8/2012 | Schiemann et al. | |
| 2012/0316162 A1 | 12/2012 | Schiemann et al. | |
| 2013/0012505 A1 | 1/2013 | Staehle et al. | |
| 2013/0023556 A1 | 1/2013 | Schultz et al. | |
| 2013/0029948 A1 | 1/2013 | Roppe et al. | |
| 2013/0150326 A1 | 6/2013 | Roppe et al. | |
| 2013/0251728 A1 | 9/2013 | Harp et al. | |
| 2013/0270634 A1 | 10/2013 | Huang et al. | |
| 2014/0086839 A1 | 3/2014 | Achiron et al. | |
| 2014/0113953 A1 | 4/2014 | Stoffel et al. | |
| 2014/0171361 A1 | 6/2014 | Jonker et al. | |
| 2014/0171403 A1 | 6/2014 | Legrand et al. | |
| 2014/0171404 A1 | 6/2014 | Furminger et al. | |
| 2014/0200231 A1 | 7/2014 | Beauchamp et al. | |
| 2016/0264575 A1 | 9/2016 | Hutchinson et al. | |
| 2018/0147185 A1 | 5/2018 | Bain et al. | |
| 2018/0162859 A1 | 6/2018 | Hutchinson et al. | |
| 2018/0243267 A1 | 8/2018 | Hutchinson et al. | |
| 2020/0215034 A1 | 7/2020 | Bain et al. | |

FOREIGN PATENT DOCUMENTS

| | | |
|---|---|---|
| CL | 2016001080 A1 | 1/2017 |
| CN | 1095841 C | 12/2002 |
| JP | 2012522733 A | 9/2012 |
| JP | 2013523607 A | 6/2013 |
| JP | 2013129632 A | 7/2013 |
| WO | WO-199632003 A1 | 10/1996 |
| WO | WO-200130343 A1 | 5/2001 |
| WO | WO-200228865 A2 | 4/2002 |
| WO | WO-2002083126 A1 | 10/2002 |
| WO | WO-2003029212 A1 | 4/2003 |
| WO | WO-2004019869 A2 | 3/2004 |
| WO | WO-2004020408 A1 | 3/2004 |
| WO | WO-2004020409 A1 | 3/2004 |
| WO | WO-2005061455 A1 | 7/2005 |
| WO | WO-2006041961 A1 | 4/2006 |
| WO | WO-2006050236 A2 | 5/2006 |
| WO | WO-2006134499 A2 | 12/2006 |
| WO | WO-2007134169 A2 | 11/2007 |
| WO | WO-2008157361 A1 | 12/2008 |
| WO | WO-2009046804 A1 | 4/2009 |
| WO | WO-2009046841 A2 | 4/2009 |
| WO | WO-2009046842 A2 | 4/2009 |
| WO | WO-2009151644 A2 | 12/2009 |
| WO | WO-2010040080 A1 | 4/2010 |
| WO | WO-2010060532 A1 | 6/2010 |
| WO | WO-2010063352 A1 | 6/2010 |
| WO | WO-2010112116 A1 | 10/2010 |
| WO | WO-2010112124 A1 | 10/2010 |
| WO | WO-2010115491 A2 | 10/2010 |
| WO | WO-2010132479 A2 | 11/2010 |
| WO | WO-2011002918 A1 | 1/2011 |
| WO | WO-2011006569 A1 | 1/2011 |
| WO | WO-2011044978 A1 | 4/2011 |
| WO | WO-2011049433 A1 | 4/2011 |
| WO | WO-2011053597 A1 | 5/2011 |
| WO | WO-2011103430 A1 | 8/2011 |
| WO | WO-2011116867 A1 | 9/2011 |
| WO | WO-2012024620 A2 | 2/2012 |
| WO | WO-2012100018 A1 | 7/2012 |
| WO | WO-2012112964 A1 | 8/2012 |
| WO | WO-2012112966 A1 | 8/2012 |
| WO | WO-2012166415 A1 | 12/2012 |
| WO | WO-2013054185 A1 | 4/2013 |
| WO | WO-2013061297 A1 | 5/2013 |
| WO | WO-2013186159 A1 | 12/2013 |
| WO | WO-2014031170 A1 | 2/2014 |
| WO | WO-2014048865 A1 | 4/2014 |
| WO | WO-2014097151 A2 | 6/2014 |
| WO | WO-2015042052 A1 | 3/2015 |
| WO | WO-2015042053 A1 | 3/2015 |
| WO | WO-2015048301 A1 | 4/2015 |
| WO | WO-2015075174 A1 | 5/2015 |
| WO | WO-2015077502 A1 | 5/2015 |
| WO | WO-2015077503 A1 | 5/2015 |
| WO | WO-2016028686 A1 | 2/2016 |
| WO | WO-2016191427 A1 | 12/2016 |

OTHER PUBLICATIONS

Antunes et al. In silica prediction of novel phosphodiesterase type-5 inhibitors derived from Sildenafil, Vardenafil and Tadalafil. Bioorg Med Chem. 16: 7599-7606 (2008).

Baader et al. Characterization of the properties of a selective, orally bioavailable autotaxin inhibitor in preclinical models of advanced stages of liver fibrosis. Br J Pharmacol. 175(4): 693-707 (2018).

Baker et al. Carba analogs of cyclic phosphatidic acid are selective inhibitors of autotaxin and cancer cell invasion and metastasis. J. Biol. Chem. 281:22786-22793 (2006).

Barbayianni et al. Autotaxin inhibitors: a patent review. Expert Opin Ther Pat. 23(9):1123-1132 (2013).

Berge et al. Pharmaceutical Salts. Journal of Pharmaceutical Sciences 66(1):1-19 (Jan. 1977).

Black et al. Autotaxin activity increases locally following lung injury, but is not required for pulmonary lysophosphatidic acid production or fibrosis. FASEB J 30(6): 2435-50 (2016).

Bosarge et al. Stress-induced Hyperglycemia. Is it Harmful Following Trauma? Ad Surgery 47: 287-297 (2013).

Boucher et al. Potential involvement of adipocyte insulin resistance in obesity-associated upregulation of adipocyte lysophospholipase D/autotaxin expression. Diabetologia 48:569-577 (2005).

Bundgaard. Means to Enhance Penetration: Prodrugs as a Means to Improve the Delivery of Peptide Drugs. Advanced Drug Delivery Review 8(1): 1-38 (1992).

Chalasani et al. The Diagnosis and Management of non-alcoholic fatty liver disease: practice guideline by the American Gastroenterological Association, American Association for the Study of Liver Diseases, and American College of Gastroenterology. Gastroenterology, 142(7): 1592-1609 (2012).

Cui et al. Alpha- and beta-substituted phosphonate analogs of LPA as autotaxin inhibitors. Bioorg. Med. Chem. 16:2212-2225 (2008).

(56) References Cited

OTHER PUBLICATIONS

Cui et al. Synthesis and biological evaluation of phosphonate derivatives as autotaxin (ATX) inhibitors. Bioorg. Med. Chem. Lett. 17:1634-1640 (2007).
Dougan et al. The Discovery of Tadalafil: A Novel and Highly Selective PDE5 Inhibitor. 2:2,3,6,7,12,12a-hexahydropyrazino[1',2':1,6]pyrido[3,4-b]indole-1,4-dione Analogues. J Med Chem. 46: 4525-4532 (2003).
Durgam et al. Synthesis, structure-activity relationships, and biological evaluation of fatty alcohol phosphates as lysophosphatidic acid receptor ligands, activators of PPARgamma, and inhibitors of autotaxin. J. Med. Chem. 48:4919-4930 (2005).
Durgam et al. Synthesis and pharmacological evaluation of second-generation phosphatidic acid derivatives as lysophosphatidic acid receptor ligands. Bioorg. Med. Chem. Lett. 16:633-640 (2006).
Dusaulcy et al. Adipose-specific disruption of autotaxin enhances nutritional fattening and reduces plasma lysophosphatidic acid. J Lipid Res. 52: 1247-1255 (2011).
European Association for the Study of Liver., EASL clinical guidelines: Management of alcoholic liver diseases. J Hepatol. 51(2): 237-267 (2009).
European Association for the Study of Liver., EASL clinical guidelines: Management of alcoholic liver disease. J Hepatol. 57(2): 399-420 (2012).
East et al. Synthesis and structure-activity relationships of tyrosine-based inhibitors of autotaxin (ATX). Bioorg. Med. Chem. Lett. 20:7132-7136 (2010) and suppl. Material.
Federico et al. Therapeutic potential of autotaxin/lysophospholipase d inhibitors. Curr Drug Targets 9(8):698-708 (2008).
Federico et al. Autotaxin and its product lysophosphatidic acid suppress brown adipose differentiation and promote diet-induced obesity in mice. Mol Endocr. 26: 786-797 (2012).
Ferry et al. S32826, A Nanomolar Inhibitor of Autotaxin: Discovery, Synthesis and Applications as a Pharmacological Tool. J. Pharmacol. Exp. Ther. 327:809-819 (2008).
Gajewiak et al. Synthesis, pharmacology, and cell biology of sn-2-aminooxy analogues of lysophosphatidic acid. Org. Lett. 10:1111-1114 (2008).
Gendaszewska-Darmach et al. The chemical synthesis of metabolically stabilized 2-OMe-LPA analogues and preliminary studies of their inhibitory activity toward autotaxin. Bioorg. Med. Chem. Lett. 22:2698-2700 (2012).
Gierse et al. A novel autotaxin inhibitor reduces lysophosphatidic acid levels in plasma and the site of inflammation. J. Pharmacol. Exp. 334:310-317 (2010).
Gududuru et al. Identification of Darmstoff analogs as selective agonists and antagonists of lysophosphatidic acid receptors. Bioorg. Med. Chem. Lett. 16:451-456 (2006).
Gupte et al. Benzyl and naphthalene methylphosphonic acid inhibitors of autotaxin with anti-invasive and anti-metastatic activity. ChemMedChem 6:922-935 (2011).
Gupte et al. Synthesis and pharmacological evaluation of the stereoisomers of 3-carba cyclic-phosphatidic acid. Bioorg. Med. Chem. Lett. 20:7525-7528 (2010).
Higazi et al. Immunomodulatory effects of plasminogen activators on hepatic fibrogenesis. Clin Exp Immunol 152(1):163-173 (2008).
Hoeglund et al. Characterization of non-lipid autotaxin inhibitors. Bioorg. Med. Chem. 18:769-776 (2010).
Hoeglund et al. Optimization of a pipemidic acid autotaxin inhibitor. J. Med. Chem. 53:105-1066 (2010).
Humphrey et al., Practical methodologies for the synthesis of indoles. Chem Rev. 106(7): 2875-2911 (2006).
Jiang et al. Alpha-substituted phosphonate analogues of lysophosphatidic acid (LPA) selectively inhibit production and action of LPA. ChemMedChem 2:679-690 (2007).
Jiang et al. Aromatic phosphonates inhibit the lysophospholipase D activity of autotaxin. Bioorg. Med. Chem. Lett. 21:5098-5101 (2011).
Kano et al. LPA and its analogs-attractive tools for elucidation of LPA biology and drug development. Curr. Med. Chem. 15:2122-2131 (2008).
Karlsen et al. Update on primary sclerosing cholangitis. Dig Liver Disease 42: 390-400 (2010).
Klein et al. Solid-phase synthesis of new fused tetra, penta and hexacyclic β-carboline derivatives. Tetrahedron Lett. 44: 2211-2215 (2003).
Ma et al. Efficient Asymmetric Synthesis of Biologically Important Tryptophan Analogues via a Palladium-Mediated Heteroannulation Reaction. J Org Chem 66:4525-4542 (2001) & Supplementary Information in 26 pages.
Moulharat et al. Molecular pharmacology of adipocyte-secreted autotaxin. Chem.-Biol. Interact. 172:115-124 (2008).
Nishimura et al. ENPP2 contributes to adipose tissue expansion in diet-induced obesity. Diabetes. 2014. Epub ahead of print. Published online Jun. 26, 2014. doi: 10.2337/db13-1694. 45 pages.
North et al. Pharmacophore development and application toward the identification of novel, small-molecule autotaxin inhibitors. J. Med. Chem. 53:3095-3105 (2010).
Notari R.E. Theory and Practice of Prodrug Kinetics. Method in Enzymology. 112: 309-396 (1985).
Parrill et al. Autotaxin Inhibitors: A Perspective on Initial Medicinal Chemistry Efforts. Expert Opin Ther Pat 20(12):1619-1625 (2010).
Parrill et al. Virtual screening approaches for the identification of non-lipid autotaxin inhibitors. Bioorg. Med. Chem. 16:1784-1795 (2008).
Poupon, R. Primary biliary cirrhosis: A 2010 update. J Hepatol. 52(2): 745-758 (2010).
Rancoule et al. Depot-specific regulation of autotaxin with obesity in human adipose tissue. J Physiol Biochem.68:635-644 (2012).
Rancoule et al. Lysophosphatidic acid impairs glucose homeostasis and inhibits insulin secretion in high-fat diet obese mice. Diabetolgia (9 pgs) (2013).
Ratziu et al. Current efforts and trends in the treatment of NASH. J Hepatol., 62(1): S65-S75 (2015).
Rehman et al. Drug-Induced Glucose Alterations Part 2: Drug-Induced Hyperglycemia. Diabetes Spectrum 24(4):234-238 (2011).
Saunders et al. Identification of small-molecule inhibitors of autotaxin that inhibit melanoma cell migration and invasion. Mol. Cancer Ther. 7:3352-3362 (2008).
Skyler. Effects of Glycemic Control on Diabetes Complications and on the Prevention of Diabetes. Clinical Diabetes 22(4): 162-166 (2004).
Serajuddin et al. "Salt-Selection Strategies", Chapter 6 in Handbook of Pharmaceutical Salts, Stahl et al. [Eds.]; Verlag Helvetica Chimica Acta, Zürich, 138-139 (2002).
Stein et al. Structural Basis for Inhibition of Human Autotaxin by Four Potent Compounds with Distinct Modes of Binding. Mol Pharmacol. 88(6): 982-992 (2015).
Tanaka et al. Efficient synthesis of 3-O-thia-cPA and preliminary analysis of its biological activity toward autotaxin. Bioorg. Med. Chem. Lett. 21:4180-4182 (2011).
Turner et al. Glycemic Control with Diet, Sulfonylurea, Metformin, or Insulin in Patients With Type 2 Diabetes Mellitus: Progressive Requirement for Multiple Therapies (UUKPDS 49). JAMA 281(21): 2005-2012 (1999).
Van Meeteren et al. Anticancer activity of FTY720: phosphorylated FTY720 inhibits autotaxin, a metastasis-enhancing and angiogenic lysophospholipase D. Cancer Lett. 266:203-208 (2008).
Van Meeteren et al. Inhibition of autotaxin by lysophosphatidic acid and sphingosine 1-phosphate. J. Biol. Chem. 280:21155-21161 (2005).
Yamamoto et al. Animal Model of Sclerotic Skin. I: Local Injections of Bleomycin Induce Sclerotic Skin Mimicking Scleroderma. J Invest Dermatol 112(4):456-462 (1999).
Zhang et al. Dual activity lysophosphatidic acid receptor pan-antagonist/autotaxin inhibitor reduces breast cancer cell migration in vitro and causes tumor regression in vivo. Cancer Res 69:5441-5449 (2009).
Zou et al. Use of pioglitazone in the treatment of diabetes: effect on cardiovascular risk. Vasc. Health and Risk Management 9: 429-433 (2013).

(56) References Cited

OTHER PUBLICATIONS

International Search Report and Written Opinion dated Mar. 13, 2015 for Application No. PCT/US2014/066706.
Extended European Search Report dated Jun. 21, 2021 for Application No. 21156420.8.
Nema et al., Excipients and their role in approved injectable products: Current usage and future directions, PDA J. Pharm. Sci. Tech. May 1, 2011;65(3): 287-332.
Powell et al., Compendium of excipients for parenteral formulations, PDA J Pharm Sci and Tech Sep. 1, 1998;52(5): 238-311.

* cited by examiner

AUTOTAXIN INHIBITOR COMPOUNDS

RELATED APPLICATIONS

This application is a continuation of U.S. patent application Ser. No. 16/874,073, filed May 14, 2020, which is a continuation of U.S. patent application Ser. No. 15/970,337, filed May 3, 2018, which is a continuation of U.S. patent application Ser. No. 15/261,659, filed on Sep. 9, 2016, now U.S. Pat. No. 9,999,615 which is a continuation of U.S. patent application Ser. No. 15/060,398, filed on Mar. 3, 2016, now U.S. Pat. No. 9,468,628, which is a divisional of U.S. patent application Ser. No. 14/926,877, filed on Oct. 29, 2015, now U.S. Pat. No. 9,334,261, which is a continuation of International Application No. PCT/US2014/066706, filed on Nov. 20, 2014, which claims the benefit of U.S. Provisional Patent Application No. 62/038,121, filed on Aug. 15, 2014, and U.S. Provisional Patent Application No. 61/907,965, filed on Nov. 22, 2013, each of which is herein incorporated by reference in its entirety.

FIELD OF THE INVENTION

Described herein are compounds that are autotaxin inhibitors, methods of making such compounds, pharmaceutical compositions and medicaments comprising such compounds, and methods of using such compounds in the treatment of conditions, diseases, or disorders associated with autotaxin activity.

BACKGROUND OF THE INVENTION

Lysophosphatidic acid (LPA) is a lipid mediator that functions, for example, as a mitogen, chemoattractant, and survival factor for many cell types. LPA signaling is implicated in, for example, cancer and fibrotic diseases.

SUMMARY OF THE INVENTION

Compounds described herein are autotaxin (ATX) inhibitors. In some embodiments, the autotaxin inhibitors described herein are useful as agents for the treatment or prevention of diseases or conditions in which ATX and/or LPA participates, is involved in the etiology or pathology of the disease, or is otherwise associated with at least one symptom of the disease. Inhibition of the physiological activity of ATX and/or LPA is useful in a variety of diseases or conditions. The ATX-LPA signaling pathway has been implicated in fibrotic diseases and cancer.

Compounds described herein are used in the treatment of diseases or conditions in which autotaxin activity contributes to the symptomology or progression of the disease, disorder or condition. In one aspect, the methods, compounds, pharmaceutical compositions, and medicaments described herein comprise autotaxin inhibitors.

In one aspect, described herein is a compound of Formula (I), or a pharmaceutically acceptable salt, or solvate thereof:

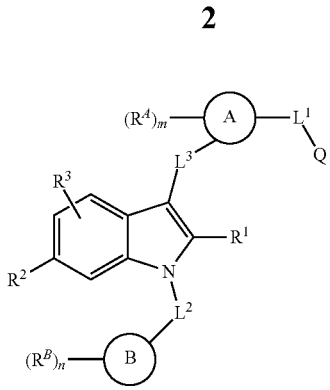

Formula (I)

wherein, $R^1$ is —F, —Cl, —Br, —CN, vinyl, $C_3$-$C_6$cycloalkyl, —$NH_2$, —$NH(C_1$-$C_4$ alkyl), —$N(C_1$-$C_4$ alkyl)$_2$, —O—$C_1$-$C_4$ alkyl, or —S—$C_1$-$C_4$ alkyl;

$R^2$ is H—, halogen, —CN, —$NO_2$, —OH, —$OR^9$, —$SR^9$, —$S(O)R^9$, —$S(O)_2R^9$, —$S(=O)_2N(R^{10})_2$, —$NR^{10}S(=O)_2R^9$, —$C(=O)R^9$, —$OC(=O)R$, —$CO_2R^9$, $R^{10}$, —$OCO_2R^9$, —$N(R^{10})_2$, —$C(=O)N(R^{10})_2$, —$OC(=O)N(R^{10})_2$, —$NC(=O)R^9$, —$NHC(=O)R^9$, $C_1$-$C_4$alkyl, $C_1$-$C_4$fluoroalkyl, $C_1$-$C_4$deuteroalkyl, $C_1$-$C_4$hydroxyalkyl, $C_1$-$C_4$heteroalkyl, $C_3$-$C_6$cycloalkyl, substituted or unsubstituted phenyl, or substituted or unsubstituted monocyclic heteroaryl;

Ring A is a monocyclic aryl, bicyclic aryl, monocyclic heterocycloalkyl, monocyclic heteroaryl or bicyclic heteroaryl;

each $R^A$ is H, halogen, —CN, —$NO_2$, —OH, —$OR^9$, —$SR^9$, —$S(O)R^9$, —$S(=O)_2R^9$, —$S(=O)_2N(R^{10})_2$, —$NR^{10}S(=O)_2R^9$, —$C(=O)R^9$, —$OC(=O)R^9$, —$CO_2R^{10}$, —$OCO_2R^9$, —$N(R^{10})_2$, —$C(=O)N(R^{10})_2$, —$OC(=O)N(R^{10})_2$, —$NHC(=O)R^9$, —$NHC(=O)OR^9$, $C_1$-$C_6$alkyl $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, or substituted or unsubstituted monocyclic heteroaryl;

m is 0, 1, or 2;

$L^1$ is absent, $C_1$-$C_6$alkylene, $C_1$-$C_6$fluoroalkylene, or $C_3$-$C_6$cycloalkylene;

Q is —$CO_2H$, —$CO_2(C_1$-$C_6$alkyl), —OH, —CN, —$B(OH)_2$, —$C(=O)NHSO_2R^9$, —$C(=O)N(R^{10})_2$, —$SO_2NHC(=O)R^9$, —CN, tetrazolyl, —$OP(=O)(OH)_2$, —$P(=O)(OH)_2$ or carboxylic acid bioisostere;

$L^2$ is absent, $C_1$-$C_4$alkylene, or $C_3$-$C_7$cycloalkylene;

$L^3$ is —S—, S(=O), S(=O)$_2$, or —O—;

Ring B is a monocyclic aryl, bicyclic aryl, monocyclic heteroaryl or bicyclic heteroaryl;

each $R^B$ is independently H, halogen, —CN, —$NO_2$, —OH, —$OR^9$, —$SR^9$, —$S(=O)R^9$, —$S(=O)_2R^9$, —$S(=O)_2N(R^{10})_2$, —$NR^{10}S(=O)_2R^9$, —$C(=O)R^9$, —$OC(=O)R^9$, —$CO_2R^{10}$, —$OCO_2R^9$, —$N(R^{10})_2$, —$C(=O)N(R^{10})_2$, —$OC(=O)N(R^{10})$, —$NHC(=O)R^9$, —$NHC(=O)OR^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, $C_1$-$C_4$alkylene-(substituted or unsubstituted phenyl), substituted unsubstituted monocyclic heteroaryl, $C_1$-$C_4$alkylene-(substituted or unsubstituted monocyclic heteroaryl), a substituted or unsubstituted bicyclic heteroaryl, or $C_1$-$C_4$alkylene-(substituted or unsubstituted bicyclic heteroaryl);

n is 0, 1, or 2;

$R^9$ is $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, a substituted or unsubstituted monocyclic heteroaryl, or a substituted or unsubstituted bicyclic heteroaryl;

each $R^{10}$ is independently selected from H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, or a substituted or unsubstituted monocyclic heteroaryl; or two $R^{10}$ groups attached to the same N atom are taken together with the N atom to which they are attached to form a substituted or unsubstituted heterocycle.

For any and all of the embodiments, substituents are selected from among a subset of the listed alternatives. For example, in some embodiments, X is —O—, —S—, —S(=O)—, or —S(=O)$_2$. In other embodiments, X is —O— or —S—. In other embodiments, X is —S—, —S(=O)—, or —S(=O)$_2$—. In some embodiments, X is —S—.

In some embodiments, $R^1$ is —F, —Cl, —Br, —CN, vinyl, cyclopropyl, cyclobutyl, —NH$_2$, —NH(CH$_3$), —N(CH$_3$)$_2$, —O—CH$_3$, or —S—CH$_3$.

In some embodiments, $R^1$ is vinyl, cyclopropyl, or cyclobutyl.

In some embodiments, $R^1$ is cyclopropyl, or cyclobutyl.

In some embodiments, $R^1$ is —F, —Cl, or —Br.

In some embodiments, U is absent, or $C_1$-$C_4$alkylene; $L^3$ is —S— S(=O), or S(=O)$_2$.

In some embodiments, $L^2$ is absent, —CH$_2$—, —CH$_2$CH$_2$—, —CH$_2$CH$_2$CH$_2$—, or —CH(CH$_3$)—.

In some embodiments, $L^1$ is absent, —CH$_2$—, —CH$_2$CH$_2$—, —CH$_2$CH$_2$CH$_2$—, —CH(CH$_3$)—, —CH(CH$_2$CH$_2$—, —C(CH$_3$)$_2$—, —C(CH$_2$CH)$_2$—, cyclopropyl-1,1-diyl, cyclobutyl-1,1-diyl, cyclopentyl-1,1-diyl or cyclohexyl-1,1-diyl; Q is —CO$_2$H, —CO$_2$(C$_1$-C$_6$alkyl), —C(=O)NHSO$_2$R$^9$ or tetrazolyl.

In some embodiments, $L^1$ is absent or —CH$_2$—; Q is —CO$_2$H, or —CO$_2$(C$_1$-C$_6$alkyl).

In some embodiments, the compound of Formula (I) has the following structure of Formula

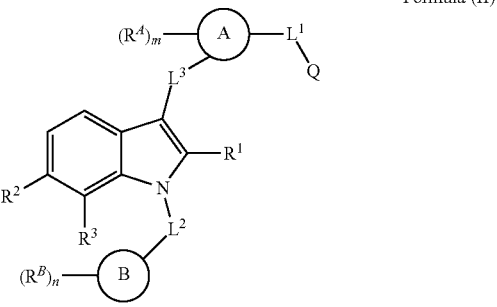

Formula (II)

or a pharmaceutically acceptable salt, or solvate thereof.

In some embodiments, Ring A is phenyl, naphthyl, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms; Ring B is phenyl, naphthyl, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms.

In some embodiments, Ring A is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, Ring A is phenyl or naphthyl.

In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

In some embodiments, Ring A is pyridinyl, pyrimidinyl, pyrazinyl, pyridazinyl, or triazinyl.

In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments, Ring A is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, each $R^4$ is H, halogen, —CN, —OH, —OR$^9$, —SR$^9$, $C_1$-$C_6$alkyl, $C_1$-$C_6$fluoroalkyl, $C_1$-$C_6$deuteroalkyl, $C_1$-$C_6$heteroalkyl.

In some embodiments, $L^3$ is —S—.

In some embodiments, $L^1$ is absent.

In some embodiments, the compound of Formula (I) or Formula (II) has the following structure of Formula (III):

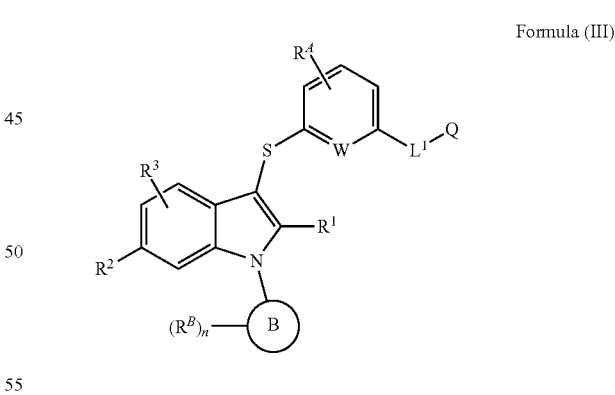

Formula (III)

wherein,

W is CH, CF or N;

or a pharmaceutically acceptable salt, or solvate thereof.

In some embodiments, $L^1$ is absent; and Q is —CO$_2$H.

In some embodiments, described herein is a compound of Formula (III), or a pharmaceutically acceptable salt, or solvate thereof:

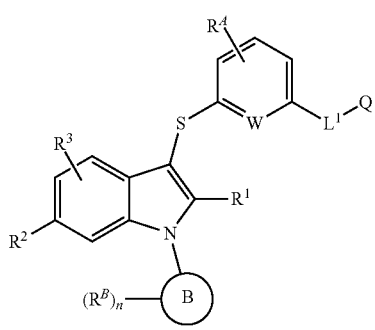

Formula (III)

wherein.
R$^1$ is —Cl, —Br, —CN, or C$_3$-C$_6$cycloalkyl;
R$^2$ is H, halogen, —CN, —NO$_2$, —OH, —OR$^9$, —SR$^9$, —S(=O)R$^9$, —S(=O)$_2$R$^{10}$, —S(=O)$_2$N(R$^{10}$)$_2$, C$_1$-C$_4$alkyl, C$_1$-C$_4$fluoroalkyl, C$_1$-C$_4$deuteroalkyl, or C$_3$-C$_6$cycloalkyl
R$^3$ is H, halogen, —CN, —OH, C$_1$-C$_4$alky(C$_1$-C$_4$fluoroalkyl, C$_1$-C$_4$deuteroalkyl, C$_1$-C$_4$alkoxy, or C$_1$-C$_4$fluoroalkoxy;
W is CH, CF or N
each R$^A$ is H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, C$_1$-C$_6$alkyl, or C$_1$-C$_6$fluoroalkyl,
L$^1$ is absent, C$_1$-C$_6$alkylene, or C$_3$-C$_6$cycloalkylene;
Q is —CO$_2$H, —CO$_2$(C$_1$-C$_6$alkyl), —OH, —CN, —B(OH)$_2$, —C(=O)NHSO$_2$R$^9$, —C(=O)N(R$^{10}$)$_2$, —SO$_2$NHC(=O)R$^9$, —CN, tetrazolyl, —OP(=O)(OH), —P(=O)(OH)$_2$ or carboxylic acid bioisostere;
Ring B is a monocyclic heteroaryl;
each R$^B$ is independently H, halogen, —CN, —NO$_2$, —OH, —OR$^9$, —SR$^9$, —S(=O)R$^9$, —S(=O)R$^9$, —S(=O)$_2$N(R$^{10}$)$_2$, C$_1$-C$_6$alkyl, C$_1$-C$_6$fluoroalkyl, C$_1$-C$_6$deuteroalkyl, C$_1$-C$_6$heteroalkyl, substituted or unsubstituted C$_3$-C$_{10}$cycloalkyl, substituted or unsubstituted C$_2$-C$_4$heterocycloalkyl, substituted or unsubstituted phenyl, C$_1$-C$_4$alkylene-(substituted or unsubstituted phenyl), substituted unsubstituted monocyclic heteroaryl, C$_1$-C$_4$alkylene-(substituted or unsubstituted monocyclic heteroaryl), a substituted or unsubstituted bicyclic heteroaryl, or C$_1$-C$_4$alkylene-(substituted or unsubstituted bicyclic heteroaryl);
n is 0, 1, or 2;
R$^9$ is C$_1$-C$_6$alkyl, C$_1$-C$_6$fluoroalkyl, C$_1$-C$_6$deuteroalkyl, C$_3$-C$_6$cycloalkyl, a substituted or unsubstituted phenyl, a substituted or unsubstituted monocyclic heteroaryl, or a substituted or unsubstituted bicyclic heteroaryl;
each R$^{10}$ is independently H, C$_1$-C$_6$alkyl, C$_1$-C$_6$fluoroalkyl, C$_1$-C$_6$deuteroalkyl, C$_3$-C$_6$cycloalkyl, a substituted or unsubstituted phenyl, or a substituted or unsubstituted monocyclic heteroaryl; or
two R$^{10}$ groups attached to the same N atom are taken together with the N atom to which they are attached to form a substituted or unsubstituted heterocycle.

In some embodiments, R$^1$ is —Cl, —Br, —CN, or cyclopropyl. In some embodiments, R$^1$ is cyclopropyl. In some embodiments, R$^1$ is —Cl.

In some embodiments, L$^1$ is absent, —CH$_2$—, —CH$_2$CH$_2$—, —CH$_2$C—2CH$_2$—, —CH(CH$_3$)—, —CH(CH$_2$CH$_3$)—, —C(CH$_3$)$_2$—, —C(CH$_2$CH$_3$)$_2$—, cyclopropyl-1,1-diyl, cyclobutyl-1,1-diyl, cyclopentyl-1,1-diyl or cyclohexyl-1,1-diyl; and Q is —CO$_2$H, —CO$_2$(C$_1$-C$_6$alkyl), —C(=O)NHSO$_2$R$^9$ or tetrazolyl.

In some embodiments, L$^1$ is absent, —CH$_2$—, —CH(CH$_3$—, —C(CH$_3$)$_2$—, or cyclopropyl-1,1-diyl; and Q is —CO$_2$H, or —CO$_2$(C$_1$-C$_6$alkyl).

In some embodiments, L$^1$ is absent or —CH$_2$—; and Q is —CO$_2$, or —CO$_2$(C$_1$-C$_6$alkyl).

In some embodiments, Ring B is monocyclic heteroaryl containing 1-4 N atoms and 0 or 1 O or S atoms, or monocyclic heteroaryl containing 0-4 N atoms and 1 O or S atoms.

In some embodiments, Ring B is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

In some embodiments, each R$^A$ is 1-1, halogen, —CN, —OH, —OR$^9$, —SR$^9$, C$_1$-C$_6$alkyl, or C$_1$-C$_6$fluoroalkyl.

In some embodiments, L$^1$ is absent, —CH$_2$—, —CH(CH$_3$)—, —C(CH$_3$)$_2$—, or cyclopropyl-1,1-diyl; and Q is —CO$_2$H.

In some embodiments, L$^1$ is absent; and Q is —CO$_2$H.

In some embodiments, the compound or Formula (III) has the following structure:

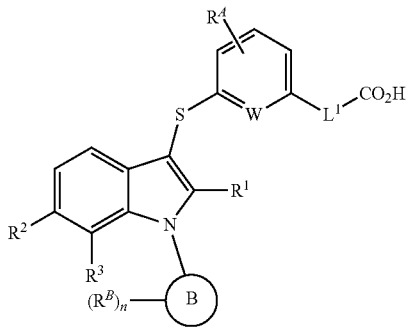

or a pharmaceutically acceptable salt, or solvate thereof.

In some embodiments, R$^2$ is H, F, Cl, Br, I, —CN, —OH, —CH$_3$, —CF$_3$, —CD$_3$, —OCH$_3$, —OCH$_2$CH$_3$, —OCF$_3$, or —OCH$_2$CF$_3$; R$^3$ is H, F, Cl, Br, I, —CN, —OH, —CH$_3$, —CF$_3$, —CD$_3$, —OCH$_2$, —OCH$_2$CH$_3$, —OCF$_3$, or —OCH$_2$CF$_3$.

In some embodiments, R$^2$ is Cl; R$^3$ is H, F, or Cl.

In some embodiments, Ring B is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

In some embodiments, Ring B is pyrazolyl.

In some embodiments, the compound of Formula (III) has the following structure:

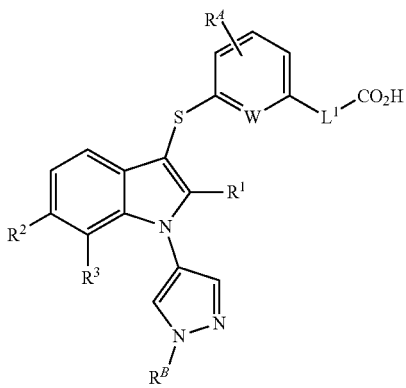

or a pharmaceutically acceptable salt, or solvate thereof.

In some embodiments, $R^A$ is H, halogen, —CN, —OH—, —$OR^9$, —$SR^9$, $C_1$-$C_6$alkyl, or $C_1$-$C_6$fluoroalkyl; $R^B$ is H, $C_1$-$C_6$alkyl, $C_1$-$C_6$fluoroalkyl, or $C_1$-$C_6$deuteroalkyl; $R^1$ is —Cl, —Br, —CN, or cyclopropyl; $R^2$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, or $C_1$-$C_4$fluoroalkoxy; and $R^3$ is H, halogen, —CN, —OH, $C_1$-$C_4$alkyl, $C_1$-$C_4$ fluoroalkyl, $C_1$-$C_4$deuteroalkyl, $C_1$-$C_4$alkoxy, or $C_1$-$C_4$fluoroalkoxy.

In some embodiments, $R^1$ is —Cl, or —Br. In some embodiments, $R^1$ is cyclopropyl.

In some embodiments, the compound of Formula (III) has the following structure:

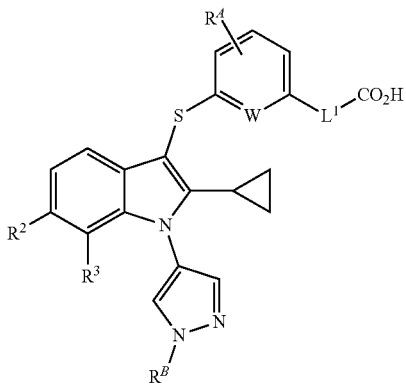

or a pharmaceutically acceptable salt, or solvate thereof.

In some embodiments, the compound of Formula (III) has the following structure:

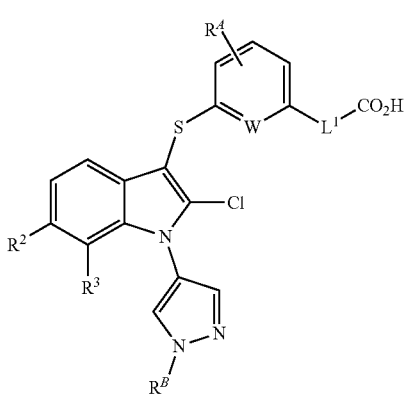

or a pharmaceutically acceptable salt, or solvate thereof.

In some embodiments, $R^4$ is H, F, Cl, Br, I, —CN, —OH, —$OCH_3$, —$OCH_2CH_3$, —$OCF_3$, —$OCH_2CF_3$, —$CH_3$, —$CH_2CH_3$, —$CF_3$, or —$CD_3$.

In some embodiments, $R^B$ is $C_1$-$C_6$alkyl.

In some embodiments, $R^2$ is H, F, Cl, Br, I, —CN, —OH, —$CH_3$, —$CF_3$, —$CD_3$, —$OCH_3$, —$OCH_2CH_3$, —$OCF_3$, or —$OCH_2CF_3$; $R^1$ is H, F, Cl, Br, I, —CN, —OH, —$CH_3$, —$CF_3$, —$CD_3$, —$OCH_3$, —$OCH_2CH_3$, —$OCF_3$, or —$OCH_2CF_3$.

In some embodiments, R, is C; $R^3$ is Cl, F, or Cl.

In some embodiments, $L^1$ is absent, —$CH_2$—, —CH($CH_3$)—, —$C(CH_3)_2$—, or cyclopropyl-1,1-diyl.

In some embodiments, $L^1$ is absent.

In some embodiments, the compound of Formula (I), Formula (II), or Formula (III) has the following structure of Formula (IV):

wherein

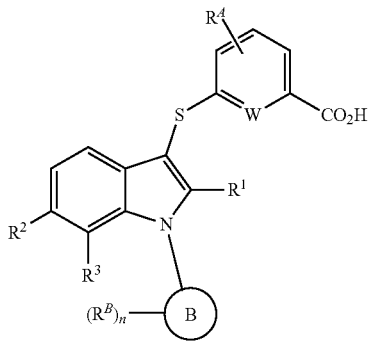

W is CH, CF or N;

or a pharmaceutically acceptable salt, or solvate thereof.

In some embodiments, $R^1$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl.

In some embodiments, $R^2$ is H, F, Cl, Br, I, —CN, —OH, —$CH_3$, —$CF_3$, —$CD_3$, —$OCH_3$, —$OCH_2CH_3$, —$OCF_3$, —$OCH_2CF_3$, or —$CH_2OH$.

In some embodiments, $R^2$ is Cl.

In some embodiments, $R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl.

In some embodiments, $R^3$ is H, F, Cl, Br, I, —CN, —OH, —$CH_3$, —$CF_3$, —CDs, —$OCH_3$, —$OCH_2CH_3$, —$OCF_3$, —$OCH_2CF_3$, or —$CH_2OH$.

In some embodiments, $R^3$ is H, F, or Cl.

In some embodiments, Ring B is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, Ring B is phenyl or naphthyl.

In some embodiments, Ring B is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

In some embodiments, Ring B is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments, Ring B is pyrazolyl.

In some embodiments, Ring B is pyrazolyl; and each $R^B$ is independently, H, $C_1$-$C_6$alkyl, $C_1$-$C_6$fluoroalkyl, or $C_1$-$C_6$deuteroalkyl; n is 1.

In some embodiments, Ring B is pyridinyl, pyrimidinyl, pyrazinyl, pyridazinyl, or triazinyl.

In some embodiments, Ring B is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, the compound of Formula (I) has the following structure of Formula (V):

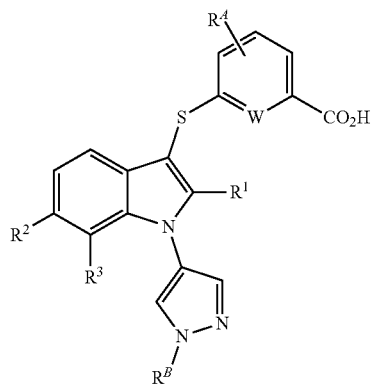

Formula (V)

wherein,

W is CH, CF or N;

or a pharmaceutically acceptable salt, or solvate thereof.

In some embodiments, $R^A$ is H, halogen, —CN, —OH, —$OR^9$, —$SR^9$, $C_1$-$C_6$alkyl, $C_1$-$C_6$fluoroalkyl, $C_1$-$C_6$deuteroalkyl, $C_1$-$C_6$heteroalkyl; $R^B$ is H, $C_1$-$C_6$alkyl, $C_1$-$C_6$fluoroalkyl, or $C_1$-$C_6$deuteroalkyl; $R^1$ is —F, —Cl, —Br, —CN, $C_3$-$C_6$cycloalkyl, —$NH_2$, or —O—$C_1$-$C_4$ alkyl; $R^2$ is H, halogen, CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl; $R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_6$fluoroalkoxy, or $C_1$-$C_4$hydroxyalkyl.

In some embodiments, $R^1$ is —F, —Cl, —Br, —CN, cyclopropyl, —$NH_2$, or —O—$CH_3$. In some embodiments, $R^1$ is —F, —Cl, or —Br. In some embodiments, $R^1$ is $C_3$-$C_6$cycloalkyl. In some embodiments, $R^1$ is cyclopropyl.

In some embodiments, the compound of Formula (I) or Formula (V) has the following structure of Formula (yl):

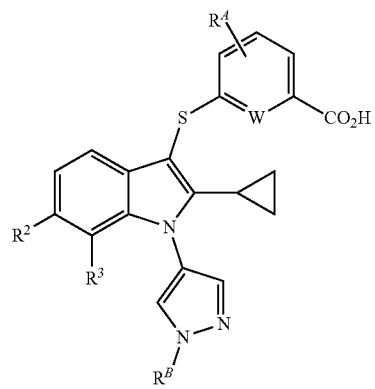

(Formula (VI))

wherein,

W is CH, CF or N;

or a pharmaceutically acceptable salt, or solvate thereof.

In some embodiments, $R^A$ is H, F, Cl, Br, I, —CN, —OH, —$OCH_3$, —$OCH_2CH_3$, —$OCF_3$, —$OCH_2CF_3$, —$CH_3$, —$CH_2CH_3$, —$CF_3$, or —$CD_3$. In some embodiments, $R^A$ is H.

In some embodiments, $R^B$ is $C_1$-$C_6$alkyl. In some embodiments, $R^B$ is —$CH_3$, —$CH_2CH_3$, or —$CH_2CH_2CH_3$, or —$CH(CH_3)_2$.

In some embodiments, $R^2$ is H, F, Cl, Br, I, —CN, —OH, —$CH_3$, —$CF_3$, —$CD_3$, —$OCH_3$, —$OCH_2CH_3$, —$OCF_3$, —$OCH_2CF_3$, or —$CH_2OH$. In some embodiments, $R^2$ is $C_1$.

In some embodiments, $R^3$ is H, F, Cl, Br, I, —CN, —OH, —$CH_3$, —$CF_3$, —$CD_3$, —$OCH_3$, —$OCH_2CH_3$, —$OCF_3$, —$OCH_2CF_3$, or —$CH_2OH$. In some embodiments, $R^3$ is H, F, or Cl.

In some embodiments, a compound of Formula (I), or a pharmaceutically acceptable salt, or solvate there, is:

3-((2,6-dichloro-1-(1-propyl-1H-pyrazol-4-yl)-1H-indol-3-yl)thio)benzoic acid (Compound no. 1-1);

3-((6-chloro-2-cyano-1-(1-propyl-1H-pyrazol-4-yl)-1H-indol-3-yl)thio)benzoic acid (Compound no. 1-3);

3-((6-chloro-2-cyclopropyl-1-(1-propyl-1H-pyrazol-4-yl)-1H-indol-3-yl)thio)benzoic acid (Compound no. 1-4);

3-((2,6-dichloro-7-fluoro-1-(1-propyl-1H-pyrazol-4-yl)-1H-indol-3-yl)thio)benzoic acid (Compound no. 1-7);

3-((2-bromo-6-chloro-1-(1-propyl-1H-pyrazol-4-yl)-1H-indol-3-yl)thio)benzoic acid (Compound no. 1-2);

3-((6-chloro-2-cyclopropyl-7-fluoro-1-(1-propyl-1H-pyrazol-4-yl)-1H-indol-3-yl)thio)benzoic acid (Compound no. 1-10);

3-((6-chloro-2-cyclopropyl-7-fluoro-1-((1-propyl-1H-pyrazol-4-yl)-1H-indol-3-yl)thio)-2-fluorobenzoic acid (Compound no. 1-16);

3-((2,6-dichloro-7-fluoro-1H-(1-propyl-1H-pyrazol-4-yl)-1H-indol-3-yl)thio)-2-fluorobenzoic acid (Compound no. 1-13);

3-((6-chloro-2-cyclopropyl-1-(1-ethyl-1H-pyrazol-4-yl)-7-fluoro-1H-indol-3-yl)thio)-2-fluorobenzoic acid (Compound no. 1-34);

6-((6-chloro-2-cyclopropyl-1-(1-ethyl-1H-pyrazol-4-yl)-1H-fluoro-1H-indol-3-yl)thio)picolinic acid (Compound no. 1-92);

3-((6-chloro-2-cyclopropyl-7-fluoro-1-(1H-pyrazol-4-yl)-1H-indol-3-yl)thio)-2-fluorobenzoic acid (Compound no. 1-119);

3-((6-chloro-2-cyclopropyl-7-fluoro-1-(1-(2-hydroxyethyl)-1H-pyrazol-4-yl)-1H-indol-3-yl)thio)-2-fluorobenzoic acid (Compound no. 1-120);

3-((1-(1-(2-(carbamoyloxy)ethyl)-1H-pyrazol-4-yl)-6-chloro-2-cyclopropyl-7-fluoro)-1H-indol-3-yl)thio)-2-fluorobenzoic acid (Compound no. 1-121);

3-((1-(1-(2-aminoethyl)-1H-pyrazol-4-yl)-6-chloro-2-cyclopropyl-7-fluoro-1H-indol-3-yl)thio)-2-fluorobenzoic acid (Compound no. 1-122);

3-((6-chloro-2-cyclopropyl-7-fluoro-1-(1-(2-ureidoethyl)-1H-pyrazol-4-yl)-1H-indol-3-yl)thio)-2-fluorobenzoic acid (Compound no. 1-123);

3-((1-(1-(3-carboxypropyl)-1H-pyrazol-4-yl)-6-chloro-2-cyclopropyl-7-fluoro-1H-indol-3-yl)thio)-2-fluorobenzoic acid (Compound no. 1-124);

3-((1-(1-(4-amino-4-oxobutyl)-1H-pyrazol-4-yl)-6-chloro-2-cyclopropyl-7-fluoro-1H-indol-3-yl)thio)-2-fluorobenzoic acid (Compound no. 1-125);

3-((2,6-dichloro-7-fluoro-1-(1-methyl-1H-pyrazol-4-yl)-1H-indol-3-yl)thio)-2-fluorobenzoic acid (Compound no. 1-49);

3-((6-chloro-2-cyclopropyl-7-fluoro-1-(1-(2,2,2-trifluoroethyl)-1H-pyrazol-4-yl)-1H-indol-3-yl)thio)-2-fluorobenzoic acid (Compound no. 1-126);

3-((6-chloro-2-cyclopropyl-1-(1-(ethyl-$d_5$)-1H-pyrazol-4-yl)-7-fluoro-1H-indol-3-yl)thio)-2-fluorobenzoic acid (Compound no. 1-127);

3-((2,6-dichloro-1-(1-ethyl-1H-pyrazol-4-yl)-7-fluoro-1H-indol-3-yl)thio)-2-fluorobenzoic acid (Compound no. 1-31);

3-((2,6-dichloro-7-fluoro-1-(pyridin-3-yl)-1H-indol-3-yl)thio)-2-fluorobenzoic acid (Compound no. 2-1);

3-((2-bromo-6-chloro-7-fluoro-1-(pyridin-3-yl)-1H-indol-3-yl)thio)-2-fluorobenzoic acid (Compound no. 2-2);

3-((6-chloro-2-cyclopropyl-7-fluoro-1-(pyridin-3-yl)-1l-indol-3-yl)thio)-2-fluorobenzoic acid (Compound no. 2-3);

3-((1-(1-(6-aminoethyl)-1H-pyrazol-4-yl)-6-chloro-2-cyclopropyl-7-fluoro-1H-indol-3-yl)thio)-2-fluorobenzoic acid (Compound no. 1-128);

3-((6-chloro-2-cyclopropyl-7-fluoro-1-(1-(hex-5-yn-1-yl)-1-H-pyrazol-4-yl)-1H-indol-3-yl)thio)-2-fluorobenzoic acid (Compound no. 1-129);

3-((1-(1-(3-hydroxy-2,2-dimethylpropyl)-1N-pyrazol-4-yl)-6-chloro-2-cyclopropyl-7-fluoro-1H-indol-3-yl)thio)-2-fluorobenzoic acid (Compound no. 1-130); or 3-((6-chloro-2-cyclopropyl-1-(1-(6-(3-(3',6-dihydroxy-3-oxo-3H-spiro[isobenzofuran-1,9'-xanthen]-5-yl)ureido)hexyl)-1H-pyrazol-4-yl)-7-fluoro-1H-indol-3-yl)thio)-2-fluorobenzoic acid (Compound 1-131).

Any combination of the groups described above for the various variables is contemplated herein. Throughout the specification, groups and substituents thereof are chosen by one skilled in the field to provide stable moieties and compounds.

In one aspect, described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is in the form of a tablet, a pill, a capsule, a liquid, a suspension, a gel, a dispersion, a solution, an emulsion, an ointment, or a lotion.

In one aspect, described herein is a method of treating or preventing any one of the diseases or conditions described herein comprising administering a therapeutically effective amount of a compound described herein, or a pharmaceutically acceptable salt, or solvate thereof, to a mammal in need thereof.

In another aspect, described herein is a method for treating or preventing cancer, or fibrosis, or combinations thereof in a mammal comprising administering a therapeutically effective amount of a compound described herein, or a pharmaceutically acceptable salt, or solvate thereof, to the mammal in need thereof.

In one aspect, described herein is a method for treating or preventing cancer in a mammal comprising administering a therapeutically effective amount of a compound described herein, or a pharmaceutically acceptable salt, or solvate thereof, to the mammal in need thereof. In some embodiments, the cancer is amenable to treatment with an autotaxin inhibitor. In some embodiments, the method further comprises administering a second therapeutic agent to the mammal in addition to the compound described herein, or a pharmaceutically acceptable salt, or solvate thereof.

In one aspect, described herein is a method for the treatment or prevention of fibrosis in a mammal comprising administering a therapeutically effective amount of a compound described herein, or a pharmaceutically acceptable salt, or solvate thereof, to the mammal in need thereof. In other embodiments, the fibrosis is amenable to treatment with an autotaxin inhibitor. In some embodiments, the method further comprises administering a second therapeutic agent to the mammal in addition to the compound described herein, or a pharmaceutically acceptable salt, or solvate thereof.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by inhalation; and/or I t administered by nasal administration; or and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the aforementioned aspects involving the treatment of ATX dependent diseases or conditions are further embodiments comprising administering at least one additional agent in addition to the administration of a compound described herein, or a pharmaceutically acceptable salt thereof. In various embodiments, each agent is administered in any order, including simultaneously.

In any of the embodiments disclosed herein, the mammal is a human.

In some embodiments, compounds provided herein are administered to a human.

In some embodiments, compounds provided herein are orally administered.

Articles of manufacture, which include packaging material, a compound described herein, or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for inhibiting the activity of autotaxin, or for the treatment, prevention or amelioration of one or more symptoms of a disease or condition that would benefit from inhibition of the activity of autotaxin, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Autotaxin and LPA

Autotaxin (ATX, NPP2, or E-NPP2), an approximately 120 kDa glycoprotein, is a secreted nucleotide pyrophosphatase/phosphodiesterase (NPP) with lysophospholipase D activity that converts extracellular lysophosphatidylcholine (LPC) and other lysophospholipids to lysophosphatidic acid (LPA). ATX is considered to be responsible for the majority of circulating LPA production.

LPA acts through sets of specific G protein-coupled receptors (GPCRs), such as LPA1, LPA2, LPA3, LPA4, LPA5, LPA6, LPA7, LPA8, in an autocrine and paracrine fashion to produce a variety of biological responses. For example, lysophospholipids, such as lysophosphatidic acid (LPA), are known to affect such biological functions as cellular proliferation, differentiation, survival, migration, adhesion, invasion, and morphogenesis. In addition, LPA is known to play a role in such processes as platelet activation, smooth muscle contraction, actin stress fiber formation, and cell migration.

ATX and LPA have been detected in various biological fluids such as serum, plasma, cerebrospinal fluid, seminal fluid, urine, and saliva, both in animals and humans, suggesting that they are potential biomarkers to predict certain diseases. For example, serum ATX concentration and activity is elevated in patients with chronic liver diseases and in pregnant women. In addition, ATX concentration has been found to be lower in postoperative cancer patients as a result of postoperative damage or poor nutritional state. In addition, ATX is known to be essential for normal development. For example, ATX-deficient mice die at embryonic day 9.5 with profound vascular defects in both the yolk sac and the embryo. Furthermore, at embryonic day 8.5 ATX-deficient embryos were found to have malformed allantois, neural tube defects, and assymetric headfolds.

Cancer

ATX has been demonstrated to increase cell motility, neovascularization, proliferation and aggressiveness of tumors. It is upregulated in numerous tumor lineages, such as breast, renal, liver, glioblastoma, ovarian and prostate cancer.

In some embodiments, disclosed herein are methods of treating cancer with a compound disclosed herein.

ATX is a prometastatic enzyme initially isolated from the conditioned medium of human melanoma cells. In addition, ATX overexpression is frequently observed in malignant tumor tissues such as breast cancer, renal cancer, Hodgkin lymphoma, hepatocellular carcinoma, pancreatic cancer and glioblastoma. LPA also contributes to tumorigenesis by increasing motility and invasiveness of cells.

The term "cancer" as used herein, refers to an abnormal growth of cells that tend to proliferate in an uncontrolled way and, in some cases, to metastasize (spread). Types of cancer include, but are not limited to, solid tumors (such as those of the bladder, bowel, brain, breast, endometrium, heart, kidney, lung, liver, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Fibrosis

In some embodiments, disclosed herein are methods of treating fibrosis with a compound disclosed herein.

"Fibrosis," as used herein, refers to the accumulation of extracellular matrix constituents that occurs following trauma, inflammation, tissue repair, immunological reactions, cellular hyperplasia, and neoplasia.

In some embodiments, disclosed herein is a method of reducing fibrosis in a tissue comprising contacting a fibrotic cell or tissue with a compound disclosed herein, in an amount sufficient to decrease or inhibit the fibrosis. In some embodiments, the fibrosis includes a fibrotic condition.

In some embodiments, reducing fibrosis, or treatment of a fibrotic condition, includes reducing or inhibiting one or more of: formation or deposition of extracellular matrix proteins; the number of pro-fibrotic cell types (e.g., fibroblast or immune cell numbers); cellular collagen or hydroxyproline content within a fibrotic lesion; expression or activity of a fibrogenic protein; or reducing fibrosis associated with an inflammatory response.

In some embodiments, the fibrotic condition is primary fibrosis. In some embodiments, the fibrotic condition is idiopathic. In some embodiments, the fibrotic condition is associated with (e.g., is secondary to) a disease; a toxin; an insult (e.g., an environmental hazard); a medical treatment, or a combination thereof.

In some embodiments, the fibrotic condition is a fibrotic condition of the lung (pulmonary fibrosis), a fibrotic condition of the liver (renal fibrosis), a fibrotic condition of the heart or vasculature (cardiac fibrosis), a fibrotic condition of the kidney (renal fibrosis), a fibrotic condition of the skin, a fibrotic condition of the gastrointestinal tract, or a combination thereof.

In some embodiments, the fibrotic condition is a fibrotic condition of the lung. In some embodiments, the fibrotic condition of the lung is chosen from one or more of: pulmonary fibrosis, idiopathic pulmonary fibrosis (IPF), usual interstitial pneumonitis (UIP), interstitial lung disease, cryptogenic fibrosing alveolitis (CFA), bronchiolitis obliterans, or bronchiectasis. In some embodiments, the fibrotic condition of the lung treated with the methods of the invention is associated with (e.g., secondary to) a cancer treatment.

In some embodiments, the fibrotic condition is a fibrotic condition of the liver.

In some embodiments, the fibrotic condition is a fibrotic condition of the heart.

In some embodiments, the fibrotic condition is a fibrotic condition of the kidney.

In some embodiments, the fibrotic condition is a fibrotic condition of the skin.

In some embodiments, the fibrotic condition is a fibrotic condition of the gastrointestinal tract.

Compounds

Compounds described herein, including pharmaceutically acceptable salts, prodrugs, active metabolites and pharmaceutically acceptable solvates thereof, are autotaxin inhibitors.

In one aspect, described herein is a compound of Formula (I), or a pharmaceutically acceptable salt, or solvate thereof:

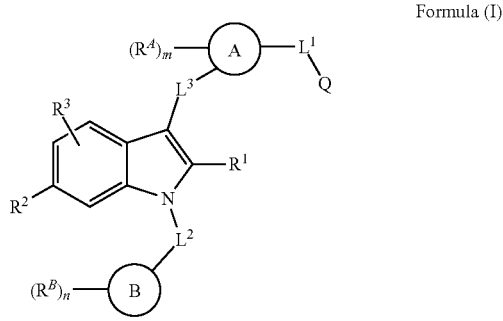

Formula (I)

wherein, $R^1$ is —F, —Cl, —Br, —CN, vinyl, $C_3$-$C_6$cycloalkyl, —$NH_2$, —$NH(C_1$-$C_4$ alkyl), —$N(C_1$-$C_4$ alkyl)$_2$, —O—$C_1$-$C_4$ alkyl, or —S—$C_1$-$C_4$ alkyl;

$R^2$ is H, halogen, —CN, —$NO_2$, —OH, —$OR^9$, —$SR^9$, —S(=O)$R^9$, —S(=O)$_2R^9$, —S(=O)$_2N(R^{10})_2$, $NR^{10}S(=O)_2R^9$, —C(O)$R^9$—OC(O)$R^9$, —$CO_2R^{10}$, —$OCO_2R^9$, —$N(R^{10})_2$, —C(=O)$N(R^{10})_2$, —OC(=O)$N(R^{10})_2$, —NHC(=O)$R^9$, —NHC(=O)$OR^9$, $C_1$-$C_4$alkyl, $C_1$-$C_4$fluoroalkyl, $C_1$-$C_4$deuteroalkyl, $C_1$-$C_4$hydroxyalkyl, $C_1$-$C_4$heteroalkyl, $C_3$-$C_6$cycloalkyl, substituted or unsubstituted phenyl, or substituted or unsubstituted monocyclic heteroaryl;

Ring A is a monocyclic aryl, bicyclic aryl, monocyclic heterocycloalkyl, monocyclic heteroaryl or bicyclic heteroaryl;

each $R^A$ is H, halogen, —CN, —$NO_2$, —OH, —$OR^9$, —$SR^9$, —S(=O)$R^9$, —S(=O)$_2R^9$—S(=O)$_2N(R^{10})_2$, —$NR^{10}S(=OC)_2R^9$, —C(=O)$R^9$, —OC(=O)$R^9$, —$CO_2R^{10}$, —$OCO_2R^9$, —$N(R^{10})_2$, —C(=O)$N(R^{10})_2$, —OC(=O)$N(R^9)_2$, —NHC(=O)$R^9$, —NHC(=O)$OR^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, or substituted or unsubstituted monocyclic heteroaryl;

m is 0, 1, or 2;

$L^1$ is absent, $C_1$-$C_6$alkylene, $C_1$-$C_6$fluoroalkylene, or $C_3$-$C_6$cycloalkylene;

Q is —$CO_2H$, —CO($C_1$-$C_6$alkyl), —OH, —CN, —B(OH)$_2$, —C(=O)NHSO$_2R^9$, —C(=O)$N(R^{10})_2$, —SO$_2$NHC(=O)$R^9$, —CN, tetrazolyl, —OP(=O)(OH)$_2$, —P(=O)(OH)$_2$ or carboxylic acid bioisostere;

$L^2$ is absent, $C_1$-$C_4$alkylene, or $C_3$-$C_7$cycloalkylene;

$L^3$ is —S—, S(=O), S(=O)$_2$ or —O—;

Ring B is a monocyclic aryl, bicyclic aryl, monocyclic heteroaryl or bicyclic heteroaryl;

each $R^B$ is independently H, halogen, —CN, —$NO_2$, —OH, —$OR^9$, —$SR^9$, —S(O)$R^9$, —S(=O)$_2R^9$, —S(O)$_2N(R^{10})_2$, —$NR^{10}S(=O)_2R^9$, —S(=O)$R^9$, —OC(=O)$R^9$, —$CO_2R^{10}$, —$OCO_2R^9$, —$N(R^{10})_2$, —C(=O)$N(R^{10})_2$, —OC(=O)$N(R^9)_2$, —NHC(=O)$R^9$, —NHC(=O)$OR^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, $C_1$-$C_4$alkylene-(substituted or unsubstituted phenyl), substituted unsubstituted monocyclic heteroaryl, $C_1$-$C_4$alkylene-(substituted or unsubstituted monocyclic heteroaryl), a substituted or unsubstituted bicyclic heteroaryl, or $C_1$-$C_4$alkylene-(substituted or unsubstituted bicyclic heteroaryl);

n is 0, 1, or 2;

$R^9$ is $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, a substituted or unsubstituted monocyclic heteroaryl, or a substituted or unsubstituted bicyclic heteroaryl;

each $R^{10}$ is independently selected from H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, or a substituted or unsubstituted monocyclic heteroaryl; or two $R^{10}$ groups attached to the same N atom are taken together with the N atom to which they are attached to form a substituted or unsubstituted heterocycle.

For any and all of the embodiments, substituents are selected from among a subset of the listed alternatives. For example, in some embodiments, X is —O—, —S—, —S(=O)—, or —S(=O)$_2$— In other embodiments, X is —O— or —S—. In other embodiments, X is —S—, —S(=O)—, or —S(=O)$_2$—. In some embodiments, X is —S—.

In some embodiments, $R^1$ is —F, —Cl, —Br, —CN, vinyl, cyclopropyl, cyclobutyl, —$NH_2$, —NH(CHO), —$N(CH_3)_2$, —O—$CH_3$, or —S—$CH_3$.

In some embodiments, $R^1$ is vinyl, cyclopropyl, or cyclobutyl.

In some embodiments, $R^1$ is cyclopropyl, or cyclobutyl.

In some embodiments, $R^1$ is —F, —Cl, or —Br.

In some embodiments, $L^1$ is absent, or $C_1$-$C_4$alkylene; $L^3$ is —S—, S(=O), or S(=O)$_2$.

In some embodiments, $L^2$ is absent, —$CH_2$—, —$CH_2CH_2$—, —$CH_2CH_2CH_2$—, or —CH($CH_3$)—.

In some embodiments, $L^1$ is absent, —$CH_2$—, —$CH_2CH_2$—, —$CH_2C$—2$CH_2$—, —CH($CH_3$)—, —CH($CH_2CH_3$)—, —C($CH_3)_2$—, —C($CH_2CH_3)_2$—, cyclopropyl-1,1-diyl, cyclobutyl-1,1-diyl, cyclopentyl-1,1-diyl or cyclohexyl-1,1-diyl; Q is —$CO_2H$, —$CO_2(C_1$-$C_6$alkyl), —C(=O)NHSO$_2R^9$ or tetrazolyl.

In some embodiments, $L^1$ is absent or —$CH_2$—; Q is —$CH_2$—, or —$CO_2(C_1$-$C_6$alkyl).

In some embodiments, the compound of Formula (I) has the following structure of Formula (II)

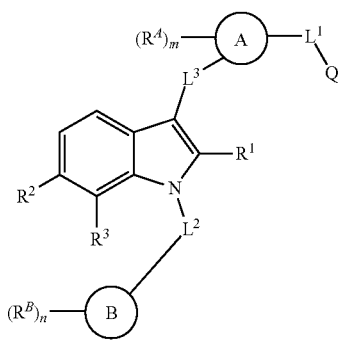

Formula (II)

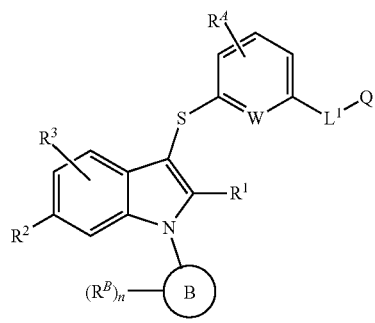

Formula (III)

wherein.

W is CH, CF or N;

or a pharmaceutically acceptable salt, or solvate thereof.

In some embodiments, $L^1$ is absent; and Q is —CO$_2$H.

In some embodiments, described herein is a compound of Formula (III), or a pharmaceutically acceptable salt, or solvate thereof:

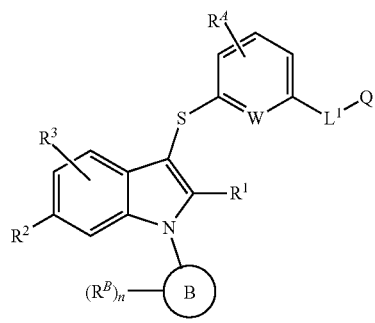

Formula (III)

wherein.

R$^1$ is —Cl, —Br, —CN, or C$_3$-C$_6$cycloalkyl;

R$^2$ is H, halogen, —CN, —NO$_2$, —OH, —OR$^9$, —SR$^9$, —S(=O)R$^9$, —S(=O)$_2$R$^{10}$, —S(=O)$_2$N(R$^{10}$)$_2$, C$_1$-C$_4$alkyl, C$_1$-C$_4$fluoroalkyl, C$_1$-C$_4$deuteroalkyl, or C$_3$-C$_6$cycloalkyl;

R$^3$ is 1, halogen, —CN, —OH, C$_1$-C$_4$alkyl, C$_1$-C$_4$fluoroalkyl, C$_1$-C$_4$deuteroalkyl, C$_1$-C$_4$alkoxy, or C$_1$-C$_4$fluoroalkoxy;

W is CH, CF or N;

each R$^A$ is H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, C$_1$-C$_6$alkyl, or C$_1$-C$_6$fluoroalkyl;

L$^1$ is absent, C$_1$-C$_6$alkylene, or C$_3$-C$_6$cycloalkylene;

Q is —CO$_2$H, —CO$_2$(C$_1$-C$_6$alkyl), —OH, —CN, —B(OH)$_2$, —C(=O)NHSO$_2$R$^9$, —C(=O)N(R$^{10}$), —SO$_2$NHC(=O)R$^9$, —CN, tetrazolyl, —OP(=O)(OH)$_2$, —P(=O)(OH)$_2$ or carboxylic acid bioisostere;

Ring B is a monocyclic heteroaryl;

each R$^8$ is independently H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, C$_1$-C$_6$alkyl, C$_1$-C$_1$fluoroalkyl, C$_1$-C$_6$deuteroalkyl, C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted phenyl, C$_1$-C$_4$alkylene-(substituted or unsubstituted phenyl), substituted unsubstituted monocyclic heteroaryl, C$_1$-C$_4$alkylene-(substituted or a pharmaceutically acceptable salt, or solvate thereof.

In some embodiments, Ring A is phenyl, naphthyl, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms; Ring B is phenyl, naphthyl, monocyclic heteroaryl containing 1-4 N atoms and 0 or 10 or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms.

In some embodiments, Ring A is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, Ring A is phenyl or naphthyl.

In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

In some embodiments, Ring A is pyridinyl, pyrimidinyl, pyrazinyl, pyridazinyl, or triazinyl.

In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments, Ring A is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, each R$^A$ is H, halogen, —CN, —OH, —OR$^9$. —SR$^9$, C$_1$-C$_6$alkyl, C$_1$-C$_6$fluoroalkyl, C$_1$-C$_6$deuteroalkyl, C$_1$-C$_6$heteroalkyl.

In some embodiments, L$^3$ is —S—.

In some embodiments, L$^2$ is absent.

In some embodiments, the compound of Formula (I) or Formula (II) has the following structure of Formula (III):

or unsubstituted monocyclic heteroaryl), a substituted or unsubstituted bicyclic heteroaryl, or $C_1$-$C_4$alkylene-(substituted or unsubstituted bicyclic heteroaryl);

n is 0, 1, or 2;

$R^9$ is $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, a substituted or unsubstituted monocyclic heteroaryl, or a substituted or unsubstituted bicyclic heteroaryl;

each $R^{10}$ is independently H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, or a substituted or unsubstituted monocyclic heteroaryl; or two $R^{10}$ groups attached to the same N atom are taken together with the N atom to which they are attached to form a substituted or unsubstituted heterocycle.

In some embodiments, $R^1$ is —Cl, —Br, —CN, or cyclopropyl. In some embodiments, $R^1$ is cyclopropyl. In some embodiments, $R^1$ is —Cl.

In some embodiments, $L^1$ is absent, —$CH_2$—, —$CH_2CH_2$—, —$CH_2CH_2CH_2$—, —$CH(CH_3)$—, —CH($CH_2CH_3$)—, —C($CH_3$)$_2$—, —C($CH_2CH_3$)$_2$—, cyclopropyl-1,1-diyl, cyclobutyl-1,1-diyl, cyclopentyl-1,1-diyl or cyclohexyl-1,1-diyl; and Q is —$CO_2$H, —$CO_2$($C_1$-$C_6$alkyl), —C(=O)NHSO$_2$R$^9$ or tetrazolyl.

In some embodiments, $L^1$ is absent, —$CH_2$—, —CH($CH_3$)—, —C($CH_3$)$_2$—, or cyclopropyl-1,1-diyl; and Q is —$CO_2$H, or —$CO_2$($C_1$-$C_6$alkyl).

In some embodiments, $L^1$ is absent, —$CH_2$—, —$CH_2CH_2$—, —$CH_2CH_2CH_2$—, —CH(CH)—, —CH($CH_2CH_3$)—, —C($CH_3$)$_2$—, or —C($CH_2CH_3$)$_2$—. In some embodiments, $L^1$ is absent, —$CH_2$—, —CH($CH_3$)—, —CH($CH_2CH_3$)—, —C($CH_3$)$_2$—, or —C($CH_2CH_3$)$_2$—. In some embodiments, $L^1$ is absent, —$CH_2$—, —CH($CH_3$) or —C($CH_3$)$_2$— In some embodiments, $L^1$ is absent, or —$CH_2$—.

In some embodiments, $L^1$ is —$CH_2$—, —$CH_2CH_2$—, —$CH_2CH_2CH_2$—, —CH($CH_3$)—, —CH($CH_2CH_3$)—, —C($CH_3$)$_2$—, or —C($CH_2CH_3$)$_2$—. In some embodiments, $L^1$ is —$CH_2$—, —CH($CH_3$)—, —C($CH_2CH_2$)—, —C($CH_3$)$_2$—, or —C($CH_2CH_3$)$_2$—. In some embodiments, $L^1$ is —$CH_2$—, —CH($CH_3$)—, or —C($CH_3$)$_2$—. In some embodiments, $L^1$ is —$CH_2$—.

In some embodiments, $L^1$ is absent or —$CH_2$—; and Q is —$CO_2$H, or —$CO_2$($C_1$-$C_6$alkyl).

In some embodiments, Ring B is monocyclic heteroaryl containing 1-4 N atoms and 0 or 1 O or S atoms, or monocyclic heteroaryl containing 0-4 N atoms and 1 O or S atoms.

In some embodiments, Ring B is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimindinyl, pyrazinyl, pyridazinyl, or triazinyl.

In some embodiments, each $R^A$ is H, halogen, —CN, —OH, —OR, —SR$^9$, $C_1$-$C_6$ alkyl, or $C_1$-$C_6$fluoroalkyl.

In some embodiments, $L^1$ is absent, —$CH_2$—, —CH(CH—)—, —C(CH—)$_2$—, or cyclopropyl-1,1-diyl; and Q is —$CO_2$H.

In some embodiments, $L^1$ is absent; and Q is —$CO_2$—.

In some embodiments, the compound or Formula (III) has the following structure:

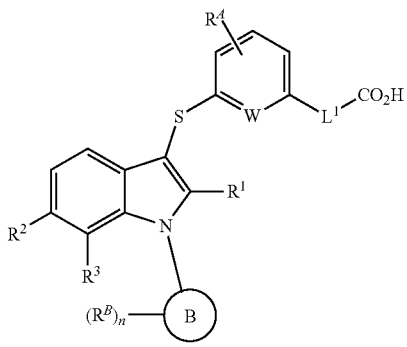

or a pharmaceutically acceptable salt, or solvate thereof.

In some embodiments, $R^2$ is H, F, Cl, Br, I, —CN, —OH, —$CH_3$, —$CF_3$, —$CD_3$, —$OCH_3$, —$OCH_2CH_3$, —$OCF_3$, or —$OCH_2CF_3$; $R^3$ is H, F, Cl, Br, I, —CN, —OH, —$CH_3$, —$CF_3$, —$CD_3$, —$OCH_3$, —$OCH_2CH_3$, —$OCF_3$, or —$OCH_2CF_3$.

In some embodiments, $R^2$ is Cl; $R^3$ is H, F, or Cl.

In some embodiments, Ring B is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

In some embodiments, Ring B is pyrazolyl.

In some embodiments, the compound of Formula (II) has the following structure:

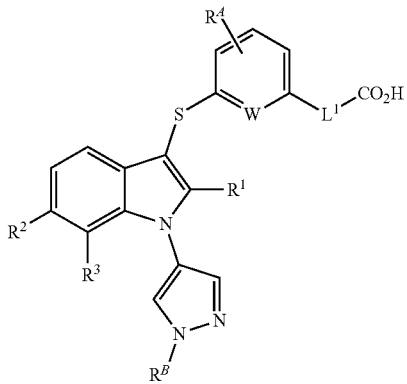

or a pharmaceutically acceptable salt, or solvate thereof.

In some embodiments, $R^A$ is H, halogen, —CN, —O—I, —OR$^9$, —SR$^9$, $C_1$-$C_6$alkyl, or $C_1$-$C_6$fluoroalkyl;

$R^B$ is H, $C_1$-$C_6$alkyl, $C_1$-$C_6$fluoroalkyl, or $C_1$-$C_6$deuteroalkyl, $R^1$ is —Cl, —Br, —CN, or cyclopropyl; $R^2$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, or $C_1$-$C_4$fluoroalkoxy; and $R^3$ is —I, halogen —CN, —O—I, $C_1$-$C_4$alkyl, $C_1$-$C_4$fluoroalkyl, $C_1$-$C_4$deuteroalkyl, $C_1$-$C_4$alkoxy, or $C_1$-$C_4$fluoroalkoxy.

In some embodiments, $R^1$ is —Cl, or —Br. In some embodiments, $R^1$ is cyclopropyl.

In some embodiments, the compound of Formula (III) has the following structure:

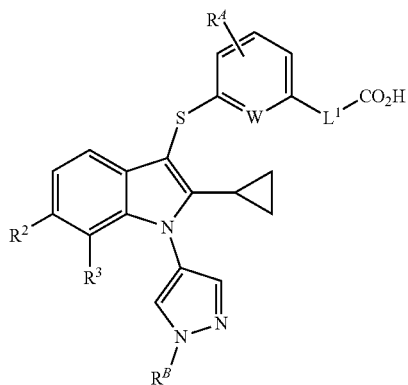

or a pharmaceutically acceptable salt, or solvate thereof.

In some embodiments, the compound of Formula (III) has the following structure:

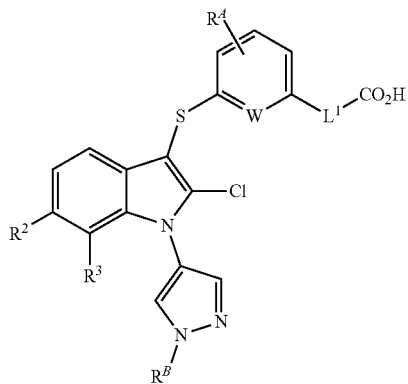

or a pharmaceutically acceptable salt, or solvate thereof.

In some embodiments, $R^A$ is H, F, Cl, Br, I, —CN, —OH, —OCH$_3$, —OCH$_2$CH$_3$, —OCF$_3$, OCH$_2$CF$_3$, —CH$_3$, —CH$_2$CH$_3$, —CF$_3$, or —CD$_3$.

In some embodiments, $R^B$ is $C_1$-$C_6$alkyl.

In some embodiments, $R^2$ is H, F, Cl, Br, I, —CN, —OH, —CH$_3$, —CF$_3$, —CD$_3$, —OCH$_3$, —OCH$_2$CH$_3$, —OCF$_3$, or —OCH$_2$CF$_3$; $R^3$ is H, F, Cl, Br, I, —CN, —OH, —CH$_3$, —C, —CD$_3$, —OCH$_3$, —OCH$_2$CH$_3$, —OCF$_3$, or —OCH$_2$CF$_3$.

In some embodiments, $R^2$ is Cl; $R^3$ is H, F, or Cl.

In some embodiments, $L^1$ is absent, —CH$_2$—, —CH(CH$_3$)—, —C(CH$_3$)$_2$—, or cyclopropyl-1,1-diyl.

In some embodiments, $L^1$ is absent.

In some embodiments, the compound of Formula (I), Formula (II), or Formula (III) has the following structure of Formula (IV):

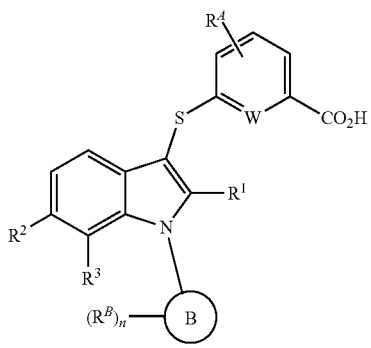

wherein,

W is CH, CF or N;

or a pharmaceutically acceptable salt, or solvate thereof.

In some embodiments, $R^2$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl.

In some embodiments, $R^2$ is H, F, Cl, Br, I, —CN, —OH, —CH$_3$, —CF$_3$, —CD$_3$, —OCH$_3$, —OCH$_2$CH$_3$, —OCF$_3$, —OCH$_2$CF$_3$, or —CH$_2$OH.

In some embodiments, $R^2$ is C.

In some embodiments, $R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl.

In some embodiments, $R^3$ is H, F, Cl, Br, I, —CN, —OH, —CH$_3$, —CF$_3$, —CD$_3$, —OCH$_3$, —OCH$_2$CH$_3$, —OCF$_3$, —OCH$_2$CF$_3$, or —CH$_2$OH.

In some embodiments, $R^1$ is H, F, or Cl.

In some embodiments, Ring B is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, Ring B is phenyl or naphthyl.

In some embodiments, Ring B is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

In some embodiments, Ring B is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments, Ring B is pyrazolyl.

In some embodiments, Ring B is pyrazolyl; and each $R^B$ is independently H, $C_1$-$C_6$alkyl, $C_1$-$C_6$fluoroalkyl, or $C_1$-$C_6$deuteroalkyl; n is 1.

In some embodiments, Ring B is pyridinyl, pyrimidinyl, pyrazinyl, pyridazinyl, or triazinyl.

In some embodiments, Ring B is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, the compound of Formula (I) has the following structure of Formula (V):

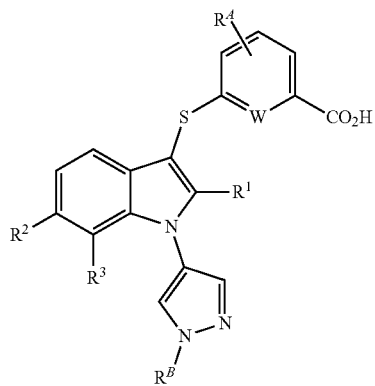

Formula (V)

wherein,

W is CH, CF or N;

or a pharmaceutically acceptable salt, or solvate thereof.

In some embodiments, $R^4$ is H, halogen, —CN, —OH, —$OR^9$, —$SR^9$, $C_1$-$C_6$alkyl, $C_1$-$C_6$fluoroalkyl, $C_1$-$C_6$deuteroalkyl, $C_1$-$C_6$heteroalkyl; $R^B$ is H, $C_1$-$C_6$alkyl, $C_1$-$C_6$fluoroalkyl, or $C_1$-$C_6$deuteroalkyl; $R^1$ is —F, —Cl, —Br, —CN, $C_3$-$C_6$cycloalkyl, —$NH_2$, or —O—$C_1$-$C_4$ alkyl; $R^2$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl; $R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl.

In some embodiments, $R^1$ is —F, —Cl, —Br, —CN, cyclopropyl, —$NH_2$, or —O—$CH_3$. In some embodiments, $R^1$ is —F, —Cl, or —Br. In some embodiments, $R^1$ is —Cl. In some embodiments, $R^1$ is $C_3$-$C_6$cycloalkyl. In some embodiments, $R^1$ is cyclopropyl.

In some embodiments, the compound of Formula (I) or Formula (V) has the following structure of Formula (yl):

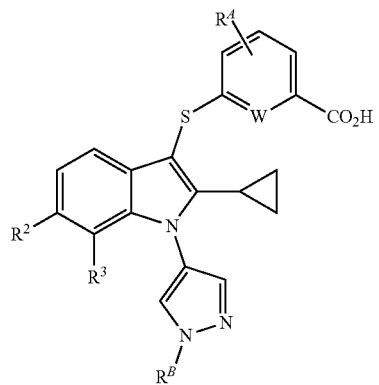

Formula (VI)

wherein,

W is CH, CF or N;

or a pharmaceutically acceptable salt, or solvate thereof.

In some embodiments, the compound of Formula (I) or Formula (V) has the following structure of Formula (VII):

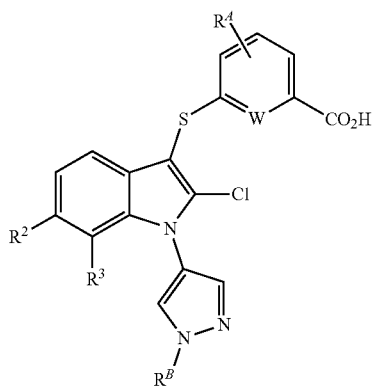

Formula (VII)

wherein,

W is CH, CF or N;

or a pharmaceutically acceptable salt, or solvate thereof.

In some embodiments, $R^4$ is H, F, Cl, Br, I, —CN, —OH, —$OCH_3$, —$OCH_2C_3$, —$OCF_3$, —$OCH_2CF_3$, —$CH_3$, —$CH_2CH_3$, —$CF_3$, or —$CD_3$. In some embodiments, $R^4$ is H.

In some embodiments, $R^B$ is $C_1$-$C_6$alkyl. In some embodiments, $R^B$ is —$CH$—$_3$, —$CH_2CH_3$, or —$CH_2CH_2CH_3$, or —$CH(CH_3)_2$.

In some embodiments, $R^2$ is H, F, Cl, Br, I, —CN, —OH, —$CH_3$, —$CF_3$, —$CD_3$, —$OCH_3$, —$OCH_2CH_3$, —$OCF_3$, —$OCH_2CF_3$, or —$CH_2OH$. In some embodiments, $R^2$ is $C_1$.

In some embodiments, $R^3$ is H, F, Cl, Br, I, —CN, —OH, —$CH_3$, —$CF_3$, —$CD_3$, —$OCH_3$, —$OCH_2CH_3$, —$OCF_3$, —$OCH_2CF_3$, or —$CH_2OH$. In some embodiments, $R^3$ is H, F, or Cl.

In some embodiments, W is CH, CF or N. In some embodiments, W is CH. In some embodiments, W is CH or CF. In some embodiments, W is CF. In some embodiments, W is N.

In some embodiments, the compound of Formula (I) has the following structure:

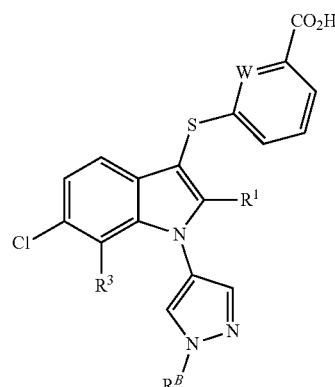

wherein,

W is CH, CF or N;

or a pharmaceutically acceptable salt, or solvate thereof.

In some embodiments, $R^1$ is —Cl or cyclopropyl. In some embodiments, $R^1$ is —Cl. In some embodiments, $R^1$ is cyclopropyl.

In some embodiments, $R^1$ is as described in Tables 1 and 2. In some embodiments, $R^3$ is as described in Tables 1 and 2. In some embodiments, $R^B$ is as described in Tables 1 and 2. In some embodiments, R, $R^3$ and $R^B$ are as described in Tables 1 and 2. In some embodiments, $L^1$ is as described in Table 2.

Any combination of the groups described above for the various variables is contemplated herein. Throughout the specification, groups and substituents thereof are chosen by one skilled in the field to provide stable moieties and compounds.

Exemplary compounds include the following compounds:

TABLE 1

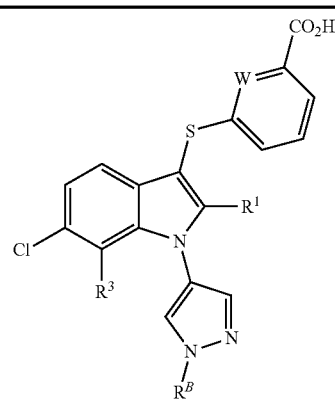

TABLE 1-continued

| Compound no. | $R^B$ | $R^1$ | W | $R^3$ |
|---|---|---|---|---|
| 1-1 | 1-propyl | —Cl | CH | H |
| 1-2 | 1-propyl | —Br | CH | H |
| 1-3 | 1-propyl | —CN | CH | H |
| 1-4 | 1-propyl | c-C$_3$H$_5$ | CH | H |
| 1-5 | 1-propyl | —NH$_2$ | CH | H |
| 1-6 | 1-propyl | —OMe | CH | H |
| 1-7 | 1-propyl | —Cl | CH | F |
| 1-8 | 1-propyl | —Br | CH | F |
| 1-9 | 1-propyl | —CN | CH | F |
| 1-10 | 1-propyl | c-C$_3$H$_5$ | CH | F |
| 1-11 | 1-propyl | —NH$_2$ | CH | F |
| 1-12 | 1-propyl | —OMe | CH | F |
| 1-13 | 1-propyl | —Cl | CF | F |
| 1-14 | 1-propyl | —Br | CF | F |
| 1-15 | 1-propyl | —CN | CF | F |
| 1-16 | 1-propyl | c-C$_3$H$_5$ | CF | F |
| 1-17 | 1-propyl | —NH$_2$ | CF | F |
| 1-18 | 1-propyl | —OMe | CF | F |
| 1-19 | ethyl | —Cl | CH | H |
| 1-20 | ethyl | —Br | CH | H |
| 1-21 | ethyl | —CN | CH | H |
| 1-22 | ethyl | c-C$_3$H$_5$ | CH | H |
| 1-23 | ethyl | —NH$_2$ | CH | H |
| 1-24 | ethyl | —OMe | CH | H |
| 1-25 | ethyl | —Cl | CH | F |
| 1-26 | ethyl | —Br | CH | F |
| 1-27 | ethyl | —CN | CH | F |
| 1-28 | ethyl | c-C$_3$H$_5$ | CH | F |
| 1-29 | ethyl | —NH$_2$ | CH | F |
| 1-30 | ethyl | —OMe | CH | F |
| 1-31 | ethyl | —Cl | CF | F |
| 1-32 | ethyl | —Br | CF | F |
| 1-33 | ethyl | —CN | CF | F |
| 1-34 | ethyl | c-C$_3$H$_5$ | CF | F |
| 1-35 | ethyl | —NH$_2$ | CF | F |
| 1-36 | ethyl | —OMe | CF | F |
| 1-37 | methyl | —Cl | CH | H |
| 1-38 | methyl | —Br | CH | H |
| 1-39 | methyl | —CN | CH | H |
| 1-40 | methyl | c-C$_3$H$_5$ | CH | H |
| 1-41 | methyl | —NH$_2$ | CH | H |
| 1-42 | methyl | —OMe | CH | H |
| 1-43 | methyl | —Cl | CH | F |
| 1-44 | methyl | —Br | CH | F |
| 1-45 | methyl | —CN | CH | F |
| 1-46 | methyl | c-C$_3$H$_5$ | CH | F |
| 1-47 | methyl | —NH$_2$ | CH | F |
| 1-48 | methyl | —OMe | CH | F |
| 1-49 | methyl | —Cl | CF | F |
| 1-50 | methyl | —Br | CF | F |
| 1-51 | methyl | —CN | CF | F |
| 1-52 | methyl | c-C$_3$H$_5$ | CF | F |
| 1-53 | methyl | —NH$_2$ | CF | F |
| 1-54 | 2-propyl | —Cl | CH | H |
| 1-55 | 2-propyl | —Br | CH | H |
| 1-56 | 2-propyl | —CN | CH | H |
| 1-57 | 2-propyl | c-C$_3$H$_5$ | CH | H |
| 1-58 | 2-propyl | —NH$_2$ | CH | H |
| 1-59 | 2-propyl | —OMe | CH | H |
| 1-60 | 2-propyl | —Cl | CH | F |
| 1-61 | 2-propyl | —Br | CH | F |
| 1-62 | 2-propyl | —CN | CH | F |
| 1-63 | 2-propyl | c-C$_3$H$_5$ | CH | F |
| 1-64 | 2-propyl | —NH$_2$ | CH | F |
| 1-65 | 2-propyl | —OMe | CH | F |
| 1-66 | 2-propyl | —Cl | CF | F |
| 1-67 | 2-propyl | —Br | CF | F |
| 1-68 | 2-propyl | —CN | CF | F |
| 1-69 | 2-propyl | c-C$_3$H$_5$ | CF | F |
| 1-70 | 2-propyl | —NH$_2$ | CF | F |
| 1-71 | 1-propyl | —Cl | N | H |
| 1-72 | 1-propyl | —Br | N | H |
| 1-73 | 1-propyl | —CN | N | H |
| 1-74 | 1-propyl | c-C$_3$H$_5$ | N | H |
| 1-75 | 1-propyl | —NH$_2$ | N | H |
| 1-76 | 1-propyl | —OMe | N | H |
| 1-77 | 1-propyl | —Cl | N | F |
| 1-78 | 1-propyl | —Br | N | F |
| 1-79 | 1-propyl | —CN | N | F |
| 1-80 | 1-propyl | c-C$_3$H$_5$ | N | F |
| 1-81 | 1-propyl | —NH$_2$ | N | F |
| 1-82 | 1-propyl | —OMe | N | F |
| 1-83 | ethyl | —Cl | N | H |
| 1-84 | ethyl | —Br | N | H |
| 1-85 | ethyl | —CN | N | H |
| 1-86 | ethyl | c-C$_3$H$_5$ | N | H |
| 1-87 | ethyl | —NH$_2$ | N | H |
| 1-88 | ethyl | —OMe | N | H |
| 1-89 | ethyl | —Cl | N | F |
| 1-90 | ethyl | —Br | N | F |
| 1-91 | ethyl | —CN | N | F |
| 1-92 | ethyl | c-C$_3$H$_5$ | N | F |
| 1-93 | ethyl | —NH$_2$ | N | F |
| 1-94 | ethyl | —OMe | N | F |
| 1-95 | methyl | —Cl | N | H |
| 1-96 | methyl | —Br | N | H |
| 1-97 | methyl | —CN | N | H |
| 1-98 | methyl | c-C$_3$H$_5$ | N | H |
| 1-99 | methyl | —NH$_2$ | N | H |
| 1-100 | methyl | —OMe | N | H |
| 1-101 | methyl | —Cl | N | F |
| 1-102 | methyl | —Br | N | F |

TABLE 1-continued

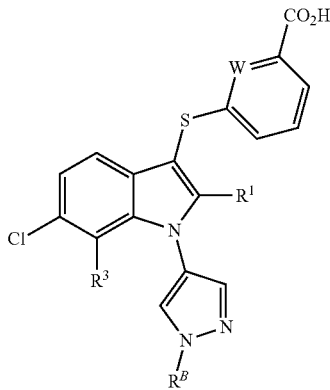

| Compound no. | $R^B$ | $R^1$ | W | $R^3$ |
|---|---|---|---|---|
| 1-103 | methyl | —CN | N | F |
| 1-104 | methyl | c-$C_3H_5$ | N | F |
| 1-105 | methyl | —$NH_2$ | N | F |
| 1-106 | methyl | —OMe | N | F |
| 1-107 | 2-propyl | —Cl | N | H |
| 1-108 | 2-propyl | —Br | N | H |
| 1-109 | 2-propyl | —CN | N | H |
| 1-110 | 2-propyl | c-$C_3H_5$ | N | H |
| 1-111 | 2-propyl | —$NH_2$ | N | H |
| 1-112 | 2-propyl | —OMe | N | H |
| 1-113 | 2-propyl | —Cl | N | F |
| 1-114 | 2-propyl | —Br | N | F |
| 1-115 | 2-propyl | —CN | N | F |
| 1-116 | 2-propyl | c-$C_3H_5$ | N | F |
| 1-117 | 2-propyl | —$NH_2$ | N | F |
| 1-118 | 2-propyl | —OMe | N | F |
| 1-119 | H | c-$C_3H_5$ | CF | F |
| 1-120 | —$CH_2CH_2OH$ | c-$C_3H_5$ | CF | F |
| 1-121 | —$CH_2CH_2OC(O)NH_2$ | c-$C_3H_5$ | CF | F |
| 1-122 | —$CH_2CH_2NH_2$ | c-$C_3H_5$ | CF | F |
| 1-123 | —$CH_2CH_2NHC(O)NH_2$ | c-$C_3H_5$ | CF | F |
| 1-124 | —$CH_2CH_2CH_2CO_2H$ | c-$C_3H_5$ | CF | F |
| 1-125 | —$CH_2CH_2CH_2CONH_2$ | c-$C_3H_5$ | CF | F |
| 1-126 | —$CH_2CF_3$ | c-$C_3H_5$ | CF | F |
| 1-127 | —$CD_2CD_3$ | c-$C_3H_5$ | CF | F |
| 1-128 | —$(CH_2)_6NH_2$ | c-$C_3H_5$ | CF | F |
| 1-129 | —$(CH_2)_4CCH$ | c-$C_3H_5$ | CF | F |
| 1-130 | —$CH_2C(CH_3)_2CH_2OH$ | c-$C_3H_5$ | CF | F |
| 1-131 | —$(CH_2)_6NHC(O)N$-fluorescein | c-$C_3H_5$ | CF | F |
| 1-132 | —$CH_2CH_2CH_2C(O)NHCH_3$ | c-$C_3H_5$ | CF | F |
| 1-133 | —$CH_2CH_2CH_2C(O)N(CH_3)_2$ | c-$C_3H_5$ | CF | F |
| 1-134 | —$CH_2CH_2C(CH_3)_2C(O)NH_2$ | c-$C_3H_5$ | CF | F |
| 1-135 | —$CH_2CH_2CH_2C(O)NH_2$ | c-$C_3H_5$ | N | F |
| 1-136 | —$CH_2CH_2CH_2C(O)NHCH_3$ | c-$C_3H_5$ | N | F |
| 1-137 | —$CH_2CH_2CH_2C(O)NH(CH_3)_2$ | c-$C_3H_5$ | N | F |
| 1-138 | —$CH_2CH_2C(CH_3)_2C(O)NH_2$ | c-$C_3H_5$ | N | F |

Compounds in Table 1 are named:
3-((2,6-dichloro-1-(1-propyl-1H-pyrazol-4-yl)-1H-indol-3-yl)thio)benzoic acid (compound no. 1-1);
3-((2-bromo-6-chloro-1-(1-propyl-1H-pyrazol-4-yl)-1H-indol-3-yl)thio)benzoic acid (compound no. 1-2);
3-((6-chloro-2-cyano-1-(1-propyl-1H-pyrazol-4-yl)-1H-indol-3-yl)thio)benzoic acid (compound no. 1-3);
3-((6-chloro-2-cyclopropyl-1-(1-propyl-1H-pyrazol-4-yl)-1-H-indol-3-yl)thio)benzoic acid (compound no. 1-4);
3-((2-amino-6-chloro-1-(1-propyl-1H-pyrazol-4-yl)-1H-indol-3-yl)thio)benzoic acid (compound no. 1-5);
3-((6-chloro-2-methoxy-1-(1-propyl-1H-pyrazol-4-yl)-1H-indol-3-yl)thio)benzoic acid (compound no. 1-6);
3-((2,6-dichloro-7-fluoro-1-(1-propyl-1H-pyrazol-4-yl)-1H-indol-3-yl)thio)benzoic acid (compound no. 1-7);
3-((2-bromo-6-chloro-7-fluoro-1-(1-propyl-1H-pyrazol-4-yl)-1H-indol-3-yl)thio)benzoic acid (compound no. 1-8);
3-((6-chloro-2-cyano-7-fluoro-1-(1-propyl-1H-pyrazol-4-yl)-1H-indol-3-yl)thio)benzoic acid (compound no. 1-9);
3-((6-chloro-2-cyclopropyl-7-fluoro-1-(1-propyl-1H-pyrazol-4-yl)-1H-indol-3-yl)thio)benzoic acid (compound no. 1-10);
3-((2-amino-6-chloro-7-fluoro-1-(1-propyl-1H-pyrazol-4-yl)-1H-indol-3-yl)thio)benzoic acid (compound no. 1-11);
3-((6-chloro-7-fluoro-2-methoxy-1-(1-propyl-1H-pyrazol-4-yl)-1H-indol-3-yl)thio)benzoic acid (compound no. 1-12);
3-((2,6-dichloro-7-fluoro-1-(1-propyl-1H-pyrazol-4-yl)-1H-indol-3-yl)thio)-2-fluorobenzoic acid (compound no. 1-13);
3-((2-bromo-6-chloro-7-fluoro-1-(1-propyl-1H-pyrazol-4-yl)-1H-indol-3-yl)thio)-2-fluorobenzoic acid (compound no. 1-14);
3-((6-chloro-2-cyano-7-fluoro-1-(1-propyl-1H-pyrazol-4-yl)-1H-indol-3-yl)thio)-2-fluorobenzoic acid (compound no. 1-15);
3-((6-chloro-2-cyclopropyl-7-fluoro-1-(1-propyl-1-H-pyrazol-4-yl)-1H-indol-3-yl)thio)-2-fluorobenzoic acid (compound no. 1-16);
3-((2-amino-6-chloro-7-fluoro-1-(1-propyl-1H-pyrazol-4-yl)-1H-indol-3-yl)thio)-2-fluorobenzoic acid (compound no. 1-17);
3-((6-chloro-7-fluoro-2-methoxy-1-(1-propyl-1H-pyrazol-4-yl)-1H-indol-3-yl)thio)-2-fluorobenzoic acid (compound no. 1-18);
3-((2,6-dichloro-1-(1-ethyl-1H-pyrazol-4-yl)-1H-indol-3-yl)thio)benzoic acid (compound no. 1-19);
3-((2-bromo-6-chloro-1-(1-ethyl-1H-pyrazol-4-yl)-1H-indol-3-yl)thio)benzoic acid (compound no. 1-20);
3-((6-chloro-2-cyano-1-(1-ethyl-1H-pyrazol-4-yl)-1H-indol-3-yl)thio)benzoic acid (compound no. 1-21);
3-((6-chloro-2-cyclopropyl-1-(1-ethyl-1H-pyrazol-4-yl)-1H-indol-3-yl)thio)benzoic acid (compound no. 1-22);
3-((2-amino-6-chloro-1-(1-ethyl-1H-pyrazol-4-yl)-1H-indol-3-yl)thio)benzoic acid (compound no. 1-23);
3-((6-chloro-2-methoxy-1-(1-ethyl-1H-pyrazol-4-yl)-1H-indol-3-yl)thio)benzoic acid (compound no. 1-24);
3-((2,6-dichloro-1-(1-ethyl-1H-pyrazol-4-yl)-7-fluoro-1H-indol-3-yl)thio)benzoic acid (compound no. 1-25);
3-((2-bromo-6-chloro-1-(1-ethyl-1H-1-pyrazol-4-yl)-7-fluoro-1-1H-indol-3-yl)thio)benzoic acid (compound no. 1-26);
3-((6-chloro-2-cyano-1-(1-ethyl-1H-pyrazol-4-yl)-7-fluoro-1H-indol-3-yl)thio)benzoic acid (compound no. 1-27);
3-((6-chloro-2-cyclopropyl-1-(1-ethyl-1H-pyrazol-4-yl)-7-fluoro-1H-indol-3-yl)thio)benzoic acid (compound no. 1-28);
3-((2-amino-6-chloro-1-(1-ethyl-1H-pyrazol-4-yl)-7-fluoro-1H-indol-3-yl)thio)benzoic acid (compound no. 1-29);
3-((6-chloro-1-(1-ethyl-1H-pyrazol-4-yl)-7-fluoro-2-methoxy-1H-indol-3-yl)thio)benzoic acid (compound no. 1-30);
3-((2,6-dichloro-1-(1-ethyl-1H-pyrazol-4-yl)-7-fluoro-1H-indol-3-yl)thio)-2-fluorobenzoic acid (compound no. 1-31);
3-((2-bromo-6-chloro-1-(1-ethyl-1H-pyrazol-4-yl)-7-fluoro-1H-indol-3-yl)thio)-2-fluorobenzoic acid (compound no. 1-32);

3-((6-chloro-2-cyano-1-(1-ethyl-1H-pyrazol-4-yl)-7-fluoro-1H-indol-3-yl)thio)-2-fluorobenzoic acid (compound no. 1-33);
3-((6-chloro-2-cyclopropyl-1-(1-ethyl-1H-pyrazol-4-yl)-7-fluoro-1H-indol-3-yl)thio)-2-fluorobenzoic acid (compound no. 1-34);
3-((2-amino-6-chloro-1-(1-ethyl-1H-pyrazol-4-yl)-7-fluoro-1H-indol-3-yl)thio)-2-fluorobenzoic acid (compound no. 1-35);
3-((6-chloro-2-methoxy-1-(1-ethyl-1H-pyrazol-4-yl)-7-fluoro-1H-indol-3-yl)thio)-2-fluorobenzoic acid (compound no. 1-36);
3-((2,6-dichloro-1-(1-methyl-1H-pyrazol-4-yl)-1H-indol-3-yl)thio)benzoic acid (compound no. 1-37);
3-((2-bromo-6-chloro-1-(1-methyl-1H-pyrazol-4-yl)-1-H-indol-3-yl)thio)benzoic acid (compound no. 1-38);
3-((6-chloro-2-cyano-1-(1-methyl-1H-pyrazol-4-yl)-1H-indol-3-yl)thio)benzoic acid (compound no. 1-39);
3-((6-chloro-2-cyclopropyl-1-(1-methyl-1H-pyrazol-4-yl)-1H-indol-3-yl)thio)benzoic acid (compound no. 1-40);
3-((2-amino-6-chloro-1-(1-methyl-1H-pyrazol-4-yl)-1H-indol-3-yl)thio)benzoic acid (compound no. 1-41);
3-((6-chloro-2-methoxy-1-(1-methyl-1H-pyrazol-4-yl)-1H-indol-3-yl)thio)benzoic acid (compound no. 1-42);
3-((2,6-dichloro-7-fluoro-1-(1-methyl-1H-pyrazol-4-yl)-1H-indol-3-yl)thio)benzoic acid (compound no. 1-43);
3-((2-bromo-6-chloro-7-fluoro-1-(1-methyl-1H-pyrazol-4-yl)-1H-indol-3-yl)thio)benzoic acid (compound no. 1-44);
3-((6-chloro-2-cyano-7-fluoro-1-(1-methyl-1H-pyrazol-4-yl)-1H-indol-3-yl)thio)benzoic acid (compound no. 1-45);
3-((6-chloro-2-cyclopropyl-7-fluoro-1H-(1-methyl-1H-pyrazol-4-yl)-1H-indol-3-yl)thio)benzoic acid (compound no. 1-46);
3-((2-amino-6-chloro-7-fluoro-1H-(1-methyl-1H-pyrazol-4-yl)-1H-indol-3-yl)thio)benzoic acid (compound no. 1-47);
3-((6-chloro-7-fluoro-1-(1-methyl-1H-pyrazol-4-yl)-2-methoxy-1H-indol-3-yl)thio)benzoic acid (compound no. 1-48);
3-((2,6-dichloro-7-fluoro-1-(1-methyl-1H-pyrazol-4-yl)-1H-indol-3-yl)thio)-2-fluorobenzoic acid (compound no. 1-49);
3-((2-bromo-6-chloro-7-fluoro-1-(1-methyl-1H-pyrazol-4-yl)-1H-indol-3-yl)thio)-2-fluorobenzoic acid (compound no. 1-50);
3-((6-chloro-2-cyano-7-fluoro-1-(1-methyl-1H-pyrazol-4-yl)-1H-indol-3-yl)thio)-2-fluorobenzoic acid (compound no. 1-51);
3-((6-chloro-2-cyclopropyl-7-fluoro-1H-(1-methyl-1H-pyrazol-4-yl)-1H-indol-3-yl)thio)-2-fluorobenzoic acid (compound no. 1-52);
3-((2-amino-6-chloro-7-fluoro-1-(1-methyl-1H-pyrazol-4-yl)-1H-indol-3-yl)thio)-2-fluorobenzoic acid (compound no. 1-53);
3-((2,6-dichloro-1-(1-isopropyl-1H-pyrazol-4-yl)-1H-indol-3-yl)thio)benzoic acid (compound no. 1-54);
3-((2-bromo-6-chloro-1-(1-isopropyl-1H-pyrazol-4-yl)-1H-indol-3-yl)thio)benzoic acid (compound no. 1-55);
3-((6-chloro-2-cyano-1-(1-isopropyl-1H-pyrazol-4-yl)-1H-indol-3-yl)thio)benzoic acid (compound no. 1-56);
3-((6-chloro-2-cyclopropyl-1-(1-isopropyl-1H-pyrazol-4-yl)-1H-indol-3-yl)thio)benzoic acid (compound no. 1-57);
3-((2-amino-6-chloro-1-(1-isopropyl-1H-pyrazol-4-yl)-1H-indol-3-yl)thio)benzoic acid (compound no. 1-58);
3-((6-chloro-2-methoxy-1-(1-isopropyl-1H-pyrazol-4-yl)-1H-indol-3-yl)thio)benzoic acid (compound no. 1-59);
3-((2,6-dichloro-7-fluoro-1-(1-isopropyl-1H-pyrazol-4-yl)-1H-indol-3-yl)thio)benzoic acid (compound no. 1-60);
3-((2-bromo-6-chloro-7-fluoro-1-(1-isopropyl-1H-pyrazol-4-yl)-1H-indol-3-yl)thio)benzoic acid (compound no. 1-61);
3-((6-chloro-2-cyano-7-fluoro-1H-(1-isopropyl-1H-pyrazol-4-yl)-1H-indol-3-yl)thio)benzoic acid (compound no. 1-62);
3-((6-chloro-2-cyclopropyl-7-fluoro-1-(1-isopropyl-1H-pyrazol-4-yl)-1H-indol-3-yl)thio)benzoic acid (compound no. 1-63);
3-((2-amino-6-chloro-7-fluoro-1-(1-isopropyl-1H-pyrazol-4-yl)-1H-indol-3-yl)thio)benzoic acid (compound no. 1-64);
3-((6-chloro-7-fluoro-1-(1-isopropyl-1H-pyrazol-4-yl)-2-methoxy-1H-indol-3-yl)thio)benzoic acid (compound no. 1-65);
3-((2,6-dichloro-1H-fluoro-1-(1-isopropyl-1H-pyrazol-4-yl)-1H-indol-3-yl)thio)-2-fluorobenzoic acid (compound no. 1-66);
3-((2-bromo-6-chloro-7-fluoro-1-(1-isopropyl-1H-pyrazol-4-yl)-1H-indol-3-yl)thio)-2-fluorobenzoic acid (compound no. 1-67);
3-((6-chloro-2-cyano-7-fluoro-1-(1-isopropyl-1H-pyrazol-4-yl)-1H-indol-3-yl)thio)-2-fluorobenzoic acid (compound no. 1-68);
3-((6-chloro-2-cyclopropyl-7-fluoro-1-(1-isopropyl-1H-pyrazol-4-yl)-1H-indol-3-yl)thio)-2-fluorobenzoic acid (compound no. 1-69);
3-((2-amino-6-chloro-7-fluoro-1-(1-isopropyl-1H-pyrazol-4-yl)-1H-indol-3-yl)thio)-2-fluorobenzoic acid (compound no. 1-70);
6-((2,6-dichloro-1-(1-propyl-1H-pyrazol-4-yl)-1H-indol-3-yl)thio)picolinic acid (compound no. 1-71);
6-((2-bromo-6-chloro-1-(1-propyl-1H-pyrazol-4-yl)-1H-indol-3-yl)thio)picolinic acid (compound no. 1-72);
6-((6-chloro-2-cyano-1-(1-propyl-1H-pyrazol-4-yl)-1H-indol-3-yl)thio)picolinic acid (compound no. 1-73);
6-((6-chloro-2-cyclopropyl-1-(1-propyl-1H-pyrazol-4-yl)-1H-indol-3-yl)thio)picolinic acid (compound no. 1-74);
6-((2-amino-6-chloro-1-(1-propyl-1H-pyrazol-4-yl)-1H-indol-3-yl)thio)picolinic acid (compound no. 1-75);
6-((6-chloro-2-methoxy-1-(1-propyl-1H-pyrazol-4-yl)-1H-indol-3-yl)thio)picolinic acid (compound no. 1-76);
6-((2,6-dichloro-7-fluoro-1-(1-propyl-1H-pyrazol-4-yl)-1H-indol-3-yl)thio)picolinic acid (compound no. 1-77);
6-((2-bromo-6-chloro-7-fluoro-1-(1-propyl-1H-pyrazol-4-yl)-1H-indol-3-yl)thio)picolinic acid (compound no. 1-78);
6-((6-chloro-2-cyano-7-fluoro-1H-(1-propyl-1H-pyrazol-4-yl)-1H-indol-3-yl)thio)picolinic acid (compound no. 1-79);
6-((6-chloro-2-cyclopropyl-7-fluoro-1H-(1-propyl-1H-pyrazol-4-yl)-1H-indol-3-yl)thio)picolinic acid (compound no. 1-80);
6-((2-amino-6-chloro-7-fluoro-1-(1-propyl-1H-pyrazol-4-yl)-1H-indol-3-yl)thio)picolinic acid (compound no. 1-81);

6-((6-chloro-7-fluoro-2-methoxy-1-(1-propyl-1H-pyrazol-4-yl)-1H-indol-3-yl)thio)picolinic acid (compound no. 1-82);

6-((2,6-dichloro-1-(1-ethyl-1H-pyrazol-4-yl)-1H-indol-3-yl)thio)picolinic acid (compound no. 1-83);

6-((2-bromo-6-chloro-1-(1-ethyl-1H-pyrazol-4-yl)-1H-indol-3-yl)thio)picolinic acid (compound no. 1-84);

6-((6-chloro-2-cyano-1-(1-ethyl-1H-pyrazol-4-yl)-1H-indol-3-yl)thio)picolinic acid (compound no. 1-85);

6-((6-chloro-2-cyclopropyl-1-(1-ethyl-1H-pyrazol-4-yl)-1H-indol-3-yl)thio)picolinic acid (compound no. 1-86);

6-((2-amino-6-chloro-1-(1-ethyl-1H-pyrazol-4-yl)-1H-indol-3-yl)thio)picolinic acid (compound no. 1-87);

6-((6-chloro-1-(1-ethyl-1H-pyrazol-4-yl)-2-methoxy-1H-indol-3-yl)thio)picolinic acid (compound no. 1-88);

6-((2,6-dichloro-1-(1-ethyl-1H-pyrazol-4-yl)-7-fluoro-1H-indol-3-yl)thio)picolinic acid (compound no. 1-89);

6-((2-bromo-6-chloro-1-(1-ethyl-1H-pyrazol-4-yl)-7-fluoro-1H-indol-3-yl)thio)picolinic acid (compound no. 1-90);

6-((6-chloro-2-cyano-1-(1-ethyl-1H-pyrazol-4-yl)-7-fluoro-1H-indol-3-yl)thio)picolinic acid (compound no. 1-91);

6-((6-chloro-2-cyclopropyl-1-(1-ethyl-1H-pyrazol-4-yl)-1H-fluoro-1H-indol-3-yl)thio)picolinic acid (compound no. 1-92);

6-((2-amino-6-chloro-1-(1-ethyl-1H-pyrazol-4-yl)-7-fluoro-1H-indol-3-yl)thio)picolinic acid (compound no. 1-93);

6-((6-chloro-1-(1-ethyl-1H-pyrazol-4-yl)-7-fluoro-2-methoxy-1H-indol-3-yl)thio)picolinic acid (compound no. 1-94);

6-((2,6-dichloro-1-(1-methyl-1H-pyrazol-4-yl)-1H-indol-3-yl)thio)picolinic acid (compound no. 1-95);

6-((2-bromo-6-chloro-(1-methyl-1H-pyrazol-4-yl)-1H-indol-3-yl)thio)picolinic acid (compound no, 1-96), 6-((6-chloro-2-cyano-1-(1-methyl-1H-pyrazol-4-yl)-1H-indol-3-yl)thio)picolinic acid (compound no. 1-97);

6-((6-chloro-2-cyclopropyl-1-(1-methyl-1H-pyrazol-4-yl)-1H-indol-3-yl)thio)picolinic acid (compound no. 1-98);

6-((2-amino-6-chloro-1-(1-methyl-1H-pyrazol-4-yl)-1H-indol-3-yl)thio)picolinic acid (compound no. 1-99);

6-((6-chloro-2-methoxy-1-(1-methyl-1H-pyrazol-4-yl)-1H-indol-3-yl)thio)picolinic acid (compound no. 1-100);

6-((2,6-dichloro-7-fluoro-1-(1-methyl-1H-pyrazol-4-yl)-1H-indol-3-yl)thio)picolinic acid (compound no. 1-101);

6-((2-bromo-6-chloro-7-fluoro-1H-(1-methyl-1H-pyrazol-4-yl)-1H-indol-3-yl)thio)picolinic acid (compound no. 1-102);

6-((6-chloro-2-cyano-7-fluoro-1-(1-methyl-1H-pyrazol-4-yl)-1H-indol-3-yl)thio)picolinic acid (compound no. 1-103);

6-((6-chloro-2-cyclopropyl-7-fluoro-1-(1-methyl-1H-pyrazol-4-yl)-1H-indol-3-yl)thio)picolinic acid (compound no. 1-104);

6-((2-amino-6-chloro-7-fluoro-1-(1-methyl-1H-pyrazol-4-yl)-1H-indol-3-yl)thio)picolinic acid (compound no. 1-105);

6-((6-chloro-7-fluoro-2-methoxy-1-(1-methyl-1H-pyrazol-4-yl)-H-indol-3-yl)thio)picolinic acid (compound no. 1-106);

6-(2,6-dichloro-1-(1-isopropyl-1H-pyrazol-4-yl)-1H-indol-3-yl)thio)picolinic acid (compound no. 1-107);

6-((2-bromo-6-chloro-1-(1-isopropyl-1H-pyrazol-4-yl)-1H-indol-3-yl)thio)picolinic acid (compound no. 1-108);

6-((6-chloro-2-cyano-1-(1-isopropyl-1H-pyrazol-4-yl)-1H-indol-3-yl)thio)picolinic acid (compound no. 1-109);

6-((6-chloro-2-cyclopropyl-1-(1-isopropyl-1H-pyrazol-4-yl)-1H-1-indol-3-yl)thio)picolinic acid (compound no. 1-110;

6-((2-amino-6-chloro-1-(1-isopropyl-1H-pyrazol-4-yl)-1H-indol-3-yl)thio)picolinic acid (compound no. 1-111);

6-((6-chloro-1-(1-isopropyl-1H-pyrazol-4-yl)-2-methoxy-1H-indol-3-yl)thio)picolinic acid (compound no. 1-112);

6-((2,6-dichloro-7-fluoro-1-(1-isopropyl-1H-pyrazol-4-yl)-1H-indol-3-yl)thio)picolinic acid (compound no. 1-113);

6-((2-bromo-6-chloro-7-fluoro-1-(1-isopropyl-1H-pyrazol-4-yl)-1H-indol-3-yl)thio)picolinic acid (compound no. 1-114);

6-((6-chloro-2-cyano-7-fluoro-1-(1-isopropyl-1H-pyrazol-4-yl)-1H-indol-3-yl)thio)picolinic acid (compound no. 1-115);

6-((6-chloro-2-cyclopropyl-1H-fluoro-1-(1-isopropyl-1H-pyrazol-4-yl)-1H-indol-3-yl)thio)picolinic acid (compound no. 1-116);

6-((2-amino-6-chloro-7-fluoro-1-(1-isopropyl-1H-pyrazol-4-yl)-1H-indol-3-yl)thio)picolinic acid (compound no. 1-117);

6-((6-chloro-7-fluoro-1-(1-isopropyl-1H-pyrazol-4-yl)-2-methoxy-1 f-indol-3-yl)thio)picolinic acid (compound no. 1-118);

3-((6-chloro-2-cyclopropyl-7-fluoro-1H-(1H-pyrazol-4-yl)-H-indol-3-yl)thio)-2-fluorobenzoic acid (compound no. 1-119);

3-((6-chloro-2-cyclopropyl-7-fluoro-1-(1-(2-hydroxyethyl)-1H-L-pyrazol-4-yl)-1H-indol-3-yl)thio)-2-fluorobenzoic acid (compound no. 1-120);

3-(1-(1-(2-(carbamoyloxy)ethyl)-1H-pyrazol-4-yl)-(6-chloro-2-cyclopropyl-7-fluoro-1H-indol-3-yl)thio)-2-fluorobenzoic acid (compound no. 1-121);

3-(1-(1-(2-aminoethyl)-1H-pyrazol-4-yl)-(6-chloro-2-cyclopropyl-7-fluoro-1H-indol-3-yl)thio)-2-fluorobenzoic acid (compound no. 1-122);

3-((6-chloro-2-cyclopropyl-7-fluoro-1-(1-(2-ureidoethyl)-1H-pyrazol-4-yl)-1H-indol-3-yl)thio)-2-fluorobenzoic acid (compound no. 1-123);

3-(1-(1-(3-carboxypropyl)-1H-pyrazol-4-yl)-(6-chloro-2-cyclopropyl-7-fluoro-1H-indol-3-yl)thio)-2-fluorobenzoic acid (compound no. 1-124);

3-(1-(1-(4-amino-4-oxobutyl)-1H-pyrazol-4-yl)-(6-chloro-2-cyclopropyl-7-fluoro-1 f-indol-3-yl)thio)-2-fluorobenzoic acid (compound no. 1-125);

3-((6-chloro-2-cyclopropyl-7-fluoro-1-(1-(2,2,2-trifluoroethyl)-1H-pyrazol-4-yl)-1 I-indol-3-yl)thio)-2-fluorobenzoic acid (compound no. 1-126);

3-((6-chloro-2-cyclopropyl-1-(1-(2H$_5$)ethyl-1H-pyrazol-4-yl)-7-fluoro-1H-indol-3-yl)thio)-2-fluorobenzoic acid; (compound no. 1-127);

3-(1-(1-(6-aminohexyl)-1H-pyrazol-4-yl)-(6-chloro-2-cyclopropyl-7-fluoro-1H-indol-3-yl)thio)-2-fluorobenzoic acid (compound no. 1-128);

3-((6-chloro-2-cyclopropyl-7-fluoro-1-(1-(hex-5-ynyl)-1H-pyrazol-4-yl)-1H-indol-3-yl)thio)-2-fluorobenzoic acid (compound no. 1-129);

3-((6-chloro-2-cyclopropyl-7-fluoro-1-(1-(3-hydroxy-2,2-dimethylpropyl)-1H-pyrazol-4-yl)-1H-indol-3-yl)thio)-2-fluorobenzoic acid (compound no. 1-130);

3-((6-chloro-2-cyclopropyl-1-(1-(6-(3-(3',6'-dihydroxy-3-oxo-3H-spiro[isobenzofuran-1,9'-xanthen]-5-yl)ureido)hexyl)-1H-pyrazol-4-yl)-7-fluoro-1H-indol-3-yl)thio)-2-fluorobenzoic acid (compound no. 1-131);

3-((6-chloro-2-cyclopropyl-7-fluoro-1-(1-(4-(methyl-amino)-4-oxobutyl)-1H-pyrazol-4-yl)-1H-indol-3-yl)thio)-2-fluorobenzoic acid (compound no. 1-132);

3-(6-chloro-2-cyclopropyl-1-(1-(4-(dimethylamino)-4-oxobutyl)-1H-pyrazol-4-yl)-7-fluoro-1H-indol-3-ylthio)-2-fluorobenzoic acid (compound no. 1-133);

3-(1-(1-(4-amino-3,3-dimethyl-4-oxobutyl)-1H-pyrazol-4-yl)-6-chloro-2-cyclopropyl-7-fluoro-1H-indol-3-ylthio)-2-fluorobenzoic acid (compound no. 1-134);

6-(1-(1-(4-amino-4-oxobutyl)-1H-pyrazol-4-yl)-(6-chloro-2-cyclopropyl-7-fluoro-1H-indol-3-yl)thio)picolinic acid (compound no. 1-135);

6-((6-chloro-2-cyclopropyl-7-fluoro-1-(1-(4-(methyl-amino)-4-oxobutyl)-1-pyrazol-4-yl)-1H-1-indol-3-yl)thio)picolinic acid (compound no. 1-136);

6-((6-chloro-2-cyclopropyl-1-(1-(4-(dimethylamino)-4-oxobutyl)-1H-pyrazol-4-yl)-7-fluoro-1H-indol-3-yl)thio) picolinic acid (compound no. 1-137);

6-(1-(1-(4-amino-3,3-dimethyl-4-oxobutyl)-1H-pyrazol-4-yl)-(6-chloro-2-cyclopropyl-7-fluoro-1-indol-3-yl)thio) picolinic acid (compound no. 1-138).

TABLE 2

| Compound no. | B—$R^B$ | $R^1$ | W | $L^1$ |
|---|---|---|---|---|
| 2-1 | pyridin-3-yl | —Cl | CF | absent |
| 2-2 | pyridin-3-yl | —Br | CF | absent |
| 2-3 | pyridin-3-yl | c-$C_3H_5$ | CF | absent |
| 2-4 | pyridin-3-yl | —CN | CF | absent |
| 2-5 | 1-ethyl-1H-pyrazol-4-yl | —Cl | CF | $CH_2$ |
| 2-6 | 1-ethyl-1H-pyrazol-4-yl | —Br | CF | $CH_2$ |
| 2-7 | 1-ethyl-1H-pyrazol-4-yl | c-$C_3H_5$ | CF | $CH_2$ |
| 2-8 | 1-ethyl-1H-pyrazol-4-yl | —CN | CF | $CH_2$ |
| 2-9 | 1-ethyl-1H-pyrazol-4-yl | —Cl | CF | $C(CH_3)_2$ |
| 2-10 | 1-ethyl-1H-pyrazol-4-yl | —Br | CF | $C(CH_3)_2$ |
| 2-11 | 1-ethyl-1H-pyrazol-4-yl | c-$C_3H_5$ | CF | $C(CH_3)_2$ |
| 2-12 | 1-ethyl-1H-pyrazol-4-yl | —CN | CF | $C(CH_3)_2$ |
| 2-13 | 1-ethyl-1H-pyrazol-4-yl | —Cl | CF | $C(CH_2CH_2)_2$ |
| 2-14 | 1-ethyl-1H-pyrazol-4-yl | —Br | CF | $C(CH_2CH_2)_2$ |
| 2-15 | 1-ethyl-1H-pyrazol-4-yl | c-$C_3H_5$ | CF | $C(CH_2CH_2)_2$ |
| 2-16 | 1-ethyl-1H-pyrazol-4-yl | —CN | CF | $C(CH_2CH_2)_2$ |
| 2-17 | 1-propyl-1H-pyrazol-4-yl | —Cl | CF | $CH_2$ |
| 2-18 | 1-propyl-1H-pyrazol-4-yl | —Br | CF | $CH_2$ |
| 2-19 | 1-propyl-1H-pyrazol-4-yl | c-$C_3H_5$ | CF | $CH_2$ |
| 2-20 | 1-propyl-1H-pyrazol-4-yl | —CN | CF | $CH_2$ |
| 2-21 | 1-propyl-1H-pyrazol-4-yl | —Cl | CF | $C(CH_3)_2$ |
| 2-22 | 1-propyl-1H-pyrazol-4-yl | —Br | CF | $C(CH_3)_2$ |
| 2-23 | 1-propyl-1H-pyrazol-4-yl | c-$C_3H_5$ | CF | $C(CH_3)_2$ |
| 2-24 | 1-propyl-1H-pyrazol-4-yl | —CN | CF | $C(CH_3)_2$ |
| 2-25 | 1-propyl-1H-pyrazol-4-yl | —Cl | CF | $C(CH_2CH_2)_2$ |
| 2-26 | 1-propyl-1H-pyrazol-4-yl | —Br | CF | $C(CH_2CH_2)_2$ |
| 2-27 | 1-propyl-1H-pyrazol-4-yl | c-$C_3H_5$ | CF | $C(CH_2CH_2)_2$ |
| 2-28 | 1-propyl-1H-pyrazol-4-yl | —CN | CF | $C(CH_2CH_2)_2$ |
| 2-29 | 1-ethyl-1H-pyrazol-4-yl | —Cl | N | $CH_2$ |
| 2-30 | 1-ethyl-1H-pyrazol-4-yl | —Cl | N | $C(CH_3)_2$ |
| 2-31 | 1-ethyl-1H-pyrazol-4-yl | —Cl | N | $C(CH_2CH_2)_2$ |
| 2-32 | 1-propyl-1H-pyrazol-4-yl | —Cl | N | $CH_2$ |
| 2-33 | 1-propyl-1H-pyrazol-4-yl | —Cl | N | $C(CH_3)_2$ |
| 2-34 | 1-propyl-1H-pyrazol-4-yl | —Cl | N | $C(CH_2CH_2)_2$ |

Compounds in Table 2 are named:

3-((2,6-dichloro-7-fluoro-1H-(pyridin-3-yl)-1H-indol-3-yl)thio)-2-fluorobenzoic acid (compound no. 2-1);

3-((2-bromo-6-chloro-7-fluoro-1-(pyridin-3-yl)-1H-indol-3-yl)thio)-2-fluorobenzoic acid (compound no. 2-2);

3-((6-chloro-2-cyclopropyl-7-fluoro-(pyridin-3-yl)-1H-indol-3-yl)thio)-2-fluorobenzoic acid (compound no. 2-3);

3-((6-chloro-2-cyano-7-fluoro-1-(pyridin-3-yl)-1,1-indol-3-yl)thio)-2-fluorobenzoic acid (compound no. 2-4);

2-(3-((2,6-dichloro-1-(1-ethyl-H-pyrazol-4-yl)-7-fluoro-1H-indol-3-yl)thio)-2-fluorophenyl)acetic acid (compound no. 2-5);

2-(3-((2-bromo-6-chloro-1-(1-ethyl-1H-pyrazol-4-yl)-7-fluoro-1H-indol-3-yl)thio)-2-fluorophenyl)acetic acid (compound no. 2-6);

2-(3-((6-chloro-2-cyclopropyl-1-(1-ethyl-1H-pyrazol-4-yl)-7-fluoro-1H-indol-3-yl)thio)-2-fluorophenyl)acetic acid (compound no. 2-7);

2-(3-((6-chloro-2-cyano-1-(1-ethyl-1H-pyrazol-4-yl)-7-fluoro-1H-indol-3-yl)thio)-2-fluorophenyl)acetic acid (compound no. 2-8);

2-(3-((2,6-dichloro-1-(1-ethyl-1H-pyrazol-4-yl)-7-fluoro-1H-indol-3-yl)thio)-2-fluorophenyl)-2-methylpropanoic acid (compound no. 2-9);

2-(3-((2-bromo-6-chloro-1-(1-ethyl-1H-pyrazol-4-yl)-7-fluoro-1H-indol-3-yl)thio)-2-fluorophenyl)-2-methylpropanoic acid (compound no. 2-10);

2-(3-((6-chloro-2-cyclopropyl-1-(1-ethyl-1H-pyrazol-4-yl)-7-fluoro-1H-indol-3-yl)thio)-2-fluorophenyl)-2-methylpropanoic acid (compound no. 2-11);

2-(3-((6-chloro-2-cyano-1-(1-ethyl-1H-pyrazol-4-yl)-7-fluoro-1H-indol-3-yl)thio)-2-fluorophenyl)-2-methylpropanoic acid (compound no. 2-12)

1-(3-((2,6-dichloro-1-(1-ethyl-1H-pyrazol-4-yl)-7-fluoro-1,1-indol-3-yl)thio)-2-fluorophenyl)cyclopropanecarboxylic acid (compound no. 2-13);

1-(3-((2-bromo-6-chloro-1-(1-ethyl-1H-pyrazol-4-yl)-7-fluoro-1H-indol-3-yl)thio)-2-fluorophenyl)cyclopropanecarboxylic acid (compound no. 2-14);

1-(3-((6-chloro-2-cyclopropyl-1-(1-ethyl-1H-pyrazol-4-yl)-7-fluoro-1H-indol-3-yl)thio)-2-fluorophenyl)cyclopropanecarboxylic acid (compound no. 2-15);

1-(3-((6-chloro-2-cyano-1-(1-ethyl-1H-pyrazol-4-yl)-7-fluoro-1H-indol-3-yl)thio)-2-fluorophenyl)cyclopropanecarboxylic acid (compound no. 2-16);

2-(3-((2,6-dichloro-1-(1-propyl-1H-pyrazol-4-yl)-7-fluoro-1H-indol-3-yl)thio)-2-fluorophenyl)acetic acid (compound no. 2-17);

2-(3-((2-bromo-6-chloro-1-(1-propyl-1H-pyrazol-4-yl)-7-fluoro-1H-indol-3-yl)thio)-2-fluorophenyl)acetic acid (compound no. 2-18);

2-(3-((6-chloro-2-cyclopropyl-1-(1-propyl-1H-pyrazol-4-yl)-7-fluoro-1H-indol-3-yl)thio)-2-fluorophenyl)acetic acid (compound no. 2-19);

2-(3-((6-chloro-2-cyano-1-(1-propyl-1H-pyrazol-4-yl)-7-fluoro-1H-indol-3-yl)thio)-2-fluorophenyl)acetic acid (compound no. 2-20);

2-(3-((2,6-dichloro-1-(1-propyl-1H-pyrazol-4-yl)-7-fluoro-1H-indol-3-yl)thio)-2-fluorophenyl)-2-methylpropanoic acid (compound no. 2-21);

2-(3-((2-bromo-6-chloro-1-(1-propyl-H-pyrazol-4-yl)-7-fluoro-1H-indol-3-yl)thio)-2-fluorophenyl)-2-methylpropanoic acid (compound no. 2-22);

2-(3-((6-chloro-2-cyclopropyl-1-(1-propyl-1H-pyrazol-4-yl)-7-fluoro-1H-indol-3-yl)thio)-2-fluorophenyl)-2-methylpropanoic acid (compound no. 2-23);

2-(3-((6-chloro-2-cyano-1-(1-propyl-1H-pyrazol-4-yl)-7-fluoro-1H-indol-3-yl)thio)-2-fluorophenyl)-2-methylpropanoic acid (compound no. 2-24) 1-(3-((2,6-dichloro-1-(1-propyl-1H-pyrazol-4-yl)-7-fluoro-1H-indol-3-yl)thio)-2-fluorophenyl)cyclopropanecarboxylic acid (compound no. 2-25);

1-(3-((2-bromo-6-chloro-1-(1-propyl-1H-pyrazol-4-yl)-7-fluoro-1H-indol-3-yl)thio)-2-fluorophenyl)cyclopropanecarboxylic acid (compound no. 2-26);

1-(3-((6-chloro-2-cyclopropyl-1-(1-propyl-1H-pyrazol-4-yl)-7-fluoro-1H-indol-3-yl)thio)-2-fluorophenyl)cyclopropanecarboxylic acid (compound no. 2-27);

1-(3-((6-chloro-2-cyano-1-(1-propyl-1H-pyrazol-4-yl)-7-fluoro-1H-indol-3-yl)thio)-2-fluorophenyl)cyclopropanecarboxylic acid (compound no. 2-28);

2-(6-((2,6-dichloro-1-(1-ethyl-1H-pyrazol-4-yl)-7-fluoro-1H-indol-3-yl)thio)pyridine-2-yl)acetic acid (compound no. 2-29);

2-(6-((2,6-dichloro-1-(1-ethyl-1H-pyrazol-4-yl)-7-fluoro-H-indol-3-yl)thio)pyridine-2-yl)-2-methylpropanoic acid (compound no. 2-30);

1-(6-((2,6-dichloro-1-(1-ethyl-1H-pyrazol-4-yl)-7-fluoro-1H-indol-3-yl)thio)pyridine-2-yl)cyclopropanecarboxylic acid (compound no. 2-31);

2-(6-((2,6-dichloro-1-(1-propyl-1H-pyrazol-4-yl)-7-fluoro-1H-indol-3-yl)thio)pyridine-2-yl)acetic acid (compound no. 2-32);

2-(6-((2,6-dichloro-1-(1-propyl-1H-pyrazol-4-yl)-7-fluoro-1H-indol-3-yl)thio)pyridine-2-yl)-2-methylpropanoic acid (compound no. 2-33);

1-(6-((2,6-dichloro-1H-(1-propyl-1H-pyrazol-4-yl)-7-fluoro-1H-indol-3-yl)thio)pyridine-2-yl)cyclopropanecarboxylic acid (compound no. 2-34).

In one aspect, compounds described herein are in the form of pharmaceutically acceptable salts. As well, active metabolites of these compounds having the same type of activity are included in the scope of the present disclosure. In addition, the compounds described herein can exist in unsolvated forms as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S M. Berge, L). Bighley, D.C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich: Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound described herein with an acid. In some embodiments, the compound described herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+) camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid: gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (− L); malonic acid; mandelic acid (DL); methanesulfonic acid; naphthalene-1, 5-disulfonic acid; naphthalene-2-sulfonic acid; nicotinic acid; oleic acid; oxalic acid; palmitic acid; pamoic acid; phosphoric acid; proprionic acid; pyroglutamic acid (− L); salicylic acid; sebacic acid; stearic acid; succinic acid; sulfuric acid; tartaric acid (+ L); thiocyanic acid; toluenesulfonic acid (p); and undecylenic acid.

In some embodiments, a compound described herein is prepared as a chloride salt, sulfate salt, bromide salt, mesylate salt, maleate salt, citrate salt or phosphate salt. In some embodiments, a compound described herein is prepared as a hydrochloride salt.

In some embodiments, pharmaceutically acceptable salts are obtained by reacting a compound described herein with a base. In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt. In some embodiments, the compounds provided herein are prepared as a sodium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds described herein, as well as active metabolites of these compounds having the same type of activity.

In some embodiments, sites on the organic radicals (e.g. alkyl groups, aromatic rings) of compounds described herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example $^2H$, $^3H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^3H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al, Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H, Advanced Drug Delivery Review, 1992, 8, 1-38, each of which is incorporated herein by reference.

In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein as set forth herein are included within the scope of the claims. In some cases, some of the herein-described compounds is a prodrug for another derivative or active compound.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized", as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Synthesis of Compounds

Compounds described herein are synthesized using standard synthetic techniques or using methods known in the art in combination with methods described herein.

Indoles are readily prepared by chemical synthesis using standard methodologies as described in the review "Practical methodologies for the synthesis of indoles" Humphrey and Kuethe, *Chem. Rev.*, 2006, 106, 2875-2911. Compounds are prepared using standard organic chemistry techniques such as those described in, for example, March's Advanced Organic Chemistry, 6$^{th}$ Edition, John Wiley and Sons, Inc. Alternative reaction conditions for the synthetic transformations described herein may be employed such as variation of solvent, reaction temperature, reaction time, as well as different chemical reagents and other reaction conditions. The starting materials are available from commercial sources or are readily prepared. Many functionalized indole and 2-oxindole compounds are commercially available.

In some embodiments, the preparation of indole compounds begins with the sequence of steps shown in Scheme 1.

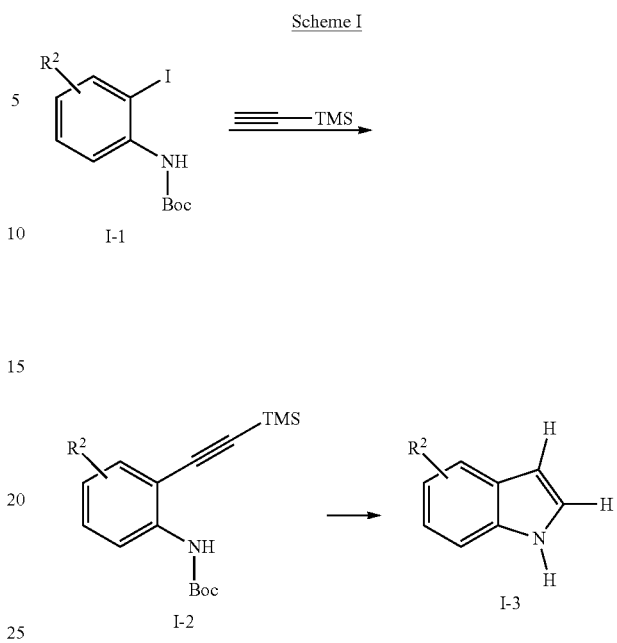

Scheme I

In some embodiments, Boc-protected 2-iodoanilines (I-1) are treated with TMS-acetylene using Sonogashira cross-coupling conditions to generate the alkyne I-2 which, upon treatment with base then cyclizes to give indoles of general structure I-3.

In other embodiments, the preparation of indole compounds begins with the sequence of steps shown in Scheme II.

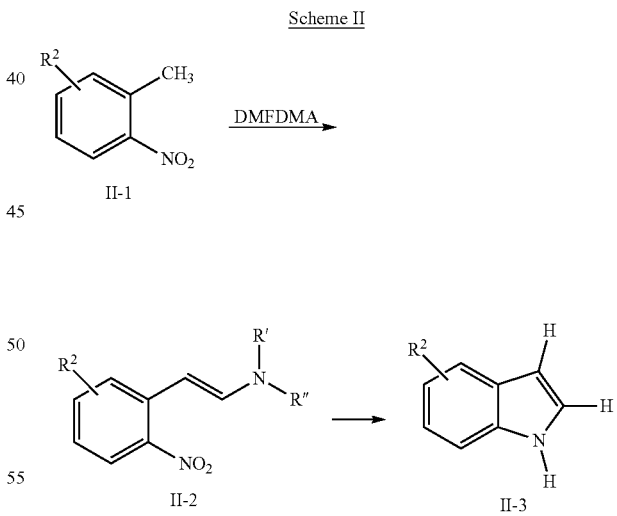

Scheme II

The Leimgruber-Batcho indole synthesis is described in Scheme II. Substituted O-nitrotoluene II-1 can be reacted with dimethylformamide dimethyl acetal (DMFDMA) to provide the vinyl intermediate II-2. Reductive cyclization using, for example, nickel boride and hydrazine then yields the indole of general structure II-3.

In other embodiments, the preparation of indole compounds begins with the sequence of steps shown in Scheme III.

Scheme III

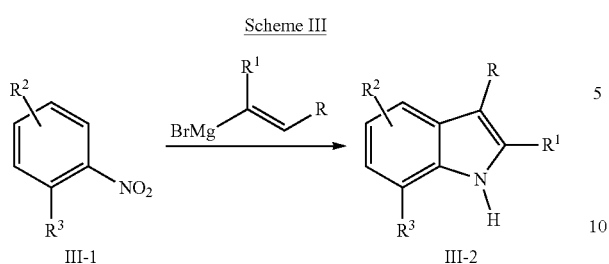

The Bartoli indole synthesis is shown in Scheme III and requires an ortho-substituted nitrobenzene (III-1). Treatment of III-1 with a vinyl magnesium Grignard reagent results in an indole of general structure III-2.

In some embodiments, 2-H Indoles are functionalized as shown in Scheme IV.

Scheme IV

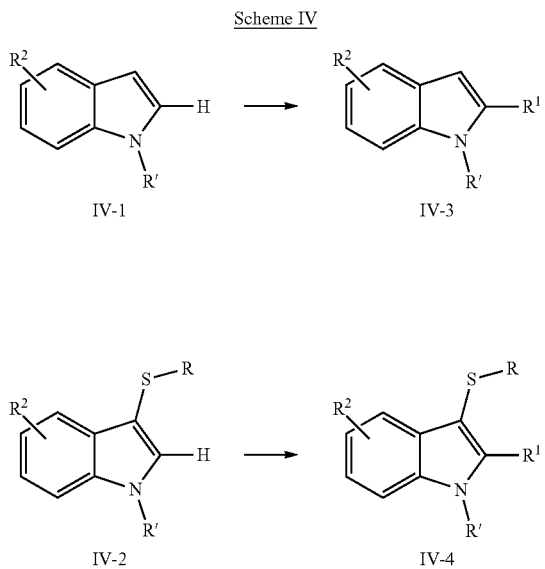

$R^1$ = Br, Cl

In some embodiments, treatment of 2H Indoles of general structure IV-1 or IV-2 with NCS or NBS in an inert solvent affords 2-chloro or bromo indoles of general structure IV-3 or IV-4.

In yet other embodiments, 2-oxindoles are used to preare compounds described herein as shown in Scheme V.

Scheme V

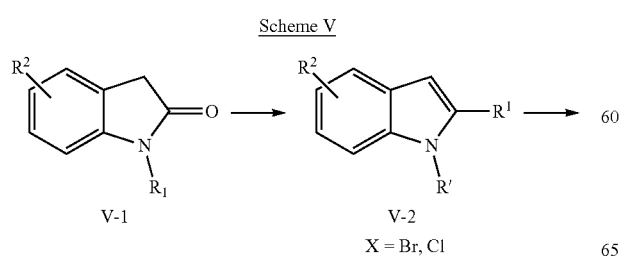

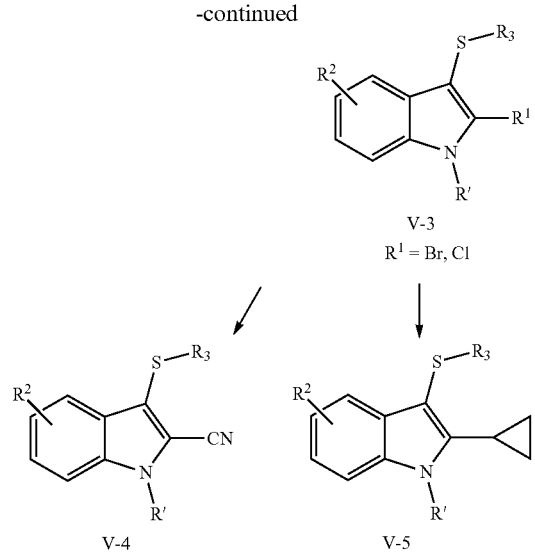

In some embodiments, 2-oxindoles such as V-1 are treated with $POCl_3$ or $POBr_3$ to yield the 2-chloro or 2-bromo derivatives V-2. In some embodiments, compound V-2 is then functionalized at C-3 of the indole to introduce a 3-thioether group by reacting with an appropriately substituted arylthiol in the presence of NCS to give compounds of structure V-3. In further embodiments, the 2-halo substituent is then be converted to V-4 containing a 2-cyano substituent. In some embodiments, this transformation is performed with the use of organometallic reagents such as, for example, $Zn(CN)_2$ in the presence of a palladium catalyst such as $Pd_2(dba)_3$ and ligand such as xantphos. Alternative CN sources may be used such as CuCN at high temperature. Other ways of preparing 2-cyanoindoles include the dehydration of the corresponding primary amide. In some embodiments, introduction of a 2-cyclopropyl group is achieved by treating V-3 with cyclopropylboronic acid under Suzuki-type couple conditions to yield V-5.

In some embodiments, indoles compounds described herein are prepared as shown in Scheme VI.

Scheme VI

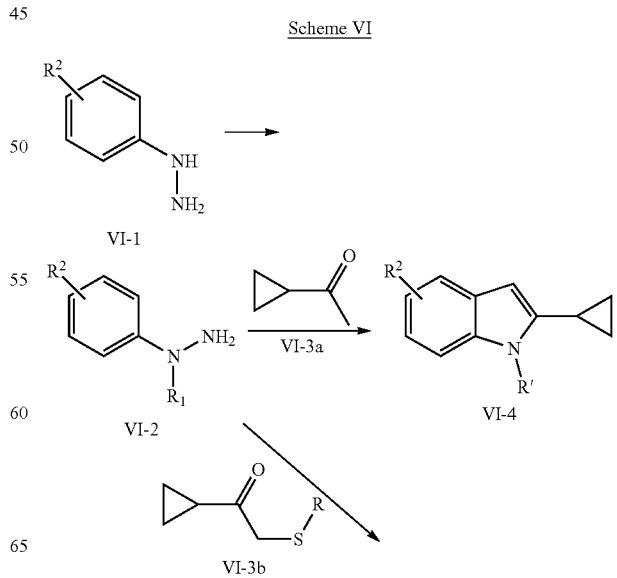

-continued

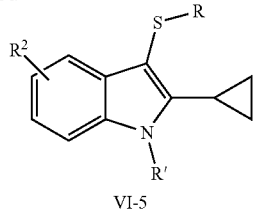

VI-5

In some embodiments, the Fisher indole reaction using the hydrazine VI-1 or VI-2 and the cyclopropylketone VI-3a is used to prepare 2-cyclopropyl indoles of general structure VI-4 (Scheme yl). In some embodiments, the 3-thio substituted 2-cyclopropyl indole VI-5 is prepared using the cyclopropylketone VI-3b.

N—H Indoles of general structure VII-1 may be further modified as shown in Scheme VII.

Scheme VII

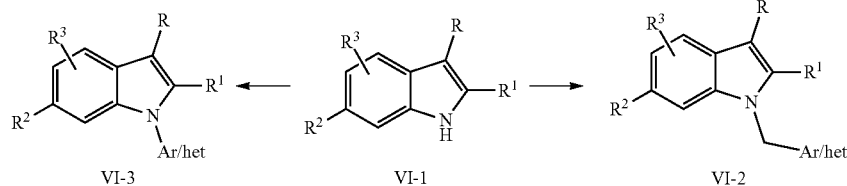

Treatment with a base such as NaH followed by alkylation with an electrophile (for example BrCH$_2$CONR'R" or BrCH$_2$CH$_2$CO$_2$tBu or ClCH$_2$Aryl) can then form compounds of general structure VII-2. Subsequent chemical modifications can then be made to the indole N-substituent using standard chemical transformations. Direct arylation or heteroarylation may be achieved using Ullman-type conditions to generate VII-3.

In some embodiments, compounds described herein are synthesized as outlined in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers refers to a divalent alkyl radical. Any of the above mentioned monovalent alkyl groups may be an alkylene by abstraction of a second hydrogen atom from the alkyl. In some embodiments, an alkelene is a $C_1$-$C_6$ alkylene. In other embodiments, an alkylene is a $C_1$-$C_6$alkylene. Typical alkylene groups include, but are not limited to, —CH$_2$—, —CH(CH$_3$)—, —C(CH$_3$)—CH$_2$CH$_2$—, —CH$_2$CH—(CH$_3$)—, —CH$_2$C(CH$_3$)$_2$—, —CH$_2$CH$_2$—, —CH$_2$CH$_2$CH$_2$CH$_2$—, and the like.

"Deuteroalkyl" refers to an alkyl group where 1 or more hydrogen atoms of an alkyl are replaced with deuterium.

The term "alkenyl" refers to a type of alkyl group in which at least one carbon-carbon double bond is present. In one embodiment, an alkenyl group has the formula —C(R)=CR$_2$, wherein R refers to the remaining portions of the alkenyl group, which may be the same or different. In some embodiments, R$^1$ is H or an alkyl. Non-limiting examples of an alkenyl group include —CH=CH$_2$, —C(CH$_3$)=CH$_2$, —CH=CHCH$_3$, —C(CH$_3$)=CHCH$_3$, and —CH$_2$CH=CH$_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R$^1$ is H or an alkyl Non-limiting examples of an alkynyl group include —C≡CH, —C≡CCH$_3$—C≡CCH$_2$CH$_3$, —CH$_2$C≡CH.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

The term "aromatic" refers to a planar ring having a delocalized π-electron system containing 4n+2π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In sonic embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1]pentyl. In some embodiments, a cycloalkyl is a $C_3$-$C_6$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoroalkyl is a $C_1$-$C_6$fluoroalkyl.

The term "heteroalkyl" refers to an alkyl group in which one or more skeletal atoms of the alkyl are selected from an atom other than carbon, e.g., oxygen, nitrogen (e. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 211-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1 (2H)-onyl, 3,4-dihydroquinolin-2 (1H)-onyl, isoindoline-1,3-dithionyl, benzo[d]oxazol-2 (3H)-onyl, 1H-benzo[d]imidazol-2 (3)-onyl, benzo[d]thiazol-2 (3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclcic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzinidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In, some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —NH$_2$, —NH—, (alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —NH$_2$, —NH (CH$_3$)—N(CH$_3$)$_2$, —OH, —CO$_2$(C$_1$-C$_4$alkyl), —C(=O) NH, —C(=O)NH((C$_1$-C$_4$alkyl), —C(=O)N(C$_1$-C$_4$alkyl), —S(=O)$_2$NH$_2$, —S(=O)$_2$NH(C$_1$-C$_4$alkyl), —S(=O)$_2$N (C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_6$alkyl. In some embodiments, optional substituents are independently selected from halogen, —CN, —NH$_2$, —OH, —NH(CH$_3$), —N(CH$_3$), —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E, Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds described herein, or a pharmaceutically acceptable salt thereof are used in the preparation of medicaments for the treatment of diseases or conditions in a mammal that would benefit from inhibition or reduction of autotaxin activity. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a, pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In some embodiments, liver toxicity can be assessed in suitable in vivo assays. In some embodiments, liver toxicity is assessed by monitoring any increases in the levels of liver markers ALT, AST, AlkP and bilirubin. For example, in a suitable dog liver toxicity study, Compound (1-34) exhibited undesired elevated liver markers whereas Compound (1-13) did not exhibit the same effects. In some embodiments, no increases in liver markers ALT, AST, AlkP and bilirubin were observed for Compound (1-13) when dosed at 100 mpk for 5 days.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple tines over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents. In certain embodiments, the pharmaceutical composition further comprises one or more anti-cancer agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound described herein, or a pharmaceutically acceptable salt thereof, is co-administered with a second therapeutic agent, wherein the compound described herein, or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, a compound described herein, or a pharmaceutically acceptable salt thereof, is administered in combination with chemotherapy, hormone blocking therapy, radiation therapy, monoclonal antibodies, or combinations thereof.

Chemotherapy includes the use of anti-cancer agents.

EXAMPLES

The following examples are provided for illustrative purposes only and not to limit the scope of the claims provided herein.

Synthesis of ethyl 2-fluoro-3-mercaptobenzoate (Intermediate A)

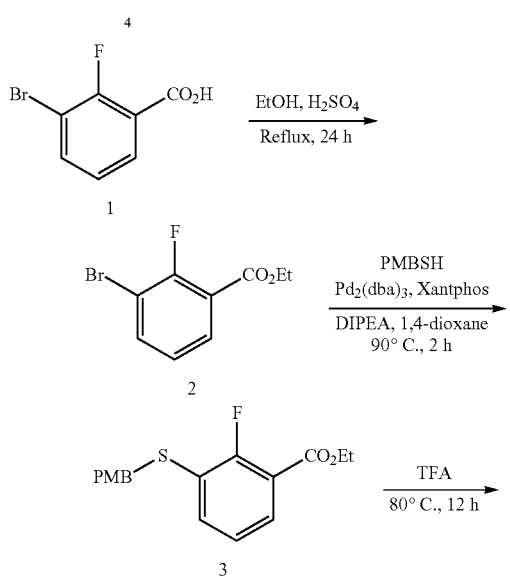

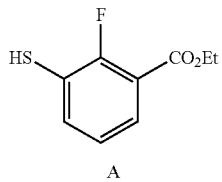

Step 1: Synthesis of ethyl 3-bromo-2-fluorobenzoate (2)

To a stirred solution of 3-bromo-2-fluorobenzoic acid 1 (25.0 g, 114.15 mmol) in ethanol (400 mL) was added conc. $H_2SO_4$ (3 mL) at RT and stirred at reflux temperature for 24 h. The reaction was monitored by LC-MS; after completion of the reaction, the reaction mixture was concentrated to obtain the residue. The residue was diluted with EtOAc (500 mL), washed with water (300 mL), brine (300 mL), dried over $Na_2SO_4$, filtered and concentrated under reduced pressure to afford compound 2 (26.0 g, 92%) as a light yellow liquid. $^1$H NMR (400 MHz, $CDCl_3$): δ 7.88-7.84 (m, 1H), 7.72-7.69 (m, 1H), 7.08-7.04 (m, 1H), 4.39 (q, J=7.2 Hz, 2H), 1.39 (t, J=7.2 Hz, 3H).

Step 2: Synthesis of ethyl 2-fluoro-3-((4-methoxybenzyl)thio)benzoate (3)

1,4-dioxane (250 mL) was degassed by purging with $N_2$ gas for 30 min and to this, were added a solution of compound 2 (13.2 g, 53.4 mmol) in 1,4-dioxane (50 mL; degassed), (4-methoxyphenyl)methanethiol (PMBSH) (8.2 g, 53.4 mmol), xantphos (1.54 g, 2.66 mmol), diisopropyl ethyl amine (19.6 mL, 106.8 mmol) and $Pd_2(dba)_3$ (1.22 g 1.33 mmol) at RT. The reaction mixture was heated to 90° C. and stirred for 2 h. The reaction was monitored by TLC; after completion of the reaction, the reaction mixture was diluted with hexane (450 mL) and stirred at RT for 15 min. The resultant solution was filtered through celite and washed with hexane (100 mL). The filtrate was washed water (250 mL) dried over $Na_2SO_4$, filtered and concentrated under reduced pressure to obtain the crude. This was purified by silica gel column chromatography using 3-4% EtOAc/Hexanes to afford compound 3 (15 g, 88%) as pale yellow solid. $^1$H NMR (500 MHz, $CDCl_3$): δ 7.78-7.74 (m, 1H), 7.43-7.39 (m, 1H), 7.19 (d, J=8.0 Hz, 2H), 7.07-7.04 (m, 1H), 6.80 (d, J=8.0 Hz, 2H), 4.41 (q, J=7.2 Hz, 2H), 4.08 (s, 2H), 3.78 (s, 3H), 141 (t, J=7.2 Hz, $^3$H). LC-MS (ESI): 89.7%; m/z 318.9 (M−H$^+$); (column: X Select CSH C-18, 50×3.0 mm, 3.5 μm); RT 4.22 min; 5 mM $NH_4OAc$: ACN; 0.8 mL/min).

Step 3: Synthesis of ethyl 2-fluoro-3-mercaptobenzoate (A)

A stirred solution of compound 3 (30.0 g, 93.75 mmol) in TFA (54.5 mL) was heated to 80° C. (and stirred for 12 h under inert atmosphere. The reaction was monitored by TLC, after completion of the reaction, the volatiles were removed under reduced pressure. The residue was dissolved in ice-cold water (100 mL), basified with solid sodium bicarbonate and extracted with EtOAc (2×200 mL). The combined organic extracts were dried over $Na_2SO_4$, filtered and concentrated under reduced pressure to obtain the crude. This was purified by silica gel column chromatography using 3% EtOAc/Hexanes to afford compound A (11.7 g, 62%) as a pale brown syrup. ¹H NMR (500 MHz, CDCl₃): δ 7.70-7.66 (m, 1H), 7.48-7.44 (m, 1H), 7.08-7.04 (m, 1H), 4.20 (q, J=75 Hz, 2F), 3.67 (s, 1H), 1.40 (t, J=7.5 Hz, 3H); LC-MS (ESI): 918%; m/z 199.0 (M–H⁺); (column: X Select CSH C-18, 50×3.0 mm, 3.5 μm); RT 2.60 min; 5 mM NH₄OAc: ACN; 0.8 mL/in).

Synthesis of 4-bromo-1-propyl-1H-pyrazole (Intermediate B

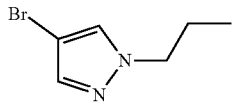

A solution of 4-bromo-1H-pyrazole (25.0 g, 170.10 mmol) in THF (100 mL) was added drop wise to NaH (10.2 g, 255.0 mmol; 60% in oil) in THF (200 mL) at 0° C. under inert atmosphere and stirred for 30 min. The reaction mixture was then warmed to rt and stirring was continued for additional 45 min. To this, iodopropane (31.8 g, 204.12 mmol) was added at 0° C.; warmed to rt and stirred for 12 h. The reaction was monitored by TLC; after completion of the reaction, the reaction mixture was quenched with water (40 mL) and extracted with EtOAc (3×50 mL). The combined organic extracts were dried over Na₂SO₄, filtered and concentrated under reduced pressure to obtain the crude. This was purified by silica gel column chromatography using 2-5% EtOAc/Hexanes to afford intermediate B (4-bromo-1-propyl-1H-pyrazole; 27.3 g, 86%) as a colorless oil. ¹H NMR (400 MHz, CDCl₃): δ 7.44 (s, 1H), 7.38 (s, 1H), 4.04 (t, J=7.2 Hz, 2H), 1.90-1.82 (m, 2H), 0.92 (t, J=7.2 Hz, 3H); MS (ESI): m/z 189 (M+H⁺).

Synthesis of 4-bromo-1-methyl-1H-pyrazole (Intermediate C)

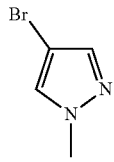

Following the procedure for Intermediate B but using EtI in place of iodopropane, Intermediate C was prepared as a pale yellow liquid. ¹H NMR (500 MHz, CDCl₃): δ 7.45 (s, 1H), 7.38 (s, 1H), 3.79 (s, 3H).

Synthesis of 4-bromo-1-((2-trimethylsilyl)ethoxy)methyl)-1H-pyrazole (Intermediate D)

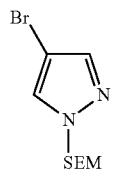

Following the procedure for Intermediate B but using SEM chloride in place of iodopropane, Intermediate D was prepared as a yellow liquid. ¹H NMR (500 MHz, DMSO-d₆): δ 8.15 (s, 1H), 7.63 (s, 1H), 5.38 (s, 2H), 3.52 (t, J=8.5 Hz, 2H), 0.82 (t, J=7.5 Hz, 2H), 0.04 (s, 9H).

Synthesis of 4-bromo-1-(ethyl-d₅)-1H-pyrazole (Intermediate E)

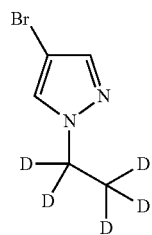

Following the procedure for Intermediate B but using ethyl iodide-d₅ in place of iodopropane, Intermediate E was prepared as a colorless oil. ¹H NMR (500 MHz, CDCl₃): δ 7.44 (s, 1H), 7.40 (s, 1H).

Synthesis of 4-bromo-1-(2,2,2-trifluoroethyl)-1H-pyrazole (Intermediate F)

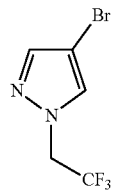

Following the procedure for Intermediate B but using 1,1,1-trifluoro-2-iodoethane in place of iodopropane and Cs₂CO₃/DMF in place of NaH/THF, Intermediate F was prepared as a colorless oil. ¹H NMR (400 MHz, CDCl₃): δ 47.55 (s, 1H), 7.54 (s, 1H), 4.67 (q, 2H).

Example 1: Synthesis of 3-((2,6-dichloro-1-(1-propyl-1H-pyrazol-4-yl)-1H-indol-3-yl)thio)benzoic acid (Compound 1-1)

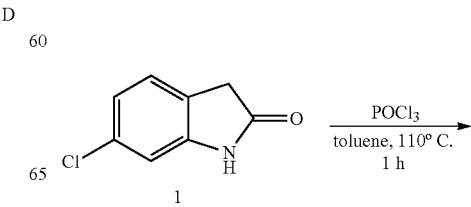

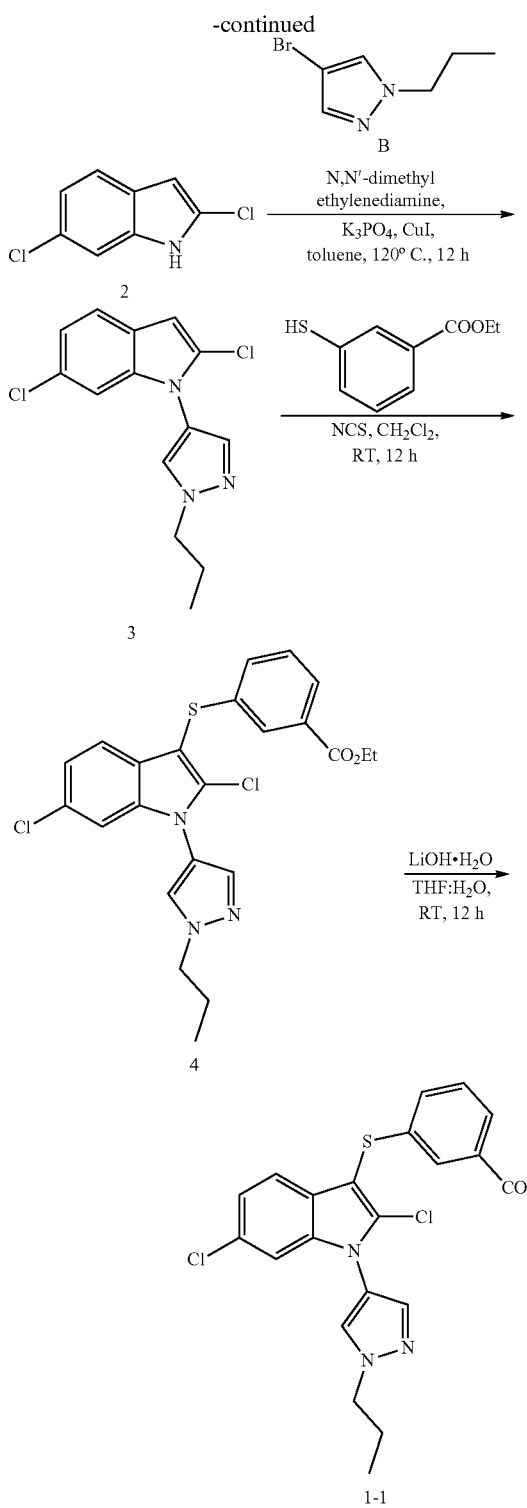

Step 1: Synthesis of 2,6-dichloro-1H-indole 2)

To a stirred solution of 6-chloroindolin-2-one 1 (500 mg, 2.99 mmol) in toluene (25 mL) tinder inert atmosphere were added N,N-dimethylaniline (362 mg, 2.99 mmol) and POCl₃ (918 g, 5.98 mmol) at RT; heated to 110° C. and stirred for 1 h. The reaction was monitored by TLC; after completion of the reaction, the reaction mixture was quenched with 10% aq. NaHCO₃ solution (30 mL) and extracted with EtOAc (2×30 mL). The combined organic extracts were dried over Na₂SO₄, filtered and concentrated under reduced pressure to obtain the crude. This was purified by silica gel column chromatography using 5% EtOAc/Hexanes to afford compound 2 (350 mg, 63%) as an off-white solid. ¹H NMR (400 MHz, CDCl₃): δ 3.8.09 (br s, 1H), 7.41 (d, J=8.4 Hz, 1H), 7.28 (s, 1H), 7.09 (d, J=8.4 Hz, 1H), 6.39 (s, 1H); MS (ESI): m/z 184 (M–H⁺).

Step 2: Synthesis of 2,6-dichloro-1-(1-propyl-1H-pyrazol-4-yl)-1H-indole (3)

To a stirred solution of compound 2 (350 mg, 1.89 mmol) in toluene (10 mL) under inert atmosphere were added 4-bromo-1-propyl-1H-pyrazole (Intermediate B; 422 mg, 2.27 mmol), potassium phosphate (1 g, 4.72 mmol), N,N'-dimethylethylene diamine (66.7 mg, 0.75 mmol) and CuI (36 mg, 0.18 mmol) at RT; heated to 120° C. and stirred for 12 h in a sealed tube. The reaction was monitored by TLC; after completion of the reaction, the volatiles were removed under reduced pressure to obtain the crude. This was purified by silica gel column chromatography using 5-7% EtOAc/Hexanes to afford compound 3 (200 mg, 36%) as colorless oil. ¹H NMR (500 MHz, CDCl₃): δ 7.63 (s, 1H), 7.59 (s, 1H), 7.44 (d, J=9.0 Hz, 1H), 7.14 (s, 1H), 7.11 (d, J=9.0 Hz, 1H), 6.55 (s, 1H), 4.18 (t, J=7.0 Hz, 2H) 2.02-1.97 (m, 2H), 0.98 (t, J=7.5 Hz, 3H); LC-MS (ESI): 59.4%; m % 294.2 (M+H⁺); (column: X Select C-18, 50×3.0 mm, 3.5 μm); RT 4.66 min; 5 mM NH₄OAc: ACN; 0.8 mL/min).

Step 3: Synthesis of ethyl 3-((2,6-dichloro-(1-propyl-1H-pyrazol-4-yl)-1H-indol-3-yl)thio) benzoate (4)

To a stirred solution of ethyl 3-mercaptobenzoate (124.9 mg, 0.68 mmol) in CH₂Cl₂ (20 mL) under inert atmosphere was added NCS (109 mg, 0.81 mmol) at 0° C.; warmed to RT and stirred for 1 h. To this, compound 3 (200 mg, 0.68 mmol) was added at 0° C.; warmed to RT and stirred for 12 h. The reaction was monitored by TLC; after completion of the reaction, the reaction mixture was diluted with water (25 mL) and extracted with CH₂Cl₂ (3×25 mL). The combined organic extracts were dried over Na₂SO₄, filtered and concentrated under reduced pressure to obtain the crude. This was purified by preparative HPLC to afford compound 4 (15 mg, 5%) as colorless oil. ¹H NMR (500 MHz, CDCl₃): δ 7.90 (s, 1H), 7.79-7.77 (m, 1H), 7.69 (s, 1H), 7.66 (s, 1H), 7.48 (d, J=9.0 Hz, 1H), 7.26-7.22 (m, 3H), 7.16 (d, J=9.0 Hz, 1H), 4.32 (q, J=7.5 Hz, 2H), 4.20 (t, J=7.0 Hz, 2H), 2.02-1.98 (m, 2H), 1.37-1.34 (t, J=7.5 Hz, 3H), 1.01 (t, J=7.0 Hz, 3H); LC-MS (ESI): 92.7%; m/z 475.8 (M+H⁺); (column: X Select C-18, 50.3.0 mm, 3.5 μm); RT 5.03 min; 5 mM NH₄OAc: ACN; 0.8 mL/min).

Step 4: Synthesis of 3-((2,6-dichloro-1-(1-propyl-1H-pyrazol-4-yl)-1H-indol-3-yl)thio) benzoic acid To a stirred solution of compound 4 (15 mg, 0.031 mmol) in THF:H₂O (1:1, 5 mL) under inert atmosphere was added LiOH·H₂O (5.3 mg, 0.12 mmol) at 0° C.; warmed to RT and stirred for 12 h. The reaction was monitored by TLC; after completion of the reaction, the volatiles were removed under reduced pressure. The residue was diluted with water (20 mL), acidified with citric acid and extracted with CH₂Cl₂ (2×20 mL). The combined organic extracts were dried over Na₂SO₄, filtered and concentrated under reduced pressure to afford the title compound 1-1 (10 mg, 71%) as an off-white solid. ¹H NMR (400 MHz, CD₃OD): δ 8.12 (s, 1H), 7.78-7.75 (m, 3H), 7.49 (d, J=8.4 Hz, 1H), 7.32-7.31 (m, 2H), 7.22-7.18 (m, 2H), 4.24 (t, J=7.2 Hz, 2H), 2.02-1.93 (m, 2H), 0.98 (t, J=7.2 Hz, 3H); MS (ESI): m/z 446.3 (M⁺); HPLC: 98.8%; (column: Acquity BEH C-18 (50×2.1 mm, 1.7μ); RT 2.94 min; ACN: 0.025% TFA (aq); 0.5 mL/min.

Example 2: Synthesis of 3-(6-chloro-2-cyano-1-(1-propyl-1H-pyrazol-4-yl)-1H-indol-3-yl)thio)benzoic acid (Compound 1-3)

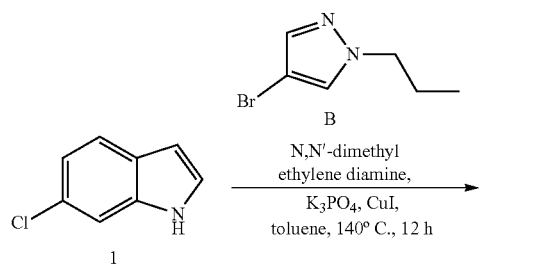

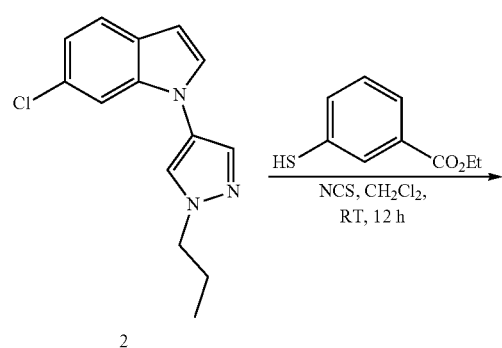

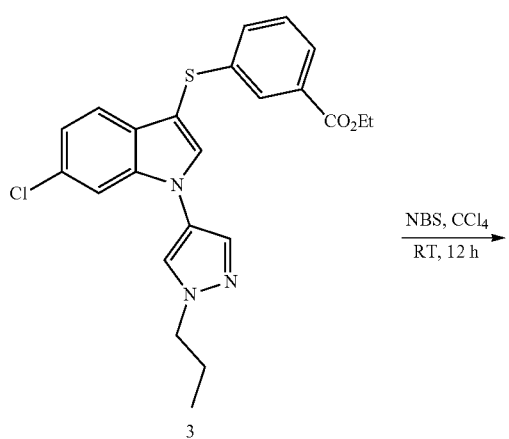

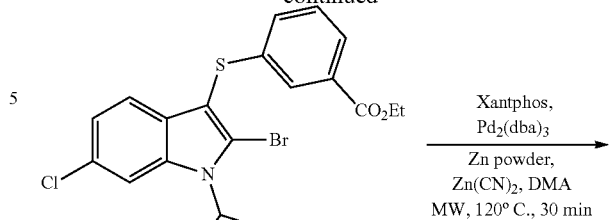

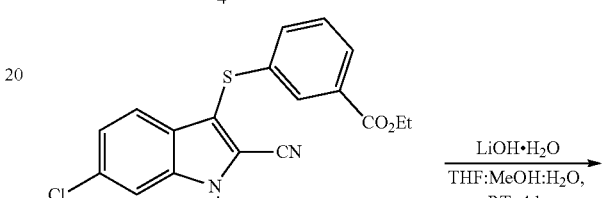

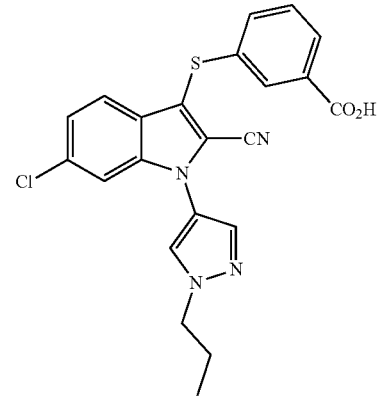

Step 1: Synthesis of 6-chloro-1-(1-propyl-1H-pyrazol-4-yl)-1H-indole 2

To a stirred solution of 6-chloro-1H-indole 1 (1.0 g, 6.62 mmol) in toluene (25 mL) under inert atmosphere were added N,N'-dimethylethylene diamine (233 mg, 2.64 mmol), potassium phosphate (3.50 g, 16.55 mmol) and 4-bromo-1-propyl-1H-pyrazole (Intermediate B, 1.23 g, 6.62 mmol) at RT and then degassed under argon for 15 min. To this, CuI (126 mg, 0.66 mmol) was added and sealed the tube. The reaction mixture was heated to 140° C. and stirred for 12 h. The reaction was monitored by TLC; after completion of the reaction, the reaction mixture was filtered and the filtrate was concentrated under reduced pressure to obtain the crude.

This was purified by silica gel column chromatography using 10-15% EtOAc/Hexanes to afford compound 2 (1.5 g, 88%) as yellow oil. $^1$H NMR (500 MHz, CDCl$_3$): δ 7.68 (s, 1H), 7.62 (s, 1H), 7.55 (d, J=10.0 Hz, 1H), 7.35 (s, 1H), 7.17 (d, J=3.5 Hz, 1H) 7.11 (d, J=10.0 Hz, 1H), 6.59 (d, J=3.5 Hz, 1H), 4.17 (t, J=7.5 Hz, 2H), 2.00-1.96 (m, 2H), 1.00 (t, J=7.5 Hz, 3H); LC-MS (ESI): 93.3%; m/z 260.2 (M+H$^+$); (column: X Select CSF C-18, 50×3.0 mm, 3.5 μm); RT 4.04 min, 5 mM NH$_4$OAc. ACN; 0.8 mL/min).

Step 2: Synthesis of ethyl 3-(6-chloro-1-(1-propyl-1H-pyrazol-4-yl)-1H-indol-3-yl)thio benzoate (3)

To a stirred solution of ethyl 3-mercaptobenzoate (372 mg, 2.03 mmol) in CH$_2$Cl$_2$ (20 mL) under inert atmosphere was added NCS (271 mg, 2.03 mmol) at 0° C.; warmed to RT and stirred for 45 min. To this, compound 2 (500 mg, 1.93 mmol) was added at 0° C.; warmed to RT and stirred for 12 h. The reaction was monitored by TLC; after completion of the reaction, the reaction mixture was diluted with water (40 mL) and extracted with CH$_2$Cl$_2$ (3×20 mL). The combined organic extracts were dried over Na$_2$SO$_4$, filtered and concentrated under reduced pressure to obtain the crude. This was purified by silica gel column chromatography using 10-15% EtOAc/Hexanes to afford compound 3 (700 mg, 83%) as a yellow oil. $^1$H NMR (400 MHz, CDCl$_3$): δ 3.7.89 (s, 1H), 7.76-7.74 (m, 1H), 7.72 (s, 1H), 7.68 (s, 1H), 7.49-7.47 (m, 2H), 7.40 (s, 1H), 7.24-7.23 (m, 2H), 7.15 (d, J=8.4 Hz, 1H), 4.32 (q, J=7.2 Hz, 2H). 4.18 (t, J=7.2 Hz, 2H), 2.01-1.96 (m, 2H), 1.34 (t, J=7.2 Hz, 3H), 1.00 (t, J=7.2 Hz, 3H); LC-MS (ESI): 72.2%; m/z 440.4 (M+H$^+$); (column: X Select CSH C-18, 50×3.0 mm, 3.5 μm); RT 4.87 min; 5 mM NH$_4$OAc: ACN; 0.8 mL/min).

Step 3: Synthesis of ethyl 3-(2-bromo-6-chloro-1-(1-propyl-1H-pyrazol-4-yl)-1H-indol-3-yl)thio) benzoate (4)

To a stirred solution of compound 3 (100 mg, 0.22 mmol) in CCl$_4$ (10 mL) was added NBS (44.85 mg, 0.25 mmol) at RT under inert atmosphere and stirred for 12 h. The reaction was monitored by TLC; after completion of the reaction, the reaction mixture was diluted with water (20 mL) and extracted with CH$_2$Cl$_2$ (3×20 mL). The combined organic extracts were dried over sodium sulphate, filtered and concentrated under reduced pressure to obtain the crude. This was purified by silica gel column chromatography using 10-15% EtOAc/Hexanes to afford compound 4 (55 mg, 47%) as an off-white solid. $^1$H NMR (500 MHz, CDCl$_3$): δ 7.90 (s, 1H), 7.78-7.77 (m, 1H), 7.68 (s, 1H), 7.66 (s, 1H), 7.49 (d, J=8.5 Hz, 1H), 7.25-7.24 (m, 2H), 7.20 (s, 1H), 7.14 (d, J=8.5 Hz, 1H), 4.35 (q, J=7.0 Hz, 2H), 4.20 (t, J=7.5 Hz, 2H), 2.03-1.98 (nm, 2H), 1.35 (t, J=7.0 Hz, 3H), 1.01 (t, J=7.5 Hz, 3H); LC-MS (ESI): 93.3%; m/z 520.8 (M$^+$+2); (column: X Select CSH C-18, 50×3.0 mm, 3.5 μm); RT 5.02 min; 5 mM N$_4$OAc: ACN; 0.8 mL/min).

Step 4: Synthesis of ethyl 3-((6-chloro-2-cyano-1-(1-propyl-1H-pyrazol-4-yl)-1H-indol-3-yl) thio) benzoate (5)

To a stirred solution of compound 4 (200 mg, 0.38 mmol) in DMA (20 mL) under inert atmosphere were added zinc powder (5.02 mg, 0.07 mmol), ZnCN$_2$ (67.8 mg, 0.58 mmol), xantphos (89.5 mg, 0.15 mmol), Pd$_2$(dba)$_3$ (70.85 mg, 0.07 mmol) at RT; heated to 120° C. under microwave for 30 min. The reaction was monitored by TLC; after completion of the reaction, the reaction mixture was diluted with water (20 mL) and extracted with CH$_2$Cl$_2$ (3×20 mL). The combined organic extracts were dried over Na$_2$SO$_4$, filtered and concentrated under reduced pressure to obtain the crude. This was purified by silica gel column chromatography using 10-15% EtOAc/Hexanes to afford compound 5 (60 mg, 33%) as an off-white solid, $^1$H NMR (500 MHz, CDCl$_3$): δ 7.99 (s, 1H), 7.87 (d, J=7.5 Hz, 1H), 7.78 (s, 2H), 7.54 (d, J=8.5 Hz, 1H), 7.42-7.27 (m, 3H), 7.24-7.22 (m, 1H), 4.36 (q, J=7.0 Hz, 2H) 4.21 (t, J=7.5 Hz, 2H), 2.02-1.98 (m, 2H) 1.36 (t, J=7.0 Hz, 3H), 1.01 (t, J=7.5 Hz, 3H); LC-MS (ESI): 92.5%; m/z 465 (M+H$^+$); (column: X Select CSH C-18, 50×3.0 mm, 3.5 μm); RT 4.92 min; 5 mM NH$_4$OAc: ACN; 0.8 mL/min).

Step 5: Synthesis of 3-((6-chloro-2-cyano-1-(1-propyl-1H-pyrazol-4-yl)-1/1-indol-3-yl) thio) benzoic acid To a stirred solution of compound 5 (60 mg, 0.12 mmol) in THF:MeOH:H$_2$O (3:1:1, 5 mL) under inert atmosphere was added LiOH·H$_2$O (16.3 mg, 0.38 mmol) at 0° C.; warmed to RT and stirred for 4 h. The reaction was monitored by TLC; after completion of the reaction, the volatiles were removed under reduced pressure. The residue was diluted with water (15 mL), acidified with citric acid to pH ~2.0. The obtained solid was filtered and dried under reduced pressure to afford the title compound 1-3 (20 mg, 35%) as an off-white solid. $^1$H NMR (400 MHz, CD$_3$OD): 4.8.23 (s, 1H), 7.88 (s, 1H), 7.87 (s, 1H), 7.82 (d, J=8.0 Hz, 1H), 7.57 (d, J=8.4 Hz, 1H), 7.43 (d, J=8.4 Hz, 1H), 7.38-7.32 (m, 2H), 7.27 (d, J=8.4 Hz, 1H), 4.25 (t, J=7.2 Hz, 2H), 2.02-1.93 (m, 2H), 0.98 (t, J=7.2 Hz, 3H); LC-MS (ESI): 96.4%; m/z 435.4 (M–H$^+$); (column: X Select CSH C-18, 50×3.0 mm, 3.5 μm); RT 3.19 min; 5 mM NH$_4$OAc: ACN; 0.8 mL/min); HPLC: 94.6%; (column: Acquity BEH C-18 (50×2.1 mm, 1.7μ); RT 2.78 min; ACN: 0.025% TFA (aq); 0.5 mL/min.

Example 3: Synthesis of 3-((6-chloro-2-cyclopropyl-1-(1-propyl-1H-pyrazol-4-yl)-1H-indol-3-yl) thio)benzoic acid (Compound 1-4)

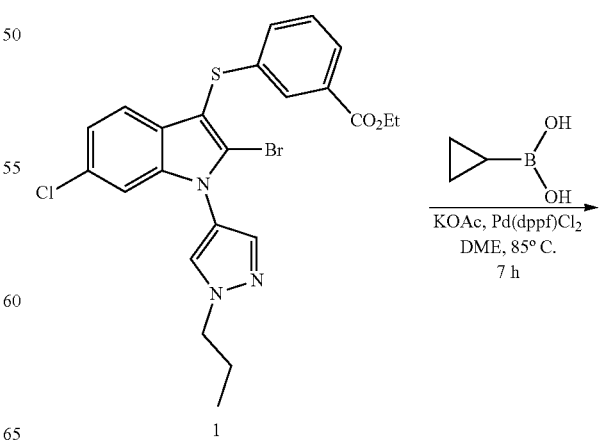

-continued

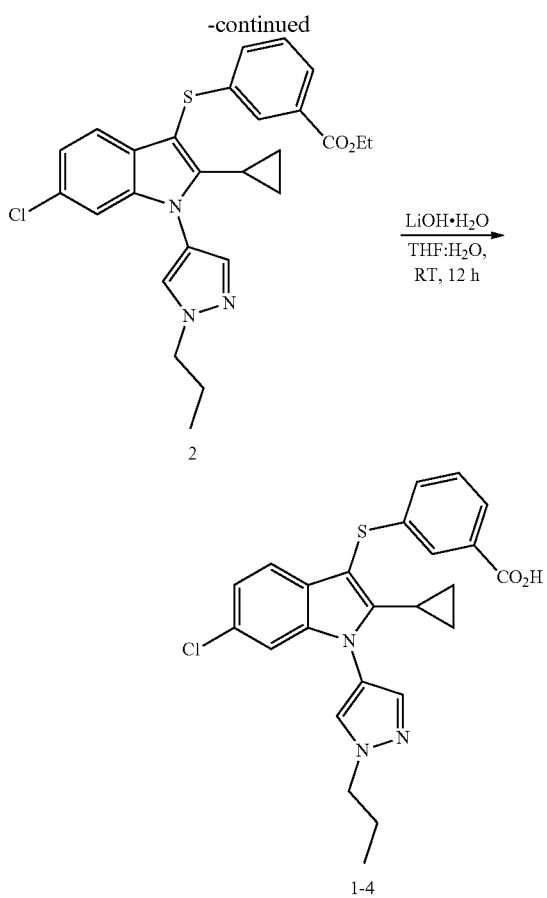

2

1-4

Step 1: Synthesis of ethyl 3-(6-chloro-2-cyclopropyl-1-(1-propyl-1H-pyrazol-4-yl-1-H-indol-3-yl)thio)benzoate (2)

To a stirred solution of ethyl 3-((2-bromo-6-chloro-1-(1-propyl-1H-pyrazol-4-yl)-1H-indol-3-yl)thio)benzoate 1 (Example 2, Step 3; 100 mg, 0.19 mmol) in DME (20 mL) under inert atmosphere were added cyclopropyl boronic acid (16.6 mg, 0.19 mmol), KOAc (56.8 mg, 0.58 mmol) at RT and degassed for 15 min. To this, was added Pd(dppf)Cl$_2$ (28.3 mg, 0.038 mmol), heated to 85° C. and stirred for 7 h. The reaction was monitored by TLC; after completion of the reaction, the reaction mixture was diluted with water (20 mL) and extracted with CH$_2$Cl$_2$ (3×20 mL). The combined organic extracts were dried over Na$_2$SO$_4$, filtered and concentrated under reduced pressure to obtain the crude. The crude was purified by silica gel column chromatography using 8-10% EtOAc/Hexanes to afford 43 mg of compound 2 with 51% purity. The impure material was further purified by preparative HPLC to afford pure compound 2 (25 mg, 27%) as a colorless oil. $^1$H NMR (500 MHz, CDCl$_3$): δ 3.7.83 (s, 1H). 7.74 (d, J=7.5 Hz, 1H), 7.69 (s, 1H), 7.65 (s, 1H), 7.41 (d, J=8.5 Hz, 1H), 7.26-7.22 (m, 2H), 7.14-7.08 (m, 2H), 4.34 (q, J=7.5 Hz, 2H), 4.21 (t, J=7.0 Hz, 2H), 2.03-1.98 (m, 2H), 1.76-1.75 (m, 1H), 1.05-1.01 (m, 2H), 1.36 (t, J=7.5 Hz, 3H), 1.00 (t, J=7.0 Hz, 3H), 0.87-0.84 (m, 2H); LC-MS (ESI): 89.7%; m/z 480.5 (M+H$^+$); (column: X Select CSH C-18, 50×3.0 mm, 3.5 turn); RT 4.83 min; 5 mM NH$_4$OAc: ACN; 0.8 mL/min).

Step 2: Synthesis of 3-((6-chloro-2-cyclopropyl-1-(1-propyl-1H-pyrazol-4-yl)-1H-indol-3-yl)thio)benzoic acid To a stirred solution of compound 2 (25 mg, 0.05 mmol) in THF:H$_2$O (1:1, 5 mL) under inert atmosphere was added LiOH·H$_2$O (6.5 mg, 0.15 mmol) at 0° C.; warmed to RT and stirred for 12 h. The reaction was monitored by TLC; after completion of the reaction, the volatiles were removed under reduced pressure. The residue was diluted with water (15 mL), acidified with citric acid and extracted with EtOAc (2×20 mL). The combined organic extracts were dried over Na$_2$SO$_4$, filtered and concentrated tinder reduced pressure to obtain the crude. The crude was triturated with n-pentane (2×5 mL) to afford the title compound 1-4 (10 mg, 43%) as an off-white solid. $^1$H NMR (400 MHz, CD$_3$OD): δ 8.07 (s, 1H), 7.76 (s, 1H), 7.71 (d, J=7.6 Hz, 1H), 7.68 (s, 1H), 7.38 (d, J=8.0 Hz, 1H), 7.31-7.28 (m, 1H), 7.21-7.18 (m, 1H), 7.09-7.05 (m, 2H), 4.24 (t, J=7.2 Hz, 2H), 2.02-1.97 (m, 2H), 1.86-1.82 (m, 1H), 1.01-0.97 (m, 5H), 0.85-0.82 (m, 2H); MS (ESI): m/z 452.3 (M+H$^+$); HPLC: 86.9%; (column: Acquity BEH C-18 (50×2.1 mm, 1.7μ) RT 3.00 min; ACN: 0.025% TFA (aq); 0.5 mL/min.

Example 4: Synthesis of 3-((2,6-dichloro-7-fluoro-1-(1-propyl-1H-pyrazol-4-yl)-1H-indol-3-yl)thio) benzoic acid (Compound 1-7)

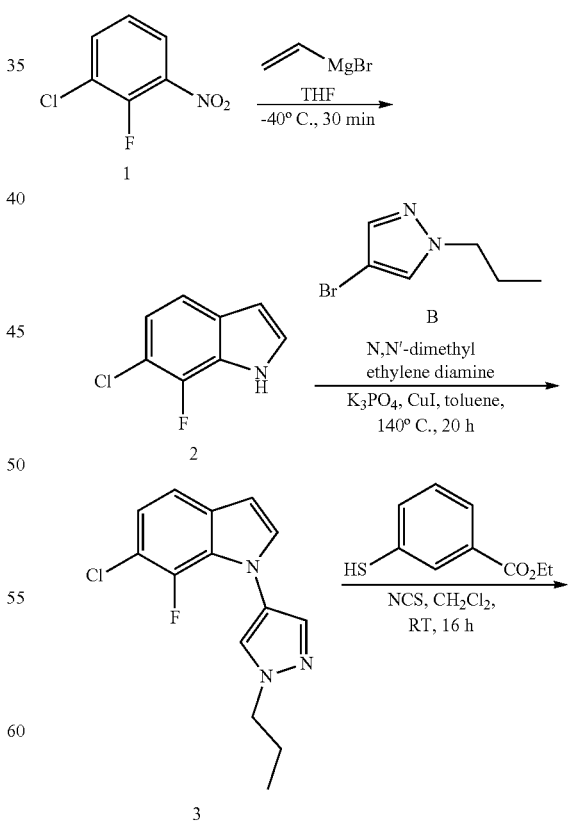

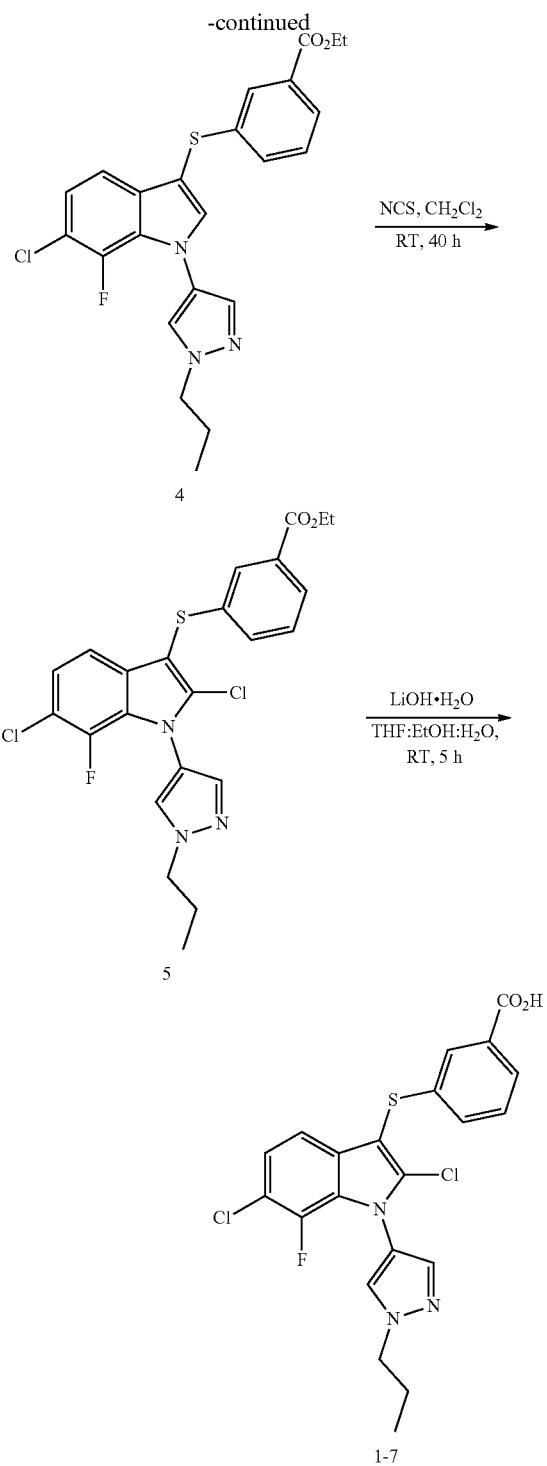

Step 1: Synthesis of 6-chloro-7-fluoro-1H-indole 2

To a stirred solution of 1-chloro-2-fluoro-3-nitrobenzene 1 (10.0 g, 56.98 mmol) in TI-F (100 mL) under inert atmosphere was added vinyl magnesium bromide (1M in THF solution; 170 mL, 170.94 mmol) at RT, cooled to −40° C. and stirred for 30 min. The reaction was monitored by TLC; after completion of the reaction, the reaction mixture was quenched with saturated NH$_4$Cl solution (50 nil), extracted with EtOAc (2×50 mL). The combined organic extracts were washed with NH$_4$Cl solution (40 mL), dried over Na$_2$SO$_4$, filtered and concentrated under reduced pressure to obtain the crude. This was purified by silica gel column chromatography using 2% EtOAc/Hexanes to afford compound 2 (1.1 g, 11.4%) as a brown oil. $^1$H NMR (500 MHz, CDCl$_3$): δ 3.8.36 (br s, 1H), 7.31 (d, J=8.0 Hz, 1H), 70.25-7.22 (m, 1H), 7.08-7.05 (m, 1H), 6.56-6.54 (m, 1H).

Step 2: Synthesis of 6-chloro-7-fluoro-1-(1-propyl-1H-pyrazol-4-yl)-1H-indole (3)

To a stirred solution of compound 2 (1.1 g, 6.48 mmol) in toluene (15 mL) under inert atmosphere were added N,N'-dimethyl ethylene diamine (229 mg, 2.60 mmol), potassium phosphate (3.44 g, 16.27 mmol), 4-bromo-1-propyl-1H-pyrazole (Intermediate B; 1.21 g, 6.50 mmol), CuI (124 mg, 0.65 mmol) at RT, degassed under argon for 15 min; heated to 140° C. and stirred for 20 ha in sealed tube. The reaction was monitored by TLC; after completion of the reaction, the reaction mixture was diluted with EtOAc (30 mL), filtered and the filtrate was concentrated under reduced pressure to obtain the crude. This was purified by silica gel column chromatography using 8-10% EtOAc/Hexanes to afford compound 3 (1.3 g, 72%) as brown liquid. $^1$H NMR (500 MHz, CDCl$_3$): δ 7.64 (s, 1H), 7.60 (s, 1H), 7.31 (d, J=7.5 Hz, 1H), 7.12-7.07 (m, 2H), 6.60 (s, 1H), 4.13 (t, J=7.0 Hz, 2H), 1.99-1.91 (m, 2H), 0.97 (t, J=8.0 Hz, 3H); LC-MS (ESI): 93.5%; m/z 278.2 (M+H$^+$); (column: X Select CSH C-18, 50×3.0 mm, 3.5 urn); RT 4.08 min; 5 mM NH$_4$OAc: ACN; 0.8 mL/min).

Step 3: Synthesis of ethyl 3-((6-chloro-7-fluoro-1-(1-propyl-1H-pyrazol-4-yl)-1H-indol-3-yl) thio) benzoate (4)

To a stirred solution of ethyl 3-mercaptobenzoate (66 mg, 0.36 mmol) in CH$_2$Cl$_2$ (5 mL) under inert atmosphere was added NCS (48.2 mg, 0.36 mmol) at RT and stirred for 50 min. To this, compound 3 (100 mg, 0.36 mmol) was added at RT and stirred for 16 h. The reaction was monitored by TLC; after completion of the reaction, the reaction mixture was diluted with water (25 mL) and extracted with CH$_2$Cl$_2$ (2×20 mL). The combined organic extracts were washed with brine (20 mL), dried over Na$_2$SO$_4$, filtered and concentrated under reduced pressure to obtain the crude. This was purified by silica gel column chromatography using 9% EtOAc/Hexanes to afford compound 4 (100 mg, 61%) as a colorless syrup. $^1$H NMR (500 MHz, CDCl$_3$): δ 6.7.88 (s, 1H), 7.77-7.76 (m, 1H), 7.69 (s, 1H), 7.67 (s, 1H), 7.43 (s, 1H), 7.27-7.24 (m, 3H), 7.15-7.12 (m, 1H), 4.33 (q, J=7.5 Hz, 2H), 4.15 (t, J=7.0 Hz, 2H), 1.98-1.94 (m, 2H), 1.35 (t, J=7.5 Hz, 3H), 0.98 (t, J=7.0 Hz, 3H); LC-MS: 94.6%; m/z 458.4 (M+H$^+$); (column: X Select CSH C-18, 50×3.0 mm, 3.5 in); RT 4.91 min; 5 mM NH$_4$OAc: ACN; 0.8 mL/min).

Step 4: Synthesis of ethyl 3-((2,6-dichloro-7-fluoro-1-(1-propyl)-1H-pyrazol-4-yl)-1H-indol-3-yl)thio) benzoate (5)

To a stirred solution of compound 4 (150 mg, 0.32 mmol) in CH$_2$Cl$_2$ (3 mL) under inert atmosphere was added NCS (87 mg, 0.65 mmol) at RT. After 16 h stirring, NCS (87 mg, 0.65 mmol) was added again at RT and stirred for additional 24 h. The reaction was monitored by TLC; after completion of the reaction, the reaction mixture was diluted with water (15 mL) and extracted with CH$_2$Cl$_2$ (2×20 mL). The combined organic extracts were washed with water (15 mL), dried over Na$_2$SO$_4$, filtered and concentrated under reduced pressure to obtain the crude. This was purified by silica gel column chromatography using 7% EtOAc/n-Hexane to afford compound 5 (100 mg, 62%) as a brown solid. $^1$H NMR (5.00 MHz, CDCl$_3$): δ 7.89 (s, 1H), 7.80-7.79 (m, 1H), 7.67 (s, 1H), 7.65 (s, 1H), 7.28-7.26 (m, 3H), 7.1.7-7.14 (m, 1H), 4.33 (q, J=7.5 Hz, 2H), 4.18 (t, J=7.5 Hz, 2H), 2.00-1.95 (m, 2H), 1.36 (t, J=7.5 Hz, 3H), 0.98 (t, J=7.5 Hz, 3H); LC-MS (ESI): 97.6%; m/z 492.4 (M+H$^+$); (column: X Select CSH C-18, 50×3.0 mm, 3.5 µm); RT 5.07 min; 5 mM NH$_4$OAc: ACN; 0.8 mL/min).

Step 5: Synthesis of 3-((2,6-dichloro-7-fluoro-1-(1-propyl-1H-pyrazol-4-yl)-1-1H-indol-3-yl)thio)benzoic acid To a stirred solution of compound 5 (100 mg, 0.20 mmol) in THF:EtOH:H$_2$O (3:1:1, 5 mL) under inert atmosphere was added LiOH·H$_2$O (25.6 mg, 0.61 mmol) at RT and stirred for 5 h. The reaction was monitored by TLC; after completion of the reaction, the volatiles were removed under reduced pressure. The residue was diluted with water (10 mL), washed with Et$_2$O (2×10 mL). The aqueous layer was acidified with 1N HCl and extracted with CH$_2$Cl$_2$ (2×20 mL). The combined organic extracts were washed with water (15 mL), dried over Na$_2$SO$_4$, filtered and concentrated tinder reduced pressure to obtain the crude. The crude was triturated with n-pentane (2×5 mL) to afford the title compound 1-7 (60 mg, 64%) as an off-white solid. $^1$H NMR (400 MHz, DMSO-d$_6$): δ 12.90 (br s, 1H), 8.31 (s, 1H), 7.82 (s, 1H), 7.72-7.70 (m, 2H), 7.37-7.28 (m, 4H), 4.16 (t, J=6.8 Hz, 2H), 1.87-1.82 (m, 2H), 0.85 (t, J=7.6 Hz, 3H); MS (ESI): m/z 464.2 (M+H$^+$); HPLC: 99.1%; (column: Acquity BEH C-18 (50×2.1 mm, 1.7); RT 2.94 min; ACN: 0.025% TFA (aq); 0.5 mL/min.

Example 5: Synthesis of 3-((2-bromo-6-chloro-1-(1-propyl-1H-pyrazol-4-yl)-1H-indol-3-yl)thio) benzoic acid (Compound 1-2)

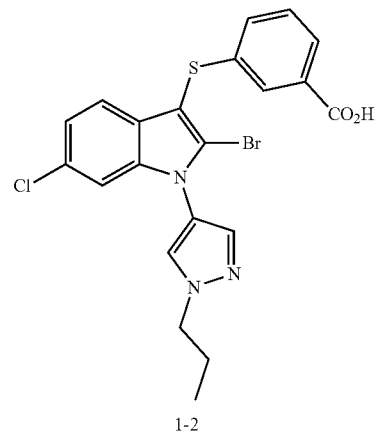

1-2

To a stirred solution of ethyl 3-((2-bromo-6-chloro-1-(1-propyl-1H-pyrazol-4-yl)-1H-indol-3-yl)thio)benzoate 1 (Example 2, Step 3; 70 Mg 0.13 mmol) in THF:H$_2$O (1:1, 10 mL) under inert atmosphere was added LiOH·H$_2$O (17 mg, 0.40 mmol) at 0° C.; warmed to RT and stirred for 12 h. The reaction was monitored by TLC; after completion of the reaction, the volatiles were removed tinder reduced pressure. The residue was diluted with water (15 mL), acidified with citric acid to pH ~2.0. The obtained solid was filtered and dried under reduced pressure to afford the title compound 1-2 (50 mg, 76%) as an off-white solid. $^1$H NMR (400 MHz, CD$_3$OD): δ 8.10 (s, 1H), 7.77-7.75 (m, 3H), 7.49 (d, J=8.4 Hz, 1H), 7.32-7.30 (m, 2H), 7.20-7.16 (m, 2H), 4.24 (t, J=7.2 Hz, 2H), 2.02-1.93 (m, 2H), 0.98 (t, J=7.2 Hz, 3H); LC-MS (ESI): 90.8%; m/z 488.8 (M−H$^+$); (column: X Select CSH C-18, 50×3.0 mm, 3.5 µm); RT 3.35 min; 5 mM NH$_4$OAc: ACN; 0.8 mL/min); HPLC: 96.4%; (column: Acquity BEH C-18 (50×2.1 mm, 1.7µ); RT 2.96 min; ACN: 0.025% TFA (aq); 0.5 mL/min.

Example 6: Synthesis of 3-((6-chloro-2-cyclopropyl-7-fluoro-(1-propyl-1H-pyrazol-4-yl)-1H-indol-3-yl)thio)benzoic acid (Compound 1-10)

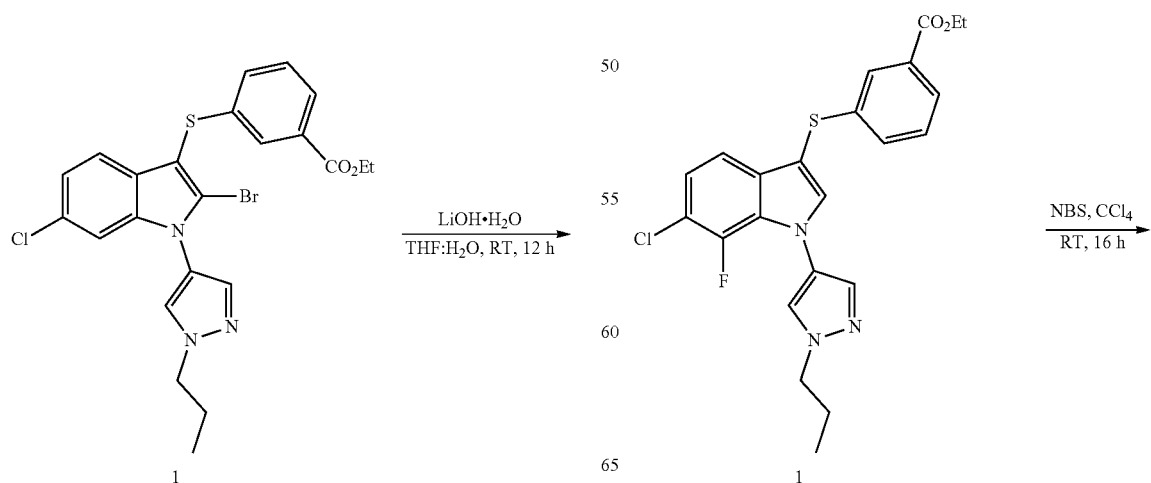

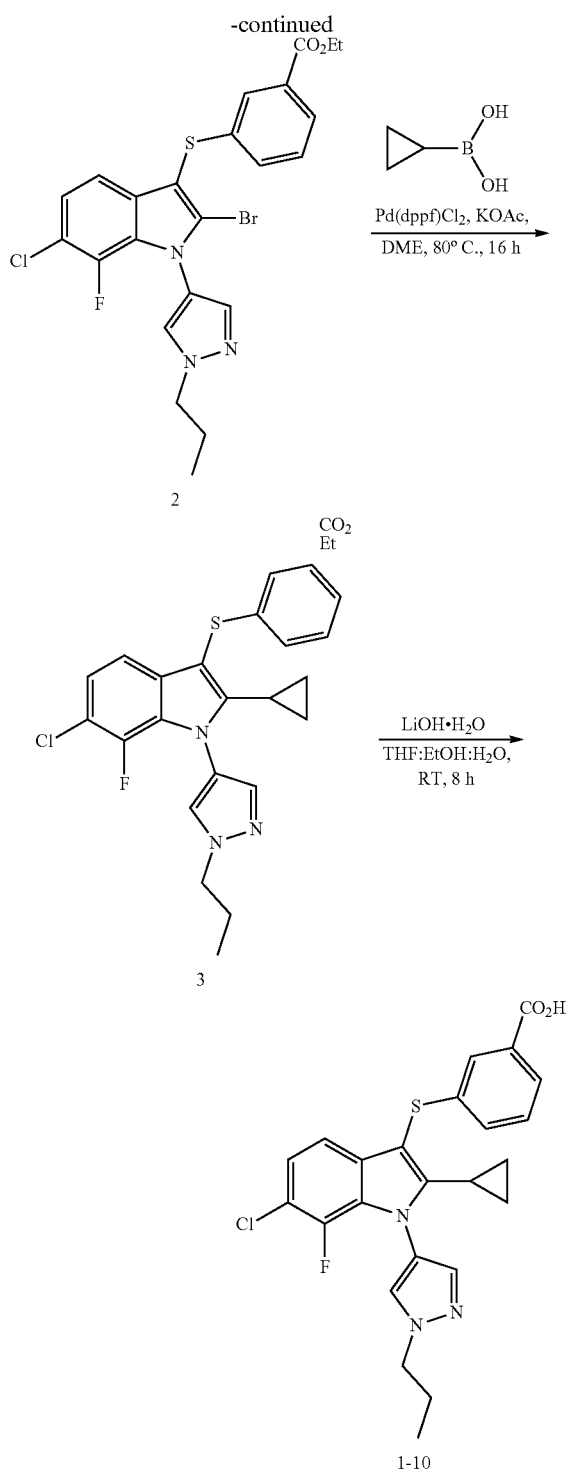

Step 1: Synthesis of ethyl 3-((2-bromo-6-chloro-7-fluoro-1 (1-propyl-1H-pyrazol-4-yl)-1H-indol-3-1 thio)benzoate (2)

To a stirred solution of ethyl 3-((6-chloro-7-fluoro-1-(1-propyl-1H-pyrazol-4-yl)-1H-indol-3-yl)thio)benzoate 1 (Example 4, Step 3; 500 mg, 1.09 mmol) in CCl$_4$ (10 mL) under inert atmosphere was added NBS (391 mg, 2.18 mmol) at RT and stirred for 16 h. The reaction was monitored by TLC; after completion of the reaction, the reaction mixture was diluted with water (30 mL) and extracted with CH$_2$Cl$_2$ (2×30 mL). The combined organic extracts were washed with water (30 mL), dried over Na$_2$SO$_4$, filtered and concentrated under reduced pressure to obtain the crude. This was purified by silica gel column chromatography using 10% EtOAc/Hexanes to afford compound 2 (360 mg, 62%) as an off-white solid. $^1$H NMR (400 MHz, CDCl$_3$): δ 7.89 (br s, 1H), 7.80-7.78 (m, 1H), 7.67 (s, 1H), 7.65 (s, 1H), 7.29-7.27 (m, 2H), 7.24-7.23 (m, 1H), 7.16-7.13 (m, 1H), 4.34 (q, J=7.2 Hz, 2H), 4.19 (t, J=6.8 Hz, 2H), 2.01-1.95 (m, 2H), 1.36 (t, J=6.8 Hz, 3H), 0.98 (t, J=72 Hz, 3H); LC-MS (ESI): 97.6%; m/z 536.8 (M+H$^+$); (column: X Select CSH C-18, 50×3.0 mm, 3.5 μm); RT 5.03 min; 5 mM NH$_4$OAc: ACN; 0.8 mL/min).

Step 2: Synthesis of ethyl 3-((6-chloro-2-cyclopropyl-7-fluoro-1-(1-propyl-1-pyrazol-4-yl-1H-indol-3-yl)thio)benzoate (3)

To a stirred solution of compound 2 (360 mg, 0.67 mmol) in DME (5 mL) under inert atmosphere were added KOAc (197 mg, 2.01 mmol), Pd(dppf)Cl$_2$ (98 mg, 0.13 mmol), cyclopropylboronic acid (57.8 mg, 0.67 mmol) at RT and degassed under Ar for 20 min; heated to 80° C. and stirred for 16 h. The reaction was monitored by TLC; after completion of the reaction, the reaction mixture was diluted with EtOAc (40 mL), filtered through celite. The filtrate was washed with water (25 mL), brine (25 mL), dried over Na$_2$SO$_4$ and concentrated under reduced pressure to obtain the crude. This was purified by silica gel column chromatography and then preparative HPLC to afford pure compound 3 (50 mg, 15%) as a white solid. $^1$H NMR (500 MHz, CDCl$_3$): δ 7.79 (s, 1H), 7.74 (d, J=7.5 Hz, 1H), 7.67 (s, 1H), 7.63 (s, 1H), 7.25-7.18 (m, 2H), 7.12 (d, J=8.0 Hz, 1H), 7.06-7.05 (m, 1H), 4.33 (q, J=7.5 Hz, 2H), 4.18 (t, J=7.5 Hz, 2H), 2.00-1.95 (m, 2H), 1.70-1.69 (m, 1H), 1.36 (t, J=7.5 Hz, 3H), 1.07-1.05 (m, 2H), 0.99-0.97 (t, J=7.5 Hz, 3H), 0.87-0.84 (m, 2H); LC-MS (ESI): 99.7%; m/z 498.5 (M+H$^+$); (column: X Select CSH C-18, 50×3.0 mm, 3.5 μm); RT 5.11 min; 5 mM NH$_4$OAc: ACN; 0.8 mL/min).

Step 3: Synthesis of 3-((6-chloro-2-cyclopropyl-7-fluoro-1-(1-propyl-1H-pyrazol-4-yl)-1H-indol-3-yl (thio)benzoic acid To a stirred solution of compound 3 (50 mg, 0.10 mmol) in THF:EtOH:H$_2$O (3:1:1, 5 mL) under inert atmosphere was added LiOH·H$_2$O (12.6 mg, 0.30 mmol) at RT and stirred for 8 h. The reaction was monitored by TLC; after completion of the reaction, the volatiles were removed under reduced pressure. The residue was diluted with water (20 mL), acidified with 1N HCl to pH ~2 and extracted with CH$_2$Cl$_2$ (2×20 mL). The combined organic extracts were dried over Na$_2$SO$_4$, filtered and concentrated under reduced pressure to obtain the crude. The crude was triturated with n-pentane (2×5 mL) and dried under reduced pressure to afford the title compound 1-10 (25 mg, 53%) as an off-white solid. 1H NMR (400 MHz, DMSO-d$_6$): δ 12.90 (br s, 1H), 8.26 (s, 1H), 7.79 (s, 1H), 7.66 (d, J=7.6 Hz, 1H), 7.61 (s, 1H), 7.34 (t, J=7.6 Hz, 1H), 7.19-7.16 (m, 3H), 4.15 (t, J=6.8 Hz, 2H), 1.87-1.78 (m, 3H), 0.95-0.92 (m, 2H), 0.87-0.80 (m, 5H); MS (ESI): m/z 470.7 (M+H$^+$); HPLC: 97.8%; (column: Acquity BEH C-18 (50×2.1 mm, 1.7μ); RT 3.00 min; ACN: 0.025% TFA (aq); 0.5 mL/min.

Example 7: Synthesis of 3-((6-chloro-2-cyclopropyl-7-fluoro-1-(1-propyl-1H-pyrazol-4-yl)-1H-indol-3-yl)thio)-2-fluorobenzoic acid (Compound 1-16)

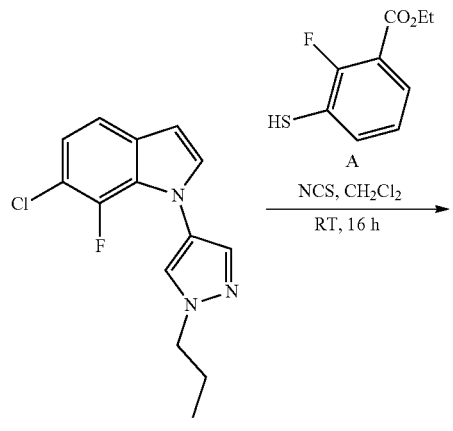

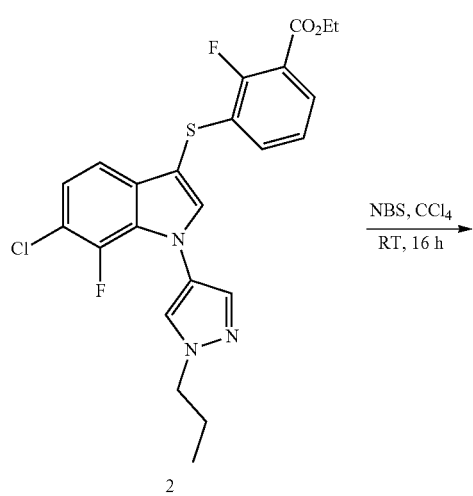

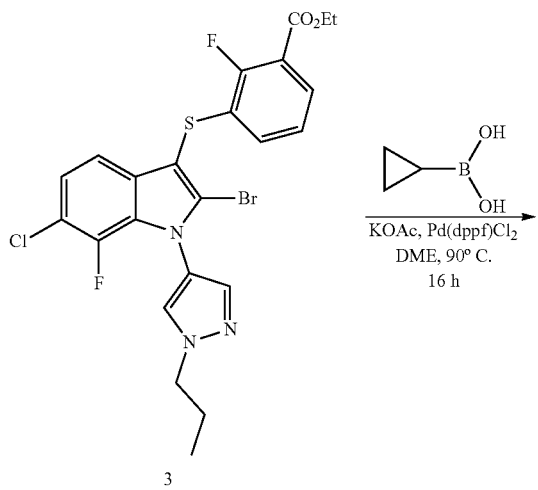

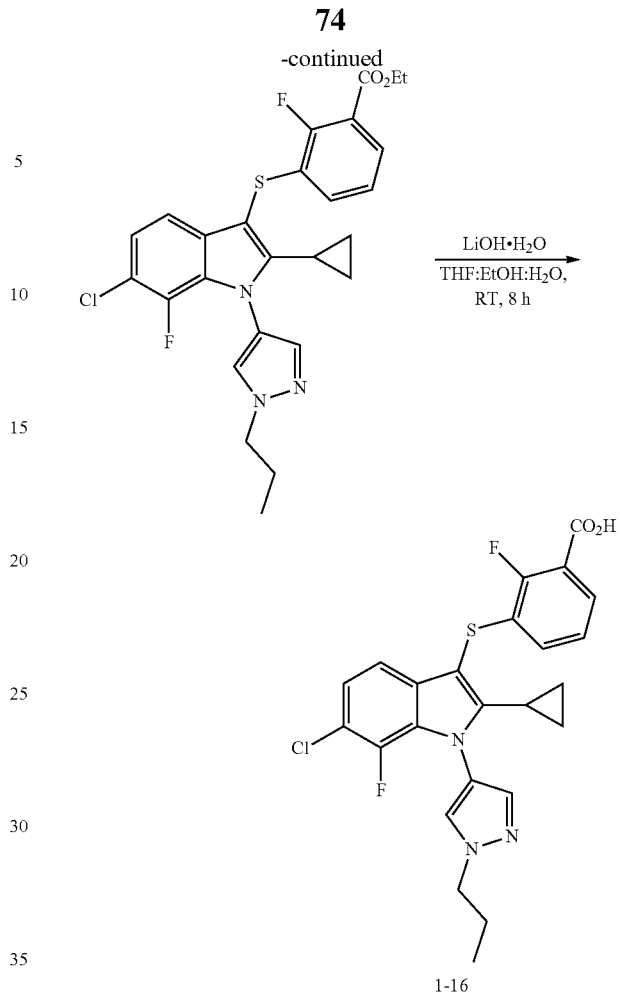

Step 1: Synthesis of ethyl 3-((6-chloro-7-fluoro-1-(1-propyl-1H-pyrazol-4-yl)-1H-indol-3-yl)thio)-2-fluorobenzoate (2)

To a stirred solution of ethyl 2-fluoro-3-mercaptobenzoate (Intermediate A; 108 mg, 0.54 mmol) in $CH_2Cl_2$ (3 mL) under inert atmosphere was added NCS (72 mg, 0.54 mmol) at RT and stirred for 1 h. To this, compound 1 (Example 4, Step 2; 150 mg, 0.54 mmol) was added and stirred for 16 h. The reaction was monitored by TLC; after completion of the reaction, the reaction mixture was diluted with water (25 mL) and extracted with $CH_2Cl_2$ (2×25 mL). The combined organic extracts were washed with brine (20 mL), dried over $Na_2SO_4$, filtered and concentrated under reduced pressure to obtain the crude. This was purified by silica gel column chromatography using 10% EtOAc/Hexanes to afford compound 2 (130 mg, 50%) as an off-white solid. $^1$H NMR (500 MHz, $CDCl_3$): δ 7.69 (s, 1H), 7.67-7.64 (m, 2H), 7.44 (s, 1H), 7.29-7.27 (m, 1H), 7.17-7.14 (m, 1H), 7.01-6.94 (m, 2H), 4.40 (q, J=7.5 Hz, 2H), 4.15 (t, J=8.0 Hz, 2H), 1.98-1.94 (m, 2H), 1.40 (t, J=7.5 Hz, 3H), 0.98 (t, J=8.0 Hz, 3H); LC-MS (ESI): 97.6%; m/z 476.7 (M+H$^+$); (column: X Select CSH C-18, 50×3.0 mm, 3.5 μm); RT 4.84 min; 5 mM $NH_4OAc$: ACN; 0.8 mL/min).

Step 2: Synthesis of ethyl 3-((2-bromo-6-chloro-7-fluoro-1-(1-propyl-1H-pyrazol-4-yl)-1H-indol-3-yl)thio)-2-fluorobenzoate (3)

To a stirred solution of compound 2 (200 mg, 0.42 mmol) in $CCl_4$ (3 mL) under inert atmosphere was added NBS (150 mg, 0.84 mmol) at RT and stirred for 16 h. The reaction was monitored by TLC and LC-MS; after completion of the reaction, the reaction mixture was diluted with water (20 mL) and extracted with CH$_2$Cl$_2$ (2×20 mL). The combined organic extracts were washed with brine (15 mL), dried over Na$_2$SO$_4$, filtered and concentrated under reduced pressure to obtain the crude. This was purified by silica gel column chromatography using 10-15% EtOAc/Hexanes to afford compound 3 (100 mg, 43%) as an off-white solid. $^1$H NMR (400 MHz, CDCl$_3$): δ 7.71-7.67 (m, 1H), 7.66 (s, 1H), 7.64 (s, 1H), 7.31 (d, J=8.8 Hz, 1H), 7.18-7.15 (m, 1H), 7.00-6.96 (m, 2H), 4.40 (q, J=7.2 Hz, 2H), 4.18 (t, J=7.2 Hz, 2H), 2.02-1.93 (m, 2H), 1.40 (t, J=7.2 Hz, 3H), 0.97 (t, J=7.2 Hz, 3H); LC-MS (ESI): 98.1%; m/z 556.2 (M$^+$+2); (column: X Select CSH C-18, 50×3.0 mm, 3.5μ); RT 4.94 min; 5 mM NH$_4$OAc: ACN; 0.8 mL/min).

Step 3: Synthesis of ethyl 3-(6-chloro-2-cyclopropyl-7-fluoro-1-(1-propyl-1H-pyrazol-4-yl)-1H-indol-3-yl)thio)-2-fluorobenzoate (4)

To a stirred solution of compound 3 (260 mg, 0.47 mmol) in DME (5 mL) under inert atmosphere were added cyclopropylboronic acid (40.4 mg, 0.47 mmol), Pd(dppf)$_2$Cl$_2$ (69 mg, 0.09 mmol), KOAc (138 mg, 1.41 mmol) at RT; heated to 90° C. and stirred for 16 h. The reaction was monitored by TLC; after completion of the reaction, the reaction mixture was diluted with water (20 mL) and extracted with EtOAc (2×25 mL). The combined organic extracts were washed with brine (20 mL), dried over Na$_2$SO$_4$, filtered and concentrated under reduced pressure to obtain the crude. This was purified by silica gel column chromatography using 7-9% EtOAc/Hexanes to afford 70 mg of compound 4 which was further purified by preparative HPLC to afford pure compound 4 (20 mg, 9%) as a yellow syrup $^1$H NMR (400 MHz, CDCl$_3$): δ 7.67 (s, 1H), 7.64-7.60 (m, 2H), 7.18 (d, J=8.8 Hz, 1H), 7.10-7.06 (m, 1H), 6.95-6.91 (m, 1H), 6.79-6.75 (m, 1H), 4.41 (q, J=7.2 Hz, 2H), 4.18 (t, J=7.2 Hz, 2H), 2.00-1.93 (m, 2H), 1.74-1.67 (m, 1H), 1.41 (t, J=7.2 Hz, 3H), 1.08-1.06 (m, 2H), 0.99 (t, J=7.2 Hz, 3H), 0.87-0.84 (m, 2H); LC-MS (ESI): 99.9%; m/z 516.5 (M+H$^+$); (column: X Select CSH C-18, 50×3.0 mm, 3.5 μm); RT 5.00 min; 5 mM NH$_4$OAc: ACN; 0.8 mL/min).

Step 4: Synthesis of 3-((6-chloro-2-cyclopropyl-7-fluoro-1-(1-propyl-1H-pyrazol-4-yl)-1H-indol-3-yl)thio)-2-fluorobenzoic acid To a stirred solution of compound 4 (30 mg, 0.058 mmol) in THF:EtOH:H$_2$O (3:1:1, 2.5 mL) under inert atmosphere was added LiOH·H$_2$O (7.3 mg, 0.17 mmol) at RT and stirred for 8 h. The reaction was monitored by TLC; after completion of the reaction, the volatiles were removed under reduced pressure. The residue was diluted with water (10 mL), washed with Et$_2$O (2×10 mL). The aqueous layer was acidified with 1N HCl solution and extracted with CH$_2$Cl$_2$ (2×15 ml). The combined organic extracts were washed with brine (15 mL), dried over Na$_2$SO$_4$, filtered and concentrated under reduced pressure to obtain the crude. This was triturated with n-pentane (5 mL) to afford the title compound 1-16 (25 mg, 89%) as an off-white solid. $^1$H NMR (400 MHz, DMSO-d$_6$): δ 8.2.5 (s, 1H), 7.80 (s, 1H), 7.18-7.14 (m, 3H), 6.81 (t, J=7.6 Hz, 1H), 6.42 (t, J=7.6 Hz, 1H), 4.15 (t, J=6.8 Hz, 2H), 1.87-1.76 (m, 3H), 0.95-0.93 (m, 2H), 0.86-0.80 (m, 5H); MS (ESI): m/z 488.4 (M+H$^+$); HPLC: 99.7%; (column: Acquity BEH C-18 (50×20.1 mm, 1.7μ); RT 2.88 min; ACN: 0.025% TFA (aq); 0.5 mL/min.

Example 8: Synthesis of 3-((2,6-dichloro-7-fluoro-1-(1-propyl-1H-pyrazol-4-yl)-1H-indol-3-yl)thio)-2-fluorobenzoic acid (Compound 1-13)

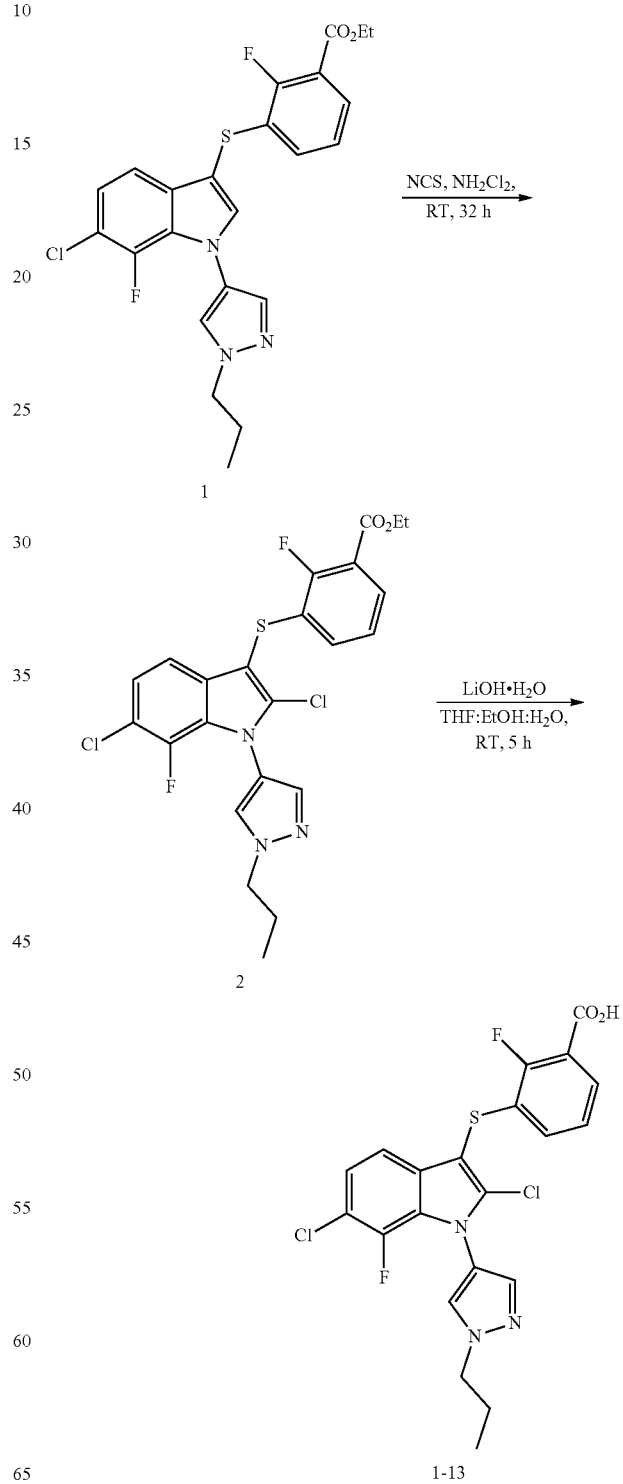

Step 1: Synthesis of ethyl 3-((2,6-dichloro-7-fluoro-1-(1-propyl-1H-pyrazol-4-yl)-1H-indol-3-yl)thio)-2-fluorobenzoate (2)

To a stirred solution of ethyl 3-((6-chloro-7-fluoro-1-(1-propyl-1H-pyrazol-4-yl)-1H-indol-3-yl)thio)-2-fluorobenzoate 1 (Example 7, Step 1; 100 mg, 0.21 mmol) in CH$_2$Cl$_2$ (3 mL) was added NC'S (33.7 mg, 0.25 mmol) at RT under inert atmosphere. After 8 h stirring, additional NCS (33.7 mg, 0.25 mmol) was added at RT and stirred again for 24 h. The reaction was monitored by TLC; after completion of the reaction, the reaction mixture was diluted with water (20 mL) and extracted with CH$_2$Cl$_2$ (2×20 mL). The combined organic extracts were washed with brine (15 mL), dried over Na$_2$SO$_4$, filtered and concentrated under reduced pressure to obtain the crude. This was purified by silica gel column chromatography using 9-11% EtOAc/Hexanes to afford compound 2 (50 mg, 47%) as an off-white solid. $^1$H NMR (400 MHz, CDCl$_3$): δ 7.71-70.67 (m, 1H), 7.66 (s, 1H), 7.64 (s, 1H), 7.30 (d, J=8.8 Hz, 1H), 7.18 (dd, J=8.4, 6.0 Hz, 1H), 7.04-6.97 (m, 2H), 4.40 (q, J=7.2 Hz, 2H), 4.18 (t, J=7.2 Hz, 2H), 2.04-1.93 (m, 2H), 1.40 (t, J=7.2 Hz, 3H), 0.97 (t, J=7.2 Hz, 3H); LC-MS (ESI): 98.8%; m/z 510.4 (M+H$^+$); (column: X Select CSH C-18, 50×3.0 mm, 3.5 μm); RT 4.94 min; 5 mM NH$_4$OAc: ACN; 0.8 mL/min).

Step 2: Synthesis of 3-((2,6-dichloro-7-fluoro-1-(1propyl-1H-pyrazol-4-yl)-1H-indol-3-yl)thio-2-fluorobenzoic acid To a stirred solution of compound 2 (50 mg, 0.09 mmol) in THF:EtOH:H$_2$O (3:1:1, 5 ml) under inert atmosphere was added LiOH·H$_2$O (12.3 mg, 0.29 mmol) at RT and stirred for 5 h. The reaction was monitored by TLC; after completion of the reaction, the volatiles were removed under reduced pressure. The residue was diluted with water (10 mL), acidified with 1N HCl and extracted with CH$_2$Cl$_2$ (2×10 mL). The combined organic extracts were washed with brine (10 mL), dried over Na$_2$SO$_4$, filtered and concentrated under reduced pressure to obtain the crude. This was triturated with n-pentane (2×5 mL) to afford the title compound 1-13 (15 mg, 34%) as an off-white solid. $^1$H NMR (400 MHz, DMSO-d$_6$): δ 13.24 (br s, 1H), 8.29 (s, 1H), 7.83 (s, 1H), 7.64-7.60 (m, 1H), 7.36-7.34 (m, 2H), 7.15-7.05 (m, 2H), 4.16 (t, J=7.2 Hz, 2H), 1.89-1.80 (m, 2H), 0.85 (t, J=7.2 Hz, 3H); MS (ESI): 480.1 (M−H$^+$); HPLC: 97.0%; (column: Acquity BEH C-18 (50×2.1 mm, 1.7); RT 2.86 min; ACN: 0.025% TFA (aq); 0.5 mL/min.

Example 9: Synthesis of 3-((6-Chloro-2-cyclopropyl-1-(1-ethyl-1H-pyrazol-4-yl)-7-fluoro-1H-indol-3-yl)thio)-2-fluorobenzoic acid (Compound 1-34)

Route 1

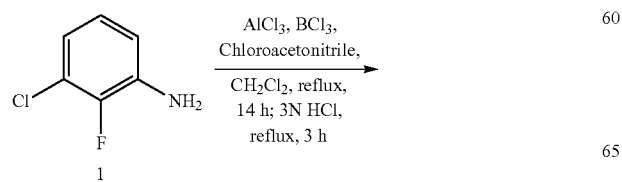

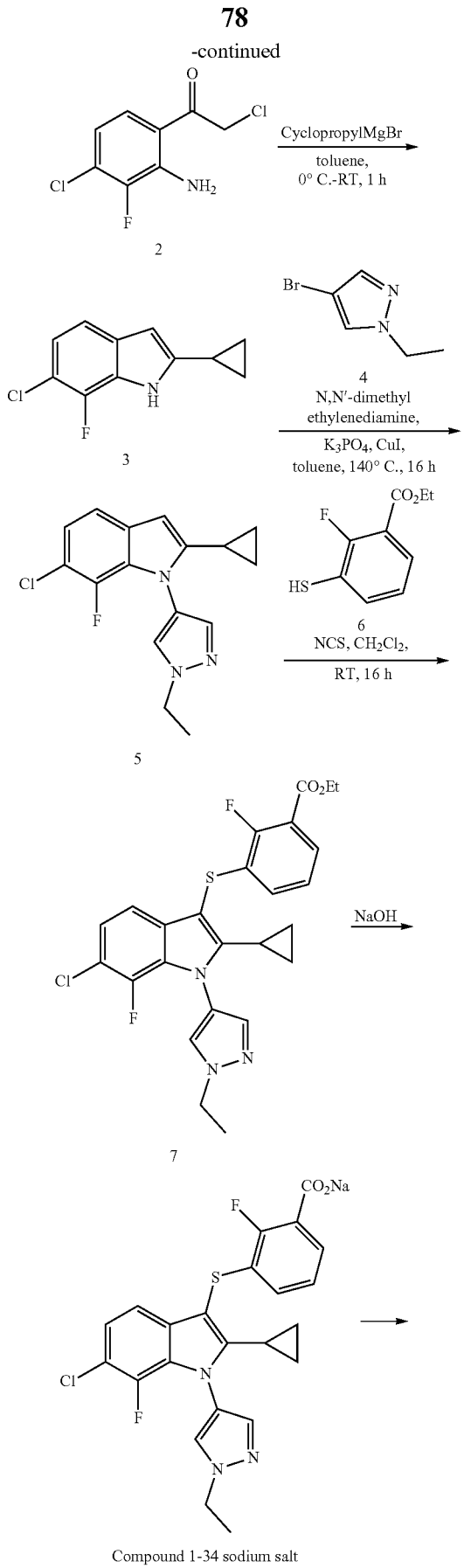

Compound 1-34 sodium salt

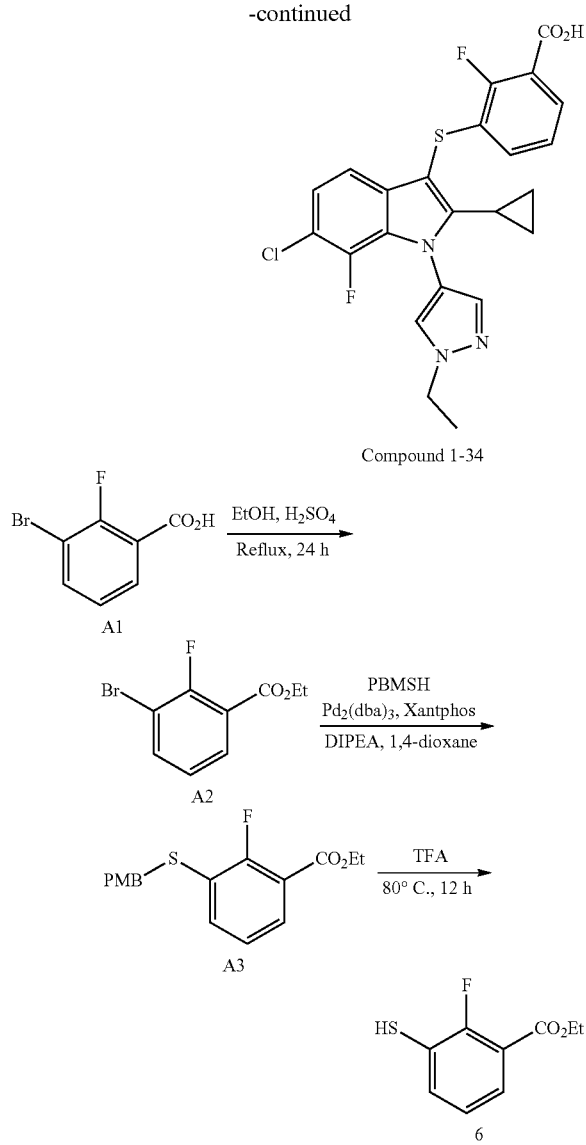

Compound 1-34

Step 1: Synthesis of 1-(2-amino-4-chloro-3-fluorophenyl)-2-chloroethan-1-one (2)

To a stirred solution of $CH_2C_3$ (10.0 g, 75.01 mmol) and $BCl_3$ (1M in n-hexane) (74 mL, 75.01 mmol) in $CH_2Cl_2$ (80 mL) was added 3-chloro-2-fluoroaniline 1 (9.0 g, 6.18 mmol) followed by a solution of chloroacetonitrile (11.6 g, 153.64 mmol) in $Cl_2Cl_2$ (20 ml) at 0° C. under inert atmosphere. The reaction mixture was allowed to stir at RT for 30 minutes; heated to reflux temperature and maintained for additional 14 h. The reaction mixture was then cooled to 0° C., added aqueous 3N HCl solution (100 mL) and raised the temperature to reflux and stirred for 3 b. After completion of the reaction by TLC, the reaction mixture was cooled RT, diluted with water (50 mL) and extracted with $CH_2Cl_2$. (2×150 mL). The combined organic extracts were dried over $Na_2SO_4$, filtered and concentrated under reduced pressure to obtain the crude. The crude was purified by triturating with n-pentane to afford compound 2 (4.5 g, 33%) as an off-white solid. $^1H$ NMR (500 MHz, DMSO-$d_5$): δ 7.61 (d, J=9.0 Hz, 1H), 7.35 (br s, 2H), 6.72 (d, J=9.0 Hz, 1H), 5.06 (s, 2H).

Step 2: Synthesis of 6-chloro-2-cyclopropyl-7-fluoro-1H-indole (3)

To a stirred solution of compound 2 (4.5 g, 20.3 mmol) in toluene (50 mL) was added cyclopropyl magnesium bromide (0.5 M in THF; 102.0 mL, 50.9 mmol) at 0° C. under inert atmosphere. The reaction mixture was stirred at 0° C. for 15 min and then warmed to RT and stirring was continued for additional 1 h. After completion of the reaction by TLC, the reaction mixture was quenched with saturated ammonium chloride solution (10 mL) and extracted with EtOAc (3×75 mL). The combined organic extracts were dried over $Na_2SO_4$, filtered and concentrated under reduced pressure to obtain the crude. The crude was purified (silica gel chromatography; 1% EtOAc/Hexanes) to afford compound 3 (2.7 g, 63%) as an off-white solid. $^1H$ NMR (500 MHz, DMSO-$d_6$): δ 11.55 (s, 1H), 7.18 (d, J=8.5 Hz, 1H), 6.97 (dd, J=8.5, 6.5 Hz, 1H), 6.16 (s, 1H), 2.03-1.99 (m, 1H), 0.99-0.96 (m, 2H), 0.83-0.80 (m, 2H); LC-MS (ESI): 91.6%; m/z 208.1 (M−H$^+$); (column: X Select CSI—C-18, 50×3.0 mm, 3.5 μm); RT 4.32 min; 5 mM $NH_4OAc$: ACN; 0.8 mL/min).

Step 3: Synthesis of 4-bromo-1-ethyl-1H-pyrazole (4)

To a stirred solution of NaH (34.0 g, 0.85 mmol; 60% in mineral oil) in THF (400 mL) was added a solution of 4-bromo-1H-pyrazole (50 g, 0.34 mmol) in THE (100 mL) at 0° C. under inert atmosphere. The reaction mixture was warmed to RT and maintained at same temperature for 1 h. The reaction mixture was cooled again to 0° C. and added EtI (63.67 g, 0.408 mol) slowly for 5 min. The resultant solution was allowed to warm to RT and then stirred for 16 h. After completion of the reaction (monitored by TLC), the reaction mixture was quenched with ice-cold water (100 mL) and extracted with EtOAc (3×250 mL). The combined organic extracts were dried over $Na_2SO_4$, filtered and concentrated under reduced pressure to obtain the crude. The crude was purified (silica gel chromatography; 4-6% EtOAc/Hexanes) to afford compound 4 (43 g, 72%) as a pale yellow liquid. $^1H$ NMR (500 MHz, $CDCl_3$): δ 7.45 (s, 1H), 7.41 (s, 1H), 4.15 (q, J=7.5 Hz, 2H), 1.47 (t, J=7.5 Hz, 3H); MS (ESI): m/z 175.0 (M+H$^+$).

Step 4: Synthesis of 6-chloro-2-cyclopropyl-1-(1-ethyl-1H-pyrazol-4-yl)-7-fluoro-1H-indole (5)

To a solution of compound 3 (4.3 g, 20.5 mmol) in toluene (50 mL) were added 4-bromo-1-ethyl-1H-pyrazole 4 (4.0 g, 22.8 mmol), potassium phosphate (11.0 g, 51.2 mmol), N,N'-dimethylethylenediamine (722 mg, 8.2 mmol) and Cu(I)I (390 mg, 2.0 mmol) at RT tinder inert atmosphere. The reaction solution was purged with argon for 15 min and then sealed the tube. The reaction mixture was heated to 140° C. and stirred for 16 h. After completion of the reaction by TLC, the reaction mixture was cooed to RT, diluted with EtOAc (50 mL) and filtered. The filtrate was washed with water (40 mL), brine (40 mL), dried over $Na_2SO_4$, filtered and concentrated under reduced pressure to obtain the crude. The crude was purified (silica gel chromatography; 9% EtOAc Hexanes) to afford compound 5 (3.9 g, 63%) as a pale brown solid. $^1H$ NMR (400 MHz, $CDCl_3$): δ 7.64 (s, 1H), 7.60 (s, 1H), 7.16 (d, J=8.4 Hz, 1H), 7.01 (dd, J=8.4, 6.4 Hz, 1H), 6.12 (s, 1H), 4.25 (q, J=7.2 Hz, 2H), 1.69-1.62 (m, 1H), 1.56 (t, J=7.2 Hz, 3H), 0.92-0.87 (m, 2H), 0.76-0.72 (m, 2H); LC-MS (ESI): 98.6%; m/z 304.3 (M+H$^+$);

(column: X Select C-18 50×3.0 mm, 3.5 μm); RT 4.23 min; 5 mM NH$_4$OAc: ACN; 0.8 mL/min).

Step 5: Synthesis of ethyl 3-bromo-2-fluorobenzoate (A2)

To a stirred solution of 3-bromo-2-fluorobenzoic acid A1 (25.0 g, 114.15 mmol) in ethanol (400 mL) was added conc. H$_2$SO$_4$ (3 mL) at RT and stirred at reflux temperature for 24 h. The reaction was monitored by LC-MS; after completion of the reaction, the reaction mixture was concentrated to obtain the residue. The residue was diluted with EtOAc (500 mL), washed with water (300 mL), brine (300 mL), dried over Na$_2$SO$_4$, filtered and concentrated under reduced pressure to afford compound A2 (26.0 g, 92%) as a light yellow liquid. $^1$H NMR (400 MHz, CDCl$_3$): δ 7.88-7.84 (m, 1H), 7.72-7.69 (m, 1H), 7.08-7.04 (m, 1H), 4.39 (q, J=7.2 Hz, 2H), 1.39 (t, J=7.2 Hz, 3H).

Step 6: Synthesis of ethyl 2-fluoro-3-((4-methoxybenzyl)thio)benzoate (A3)

1,4-dioxane (250 mL) was degassed by purging with N$_2$ gas for 30 min and to this, were added a solution of compound A2 (13.2 g, 53.4 mmol) in 1,4-dioxane (50 mL; degassed), (4-methoxyphenyl)methanethiol (PMBSH) (8.2 g, 53.4 mmol), xantphos (1.54 g, 2.66 mmol), diisopropyl ethyl amine (19.6 mL, 106.8 mmol) and Pd$_2$(dba)$_3$ 1.22 g, 1.33 mmol) at RIT. The reaction mixture was heated to 90° C. and stirred for 2 h. The reaction was monitored by TLC; after completion of the reaction, the reaction mixture was diluted with hexane (450 mL) and stirred at RT for 15 min. The resultant solution was filtered through celite and washed with hexane (100 mL). The filtrate was washed water (250 mL) dried over Na$_2$SO$_4$, filtered and concentrated under reduced pressure to obtain the crude. The crude was purified through silica gel column chromatography using 3-4% EtOAc/Hexanes to afford compound A3 (15 g, 88%) as pale yellow solid. $^1$H NMR (500 MHz, CDCl$_3$): δ 7.78-7.74 (m, 1H), 7.43-7.39 (m, 1H), 7.19 (d, J=8.0 Hz, 2H), 7.07-7.04 (m, 1H), 6.80 (d, J=8.0 Hz, 2H), 4.41 (q, J=7.2 Hz, 2H), 4.08 (s, 2H), 3.78 (s, 3H), 1.41 (t, J=7.2 Hz, 3H). LC-MS (ESI): 89.7%; m/z 318.9 (M+H$^+$); (column: X Select CSH C-18, 50×3.0 mm, 3.5 μm); RT 4.22 min; 5 mM NH$_4$OAc: ACN; 0.8 mL/min).

Step 7: Synthesis of ethyl 2-fluoro-3-mercaptobenzoate (6)

A stirred solution of compound A3 (30.0 g, 93.75 mmol) in TFA (54.5 mL) was heated to 80° C. and stirred for 12 hr under inert atmosphere. The reaction was monitored by TLC; after completion of the reaction, the volatiles were removed under reduced pressure. The residue was dissolved in ice-cold water (100 mL), basified with solid sodium bicarbonate and extracted with EtOAc (2×200 mL). The combined organic extracts were dried over Na$_2$SO$_4$, filtered and concentrated under reduced pressure to obtain the crude. The crude was purified through silica gel column chromatography using 3% EtOAc/Hexanes to afford compound 6 (11.7 g, 62%) as a pale brown syrup. $^1$H NMR (500 MHz, CDCl$_3$): δ 7.70-7.66 (m, 1H), 7.48-7.44 (m, 1H), 7.08-7.04 (m, 1H), 4.20 (q, J=7.5 Hz, 2H), 3.67 (s, 1H), 1.40 (t, J=7.5 Hz, 3H); LC-MS (ESI): 91.8%; mL/z 199.0 (M−H$^+$); (column: X Select CSH C-18, 50×3.0 mm, 3.5 μm); RT 2.60 min; 5 mM NH$_4$OAc: ACN; 0.8 mL/min).

Step 8: Synthesis of ethyl 3-((6-chloro-2-cyclopropyl-1-(1-ethyl-1H-pyrazol-4-yl)-7-fluoro-1H-indol-3-yl thio)-2-fluorobenzoate (7)

To a stirred solution of ethyl 2-fluoro-3-mercaptobenzoate 6 (2.8 g, 14.0 mmol) in CH$_2$Cl$_2$ (30 mL) under inert atmosphere was added NCS (1.9 g, 14.0 mmol) at RT and allowed to stir for 2 h. To this, compound 5 (3.9 g, 12.8 mmol) in CH$_2$Cl$_2$ (10 mL) was added at RT and stirred for 16 h. After completion of the reaction by TLC, the reaction mixture was diluted with water (100 mL) and extracted with CH$_2$Cl$_2$ (2×80 mL). The combined organic extracts were washed with water (2×200 mL), dried over Na$_2$SO$_4$, filtered and concentrated under reduced pressure to obtain the crude. The crude was purified by triturating with n-pentane (2×50 mL) to afford 7 (5.2 g, 81%) as a pale yellow solid. $^1$H NMR (400 MHz, CDCl$_3$): δ 7.66-7.7.60 (m, 3H), 7.18 (d, J=8.4 Hz, 1H), 7.08 (dd, J=8.4, 6.5 Hz, 1H), 6.93 (t, J=8.4 Hz, 1H), 6.79-6.75 (m, 1H), 4.40 (q, J=7.2 Hz, 2H), 4.26 (q, J=7.6 Hz, 2H), 1.74-1.68 (m, 1H), 1.56 (t, J=7.2 Hz, 3H), 1.41 (t, J=7.6 Hz, 3H), 1.08-1.04 (m, 2H), 0.89-0.84 (m, 2H); MS (ESI): m/z 502.5 (M+H$^+$); HPLC: 97.5%; (column: Acquity BEH C-18 (50×2.1 mm, 1.7μ); RT 3.44 min; ACN: 0.025% TFA (aq); 0.5 mL/min.

Step 9: Synthesis of 3-((6-chloro-2-cyclopropyl-1-(1-ethyl-1H-pyrazol-4-yl)-7-fluoro-1H-indol-3-yl) thio)-2-fluorobenzoic acid sodium salt (Compound 1-34 sodium salt)

1.0 M NaOH (10.25 mL, 10.2 mmol) was added to a solution of compound 7 (5.14 g, 10.2 mmol) in THF/MeOH (3:1)(56 mL). The mixture was heated at 65° C. for 1.5 h. Additional 1.0 M NaOH (0.23 mL, 0.2 mmol) was added to the reaction and heated at 65° C. for 0.5 h. The mixture was concentrated under reduced pressure to afford the crude acid sodium salt (5.12 g, 100%) as a pale pink solid. The crude solid (600 mg) in THF/EtOH (4:1) (6 mL) and a few drops of water. The mixture filtered and concentrated under reduced pressure and precipitants formed. The solids filtered off and washed with THF/EtOH (9:1) to afford 3-((6-chloro-2-cyclopropyl-1-(1-ethyl-1H-pyrazol-4-yl)-7-fluoro-1H-indol-3-yl)thio)-2-fluorobenzoic acid sodium salt (Compound 1-34 sodium salt; 449 mg) as an off white solid. $^1$H NMR (300 MHz, DMSO-d$_6$): δ 8.26 (s, 1H), 7.79 (m, 1H), 7.18-7.13 (m, 3H), 6.81 (t, 1H), 6.43-6.38 (m, 1H), 4.21 (q, 2H), 1.84-1.72 (m, 1H), 1.42 (t, 3H), 0.96-0.93 (m, 2H), 0.84-0.80 (m, 2H); LC-MS: 474 (M$^+$).

Step 9: 3-((6-Chloro-2-cyclopropyl-1-(1-ethyl-1H-pyrazol-4-yl)-7-fluoro-1H-indol-3-yl)thio)-2-fluorobenzoic acid (Compound 1-34)

To Compound 1-34 sodium salt (50 mg, 0.10 mmol) suspended in CH$_2$Cl$_2$ (1 mL) and water (1 mL) was added saturated citric acid until pH 3. The suspension stirred until clear solution. The organic layer was separated, washed with brine, dried over Na$_2$SO$_4$, filtered, and concentrated under reduced pressure to obtain the crude material to afford compound B as a white solid (33 mg, 70%) $^1$H NMR (300 MHz, DMSO-d$_6$): δ 13.39 (s, 1H), 8.24 (s, 1H), 7.79 (s, 1H), 7.57 (t, 1H), 7.22-7.06 (m, 3H), 6.80 (t, 1H), 4.21 (q, 2H), 1.84-1.72 (m, 1H), 1.42 (t, 3H), 0.96-0.88 (m, 2H), 0.86-0.80 (m, 2H); LC-MS: 474 (M).

Alternative Route to Intermediate 7

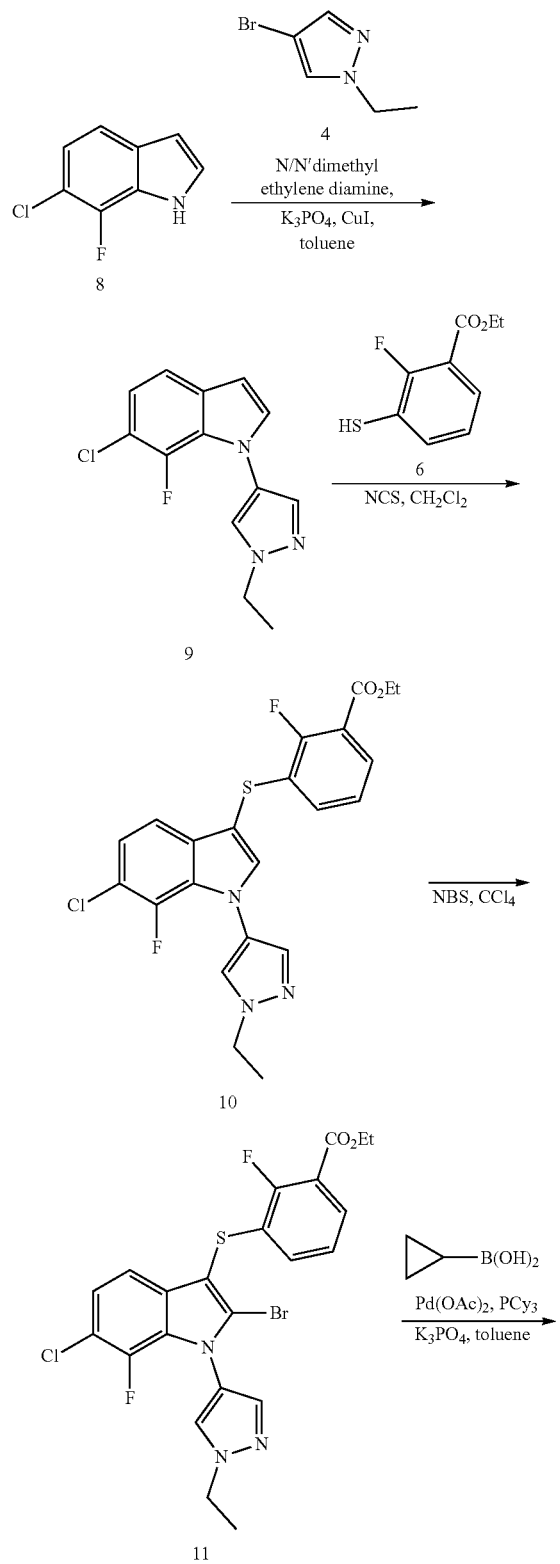
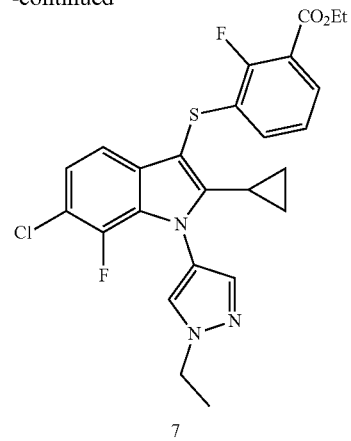

Step 1: Synthesis of 6-chloro-1-(1-ethyl-1H-pyrazol-4-yl)-7-fluoro-1H-indole (9)

To a stirred solution of 6-chloro-7-fluoro-1H-indole 8 (400 mg, 2.36 mmol) in toluene (10 mL) were added 4-bromo-1-ethyl-1H-pyrazole 4 (Step 3 above; 414 mg, 2.36 mmol), potassium phosphate (1.25 g, 5.91 mmol), N,N'-dimethylethylenediamine (84 mg, 0.95 mmol) and Cu(I)I (45 mg, 0.24 mmol) at RT under inert atmosphere. The resulted solution was purged with argon and sealed the tube. The reaction mixture was then heated to 140° C. for 16 h. After completion of the reaction (monitored by TLC), the reaction mixture was cooled to RT, diluted with hexane (10 mL) and filtered through a short pad of celite. The filtrate was washed with water (2×10 mL), dried over $Na_2SO_4$, filtered and concentrated under reduced pressure to obtain the crude. The crude was purified (silica gel chromatography; 8-1.0% EtOAc/Hexanes) to afford compound 9 (224 mg, 36%) as a light brown thick liquid. $^1$H NMR (500 MHz, CDCl$_3$): δ 7.64 (s, 1H), 7.61 (s, 1H), 7.31 (d, J=8.0 Hz, 1H), 7.12-7.07 (m, 2H), 6.60-6.59 (m, 1H), 4.22 (q, J=7.5 Hz, 2H), 1.55 (t, J=7.5 Hz, 3H) LC-MS (ESI): 94.7%; m/z 264.1 (M+H$^+$); (column: X Select C-18, 50×3.0 mm, 3.5 μm); RT 3.87 min; 5 mM NH$_4$OAc: ACN; 0.8 mL/min).

Step 2: Synthesis of ethyl 3-((6-chloro-1-(1-ethyl-1H-pyrazol-4-yl)-7-fluoro-1H-indol-3-yl)thio)-2-fluorobenzoate (10)

To a stirred solution of ethyl 2-fluoro-3-mercaptobenzoate 6 (Step 7 above; 212 mg, 1.06 mmol) in CH$_2$Cl$_2$ (4 mL) under inert atmosphere was added NCS (156 mg, 1.16 mmol) at 0° C. and allowed to stir at RT for 1 h. The reaction mixture was cooled to 0° C. and compound 3 (280 mg. 1.06 mmol) in CH$_2$Cl$_2$ (1 mL) was added slowly and stirred at RT for 16 h. After completion of the reaction by TLC, the reaction mixture was diluted with CH$_2$Cl$_2$ (15 mL) and washed with water (2×20 mL), dried over Na$_2$SO$_4$, filtered and concentrated under reduced pressure to obtain the crude. The crude was purified (silica gel chromatography; 8-10% EtOAc/Hexanes) to afford compound 10 (300 mg, 61%) as a pale brown solid, $^1$H NMR (500 MHz, CDCl$_3$): δ 7.69-7.64 (m, 3H), 7.44 (s, 1H), 7.27 (t, J=8.0 Hz, 1-1), 7.16 (dd, J=8.5, 6.0 Hz, 1H), 7.01-6.94 (m, 2H), 4.39 (q, J=75 Hz, 2H), 4.24 (q, J=7.0 Hz, 2H), 1.57 (t, J=7.0 Hz, 3H), 1.40 (t, J=7.5 Hz, 3H); LC-MS (ESI): 98.6%; m/z 462.3 (M+H$^+$);

(column: X Select C-18, 50×3.0 mm, 3.5 µm); RT 4.70 min; 5 mM NH₄OAc: ACN; 0.8 mL/min).

Step 3: Synthesis of ethyl 3-((2-bromo-6-chloro-1-(1-ethyl-1H-pyrazol-4-yl)-7-fluoro-1H-indol-3-yl)thio)-2-fluorobenzoate (11)

To a stirred solution of compound 10 (200 mg, 0.43 mmol) in CCl₄ (10 mL) under inert atmosphere was added NBS (178 mg, 0.99 mmol) at RT and stirred for 16 h. After completion of the reaction by TLC, the reaction mixture was diluted with water (10 mL) and extracted with CH₂Cl₂ (2×20 mL). The combined organic extracts were washed with brine (10 mL), dried over Na₂SO₄, filtered and concentrated tinder reduced pressure to obtain the crude. The crude was purified (silica gel chromatography; 5-7% EtOAc/Hexanes) to afford compound 11 (180 mg, 77%) as an off-white solid. ¹H NMR (500 MHz, CDCl₃): δ 7.70-7.67 (m, 1H), 7.65 (s, 2H), 7.30 (d, J=8.0 Hz, 1H), 7.1.7 (dd, J=8.5.6.0 Hz, 1H), 7.00-6.98 (m, 2H), 4.40 (q, J=7.5 Hz, 2H), 4.27 (q, J=7.5 Hz, 2H), 1.58 (t, J=7.5 Hz, 3H), 1.40 (t, J=7.5 Hz, 3H); LC-MS (ESI): 99.5%; m/z 542.4 (M⁺+2); (column: X Select CSH C-18, 50×3.0 mm, 3.5 µm); RT 4.80 min; 5 mM NH₄OAc:ACN: 0.8 mL/min).

Step 4: Synthesis of ethyl 3-((6-chloro-2-cyclopropyl-1-(1-ethyl-1H-pyrazol-4-1l-7-fluoro-1H-1-indol-3-yl)thio)-2-fluorobenzoate (7)

A solution of compound 11 (150 mg, 0.27 mmol) in toluene (10 mL) under inert atmosphere was purged with argon at RT for 10 min. To this, cyclopropylboronic acid (48 mg, 0.55 mmol), tricyclohexyl phosphine (16 mg, 0.05 mmol), Pd(OAc)₂ (6 mg, 0.02 mmol) and potassium phosphate (202 mg, 0.01 mmol) were added at RT under argon. The resultant solution was purged again with argon at RT for 5 min. The reaction mixture was then heated to reflux temperature and stirred for 3 h. The reaction was monitored by TLC & LC-MS; after completion of the reaction, the reaction was cooled to RT, diluted with EtOAc (20 mL) and filtered. The filtrate was washed with water (2×10 mL) and brine (10 mL), dried over Na₂SO₄, filtered and concentrated under reduced pressure to obtain the crude. This was purified (silica gel chromatography; 6% EtOAc/Hexanes) to afford 7 as a pale yellow solid. ¹H NMR (400 MHz, CDCl₃): δ 7.66-7.7.60 (m, 3H), 7.18 (d, J=8.4 Hz, 1H), 7.08 (dd, J=8.4, 6.5 Hz, 1H), 6.93 (t, J=8.4 Hz, 1H), 6.79-6.75 (m, 1H), 4.40 (q, J=7.2 Hz, 2H), 4.26 (q, J=7.6 Hz, 2H), 1.74-1.68 (m, 1H), 1.56 (t, J=7.2 Hz, 314), 1.41 (t, J=7.6 Hz, 3H), 1.08-1.04 (m, 2H), 0.89-0.84 (m, 2H); LC-MS (ESI): 92.9%; m/z 502.5 (M); (column: X Select CSH C-18, 50×3.0 mm, 3.5 µm); RT 4.85 min; 5 mM NH₄OAc: ACN; 0.8 mL/Min.) HPLC: 93.1%; (column: Acquity BEH-C-18 (50×2.1 mm, 1.7µ); RT 3.44 min; ACN: 0.025% TFA (aq); 0.5 mL/min.

Example 10: Synthesis of 6-((6-chloro-2-cyclopropyl-1-(1-ethyl-1H-pyrazol-4-yl)-7-fluoro-1-indol-3-yl)thio)picolinic acid (Compound 1-92)

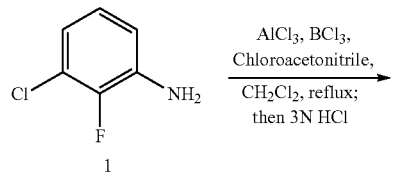

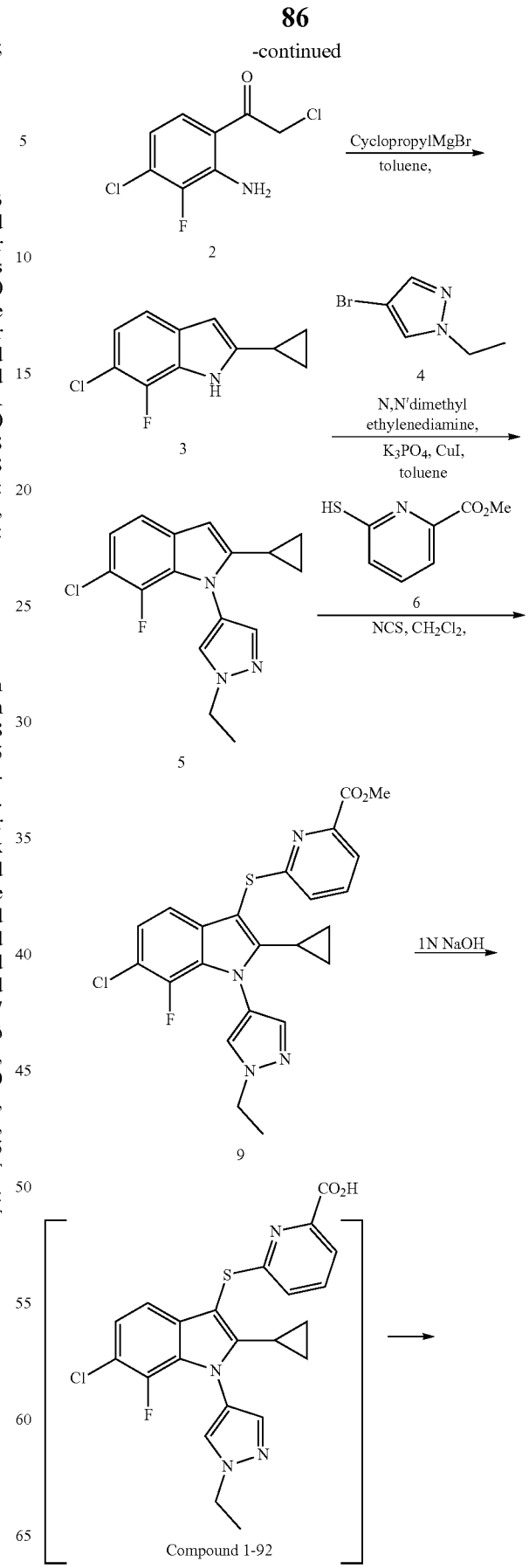

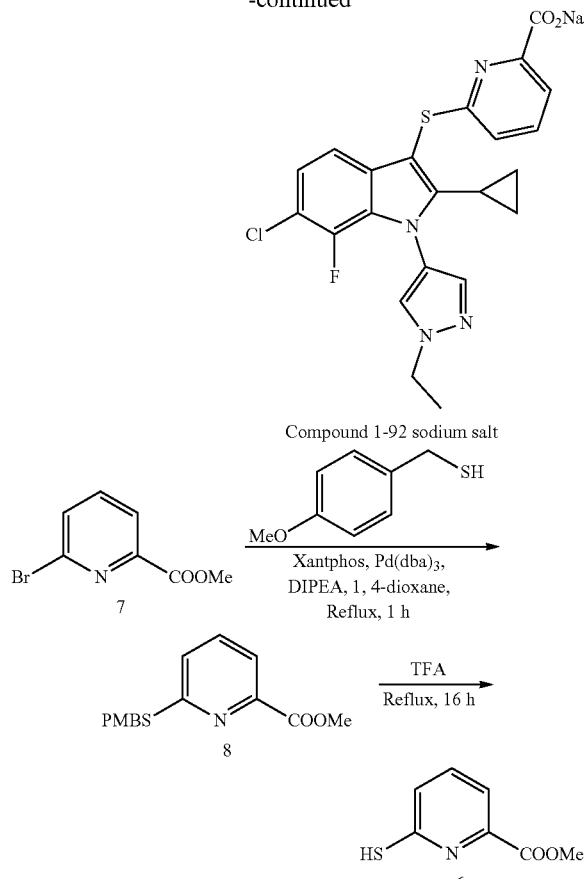

Step 1: Synthesis of 1-(2-amino-4-chloro-3-fluorophenyl)-2-chloroethan-1-one (2)

To a stirred solution of AlCl$_3$ (10.0 g, 75.01 mmol) and BCl$_3$ (1M in n-hexane) (74 mL, 75.01 mmol) in CH$_2$Cl$_2$ (80 mL) was added 3-chloro-2-fluoroaniline 1 (9.0 g, 6.18 mmol) followed by a solution of chloroacetonitrile (11.6 g, 153.64 mmol) in Cl$_2$C$_2$ (20 mL) at 0° C. tinder inert atmosphere. The reaction mixture was allowed to stir at W for 30 minutes; heated to reflux temperature and maintained for additional 14 h. The reaction mixture was then cooled to 0° C., added aqueous 3N HCl solution (100 ml) and raised the temperature to reflux and stirred for 3 h. After completion of the reaction (TLC), the reaction mixture was cooled RT, diluted with water (50 mL) and extracted with CH$_2$Cl$_2$ (2×150 mL). The combined organic extracts were dried over Na$_2$SO$_4$, filtered and concentrated under reduced pressure to obtain the crude. The crude was purified by triturating with n-pentane to afford compound 2 (4.5 g, 33%) as an off-white solid. $^1$H NMR (500 MHz, DMSO-d$_6$): δ 7.61 (d, J=9.0 Hz, 1H), 7.35 (br s, 2H), 6.72 (d, J=9.0 Hz, 1H), 5.06 (s, 2H).

Step 2: Synthesis of 6-chloro-2-cyclopropyl-7-fluoro-1H-indole (3)

To a stirred solution of compound 2 (4.5 g, 20.3 mmol) in toluene (50 mL) was added cyclopropyl magnesium bromide (0.5 M in THF; 102.0 mL, 50.9 mmol) at 0° C. under inert atmosphere. The reaction mixture was stirred at 0° C. for 15 min and then warmed to R T and stirring was continued for additional 1 h. After completion of the reaction (TLC), the reaction mixture was quenched with sat. NH$_4$Cl solution (10 mL) and extracted with EtOAc (3×75 mL). The combined organic extracts were dried over Na$_2$SO$_4$, filtered and concentrated under reduced pressure to obtain the crude. The crude was purified (silica gel column chromatography; 1% EtOAc/Hexanes to afford compound 3 (2.7 g, 63%) as an off-white solid. $^1$H NMR (500 MHz, DMSO-d$_6$): δ 11.55 (s, 1H), 7.18 (d, J=8.5 Hz, 1H), 6.97 (dd, J=8.5, 6.5 Hz, 1H), 6.16 (s, 1H), 2.03-1.99 (m, 1H), 0.99-0.96 (m, 2H), 0.83-0.80 (m, 2H); LC-MS (ESI): 91.6%; m/z 208.1 (M−H$^+$); (column: X Select CSH C-18, 50×3.0 mm, 3.5 μm); RT 4.32 min; 5 mM NH$_4$OAc: ACN; 0.8 mL/min).

Step 3: Synthesis of 6-chloro-2-cyclopropyl-1-(1-ethyl-1H-pyrazol-4-yl)-7-fluoro-1H-indole (5)

To a solution of compound 3 (4.3 g, 20.5 mmol) in toluene (50 mL) were added 4-bromo-1-ethyl-1H-pyrazole 4 (Example 2, Step 3; 4.0 g, 22.8 mmol), potassium phosphate (11.0 g, 51.2 mmol), N,N'-dimethylethylenediamine (722 mg, 8.2 mmol) and Cu(I)I (390 mg, 2.0 mmol) at RT under inert atmosphere. The reaction solution was purged with argon for 15 min and then sealed the tube. The reaction mixture was heated to 140° C. and stirred for 16 h. After completion of the reaction (TLC), the reaction mixture was cooled to RT, diluted with EtOAc (50 mL) and filtered. The filtrate was washed with water (40 mL), brine (40 mL), dried over Na$_2$SO$_4$, filtered and concentrated under reduced pressure to obtain the crude. The crude was purified (silica gel column chromatography; 9% EtOAc/Hexanes) to afford compound 5 (3.9 g, 63%) as a pale brown solid. $^1$H NMR (400 MHz, CDCl$_3$): δ 7.64 (s, 1H), 7.60 (s, 1H), 7.16 (d, J=8.4 Hz, 1H), 7.01 (dd, J=8.4, 6.4 Hz, 1H), 6.12 (s, 1), 4.25 (q, J=7.2 Hz, 2H), 1.69-1.62 (m, 1), 1.56 (t, J=7.2 Hz, 3H), 0.92-0.87 (m, 2H), 0.76-0.72 (m, 2H); LC-MS (ESI): 98.6%; m/z 304.3 (M+H$^+$); (column: X Select C-18, 50×3.0 mm, 3.5 μm); RT 4.23 min; 5 mM NH$_4$OAc: ACN; 0.8 mL/min).

Step 4: Synthesis of methyl 6-((4-methoxybenzyl)thio) picolinate (8)

To a stirred solution of methyl 6-bromopicolinate 7 (8 g, 37.2 mmol) in 1, 4-dioxane (110 mL) under inert atmosphere were added (4-methoxyphenyl) methanethiol (5.7 g, 37.0 mmol), xantphos (1.1 g, 1.9 mmol), diisopropyl ethyl amine (13.6 mL, 74.0 mmol), Pd(dba)$_3$ (847 mg, 0.9 mmol) at RT, degassed under argon for 15 min; heated to reflux and stirred for 1 h. After completion of the reaction (TLC), the reaction mixture was diluted with water (500 mL) and extracted with EtOAc (3×500 mL). The combined organic extracts were dried over Na$_2$SO$_4$, filtered and concentrated under reduced pressure to obtain the crude. The crude was purified (silica gel column chromatography; 10% EtOAc/hexanes) to afford compound 8 (8 g, 75%) as yellow solid. $^1$H NMR (400 MHz, CDCl$_3$): δ 7.78 (d, J=7.6 Hz, 1H), 7.57 (t, J=8.0 Hz, 1H), 7.42-7.40 (m, 2H), 7.29-7.25 (m, 1H), 6.82 (d, J=8.4 Hz, 2H), 4.44 (s, 2H), 4.00 (s, 3H), 3.77 (s, 3H); LC-MS: 95.7%; 290.3 (M$^+$+1); (column: X Select C-18, 50×3.0 mm, 3.5 μm); RT 4.10 min. 5 mM NH$_4$OAc: ACN; 0.8 mL/min).

Step 5: Synthesis of methyl 6-mercaptopicolinate (6)

A stirred solution of compound 8 (6 g, 20.7 mmol) in Trifluoro acetic acid (50 mL) under inert atmosphere was heated to reflux and stirred for 16 h. After completion of the reaction TLC), the volatiles were removed under reduced pressure. The residue was diluted with EtOAc (500 mL), washed with aqueous NaHCO$_3$ solution (3×250 mL). The organic extract were dried over Na$_2$SO$_4$, filtered and concentrated under reduced pressure to obtain the compound 6 (3.5 g, crude) as pale brown solid. LC-MS: 61.1%; 170 (M$^+$+1); (column: X Select C-18, 50×3.0 mm, 3.5 μm); RT 1.41 min. 5 mM NH$_4$OAc: ACN; 0.8 mL/min).

Step 6: Synthesis of methyl 6-(6-chloro-2_cyclopropyl-1-(1-ethyl-1H-pyrazol-4-yl)-7-fluoro-1H-indol-3-yl)thio)picolinate (9)

To a stirred solution of methyl 6-mercaptopicolinate 6 (3.15 g, crude) in CH$_2$Cl$_2$ (50 mL) under inert atmosphere was added NCS (2.49 g, 18.63 mmol) at RT and stirred for 1 h. To this, indole 5 (5.6 g, 18.47 mmol) in CH$_2$Cl$_2$ (50 mL) was added at RT and stirred for 16 h. After completion of the reaction (TLC), the reaction mixture was diluted CH$_2$Cl$_2$ (100 mL) washed with water (3×100 mL). The organic extract was dried over Na$_2$SO$_4$ filtered and concentrated under reduced pressure to obtain the crude. The crude was purified (silica gel column chromatography; 10% EtOAc/ hexanes) to afford 9 (28 g, 32%) as a pale brown solid. $^1$H NMR (500 MHz, DMSO-d$_6$): δ 7.79 (d, J=7.5 Hz, 1H), 7.66 (d, J=10.5 Hz, 2H), 7.51 (t, J=7.5 Hz, 1H), 7.19 (d, J=8.5 Hz, 1H), 7.10-7.07 (m, 1H), 6.78 (d, J=8.0 Hz 1H), 4.28 (q, 2N), 4.00 (s, 3H), 1.75-1.69 (m, 1H), 1.58 (t, J=7.0 Hz, 3H), 1.09-1.08 (m, 2H), 0.87-0.84 (m, 2H); LC-MS: 98.4%; m/z 471.4 (M+H$^+$); (column; X-select CSH C-18, (50×3.0 mm, 3.5 μm); RT 4.25 min 5.0 mM NH$_4$OAc (Aq): ACN; 0.8 mL/min); HPLC: 98.1%; (column: Acquity BEH C-18 (50× 2.1 mm, 1.7μ); RT 3.02 min. ACN: 0.025% TFA (aq); 0.5 mL/min).

Step 7: Synthesis of 6-((6-chloro-2-cyclopropyl-(1H-ethyl-1H-pyrazol-4-yl)-7-fluoro-1H-indol-3-yl) thio)picolinic acid sodium salt (Compound 1-92 sodium salt)

To a stirred solution of compound 9 (2.81 g, 5.97 mmol) in THF:water (4:1) (40 mL) was added 1M aq. NaOH solution (6.03 n L, 6.03 mmol) and the mixture was heated at 60° C. for 1 h. After completion of the reaction, the solvent was removed to afford Compound 1-92 (2.83 g, 100%) as a light brown solid. LC-MS: 457 (M$^+$+1).

Example 11: Synthesis of 3-((6-chloro-2-cyclopropyl-7-fluoro-1-(1H-pyrazol-4-yl)-1H-indol-3-yl) thio)-2-fluorobenzoic acid sodium salt (Compound 1-119)

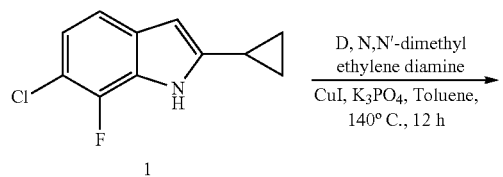

Step 1: Synthesis of ethyl 3-((6-chloro-2-cyclopropyl-7-fluoro-1-(1-((2-(trimethylsilyl) ethoxy) methyl)-1H-pyrazol-4-yl)-1H-indol-3-yl)thio)-2-fluorobenzoate (3)

Following the procedure of Example 9, Steps 3 and 4 but using Intermediate D in place of Intermediate B in Step 3,

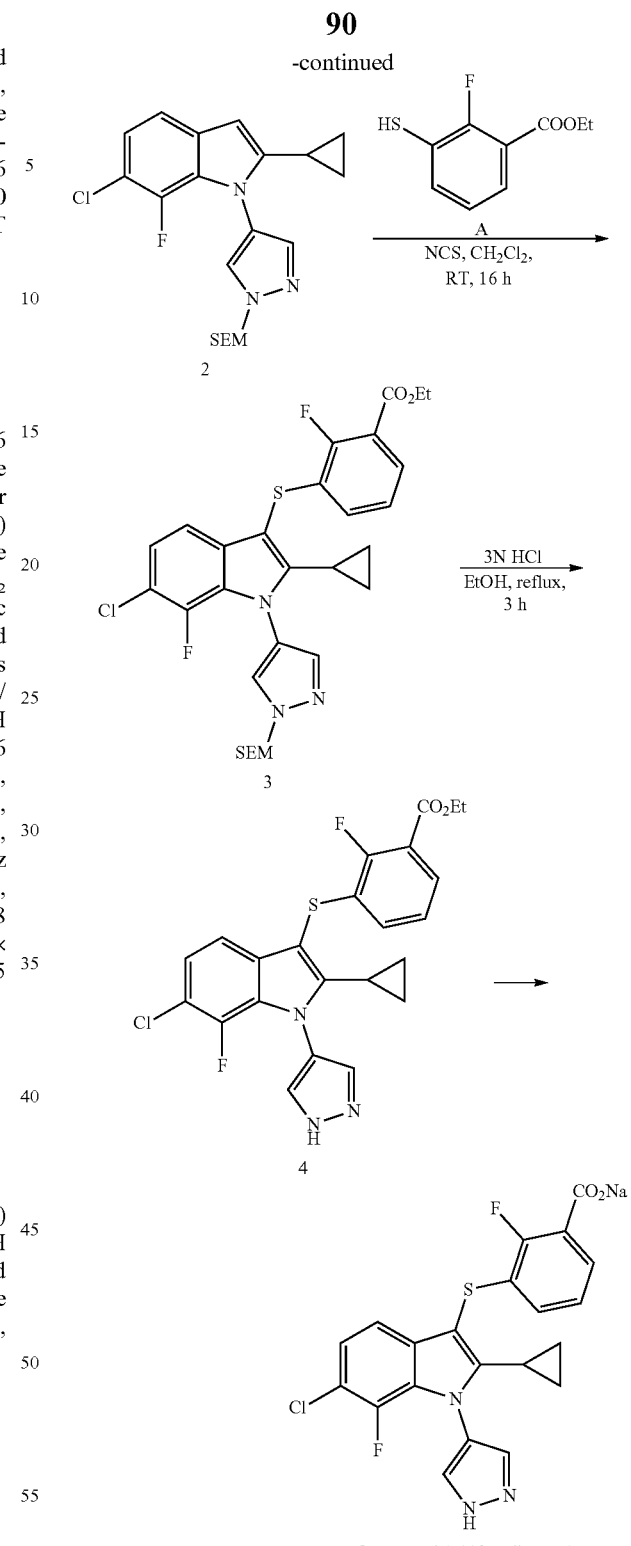

the title compound 3 was obtained as a pale brown syrup. ¹H NMR (400 MHz, CDCl₃): δ 7.85 (s, 1H), 7.73 (s, 1H), 7.64 (t, J=7.5 Hz, 1H), 7.20 (d, J=8.0 Hz, 1H), 7.12-7.09 (m, 1H), 6.95 (t, J=7.5 Hz, 1H), 6.79 (t, J=6.5 Hz, 1H), 5.54 (s, 2H), 4.42 (q, 2H), 3.62 (t, J=7.5 Hz, 2H), 1.70-1.65 (m, 1H), 1.42 (t, J=7.0 Hz, 3H), 1.06-1.05 (m, 2H), 0.96 (t, J=8.5 Hz, 2H), 0.89-0.87 (m, 2H), 0.03 (s, 9H); LC-MS (ESI): m/z 604.6 (M+H⁺).

Step 2: Synthesis of ethyl 3-((6-chloro-2-cyclopropyl-7-fluoro-1-(1H-pyrazol-4-yl)-1H-indol-3-yl)thio)-2-fluorobenzoate (4)

To a stirred solution of compound 3 (140 mg, 0.23 mmol) in EtOH (17 mL) was added 3 N HCl (4 mL) at RT and heated to reflux for 3 h. After completion of the reaction (TLC), the pH of the mixture was neutralized with Et₃N (2 mL) and extracted with EtOAc (2×30 mL). The combined organic extracts were dried (Na₂SO₄), filtered and concentrated under reduced pressure to obtain the crude. The crude was titurated with n-pentane, dried under reduced pressure to afford 4 (90 mg, 90%) as a pale brown solid. ¹H NMR (500 MHz, DMSO-d₆): δ 13.21 (br s, 1H), 8.24 (s, 1H), 7.84 (s, 1H), 7.60 (t, J=6.5 Hz, 1H), 7.21-7.11 (m, 3H), 6.84 (t, J=6.5 Hz, 1H), 4.34 (q, 2H), 1.81-1.76 (m, 1H), 1.32 (t, J=8.0 Hz, 3H), 0.93-0.90 (m, 2H), 0.84-0.79 (m, 2H); LC-MS (ESI): m/z 474.9 (M+H⁺).

Step 3: Synthesis of 3-((6-chloro-2-cyclopropyl-7-fluoro-1-(1H-pyrazol-4-yl)-1H-indol-3-yl)thio)-2-fluorobenzoic acid sodium salt (Compound 1-119)

To a solution of compound 4 (30 mg, 0.063 mmol) in THF:water (3:1) (4 mL) was added 1M aq. NaOH solution (0.063 mL, 0.063 mmol) at RT and then heat at 60° C. overnight. After the completion of the reaction, solvent was removed to afford Compound 1-119 sodium salt (29 mg, 100%) as an off-white solid. LC-MS: m/z 446 (M+H⁺).

Example 12: Synthesis of 3-((6-chloro-2-cyclopropyl-7-fluoro-1-(1-(2-hydroxyethyl)-1H-pyrazol-4-yl)-1H-indol-3-yl)thio)-2-fluorobenzoic acid sodium salt (Compound 1-120)

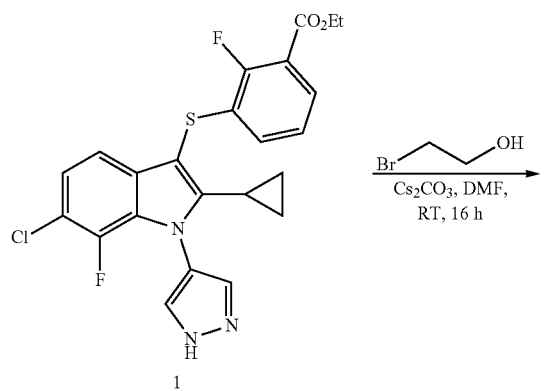

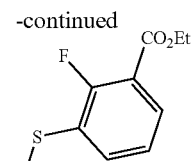

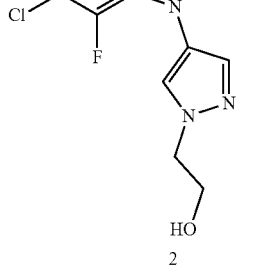

Compound 1-120
sodium salt

Step 1: Synthesis of ethyl 3-((6-chloro-2-cyclopropyl-7-fluoro-1-(1-(2-hydroxyethyl)-1-pyrazol-4-yl)-1H-indol-3-yl)thio)-2-fluorobenzoate (2)

To a stirred solution of indole 1 (Example 11, Step 3; 480 mg, 1.01 mmol) in DMF (10 mL) under inert atmosphere were added Cs₂CO₃ (0.32 g, 4.05 mmol) and 2-bromoethan-1-ol (152 mg, 1.27 mmol) at RT and stirred for 16 h. The mixture was diluted with water (20 mL) and extracted with EtOAc (3×20 mL). The combined organic extracts were dried (Na₂SO₄), filtered and concentrated under reduced pressure to obtain the crude. This was purified (silica gel; 55% EtOAc/hexanes) to obtain compound 2 (100 mg, 19%) as a colorless syrup. 1H NMR (400 MHz, CDCl₃): δ 7.72 (d, J=6.8 Hz, 2H), 7.62 (dt, J=8.0 Hz, 1.6 Hz, 1H), 7.18 (d, J=8.4 Hz, 1H), 7.10-7.07 (m, 1H), 6.94 (t, J=8.0 Hz, 1H), 6.78 (dt, J=8.0, 1.6 Hz, 1H), 4.41 (q, 2H), 4.36-4.34 (m, 2H), 4.10 (t, J=4.8 Hz, 2H), 2.72 (br s, 1H), 1.74-1.67 (m, 1H), 1.41 (t, J=7.2 Hz, 3H), 1.08-1.04 (m, 2H), 0.90-0.85 (m, 2H); LC-MS: m/z 518.7 (M+H⁺).

Step 2: Synthesis of 3-((6-chloro-2-cyclopropyl-7-fluoro-1-(1-(2-hydroxyethyl)-1H-pyrazol-4-yl)-1H-indol-3-yl)thio)-2-fluorobenzoic acid sodium salt (Compound 1-120)

Following the procedure of Example 11, Step 3 but using Intermediate 2 in place of Intermediate 4 in Step 3, the title Compound 1-120 sodium salt was obtained as a white solid. LC-MS: m/z 490 (M+H$^+$).

Example 13: Synthesis of 3-(1-(1-(2-(carbamoyloxy)ethyl)-1H-pyrazol-4-yl)-6-chloro-2-cycyclopropyl-7-fluoro-1H-indol-3-yl)thio)-2-fluorobenzoic acid sodium salt (Compound 1-121)

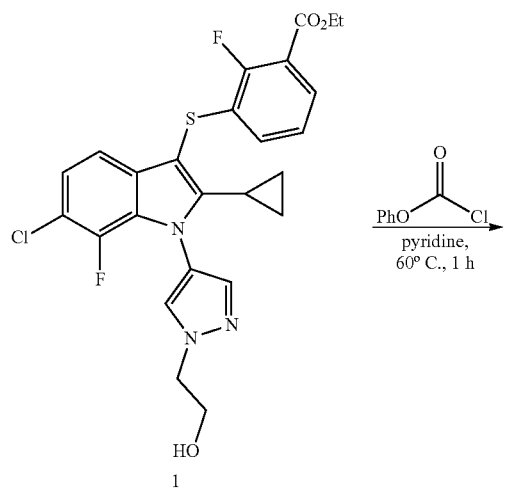

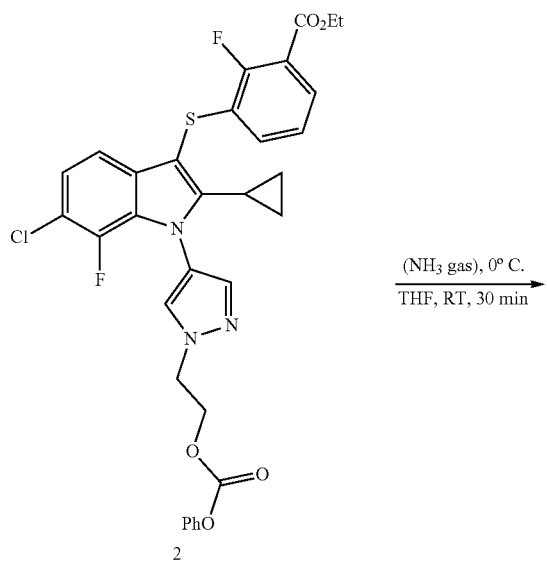

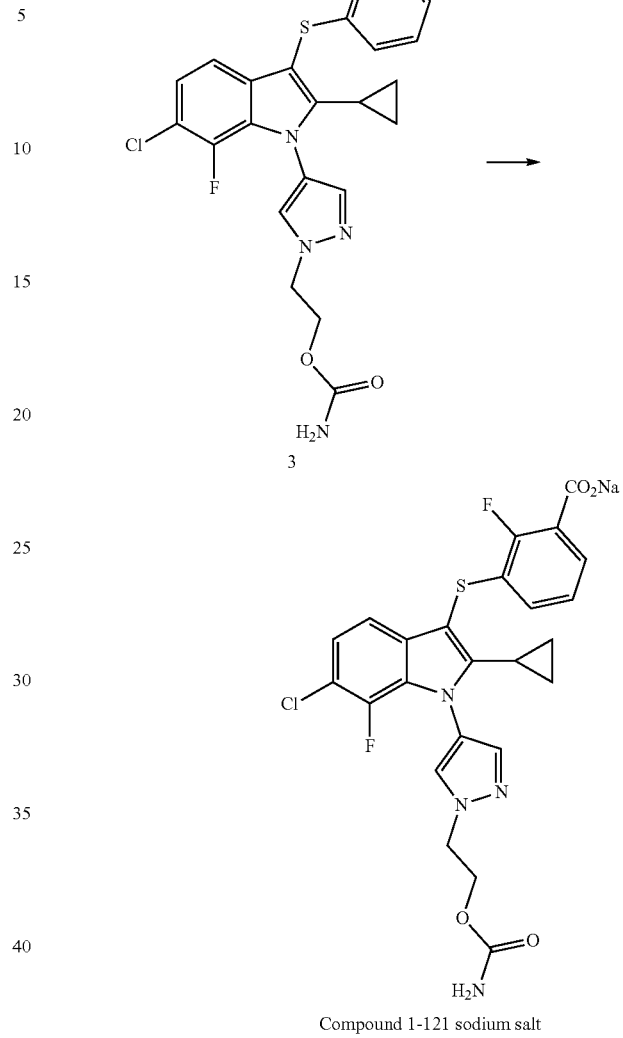

Step 1: Synthesis of ethyl 3-(6-chloro-2-cyclopropyl-7-fluoro-1-(1-(2-phenoxycarbonyl) oxy)ethyl)-1H-pyrazol-4-yl)-1H-indol-3-yl)thio)-2-fluorobenzoate (2)

To a stirred solution of indole 1 (Example 12, Step 1; 50 mg, 0.096 mmol) in pyridine (2 mL) under inert atmosphere was added phenyl chloroformate (18 mg, 0.11 mmol) at 0° C.; heated to 60° C. and stirred for 1 hr. The mixture was diluted with water (20 mL), acidified with 1 N aq. HCl (5 mL) and extracted with EtOAc (2×10 nm). The combined organic extracts were washed with brine (10 ML), dried (Na$_2$SO$_4$) filtered and concentrated under reduced pressure to obtain the crude. This was purified (silica gel; 30% EtOAc/hexanes) to afford compound 2 (20 mg, 32%) as a yellow oil. LC-MS (ESI): m/z 638.5 (M+H$^+$).

Step 2: Synthesis of ethyl 3-((1-(1-(2-(carbamoyloxy)ethyl)-1-pyrazol-4-yl)-6-chloro-2-cyclopropyl-7-fluoro-1H-indol-3-yl)thio)-2-fluorobenzoate (3)

To a stirred solution of compound 2 (20 mg, 0.031 mmol) in THF (3 mL) under inert atmosphere was passed ammonia gas at 0° C. for 15 min; warmed to RT and stirred for 30 min. The volatiles were removed under reduced pressure and the crude was purified by triturating with n-pentane (2×5 mL) and dried under reduced pressure to afford 3 (6 mg, 35%) as a pale brown oil. $^1$H NMR (500 MHz, CDCl$_3$): δ 7.73 (s, 1H), 7.70 (s, 1H), 7.64 (t, J=8.0 Hz, 1H), 7.20 (d, J=8.5 Hz, 1H), 7.11-7.08 (m, 1H), 6.95 (t, J=8.0 Hz, 1H), 6.79 (t, J=8.0 Hz, 1H), 4.65 (br s, 2H), 4.54-4.47 (m, 4H), 4.42 (q, 2H), 1.74-1.70 (m, 1H), 1.43 (t, J=7.5 Hz, 3H), 1.07-1.05 (m, 2H), 0.91-0.88 (m, 2H); LC-MS: m/z 561.7 (M+H$^+$).

Step 3: Synthesis of 3-((1-(1-(2-(carbamoyloxy)ethyl)-1H-pyrazol-4-yl)-6-chloro-2-cyclopropyl-7-fluoro-1H-indol-3-yl)thio)-2-fluorobenzoic acid sodium salt (Compound 1-121)

To a solution of compound 3 (5 mg, 0.009 mmol) in THF:water (3:1) (4 mL) was added 1M aq. NaOH solution (0.009 mL, 0.009 mmol) at RT overnight. After the completion of the reaction, solvent was removed to afford Compound 1-121 sodium salt (5 mg, 100%) as an off-white solid, LC-MS: m/z 533 (M+1).

Example 14: Synthesis of 3-((1-(1-(2-aminoethyl)-1H-pyrazol-4-yl)-6-chloro-2-cyclopropyl-7-fluoro-1H-indol-3-yl)thio)-2-fluorobenzoic acid sodium salt (Compound 1-122)

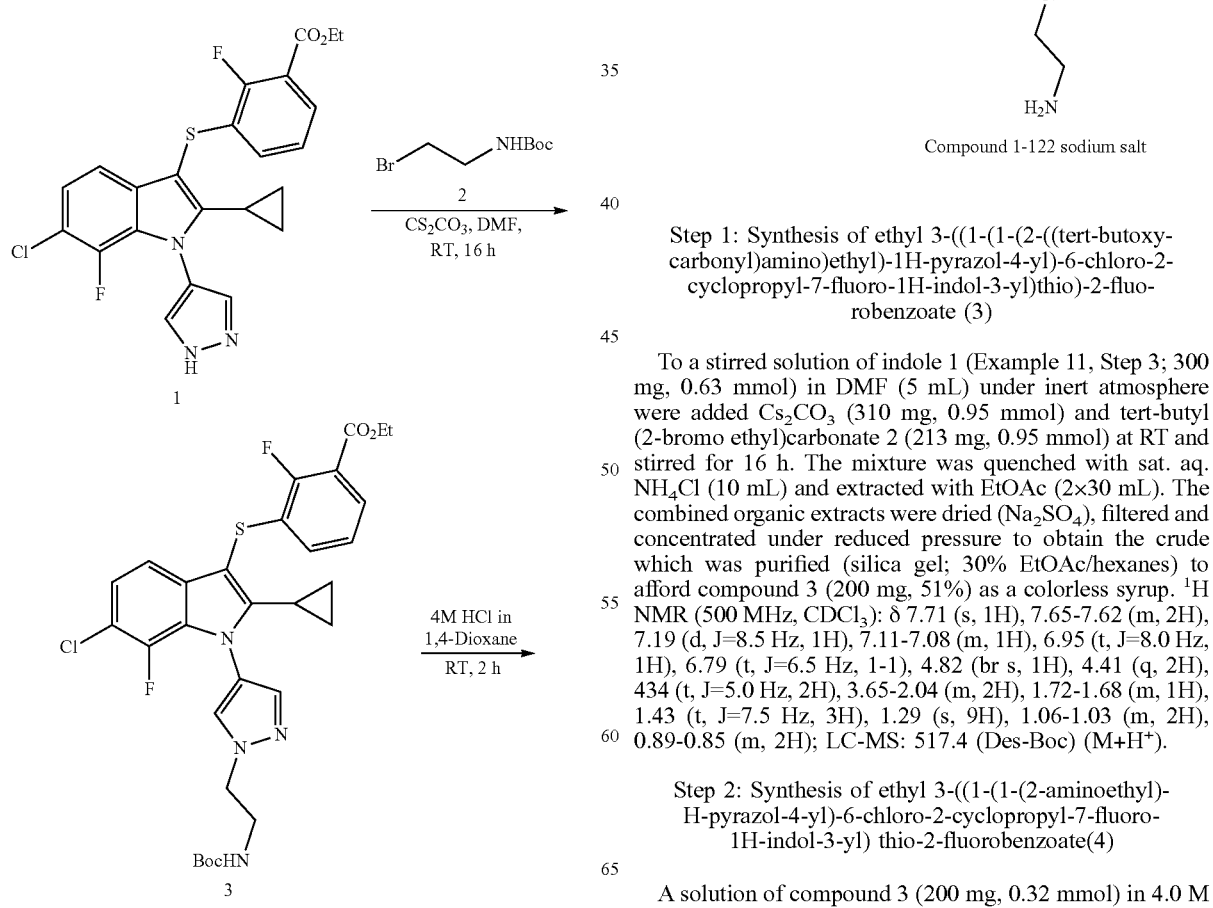

Compound 1-122 sodium salt

Step 1: Synthesis of ethyl 3-((1-(1-(2-((tert-butoxycarbonyl)amino)ethyl)-1H-pyrazol-4-yl)-6-chloro-2-cyclopropyl-7-fluoro-1H-indol-3-yl)thio)-2-fluorobenzoate (3)

To a stirred solution of indole 1 (Example 11, Step 3; 300 mg, 0.63 mmol) in DMF (5 mL) under inert atmosphere were added Cs$_2$CO$_3$ (310 mg, 0.95 mmol) and tert-butyl (2-bromo ethyl)carbonate 2 (213 mg, 0.95 mmol) at RT and stirred for 16 h. The mixture was quenched with sat. aq. NH$_4$Cl (10 mL) and extracted with EtOAc (2×30 mL). The combined organic extracts were dried (Na$_2$SO$_4$), filtered and concentrated under reduced pressure to obtain the crude which was purified (silica gel; 30% EtOAc/hexanes) to afford compound 3 (200 mg, 51%) as a colorless syrup. $^1$H NMR (500 MHz, CDCl$_3$): δ 7.71 (s, 1H), 7.65-7.62 (m, 2H), 7.19 (d, J=8.5 Hz, 1H), 7.11-7.08 (m, 1H), 6.95 (t, J=8.0 Hz, 1H), 6.79 (t, J=6.5 Hz, 1-1), 4.82 (br s, 1H), 4.41 (q, 2H), 434 (t, J=5.0 Hz, 2H), 3.65-2.04 (m, 2H), 1.72-1.68 (m, 1H), 1.43 (t, J=7.5 Hz, 3H), 1.29 (s, 9H), 1.06-1.03 (m, 2H), 0.89-0.85 (m, 2H); LC-MS: 517.4 (Des-Boc) (M+H$^+$).

Step 2: Synthesis of ethyl 3-((1-(1-(2-aminoethyl)-H-pyrazol-4-yl)-6-chloro-2-cyclopropyl-7-fluoro-1H-indol-3-yl) thio-2-fluorobenzoate(4)

A solution of compound 3 (200 mg, 0.32 mmol) in 4.0 M HCl in 1,4-dioxane (5 mL) under inert atmosphere was stirred at 0° C.-RT for 2 h. The volatiles were removed under reduced pressure. The residue was diluted with water (5 mL), basified with aq. NaHCO₃ (5 mL) and extracted with EtOAc (2×20 mL). The combined organic extracts were dried (Na₂SO₄), filtered and concentrated under reduced pressure to afford 4 (130 mg, 81%) as an off-white solid. $^1$H NMR (400 MHz, DMSO-d₆): δ 8.24 (s, 1H), 7.82 (s, 1H), 7.60 (t, J=6.8 Hz, 1H), 7.22-7.11 (m, 3H), 6.84 (t, J=6.8 Hz, 1H), 4.33 (q, 2H), 4.17 (t, J=6.0 Hz, 2H), 2.98 (t, J=6.0 Hz, 2H), 1.84-1.80 (m, 3H), 1.32 (t, J=7.2 Hz, 3H), 0.92-0.91 (m, 2H), 0.84-0.82 (m, 2H); MS: m/z 517.6 (M+H⁺).

Step 3: Synthesis of 3-((1-(1 (2-aminoethyl)-1H-pyrazol-4-yl)-6-chloro-2-cyclopropyl-7-fluoro-1H-indol-3-yl)thio)-2-fluorobenzoic acid sodium salt (Compound 1-122)

Following the procedure of Example 11, Step 3 but using Intermediate 4 in place of Intermediate 4 in Step 3, the title Compound 1-122 sodium salt was obtained as an off-white solid. LC-MS: m/z 489 (M-1).

Example 15: Synthesis of 3-((6-chloro-2-cyclopropyl-7-fluoro-1-(1-(2-ureidoethyl)-1H-pyrazol-4-yl)-1H-indol-3-yl)thio)-2-fluorobenzoic acid sodium salt (Compound 1-123)

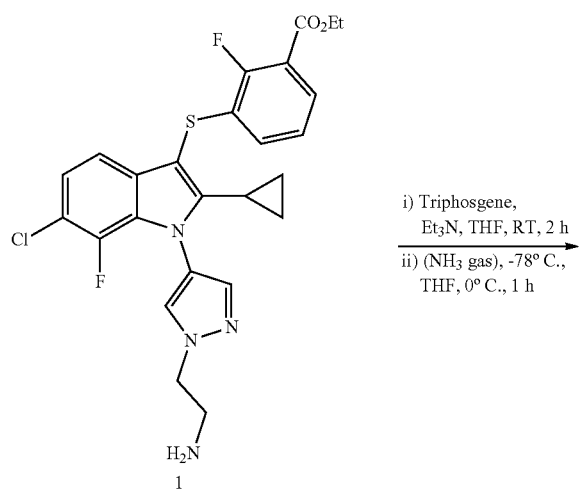

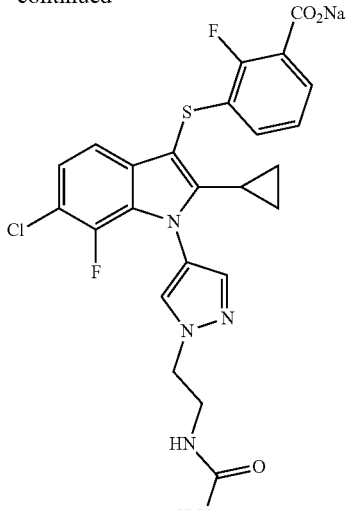

Compound 1-123 sodium salt

Step 1: Synthesis of ethyl 3-((6-chloro-2-cyclopropyl-7-fluoro-1-(1-(2-ureidoethyl)-1H-pyrazol-4-yl)-1H-indol-3-yl)thio)-2-fluorobenzoate (2)

To a stirred solution of indole 1 (Example 14, Step 2; 80 mg, 0.15 mmol) in THF (5 mL) under inert atmosphere were added Et₃N (0.04 mL, 0.31 mmol) and triphosgene (18.3 mg, 0.06 mmol) at 0° C., stirred for 1 h, warmed to RT and stirred for 2 h. To this solution of crude isocyanate was passed ammonia gas at −78° C. for 10 min; warmed to 0° C. and stirred for 1 hr. The mixture was diluted with water and extracted with EtOAc (2×20 mL). The combined organic extracts were dried (Na₂SO₄), filtered and concentrated under reduced pressure to obtain the crude. This was purified by triturating with Et₂O (2×5 mL) and dried under reduced pressure to afford 2 (30 mg, 34%) as an off-white solid. $^1$H NMR (400 MHz, DMSO-d₆): δ 8.19 (s, 1H), 7.82 (s, 1H). 7.60 (t, J=7.2 Hz, 1H), 7.22-7.11 (M, 3H), 6.84 (t, J=7.2 Hz, 1H), 6.04-6.03 (m, 1H), 5.53 (br s, 2H), 4.33 (q, 2H), 4.21 (t, J=6.0 Hz, 2H), 3.43 (t, J=6.0 Hz, 2H), 1.84-1.78 (m, 1H), 1.32 (t, J=7.2 Hz, 3H), 0.92-0.91 (m, 2H), 0.87-0.85 (m, 2H); MS: m/z 560.6 (M−H⁺).

Step 2: Synthesis of 3-(6-chloro-2-cycyclopropyl-7-fluoro-1-(1-(2-ureidoethyl-1H-pyrazol-4-yl)-1H-indol-3-yl)thio)-2-fluorobenzoic acid sodium salt (Compound 1-123)

Following the procedure of Example 13, Step 3 but using Intermediate 2 in place of Intermediate 3 in Step 3, the title Compound 1-123 sodium salt was obtained as an off-white solid. LC-MS: m/z 532 (M+H⁺).

Example 16: Synthesis of 3-(1-(1-(3-carboxypropyl)-1H-pyrazol-4-yl)-6-chloro-2-cyclopropyl-7-fluoro-1H-indol-3-yl)thio)-2-fluorobenzoic acid sodium salt (Compound 1-124)

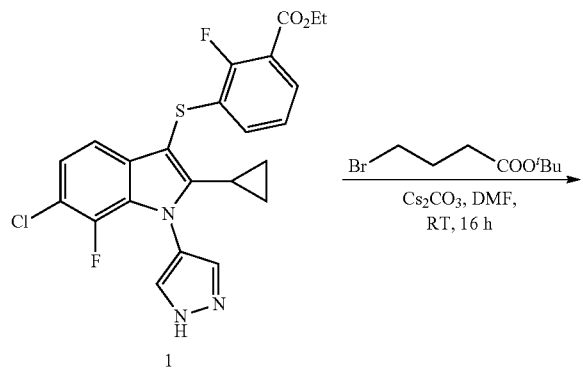

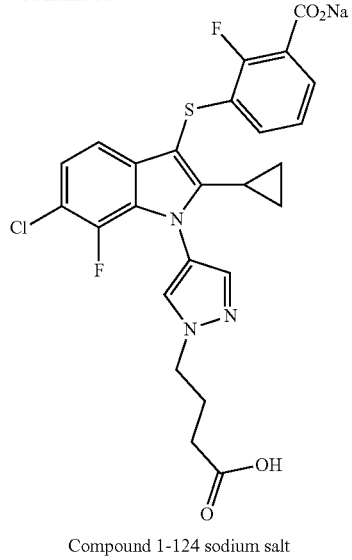

Compound 1-124 sodium salt

Step 1: Synthesis of ethyl 3-((1-(1-(4-(tert-butoxy)-4-oxobutyl)-1H-pyrazol-4-yl)-6-chloro-2-cyclopropyl-7-fluoro-1H-indol-3-yl)thio)-2-fluorobenzoate (2)

To a stirred solution of indole 1 (Example 11, Step 3; 200 mg, 0.42 mmol) in DMF (5 n L) under inert atmosphere were added $Cs_2CO_3$ (206 mg, 0.63 mmol) and tert-butyl 4-bromobutanoate (141 mg, 0.63 mmol) at RT and stirred for 16 h. The mixture was diluted with ice cold water (20 mL) and extracted with EtOAc (3×30 mL). The combined organic extracts were dried ($Na_2SO_4$), filtered and concentrated under reduced pressure to obtain the crude. This was purified (silica gel chromatography; 20% EtOAc/hexanes) to afford compound 2 (180 mg, 70%) as a pale brown oil. $^1$H NMR (400 MHz, $CDCl_3$): δ 7.67 (s, 1H), 7.64 (s, 1H), 7.63-7.60 (m, 1H), 7.18 (d, J=8.4 Hz, 1H), 7.10-7.06 (m, 1H), 6.93 (t, J=8.0 Hz, 1H), 6.77 (t, J=7.6 Hz, 1H), 4.41 (q, 2H), 4.28 (t, J=6.8 Hz, 2H), 2.28-2.19 (m, 4H), 1.74-1.66 (m, 1H), 1.46 (s, 9H), 1.41 (t, J=7.2 Hz, 3H), 1.06-1.02 (m, 2H), 0.89-0.84 (m, 2H); LC-MS (ESI): m/z 618.6 (M+H$^+$).

Step 2: Synthesis of 4-(4-(6-chloro-2-cyclopropyl-3-((3-(ethoxycarbonyl)-2-fluorophenyl)thio)-7-fluoro-1H-indol-yl)-1H-pyrazol-1-1 butanoic acid 3

A solution of compound 2 (100 rug, 0.29 mmol) in 4.0 M HC in 1,4-dioxane (2 mL) under inert atmosphere was stirred at 0° C.-RT for 16 h. The volatiles were removed in vacuo and the residue was diluted with water (5 mL), basified with aq. $NaHCO_3$ (5 mL) and extracted with EtOAc (2×20 mL). The combined organic extracts were dried ($Na_2SO_4$), filtered and concentrated under reduced pressure to obtain the crude. This was purified by acid-base treatment to afford 3 (50 mg, 56%) as a white solid. $^1$H NMR (500 MHz, DMSO-$d_6$): δ 12.75 (br s, 1H), 8.24 (s, 1H), 7.82 (s, 1H), 7.59 (t, J=7.0 Hz, 1H), 7.22-7.10 (m, 3H), 6.84 (t, J=7.5 Hz, 1H), 4.33 (q, 2H), 4.22 (t, J=7.0 Hz, 2H), 2.21 (t, J=7.5 Hz, 2H), 2.06-2.03 (m, 2H), 1.81-1.78 (m, 1H), 1.32 (t, J=7.0 Hz, 3H), 0.89-0.88 (m, 2H), 0.82-0.81 (m, 2H); MS: m/z 560.7 (M+H$^+$).

Step 3: Synthesis of 3-((1-(1-(3-carboxypropyl)-1H-pyrazol-4-yl)-6-chloro-2-cyclopropyl-7-fluoro-1H-indol-3-yl)thio)-2-fluorobenzoic acid sodium salt (Compound 1-124)

To a solution of compound 3 (10 mg, 0.018 mmol) in THF:water (3:1) (4 mL) was added 1M aq. NaOH solution (0.036 ml, 0.036 mmol) at RT and then heated at 60° C. overnight. After the completion of the reaction, solvent was removed to afford Compound 1-124 sodium salt (10 mg, 100%) as a white solid. LC-MS: m/z 532 (M+H$^+$).

Example 17: Synthesis of 3-((1-(1-(4-amino-4-oxobutyl)-1H-pyrazol-4-yl)-6-chloro-2-cycyclopropyl-7-fluoro-1H-indol-3-yl)thio)-2-fluorobenzoic acid sodium salt (Compound 1-125)

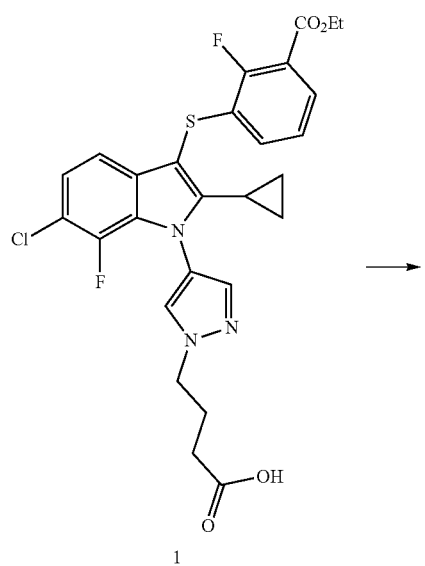

1

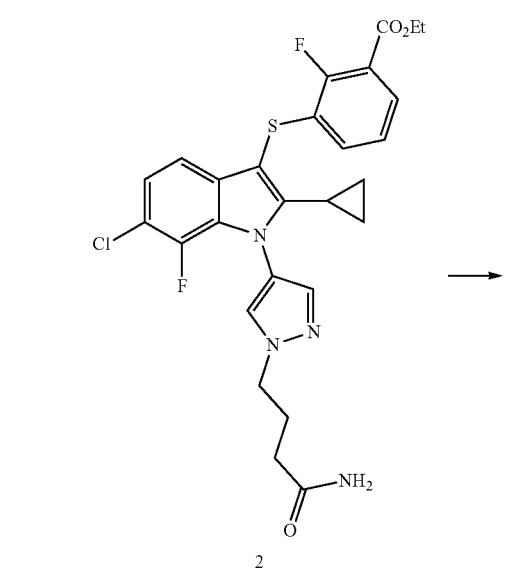

2

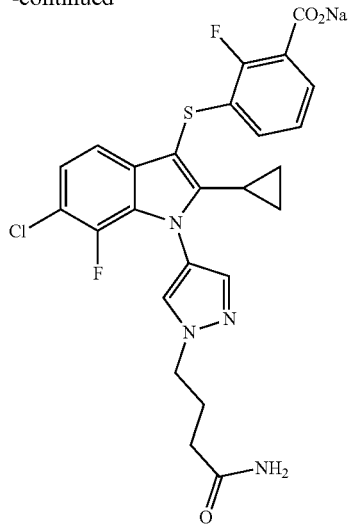

Compound 1-125 sodium salt

Step 1: Synthesis of ethyl 3-((1-(1-(4-amino-4-oxobutyl)-1H-pyrazol-4-yl-6-chloro-2-cycloprope-nyl-7-fluoro-1H-indol-3-yl)thio)-2-fluorobenzoate (2)

To a stirred solution of indole 1 (Example 16, Step 2; 150 mg, 0.26 mmol) in DMF (3 mL) under inert atmosphere were added EDCI·HCl (36 mg, 0.40 mmol), HOBt (61.5 mg, 0.40 mmol), NMM (0.07 mL, 0.67 μmmol) at RT and stirred for 10 min. To this, NH$_4$Cl (17.1 mg, 0.32 mmol) was added at RT and stirred for 16 h. The mixture was diluted with water (30 mL) and extracted with EtOAc (2×30 mL). The combined organic extracts were washed with brine (20 mL), dried (Na$_2$SO$_4$), filtered and dried under reduced pressure to obtain the crude. This was purified (silica gel; 2% MeOH/CH$_2$Cl$_2$ to afford compound 2 (15 mg, 10%) as an off-white solid. $^1$H NMR (400 MHz, DMSO-d$_6$): δ 8.23 (s, 1H), 7.81 (s, 1H), 7.60 (dt, J=8.0, 1.6 Hz, 1H), 7.29 (br s, 1H), 7.22-7.11 (m, 3H), 6.84 (dt, J=8.0, 1.6 Hz, 1H), 6.78 (br s, 1H), 4.33 (q, 2H), 4.20 (t, J=6.4 Hz, 2H), 2.08-2.02 (m, 4H), 1.82-1.77 (m, 1H), 1.32 (t, J=7.2 Hz, 3H), 0.92-0.88 (m, 2H), 0.86-0.80 (m, 2H); MS: m/z 559.6 (M+H$^+$).

Step 2: Synthesis of 3-((1-(1-(4-amino-4-oxobutyl)-1H-pyrazol-4-1H-6-chloro-2-cyclopropyl-7-fluoro-1H-indol-3-yl)thio)-2-fluorobenzoic acid sodium salt (Compound 1-125)

Following the procedure of Example 11, Step 3 but using Intermediate 2 in place of Intermediate 4 in Step 3, the title Compound 1-125 sodium salt was obtained as a white solid. LC-MS: m/z 531 (M+1).

Example 18: Synthesis of 3-((2,6-dichloro-7-fluoro-1-(1-methyl-1H-pyrazol-4-yl)-1H-indol-3-yl)thio)-2-fluorobenzoic acid sodium salt (Compound 1-49)

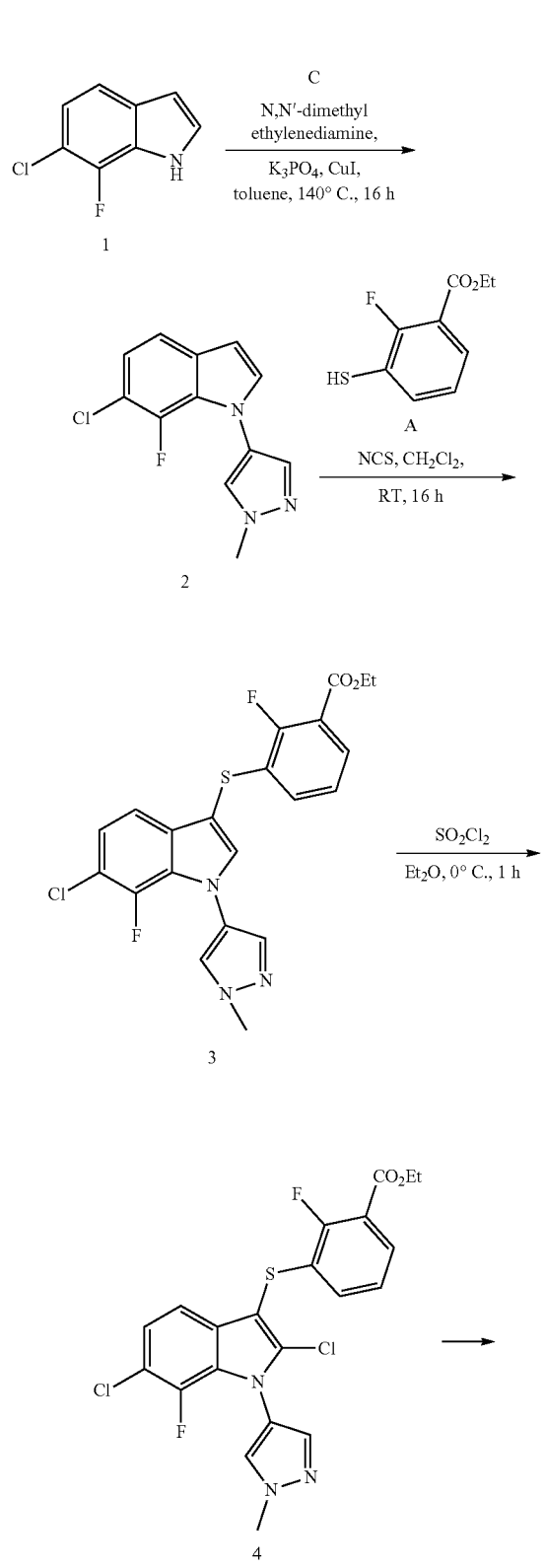

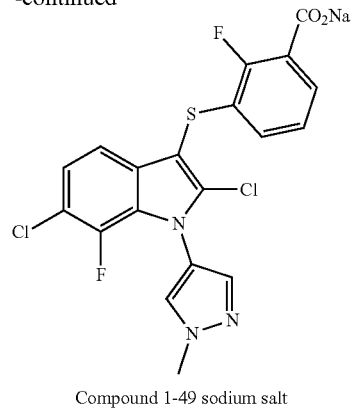

Compound 1-49 sodium salt

Step 1: Synthesis of ethyl 3-(6-chloro-7-fluoro-1-(1-methyl-1H-pyrazol-4-yl)-1H-indol-3-yl)thio)-2-fluorobenzoate (3)

Following the procedure of Example 9, Steps 3 and 4 but using Intermediate A in place of Intermediate B in Step 3, the title compound 3 was obtained as a light brown solid. $^1$H NMR (400 MHz, CDCl$_3$): δ 7.68 (s, 1H), 7.67-7.64 (m, 2H), 7.43 (s, 1H), 7.28 (d, J=18.4 Hz, 1H), 7.16 (dd, J=8.4, 6.0 Hz, 1H), 7.00-6.93 (m, 2H), 4.40 (q, J=6.8 Hz, 2H), 3.99 (s, 3H), 1.40 (t, J=6.8 Hz, 3H); LC-MS (ESI): m/z 448.4 (M+H$^+$).

Step 2: Synthesis of ethyl 3-((2,6-dichloro-7-fluoro-1-(1-methyl-1H-pyrazol-4-yl)-1H-indol-3-yl)thio)-2-fluorobenzoate (4)

To a stirred solution of compound 3 (150 mg 0.33 mmol) in Et$_2$O (10 mL) under inert atmosphere was added SO$_2$Cl$_2$ (87 mg, 0.65 mmol) at 0° C. and stirred for 1 h. The reaction mixture was quenched with water (10 mL) and extracted with EtOAc (2×20 mL). The combined organic extracts were dried over Na$_2$SO$_4$ and concentrated under reduced pressure to obtain the crude. The crude was purified (silica gel; 15% EtOAc/n-Hexane) to afford 4 (35 mg, 22%) as an off-white solid. $^1$H NMR (500 MHz, CDCl$_3$): δ 3.7.72-7.68 (m, 1H), 7.62 (s, 1H), 7.58 (s, 1H), 7.36 (d, J=8.5 Hz, 1H), 7.24-7.19 (m, 1H), 7.08-6.79 (m, 2H), 1.42 (q, J=7.0 Hz, 2H), 4.08 (s, 3H), 1.42 (t, J=7.0 Hz, 3H) LC-M S: m/z 482.4 (M$^+$).

Step 3: Synthesis of 3-((2,6-dichloro-7-fluoro-1-(1-methyl-1H pyrazol-4-yl)-1H-indol-3-yl)thio)-2-fluorobenzoic acid sodium salt (Compound 1-49)

Following the procedure of Example 11, Step 3 but using Intermediate 4 in place of Intermediate 4 in Step 3, the title Compound 1-49 sodium salt was obtained as a tan solid. LC-MS: m/z 454 (M+1).

Example 1_9: Synthesis of 3-((6-chloro-2-cyclopropyl-7-fluoro-1-(1-(2,2,2-trifluoroethyl)-1l-pyrazol-4-yl)-1H-indol-3-yl)thio)-2-fluorobenzoic acid sodium salt (Compound 1-126)

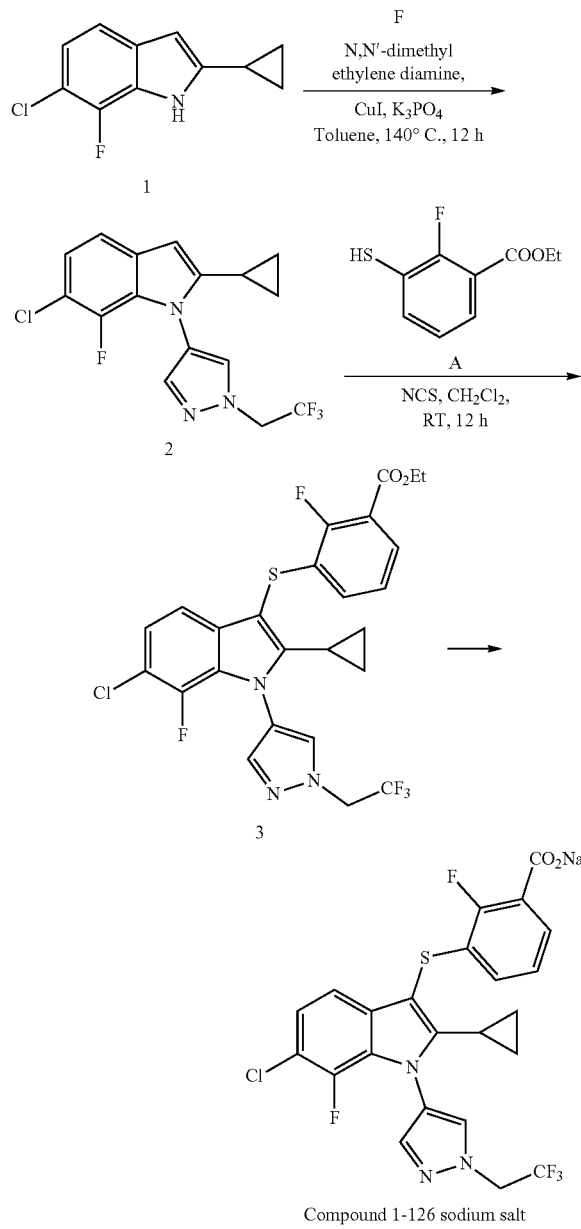

Step 1: Synthesis of ethyl 3-((6-chloro-2-cyclopropyl-7-fluoro-1-(1-((2,2,2-trifluoroethyl)-1H-pyrazol-4-yl)-1H-indol-3-yl)thio)-2-fluorobenzoate (3)

Following the procedure of Example 9, Steps 3 and 4 but using Intermediate F in place of Intermediate B in Step 3, the title compound 3 was obtained as an off-white solid. $^1$H NMR (400 MHz, CD$_3$OD): δ 8.23 (s, 1H), 7.88 (s, 1H), 7.61 (dt, J=8.0, 1.6 Hz, 1H), 7.20 (d, J=8.4 Hz, 1H), 7.15-7.11 (m, 1H), 7.02 (t, J=8.0 Hz, 1H), 6.84 (dt, J=8.4, 1.6 Hz, 1H), 5.04 (q, 2H), 4.39 (q, 2) 1.81-1.73 (m, 1H), 1.41-1.38 (m, 3H), 0.98-0.90 (m, 2H), 0.88-0.84 (m, 2H); MS: m/z 556.5 (M+H$^+$).

Step 2: Synthesis of 3-((6-chloro-2-cyclopropyl-7-fluoro-1-(1-(2,2,2-trifluoroethyl)-1H-pyrazol-4-yl)-1H-indol-3-ylthio)-2-fluorobenzoic acid sodium salt (Compound 1-126)

Following the procedure of Example 11, Step 3 but using Intermediate 3 in place of Intermediate 4 in Step 3, the title Compound 1-126 sodium salt was obtained as an off-white solid, LC-MS: m/z 528 (M+H$^+$).

Example 20: Synthesis of 3-((6-chloro-2-cyclopropyl-1-(1-ethyl-d$_5$)-1H-pyrazol-4-yl)-7-fluoro-1H-indol-3-yl)thio)-2-fluorobenzoic acid (Compound 1-127)

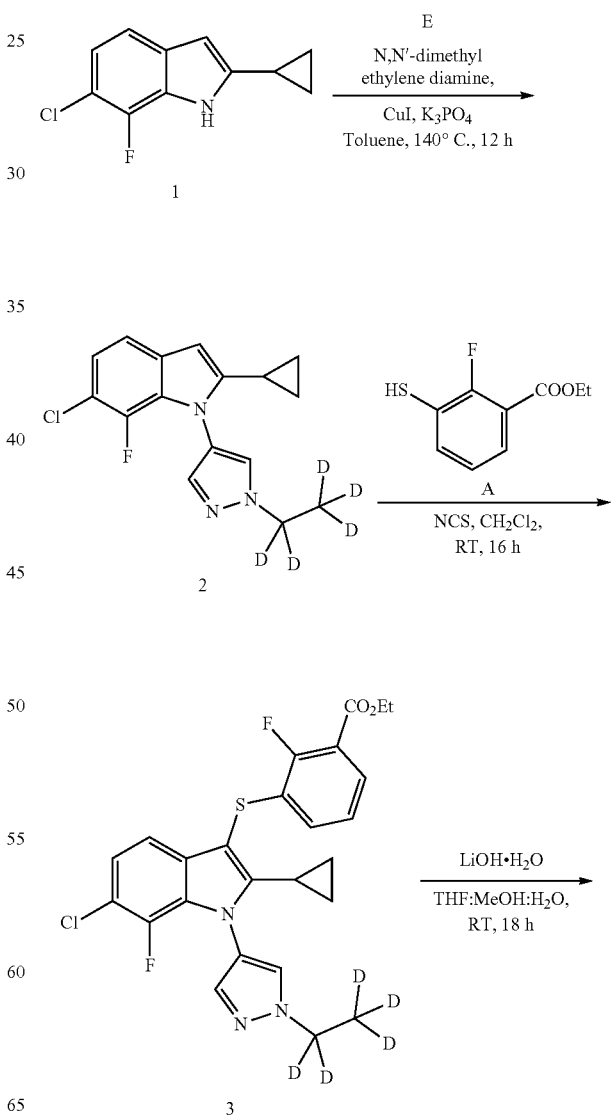

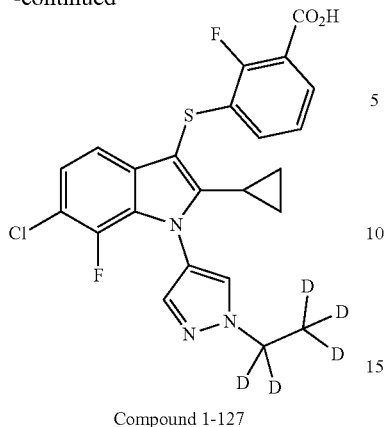

Compound 1-127

Step 1: Synthesis of ethyl 3-((6-chloro-2-cyclopropyl-1-(1-ethyl-d₅)-1H-pyrazol-4-7)-7-fluoro-1H-indol-3-yl)thio)-2-fluorobenzoate 3)

Following the procedure of Example 9, Steps 3 and 4 but using Intermediate E in place of Intermediate B in Step 3, the title compound 3 was obtained as a red solid. $^1$H NMR (500 MHz CDCl$_6$): δ 7.67-7.61 (m, 3H) 7.18 (d, J=8.0 Hz, 1H), 7.09-7.07 (m, 1H), 6.94 (t, J=8.0 Hz, 1H), 6.92-6.75 (m, 1H), 4.41 (q, 2H), 1.72-1.68 (m, 1H), 1.41 (t, J=7.5 Hz, 3H), 1.08-1.05 (m, 2H), 0.89-0.85 (m, 2H); LC-MS (ESI): 509.5 (M+H$^+$).

Step 2: Synthesis of 3-((6-chloro-2-cyclopropyl-1-((ethyl-d₅)-1H-pyrazol-4-yl)-7-fluoro-1H-indol-3-yl)thio-)-2-fluorobenzoic acid (Compound 1-127

To a stirred solution of indole 3 (200 mg, 0.39 mmol) in THF:MeO:H$_2$O (2:2:1, 5 mL) was added LiO·H$_2$O (66 mg 1.57 mmol) at RT and stirred for 8 h. The volatiles were removed in vacuo. The residue was diluted with water (5 mL), acidified with 2 M aq. HCl (5 mL); the obtained solid was filtered, washed with water (25 ml), triturated with n-pentane (2×5 mL) and dried under reduced pressure to afford the title Compound 1-127 (110 mg, 59%) as an off-white solid. $^1$H NMR (400 MHz, DMSO-d$_6$): δ 13.49 (br s, 1H), 8.22 (s, 1H), 7.73 (s, 1H), 7.51 (t, J=6.8 Hz, 1H), 7.19-7.13 (m, 2H), 7.04 (t, J=8.0 Hz, 1H), 6.74 (t, J=7.2 Hz, 1H), 1.80-1.73 (m, 1H), 0.91-0.90 (m, 2H), 0.82-0.80 (m, 2H); MS (ESI): m/z 480.8 (M+H$^+$).

Example 21: Synthesis of 3-((2,6-dichloro-1-(1-ethyl-1H-pyrazol-4-yl)-7-fluoro-1H-indol-3-yl)thio)-2-fluorobenzoic acid sodium salt (Compound 1-31)

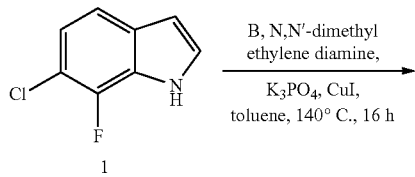

B, N,N'-dimethyl ethylene diamine, K$_3$PO$_4$, CuI, toluene, 140° C., 16 h

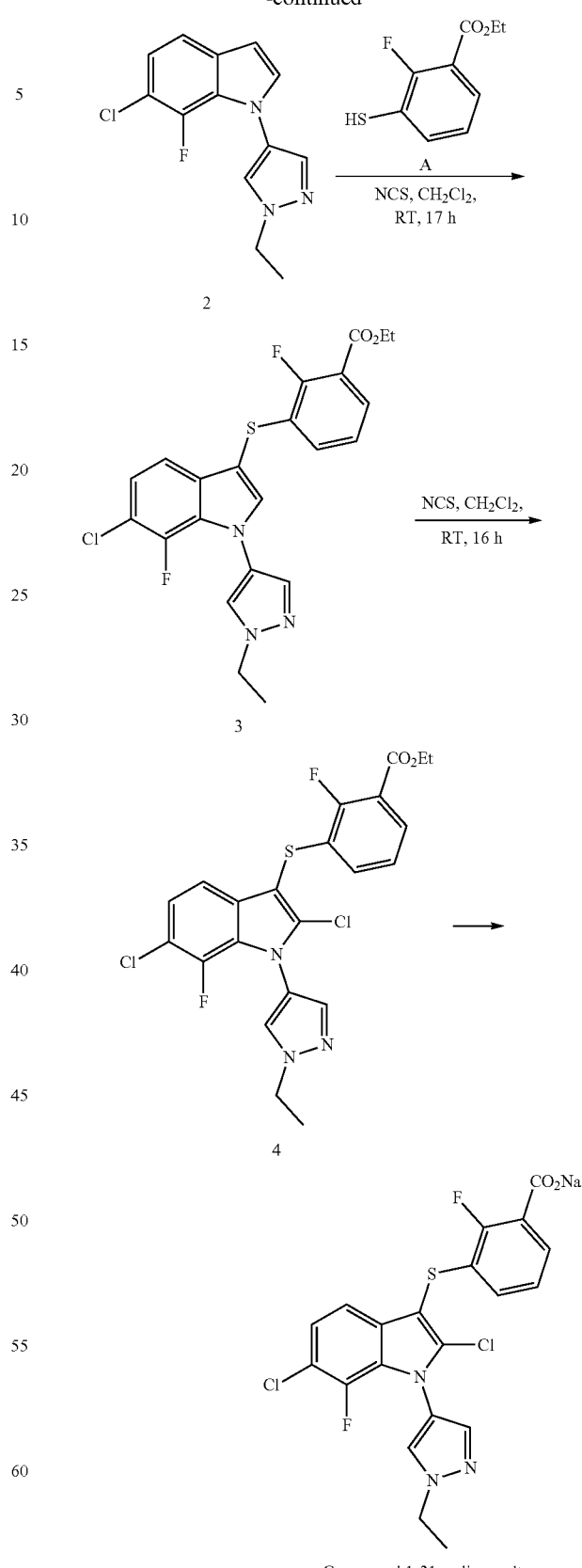

Compound 1-31 sodium salt

Step 1: Synthesis of ethyl-3-((6-chloro-1-(1-ethyl)-1H-pyrazol-4-yl)-7-fluoro-1H-indol-3-yl)thio-2-fluorobenzoate (3)

Following the procedure of Example 9, Steps 3 and 4 but using indole 1 (Example 4, Step 1) in place of indole 3 in Step 3, the title compound 3 was obtained as a light brown solid, $^1$H NMR (500 MHz, CDCl$_3$): δ 7.69-7.64 (m, 3H), 7.44 (s, 1H), 7.27 (t, J=8.0 Hz, 1H), 7.16 (dd, J=8.5, 6.0 Hz, 1H), 7.01-6.94 (m, 2H), 4.40 (q, J=7.5 Hz, 2H), 4.26 (q, 1=8.0 Hz, 2H), 1.57 (t, J=8.0 Hz, 3H), 1.57 (t, J=7.5 Hz, 3H); LC-MS (ESI): m/z 462.5 (M+H$^+$).

Step 2: Synthesis of ethyl 3-((2,6-dichloro-1-(1-ethyl)-1H-pyrazol-4-yl)-7-fluoro-1H-indol-3-yl)thio)-2-fluorobenzoate (4)

To a solution of compound 3 (100 mg, 0.21 mmol) in CH$_2$Cl$_2$ (3 mL) under inert atmosphere was added NCS (58 mg, 0.43 mmol) at RT and stirred for 16 b. The reaction mixture was diluted with water (10 mL) and extracted with CH$_2$Cl$_2$ (2×15 mL). The combined organic extracts were dried over Na$_2$SO$_4$ and concentrated under reduced pressure to obtain the crude. The crude was purified (silica gel; 14-17% EtOAc/Hexanes) to afford 5 (35 mg, 33%) as an off-white solid. $^1$H NMR (400 MHz, CDCl$_3$): δ 7.71-7.66 (m, 3H), 7.30 (d, J=7.6 Hz, 1H), 7.19 (dd, J=8.8, 6.4 Hz, 1H), 7.04-6.97 (m, 2H), 4.40 (q, J=7.2 Hz, 2H), 4.27 (q, J=7.6 Hz, 2H), 1.58 (t, J=7.6 Hz, 3H), 1.49 (t, J=7.2 Hz, 3H); LC-MS (ESI): m/z 496.7 (M+H$^+$).

Step 3: Synthesis of 3-((2,6-dichloro-1-(1-ethyl-1H-pyrazol-4-yl)-7-fluoro-1H-indol-3-yl)thio)-2-fluorobenzoic acid (Compound 1-31)

Following the procedure of Example 11, Step 3 but using Intermediate 4 in place of Intermediate 4 in Step 3, the title Compound 1-31 sodium salt was obtained as an off-white solid. LC-MS: m/z 468 (M+1).

Example 22: Synthesis of 3-((2,6-dichloro-7-fluoro-1-(pyridin-3-yl)-1H-indol-3-yl)thio)-2-fluorobenzoic acid sodium salt (Compound 2-1)

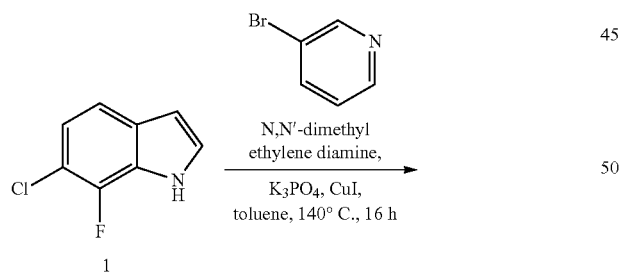

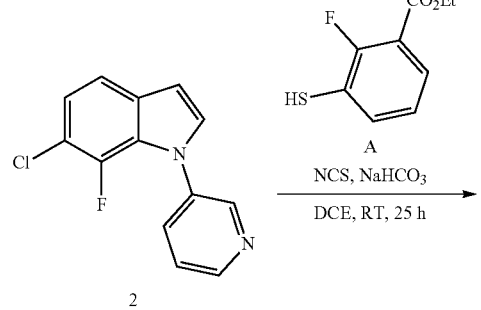

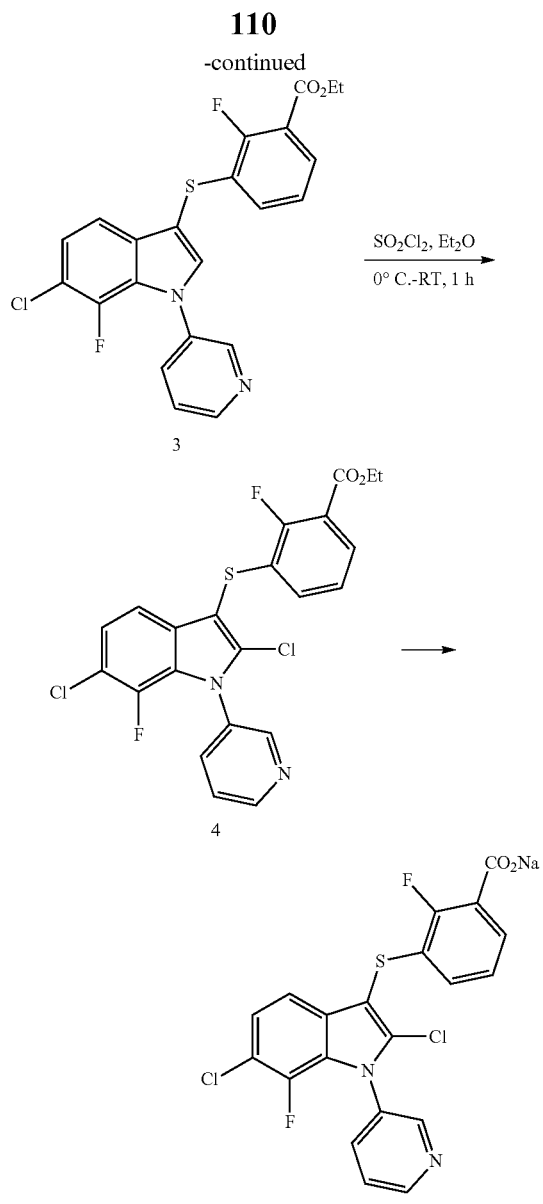

Compound 2-1 sodium salt

Step 1: Synthesis of 6-chloro-7-fluoro-1-(pyridin-3-yl)-1H-indole (2)

To a stirred solution of indole 1 (Example 4, Step 1; 2.0 g, 11.8 mmol) in toluene (50 mL) were added 3-bromopyridine (2.9 g, 17.7 mmol), N,N'-dimethylethylenediamine (418 mg, 4.73 mmol), K$_3$PO$_4$ (6.3 g, 29.5 mmol), CuI (225 mg, 1.18 mmol) at RT under inert atmosphere. The mixture was purged with argon for 15 min and heated to 140° C. in a sealed tube for 16 h. The reaction mixture was cooled to RT, added n-hexane (20 mL), stirred for 5 minutes and then filtered. The filtrate was diluted with water (20 nil) and extracted with EtOAc (2×50 mL). The combined organic extracts were washed with water and brine solution, dried over Na$_2$SO$_4$, filtered and concentrated under reduced pressure to obtain the crude. The crude was purified (silica gel; 10% EtOAc/Hexanes) to afford compound 2 (2.0 g, 69%) as light brown solid, $^1$H NMR (500 MHz, DMSO-d$_6$): δ 8.84

(s, 1H), 8.66 (d, J=5.0 Hz, 1H), 8.06-8.02 (m, 1H), 7.74-7.72 (m, 1H), 7.64-7.58 (m, 1H), 7.52 (d, J=8.0 Hz, 1H), 7.28-7.24 (m, 1H), 6.82 (m, 1H).

Step 2: Synthesis of ethyl 3-(6-chloro-7-fluoro-1-(pyridin-3-yl)-1H-indol-3-yl)thio)-2-fluorobenzoate (3)

To a stirred solution of Intermediate A (243 mg, 1.21 mmol) in 1,2-dichloroethane (8 mL) under inert atmosphere was added NCS (163 mg, 1.21 mmol) at RT and stirred for 1 h. To this, compound 2 (200 mg, 0.81 mmol) in 1,2-dichloroethane (2 mL) and NaHCO$_3$ (204 mg, 2.45 mmol) were added at RT. After 24 h stirring at RT, the reaction mixture was diluted with water (15 mL) and extracted with EtOAc (2×30 mL). The combined organic extracts were washed with water (30 mL) and brine (30 mL), dried over Na$_2$SO$_4$, filtered and concentrated under reduced pressure to obtain the crude. The crude was purified (silica gel; 10% EtOAc/Hexanes) to afford compound 3 (50 mg, 9%) as an off-white solid. $^1$H NMR (500 MHz, DMSO-d$_6$): δ 8.91 (s, 1H), 8.70 (d, J=5.0 Hz, 1H), 8.30 (s, 1H), 8.18-8.15 (m, 1H), 7.66-7.762 (m, 2H), 7.36-7.34 (m, 2H), 7.17-7.13 (m, 2H), 4.34 (q J=7.5 Hz, 2H), 1.32 (t, J=7.5 Hz, 3H).

Step 3: Synthesis of ethyl 3-((2,6-dichloro-7-fluoro-1-(pyridin-3-1H-indol-3-yl)thio-2-fluorobenzoate (4)

To a stirred solution of compound 3 (50 mg, 0.11 mmol) in Et$_2$O (10 mL) under inert atmosphere was added SO$_2$Cl$_2$ (18 mg, 0.13 mmol) slowly at 0° C. and stirred for 1 h. After completion of the reaction by TLC, the reaction mixture was quenched with water (10 mL) and extracted with EtOAc (2×20 mL). The combined organic extracts were washed with water, brine solution, dried over Na$_2$SO$_4$ and concentrated under reduced pressure to obtain the crude. The crude was purified by preparative-HPLC to afford 4 (17 mg, 32%) as an off-white solid. $^1$H NMR (400 MHz, DMSO-d$_6$): δ 8.93 (d, J=2.4 Hz, 1H), 8.80 (dd, J=4.8, 1.6 Hz, 1H), 8.23-8.21 (m, 1H), 7.71-7.66 (m, 2H), 7.39-7.38 (m, 2H), 7.20-7.18 (m, 2H), 4.34 (q, J=7.2 Hz, 2H), 1.32 (t, J=7.2 Hz, 3H); LC-MS: m/z 479.4 (M$^+$).

Step 4: Synthesis of 3-((2,6-dichloro-7-fluoro-1-pyridin-3-yl)-1H-indol-3-yl)thio)-2-fluorobenzoic acid sodium salt (Compound 2-1)

To a solution of compound 4 (16 mg, 0.033 mmol) in THF:water (3:1) (4 mL) was added 1 M aq. NaOH solution (0.033 mL, 0.033 mmol) at RT and then heated at 60° C. for 3 hours. After the completion of the reaction, solvent was removed to afford Compound 2-1 sodium salt (16 mg, 100%) as an off-white solid. LC-MS: m/z 451 (M+H$^+$).

Alternate Route for Compound 4 Preparation

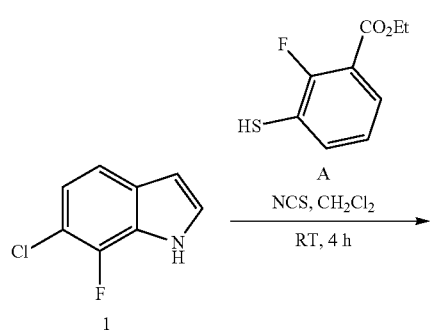

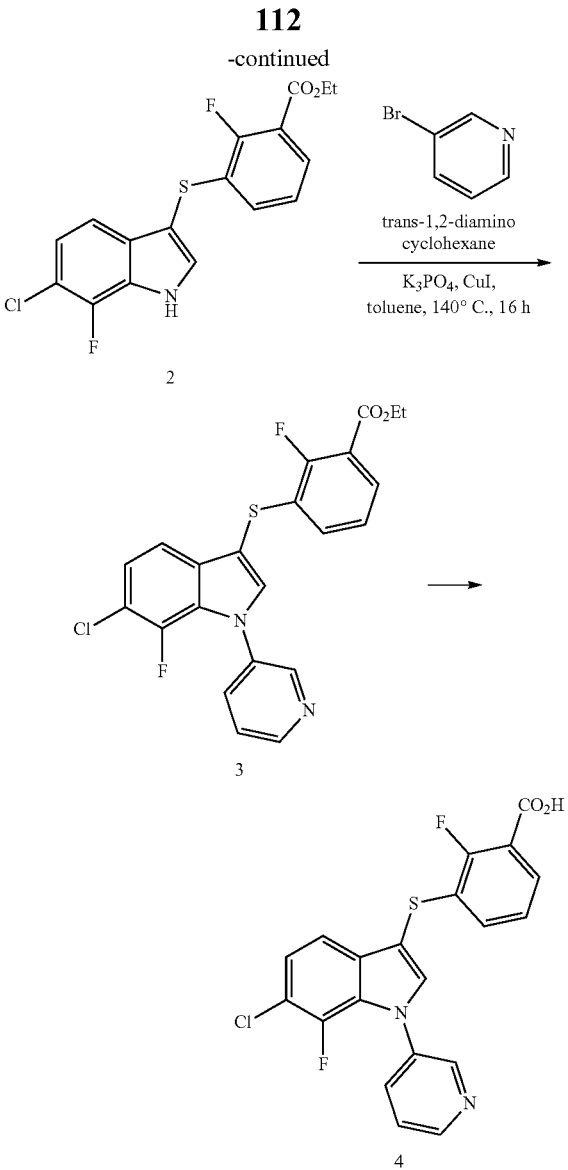

Step 1: Synthesis of ethyl 3-((6-chloro-7-fluoro-1H-indol-3-yl)thio)-2-fluorobenzoate (2)

To a stirred solution of Intermediate A (1.18 g, 5.91 mmol) in CH$_2$Cl$_2$ (30 mL) under inert atmosphere was added NCS (792 mg, 5.91 mmol) at RT and stirred for 1 h. To this, indole 1 (Example 4, Step 1; 1.0 g 5.91 mmol) in CH$_2$Cl$_2$ (20 mL) was added at RT and stirred for 4 h. After completion of the reaction by TLC, the reaction mixture was diluted with water (40 mL) and extracted with CH$_2$Cl$_2$ (2×60 mL). The combined organic extracts were washed with water (50 m L) and brine (50 mL), dried over Na$_2$SO$_4$, filtered and concentrated under reduced pressure to obtain the crude. The crude was purified (silica gel; 10% EtOAc/Hexanes) to afford compound 2 (1.2 g, 55%) as a light brown solid. $^1$H NMR (500 MHz, DMSO-d$_6$): δ 12.60 (br s, 1H), 8.00 (d, J=4.0 Hz, 1H), 7.61-7.57 (m, 1H), 7.24-7.17 (m, 2H), 7.09 (t, J=8.0 Hz, 1H), 6.90-6.86 (m, 1H), 4.34 (q, J=7.5 Hz, 2H), 1.32 (t, J=7.5 Hz, 3H); MS: m/z 368.6 (M+H$^+$).

Synthesis of ethyl 3-((6-chloro-7-fluoro-1-(pyridin-3-yl)-1H-indol-3-yl)thio)-2-fluorobenzoate To a stirred solution of compound 2 (200 mg, 0.54 mmol) in toluene (5 mL) were added 3-bromopyridine (131 mg, 0.81 mmol), trans-1,2-diaminocyclohexane (24.8 mg, 0.21 mmol), $K_3PO_4$ (288 mg, 1.35 mmol), Cu(I)I (10.3 tug, 0.05 mmol) at RT under inert atmosphere. The mixture was purged with argon for 15 min and heated to 140° C. in a sealed tube for 16 h. The reaction mixture was cooled to RT, added n-hexane (6 mL), stirred for 5 minutes and then filtered. The filtrate was diluted with water (20 mL) and extracted with EtOAc (2×50 mL). The combined organic extracts were washed with water and brine solution, dried over $Na_2SO_4$, filtered and concentrated under reduced pressure to obtain the crude. The crude was purified (silica gel; 10-12% EtOAc/Hexanes) to afford compound 3 (130 mg, 54%) as an off-white solid.

Example 23: Synthesis of 3-(2-bromo-6-chloro-7-fluoro-1H-pyridin-3-yl)-1H-indol-3-yl)thio)-2-fluorobenzoic acid (Compound 2-2)

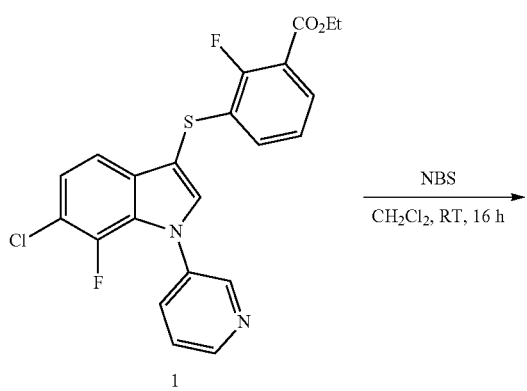

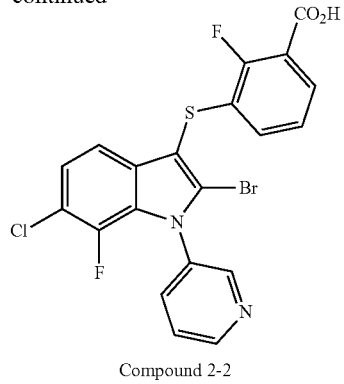

Compound 2-2

Step 1: Synthesis of ethyl 3-((2-bromo-6-chloro-7-fluoro-1-(pyridin-3-yl)-lit-indol-3-yl)thio)-2-fluorobenzoate (2)

To a stirred solution of indole 1 (Example 22, Step 2; 60 mg, 0.13 mmol) in $CH_2Cl_2$ (5 nil) under inert atmosphere was added NBS (60 mg, 0.33 mmol) at RT and stirred for 16 h. The mixture was diluted with water (10 mL) and extracted with $CH_2Cl_2$ (2×25 mL). The combined organic extracts were washed with brine (10 ml), dried ($Na_2SO_4$), filtered and concentrated under reduced pressure to obtain the crude. This was purified (silica gel; 10% EtOAc/hexanes) to afford compound 2 (35 mg, 50%) as a pale brown solid. $^1$H NMR (500 MHz, DMSO-$d_6$): δ 8.91 (s, 1H), 8.81-8.80 (m, 1H), 8.20 (d, J=8.5 Hz, 1H), 7.70-7.66 (m, 2H), 7.40-7.37 (m, 2H), 7.18 (t, J=8.0 Hz, 1H), 7.16-7.13 (m, 1H). 4.33 (q, 2H), 1.32 (t, J=7.5 Hz, 3H); MS: m/z: 525.3 (M$^+$+2).

Step 2: Synthesis of 3-((2-bromo-6-chloro-7-fluoro-1-(pyridin-3-yl)-1H-indol-3-yl)thio)-2-fluorobenzoic acid (Compound 2-2)

To a stirred solution of compound 2 (35 mg, 0.06 mmol) in THF:$H_2O$ (1:1, 4 mL) was added LiOH·$H_2O$ (11.2 mg, 0.26 mmol) at RT and stirred for 5 h. The volatiles were removed under reduced pressure and the residue was diluted with water (5 m-L), acidified with citric acid and extracted with EtOAc (2×25 mL). The combined organic extracts were washed with brine (10 mL), dried ($Na_2SO_4$), filtered and concentrated under reduced pressure to obtain the crude. This was triturated with n-pentane (2×5 mL) and dried in vacuo to afford the title Compound 2-2 (25 mg, 76%) as a pale brown solid. $^1$H NMR (500 MHz, DMSO-$d_6$): δ 13.41 (br s, 1H), 8.93 (s, 1H), 8.81-8.80 (m, 1H), 8.20 (d, J=7.5 Hz, 1H), 7.70-7.64 (m, 2H), 7.40=7.35 (m, 2H), 7.17-7.11 (m, 2H) LC-MS (ESI): m/z 497.3 (M$^+$+2).

Example 24: Synthesis of 3-(6-chloro-2=cyclopropyl-7-fluoro-1H-pyridin-3-yl) 1H-indol-3-yl)thio)-2-fluorobenzoic acid sodium salt (Compound 2-3)

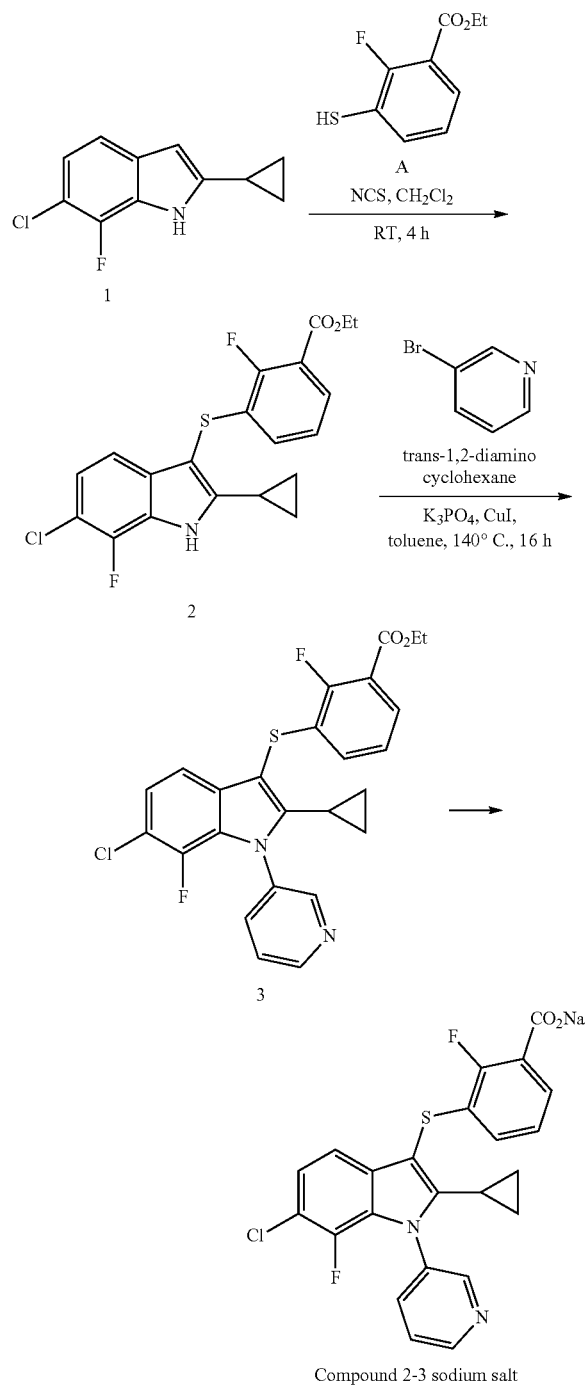

Step 1: Synthesis of ethyl 3-(6-chloro-2-cyclopropyl-7-fluoro-1H-indol-3-yl)thio)-2-fluorobenzoate (3)

To a stirred solution of Intermediate A (190 mg, 0.95 mmol) in CH$_2$Cl$_2$ (10 mL) under inert atmosphere was added NCS (128 mg, 0.95 mmol) at RT and stirred for 1 h. To this, indole 1 (Example 9, Step 2; 200 mg, 0.95 mmol) in CH$_2$Cl$_2$ (5 mL) was added at RT and stirred for 12 h. The mixture was diluted with water (50 mL) and extracted with CH$_2$Cl$_2$ (3×50 mL). The combined organic extracts were washed with brine (100 mL), dried (Na$_2$SO$_4$), filtered and concentrated under reduced pressure to obtain the crude. This was purified (silica gel chromatography; 5-10% EtOAc/hexanes) to obtain compound 2 (300 mg, 77%) as a pale pink solid. $^1$H NMR (400 MHz, DMSO-d$_6$): δ 11.91 (s, 1H), 7.89-7.84 (m, 1H), 7.57 (t, J=8.0 Hz, 1H), 7.14-7.07 (m, 2H), 6.78 (t, J=8.0 Hz, 1H), 4.35-4.29 (m, 2H), 2.32-2.25 (m, 1H), 1.33-1.28 (m, 3H), 1.15-1.10 (m, 2H), 1.08-1.03 (m, 2H); LC-MS (ESI): m/z 406.3 (M–H$^+$).

Step 2: Synthesis of ethyl 3-((6-chloro-2-cyclopropyl-7-fluoro-1-(pyridin-3-yl-1H-indol-3-yl)thio)-2-fluorobenzoate (3)

To a stirred solution of compound 2 (100 mg, 0.24 mmol) in toluene (5 mL) were added 3-bromopyridine (59.3 mg, 0.36 mmol), trans-1,2-diaminocyclohexane (11.2 mg, 0.098 mmol), K$_3$PO$_4$ (130 mg, 0.65 mmol), CuI (4.6 mg, 0.024 mmol) at RT under argon in a sealed tube. The solution was purged with argon; heated to 140° C. and stirred for 40 hr. The mixture was cooled to RT, added n-hexane (6 mL), stirred for 5 minutes and then filtered. The filtrate was diluted with water (20 mL) and extracted with EtOAc (2×50 mL). The combined organic extracts were washed with water and brine solution, dried (Na$_2$SO$_4$), filtered and concentrated under reduced pressure to obtain the crude. This was purified (silica gel; 5-10% EtOAc/hexanes) to afford compound 3 (10 mg, 8.4%) as a pale brown solid. 1H NMR (400 MHz, CDCl$_3$): δ 8.77 (br s, 2H) 7.81 (d, J=8.0 Hz, 1H), 7.68-7.62 (m, 1H), 7.53-7.50 (m, 1H), 7.25-7.23 (m, 1H), 7.17-7.11 (m, 1H), 6.96 (t, J=7.6 Hz, 1H), 6.82 (dt, J=8.4, 1.6 Hz, 1H), 4.40 (q, 2H), 1.65-1.60 (m, 1H), 1.41 (t, J=7.2 Hz, 3H), 0.91-0.82 (m, 4H); LC-MS (ESI): m/z 485.5 (M+1).

Step 3: Synthesis of 3 (6-chloro-2-cyclopropyl-7-fluoro-1-(pyridin-3-yl-1H-indol-3-yl)thio-2-fluorobenzoic acid sodium salt (Compound 2-3)

Following the procedure of Example 11, Step 3 but using Intermediate 3 in place of Intermediate 4 in Step 3, the title Compound 2-3 sodium salt was obtained as an off-white solid. LC-MS: m/z 457 (M+1).

Example 25: Synthesis of 3-((1-(1-(6-aminoethyl)-1H-pyrazol-4-yl)-6-chloro-2-cyclopropyl-7-fluoro-1H-indol-3-yl)thio)-2-fluorobenzoic acid sodium salt (Compound 1-128)

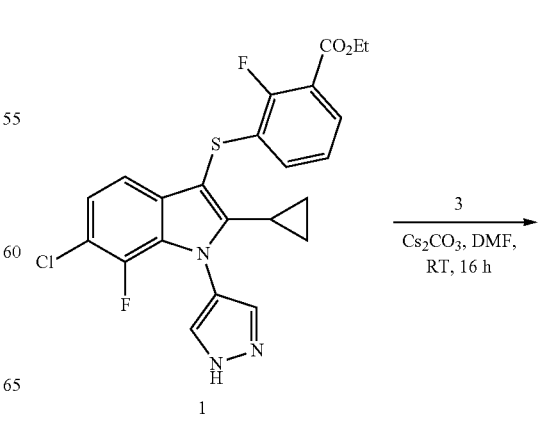

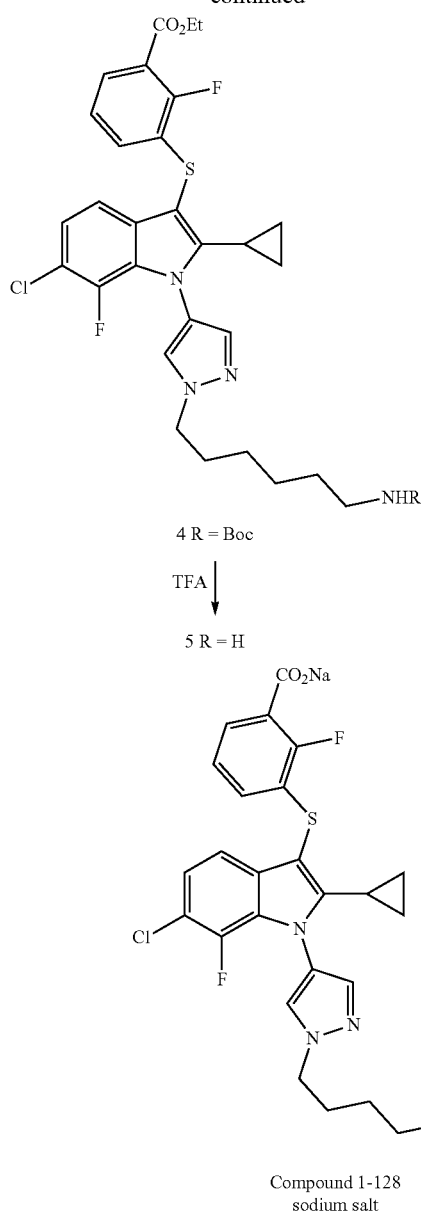

4 R = Boc

TFA ↓

5 R = H

Compound 1-128 sodium salt

Step 1: Synthesis of tert-butyl (6-hydroxyhexyl)carbamate (2)

To a stirred solution of 6-aminohexan-1H-ol (1 g, 8.55 mmol) in THF (20 mL) was added $Boc_2O$ (1.86 g, 8.55 mmol) at RT under inert, atmosphere and stirred for 6 h. The mixture was diluted with water (50 mL) and extracted with EtOAc (3×60 mL). The combined organic extracts were dried over $Na_2SO_4$, filtered and concentrated under reduced pressure to obtain the crude. The crude was purified (silica gel chromatography; 30% N EtOAc/hexanes) to afford compound 2 (1 g, 54%) as colorless syrup, $^1H$ NMR (400 MHz, $CDCl_3$): δ 4.51 (br s, 1H), 3.63 (t, J=6.4 Hz, 2H), 3.14-3.09 (m, 2H), 160-1.53 (m, 2H), 1.52-1.48 (m, 2H), 1.47 (s, 9H), 1.41-1.30 (m, 4H); LC-MS (ESI): m/z 118.1 ($M^+$-Boc).

Step 2: Synthesis of tert-butyl (6-bromohexyl)carbamate (3)

To a stirred solution of compound 2 (1 g, 4.61 mmol) in toluene (30 mL) were added $Ph_3P$ (1.81 g, 6.91 mmol) and $CBr_4$ (2.29 g, 6.91 mmol) at RT under inert atmosphere and stirred for 3 h. The mixture was diluted with water (50 mL) and extracted with EtOAc (3×60 mL). The combined organic extracts were dried over $Na_2SO_4$, filtered and concentrated in vacuo to obtain the crude. The crude was purified (silica gel; 20% EtOAc/hexanes) to afford compound 3 (1 g, 78%) as colorless oil. 1H NMR (400 MHz, $CDCl_3$): δ 3.4.51 (br s, 1H), 3.40 (t, J=6.8 Hz, 2H), 3.13-3.08 (m, 2H), 1.89-1.82 (m, 2H), 1.52-1.42 (m, 1H), 1.37-1.31 (m, 2H).

Step 3: Synthesis of 3-((1-(1-(6-aminohexyl)-1H-pyrazol-4-yl)-6-chloro-2-cycyclopropyl-7-fluoro-1H-indol-3-yl)thio)-2-fluorobenzoic acid sodium salt (Compound 1-128)

Following the procedure of Example 14 but using compound 3 in place of tert-butyl (2-bromo ethyl)carbamate, the title Compound 1-128 sodium salt was obtained as an off-white solid. LC-MS: m/z 545 (M+1).

Example 26: Synthesis of 3-(6-chloro-2-cyclopropyl-7-fluoro-(1-(1-hex-5-yn-1-yl)-1H-pyrazol-4-yl)-1H-indol-3-yl)thio)-2-fluorobenzoic acid sodium salt (Compound 1-129)

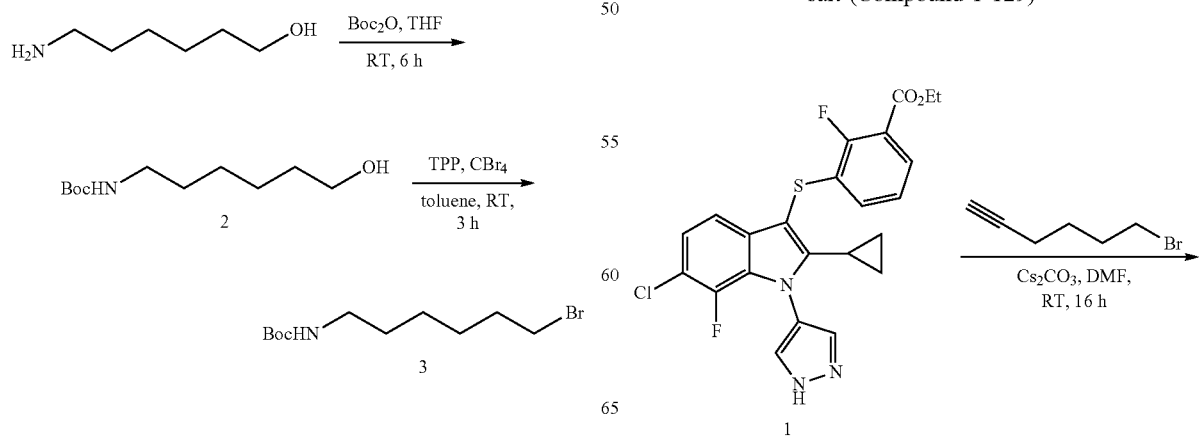

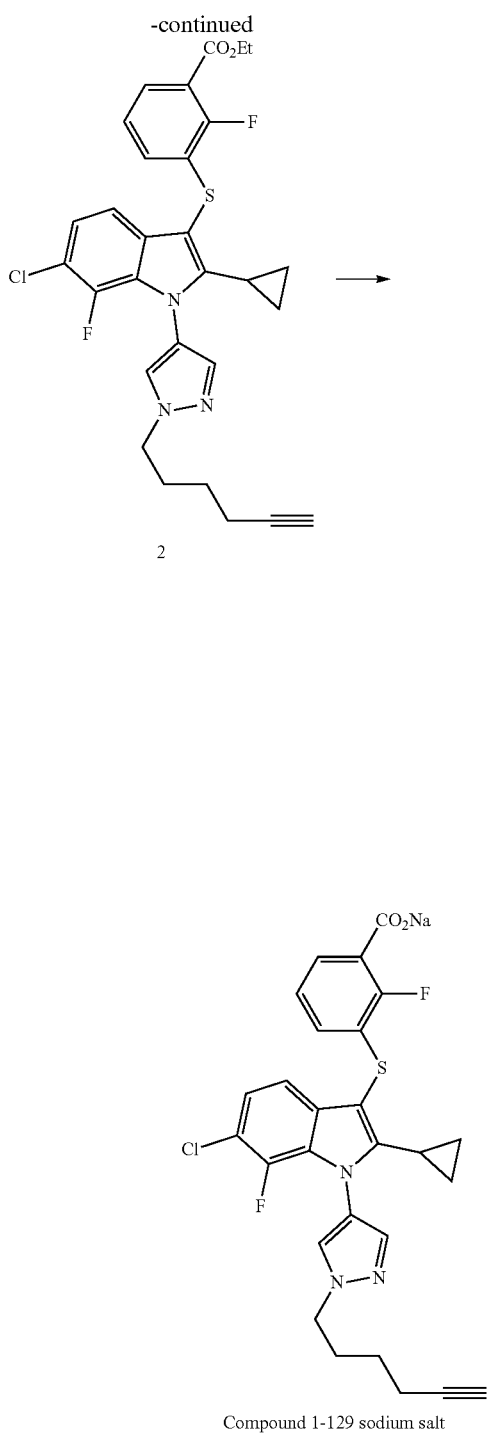

Compound 1-129 sodium salt

Following the procedure of Example 12 but using 6-bromohex-1-yne in place of 2-bromoethan-1-ol in Step 1, the title Compound 1-129 sodium salt was obtained as a white solid. LC-MS: m/z 526 (M+1).

Example 27: Synthesis of 3-((1-(1-(3-hydroxy-2,2-dimethylpropyl)-1H-pyrazol-4-yl)-6-chloro-2-cyclopropyl-7-fluoro-1H-indol-3-yl)thio)-2-fluorobenzoic acid sodium salt (Compound 1-130)

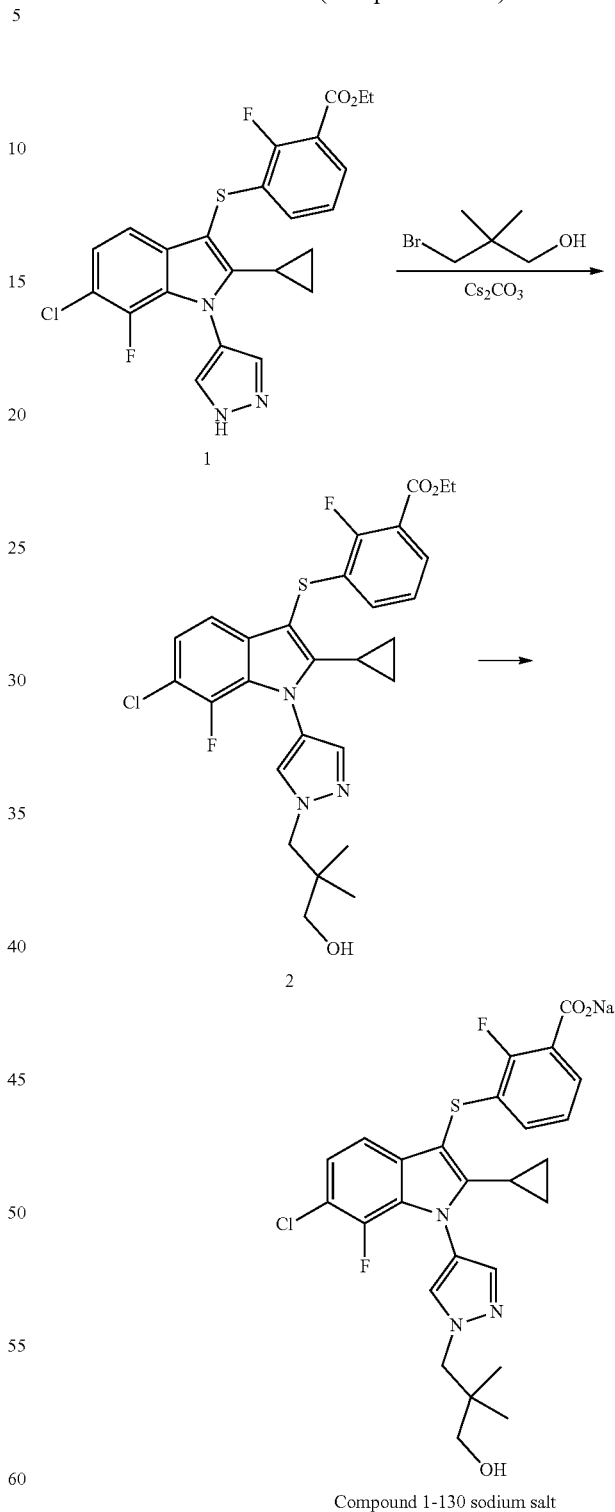

Compound 1-130 sodium salt

Following the procedure of Example 12 but using 3-bromo-2,2-dimethyl-propan-1-ol in place of 2-bromoethan-1-ol in Step 1, the title Compound 1-130 sodium salt was obtained as a white solid. LC-MS: m/z 481 (M+H$^+$).

Example 28: Synthesis of 3-((6-chloro-2-cyclopropyl-1-(1-(6-(3-(3',6'-dihydroxy-3-oxo-3H-spiroisobenzofuran-1,9'-xanthen)-5-yl)ureido)hexyl)-1H-pyrazol-4-yl)-7-fluoro-1H-indol-3-yl)thio)-2-fluorobenzoic acid sodium salt (Compound 1-131

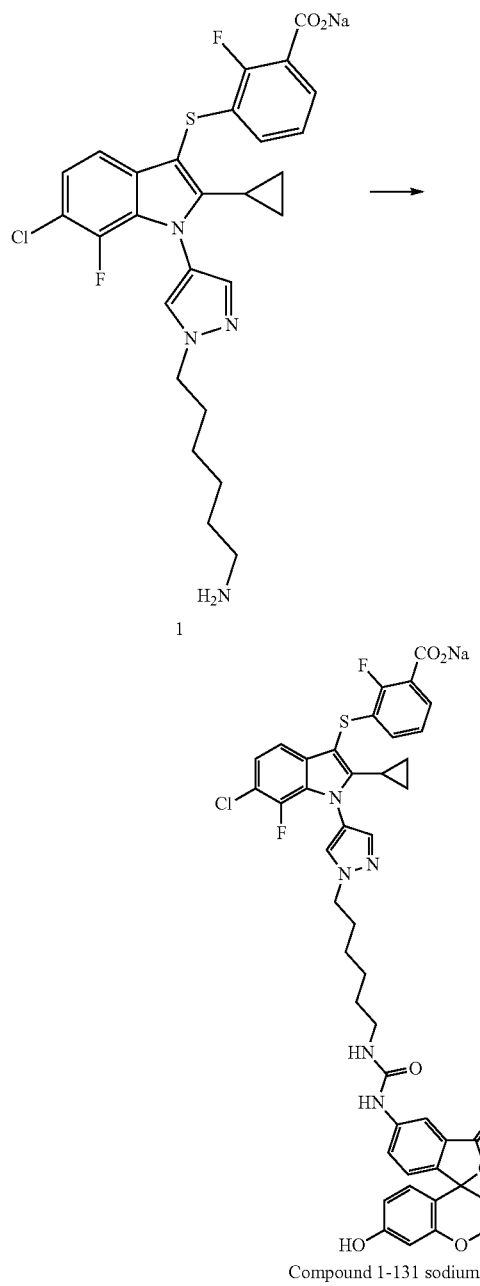

Compound 1-131 sodium salt

To a stirred solution of amine 1 (Example 25; 11.1 mg, 0.020 mmol) in CH$_2$Cl$_2$ (2 mL) under inert atmosphere was added fluorescein isothiocyante (7.6 mg, 0.020 mmol), followed by DIEA (3.4 µL, 0.020 mmol). The mixture was then stirred at room temperature under N$_2$ for overnight. After completion of the reaction, the mixture was evaporated to dryness. The crude was then purified by Prep HPLC to afford 3 mg of the title Compound 1-131 as an orange solid. LC-MS: m/z 934 (M+1).

Example 29: Synthesis of 2-(3-(6-chloro-2-cyclopropyl-7-fluoro-(1-ethyl-1H-pyrazol-4-yl)-1H-indol-3-yl)thio 2-fluorophenyl)acetic acid (compound 2-7

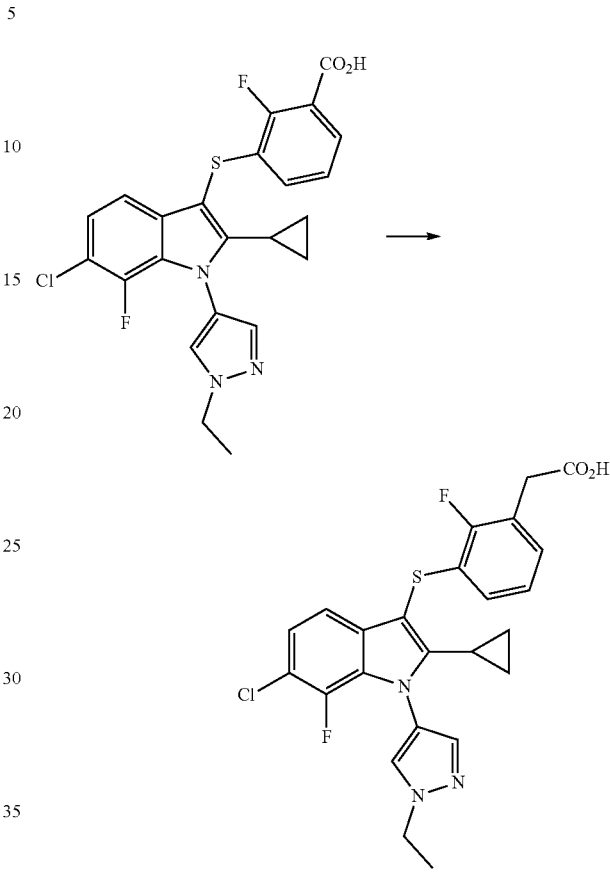

To a stirred solution of 3-((6-chloro-2-cyclopropyl-1-(1-ethyl-1H-pyrazol-4-yl)-7-fluoro-1H-indol-3-yl)thio)-2-fluorobenzoic acid compound 1-34 (Example 9; 30 mg, 0.058 mmol) in toluene (2.0 mL) under inert atmosphere was added thionyl chloride (0.22 mL, 3.0 mmol) and the mixture was heated at 85° C. for 2 h. The volatiles were removed under reduced pressure and the residue was resuspended in toluene (2.0 mL) and (trimethylsilyl)diazomethane solution (2.0 M in hexanes, 0.88 mL, 0.88 mmol). After evolution of gas, t-butylalcohol (2.0 mL) was added and the mixture was heated for 0.5 hr at 50° C. The residue was purified by silica gel chromatography (0-20% Hx/EtOAC). After evaporation of the fractions, the residue was dissolved in 4.0 M HCl in 1,4-dioxane (0.5 mL) and the solution was stirred at RT for 2 hr. The solvent was removed and the residue was purified by HPLC to give the target compound as a clear film. MS (ESI): m/z 488.0 (M.

Example 30: Parenteral Pharmaceutical Composition

To prepare a parenteral pharmaceutical composition suitable for administration by injection (subcutaneous, intravenous), 1-100 mg of a water-soluble salt of a compound described herein, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection.

Example 31: Oral Solution

To prepare a pharmaceutical composition for oral delivery, a sufficient amount of a compound described herein, or a pharmaceutically acceptable salt thereof, is added to water (with optional solubilizer(s), optional buffer(s) and taste masking excipients) to provide a 20 mg/mL solution.

Example 32: Oral Tablet

A tablet is prepared by mixing 20-50% by weight of a compound described herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example 33: Oral Capsule

To prepare a pharmaceutical composition for oral delivery, 10-500 mg of a compound described herein, or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound described herein, or a pharmaceutically acceptable salt thereof, is placed into Size 4 capsule, or size 1 capsule (hypromellose or hard gelatin) and the capsule is closed.

Example 34: Topical; Gel Composition

To prepare a pharmaceutical topical gel composition, a compound described herein, or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Example 35: Human Autotaxin Assay

ATX activity is assayed in concentrated conditioned media from Hep3B human hepatocellular carcinoma cells by measuring the amount of choline released from the substrate, lysophosphatidylcholine (LPC) as it is cleaved to LPA. Conditioned media is collected from confluent Hep3B cells and concentrated 20-fold using Centriprep-30 filter devices (Millipore). To assay for autotaxin inhibition, 10-20 μL of the concentrated conditioned media is incubated with 2.5 μL of a test compound in DMSO and 72.5-82.5 μL lyso-PLD buffer (100 mM Tris pH 9, 500 mM NaCl, 5 mM $MgCl_2$, 5 mM $CaCl_2$, 0.05% Triton X-100 in the presence or absence of 0.2% fatty-acid-free human serum albumin) for 15 min at 37° C. After the 15 min incubation, 5 ul of 2 mM LPC (14:0; Avanti Polar Lipids Cat #855575C) diluted in lyso-PLD buffer is added for a final concentration of 100 uM and the incubation continues for 1.5-3 hours at 37° C. 100 μl of a color mix containing 4.5 mM 4-aminoantipyrine, 2.7 mM N-ethyl-N-(2-hydroxy-3-sulfopropyl)-m-toluidine, 21 units/ml horseradish peroxidase and 3 units/ml choline oxidase in 50 mM Tris, pH 8, 4.5 mM $MgCl_2$ is added and the incubation continued for 15 minutes at room temperature before reading the absorbance at 555 min.

Illustrative biological activity of representative compounds in the human autotaxin assay described herein is presented in the following table:

| Compound number | $IC_{50}$ (μM) |
| --- | --- |
| 1-1 | A |
| 1-2 | A |
| 1-3 | A |
| 1-4 | A |
| 1-7 | A |
| 1-10 | A |
| 1-13 | A |
| 1-16 | A |
| 1-31 | A |
| 1-34 | A |
| 1-49 | A |
| 1-92 | A |
| 1-119 | A |
| 1-120 | A |
| 1-121 | A |
| 1-122 | A |
| 1-123 | A |
| 1-124 | A |
| 1-125 | A |
| 1-126 | A |
| 1-127 | A |
| 1-127 | A |
| 1-128 | A |
| 1-129 | A |
| 1-130 | A |
| 1-131 | A |
| 2-1 | A |
| 2-2 | A |
| 2-3 | A |
| 2-7 | A |

A is ≤0.5 μM;
B is >0.5 μM but ≤3 μM;
C >3 μM.

Example 36: Human Whole Blood Autotaxin Assay

Inhibition of ATX activity in human whole blood is assayed by measuring the concentration of 20:4 LPA in plasma after a prolonged incubation at 37° C. Blood is drawn from consenting human volunteers into heparin vacutainer tubes and 200 μl aliquots are added to 2 μl test compound in DMSO or DMSO alone. Several of the vehicle tubes are centrifuged immediately at 800× g for 10 minutes at 4° C. and the plasma removed for processing to determine the baseline concentration of 20:4 LPA. The remaining blood samples containing vehicle or test compound are incubated at 37° C. for 4 hours before centrifuging at 800× g for 10 minutes at 4° C. to obtain plasma.

Plasma is processed for LCMS as follows: 40 μl plasma is removed and 5 volumes of methanol containing 125 mg/ml 17:0 LPA as an internal standard are added and the mixture incubated at −20° C. for 10 min before centrifuging at 4000× g for 10 minutes at 4° C. 150 μl of the supernatant is transferred to a 96-well plate and diluted with 100 μl of an organic solution (90:10:0.1 of water/acetonitrile/ammonium hydroxide) for analysis of 20:4 LPA concentrations by LCMS. LPA 20:4 and the internal standard (LPA 17:0) were analyzed on a quadrupole mass spectrometer (ABI Sciex 4000QTrap) in the negative ion mode (ESI) by multiple reaction monitoring (MMI). The mobile phases contain 0.1% ammonium hydroxide in 90% water/10% acetonitrile (solvent A) and 0.1% ammonium hydroxide in 90% acetonitrile/10% water (solvent B). The flow rate was maintained at 0.8 mL/min and the total run time was 3 min, Analytes were separated using a linear gradient as follows: 1) mobile phase was held for 0.5 min at 10% B; 2) B was increased from 10% to 90% over the next 1 min; 3) B was held constant for 0.5 min at 90%; and 4) B was returned to the initial gradient conditions.

The examples and embodiments described herein are for illustrative purposes only and various modifications or changes suggested to persons skilled in the art are to be included within the spirit and purview of this application and scope of the appended claims.

What is claimed is:

1. A method for the treatment of fibrosis in a mammal comprising administering a pharmaceutical composition comprising a pharmaceutically acceptable excipient and a therapeutically effective amount of a compound of Formula (I), or a pharmaceutically acceptable salt, or solvate thereof, to the mammal in need thereof:

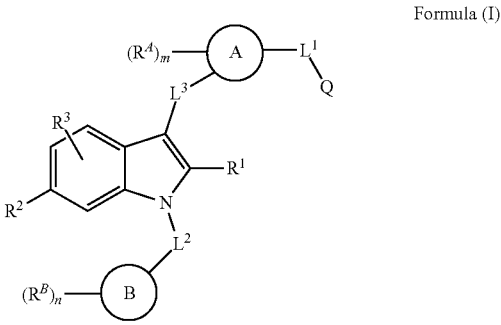

Formula (I)

wherein, $R^1$ is —F, —Cl, —Br, —CN, vinyl, $C_3$-$C_6$cyloalkyl, —NH$_2$, —NH($C_1$-$C_4$ alkyl), —N($C_1$-$C_4$ alkyl)$_2$, —O—$C_1$-$C_4$ alkyl, or —S—$C_1$-$C_4$ alkyl;

$R^2$ is H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_4$alkyl, $C_1$-$C_4$fluoroalkyl, $C_1$-$C_4$deuteroalkyl, $C_1$-$C_4$hydroxyalkyl, $C_1$-$C_4$ heteroalkyl, $C_3$-$C_6$cycloalkyl, substituted or unsubstituted phenyl, or substituted or unsubstituted monocyclic heteroaryl;

$R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, or $C_1$-$C_4$fluoroalkoxy;

Ring A is a monocyclic aryl, bicyclic aryl, monocyclic heterocycloalkyl, monocyclic heteroaryl or bi cyclic heteroaryl;

each $R^A$ is H halogen —CN—NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C (=O)R$^9$, —OC(=O) R$^9$, —CO$_2$R$^{10}$, —OCO$_2$, R$^9$, —N(R$^{10}$)$_2$, —C(=O)N(R$^{10}$)$_2$, —OC(=O)N(R$^{10}$)$_2$, —NHC(=O) R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, or substituted or unsubstituted monocyclic heteroaryl;

m is 0, 1, or 2;

$L^1$ is absent, $C_1$-$C_6$alkylene, $C_1$-$C_6$fluoroalkylene, or $C_3$-$C_6$cycloalkylene;

Q is —CO$_2$H, —CO$_2$($C_1$-$C_6$alkyl), —OH, —CN, —B(OH)$_2$, C(=O)NHSO$_2$R$^9$, —C(=O)N(R$^{10}$)$_2$, —SO$_2$NHC(=O)R$^9$, —CN, tetrazolyl, —OP(=O)(OH)$_2$, —P(=O)(OH)$_2$ or carboxylic acid bioisostere;

$L^2$ is absent, $C_1$-$C_4$alkylene, or $C_3$-$C_7$cycloalkylene;

$L^3$ is —S—, S(=O), S(=O)$_2$, or —O—;

Ring B is a monocyclic aryl, bicyclic aryl, monocyclic heteroaryl or bicyclic heteroaryl;

each $R^B$ is independently H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, $C_1$-$C_4$alkylene-(substituted or unsubstituted phenyl), substituted or unsubstituted monocyclic heteroaryl, $C_1$-$C_4$alkylene-(substituted or unsubstituted monocyclic heteroaryl), a substituted or unsubstituted bicyclic heteroaryl, or $C_1$-$C_4$alkylene-(substituted or unsubstituted bicyclic heteroaryl);

or each $R^B$ is independently hydrogen, 1-propyl, ethyl, methyl, 2-propyl, —CH$_2$CH$_2$OH, —CH$_2$CH$_2$OC(O)NH$_2$, —CH$_2$CH$_2$NH$_2$, —CH$_2$CH$_2$NHC(O)NH$_2$, —CH$_2$CH$_2$C H$_2$CO$_2$H, —CH$_2$CH$_2$CH$_2$CONH$_2$, —CH$_2$CF$_3$, —CD$_2$CD$_3$, —(CH$_2$)$_6$NH$_2$, —(CH$_2$)$_4$CCH, —CH$_2$C(CH$_3$)$_2$C H$_2$OH, —(CH$_2$)$_6$NHC(O)N-fluorescein, —CH$_2$CH$_2$CH$_2$C(O)NHCH$_3$, —CH$_2$CH$_2$CH$_2$C(O)NH(CH$_3$)$_2$, —CH$_2$CH$_2$C(CH$_3$)$_2$C(O)NH$_2$, —CH$_2$CH$_2$CH$_2$C(O)NH$_2$, —CH$_2$CH$_2$CH$_2$C(O)NHCH$_3$, —CH$_2$CH$_2$CH$_2$C(O)NH(CH$_3$)$_2$, or —CH$_2$CH$_2$C(CH$_3$)$_2$C(O)NH$_2$;

n is 0, 1, or 2;

$R^9$ is $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, a substituted or unsubstituted monocyclic heteroaryl, or a substituted or unsubstituted bi cyclic heteroaryl;

each $R^{10}$ is independently selected from H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, or a substituted or unsubstituted monocyclic heteroaryl; or two $R^{10}$ groups attached to the same N atom are taken together with the N atom to which they are attached to form a substituted or unsubstituted heterocycle;

wherein if any of $R^2$, $R^9$, $R^{10}$, $R^A$, and $R^B$ is substituted, then it is substituted with one or two groups independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$.

2. The method of claim 1, wherein the fibrosis is selected from the group consisting of lung fibrosis, liver fibrosis, heart fibrosis, kidney fibrosis, skin fibrosis, and fibrosis of the gastrointestinal tract.

3. The method of claim 2, wherein the lung fibrosis is selected from the group consisting of pulmonary fibrosis, idiopathic pulmonary fibrosis (IPF), usual interstitial pneumonitis (UIP), interstitial lung disease, cryptogenic fibrosing alveolitis (CFA), bronchiolitis obliterans, and bronchiectasis.

4. The method of claim 2, wherein the lung fibrosis is pulmonary fibrosis.

5. The method of claim 2, wherein the lung fibrosis is idiopathic pulmonary fibrosis (IPF).

6. The method of claim 2, wherein the lung fibrosis is usual interstitial pneumonitis (UIP).

7. The method of claim 2, wherein the lung fibrosis is interstitial lung disease.

8. The method of claim 2, wherein the lung fibrosis is cryptogenic fibrosing alveolitis.

9. The method of claim 2, wherein the lung fibrosis is bronchiolitis obliterans.

10. The method of claim 2, wherein the lung fibrosis is bronchiectasis.

11. The method of claim 2, wherein the lung fibrosis is associated with a cancer treatment.

12. The method of claim 1, wherein the fibrosis is liver fibrosis.

13. The method of claim 1, further comprising administering a second therapeutic agent to the mammal.

14. The method of claim 1, wherein the pharmaceutical composition is administered to the mammal by oral administration, by intravenous administration, by subcutaneous administration, by inhalation, by nasal administration, by dermal administration, or by ophthalmic administration.

15. The method of claim 1, wherein the compound of Formula (I) has the following structure of Formula (III):

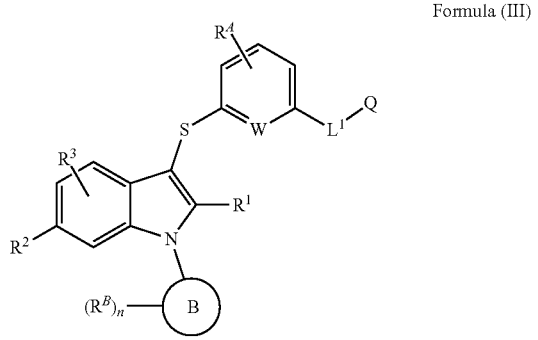

Formula (III)

wherein, $R^1$ is —Cl, —Br, —CN, or $C_3$-$C_6$cyloalkyl;

$R^2$ is H, halogen —CN, —$NO_2$, —OH, —$OR^9$, —$SR^9$, —S(=O)$R^9$, —S(=O)$_2R^9$, —S(=O)$_2$N($R^{10}$)$_2$, $C_1$-$C_4$alkyl, $C_1$-$C_4$fluoroalkyl, $C_1$-$C_4$deuteroalkyl, or $C_3$-$C_6$cycloalkyl;

$R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, or $C_1$-$C_4$fluoroalkoxy;

W is CH, CF or N;

each $R^4$ is H halogen —CN, —$NO_2$, —OH, —$OR^9$, —$SR^9$, —S(=O)$R^9$, —S(=O)$_2R^9$—S(=O)$_2$N($R^{10}$)$_2$, $C_1$-$C_6$alkyl, or $C_1$-$C_6$fluoroalkyl;

$L^1$ is absent, $C_1$-$C_6$alkylene, or $C_3$-$C_6$cycloalkylene;

Q is —$CO_2$H, —$CO_2$($C_1$-$C_6$alkyl), —OH, —CN, —B(OH)$_2$, C(=O)NHSO$_2R^9$, —C(=O)N($R^{10}$)$_2$, —$SO_2$NHC(=O)$R^9$, —CN, tetrazolyl, —OP(=O)(OH)$_2$, —P(=O)(OH)$_2$ or carboxylic acid bioisostere;

Ring B is a monocyclic heteroaryl;

each $R^B$ is independently H, halogen, —CN, —$NO_2$, —OH, —$OR^9$, —$SR^9$, —S(=O)$R^9$, —S(=O)$_2R^9$, —S(=O)$_2$N($R^{10}$)$_2$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, $C_1$-$C_4$alkylene-(substituted or unsubstituted phenyl), substituted unsubstituted monocyclic heteroaryl, $C_1$-$C_4$alkylene-(substituted or unsubstituted monocyclic heteroaryl), a substituted or unsubstituted bicyclic heteroaryl, or $C_1$-$C_4$alkylene(substituted or unsubstituted bicyclic heteroaryl);

or each $R^B$ is independently hydrogen, 1-propyl, ethyl, methyl, 2-propyl, —CH$_2$CH$_2$OH, —CH$_2$CH$_2$OC(O)NH$_2$, —CH$_2$CH$_2$NH$_2$, —CH$_2$CH$_2$NHC(O)NH$_2$, —CH$_2$CH$_2$C H$_2$CO$_2$H, —CH$_2$CH$_2$CH$_2$CONH$_2$, —CH$_2$CF$_3$, —CD$_2$CD$_3$, —(CH$_2$)$_6$NH$_2$, —(CH$_2$)$_4$CCH, —CH$_2$C(CH$_3$)$_2$C H$_2$OH, —(CH$_2$)$_6$NHC(O)N-fluorescein, —CH$_2$CH$_2$CH$_2$C(O)NHCH$_3$, —CH$_2$CH$_2$CH$_2$C(O)NH(CH$_3$)$_2$, —CH$_2$CH$_2$C(CH$_3$)$_2$C(O)NH$_2$, —CH$_2$CH$_2$CH$_2$C(O)NH$_2$, —CH$_2$CH$_2$CH$_2$C(O)NHCH$_3$, —CH$_2$CH$_2$CH$_2$C(O)NH(CH$_3$)$_2$, or —CH$_2$CH$_2$C(CH$_3$)$_2$C(O)NH$_2$;

n is 0, 1, or 2;

$R^9$ is $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, a substituted or unsubstituted monocyclic heteroaryl, or a substituted or unsubstituted bicyclic heteroaryl;

each $R^{10}$ is independently H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, or a substituted or unsubstituted monocyclic heteroaryl; or two $R^{10}$ groups attached to the same N atom are taken together with the N atom to which they are attached to form a substituted or unsubstituted heterocycle.

16. The method of claim 15, wherein:

$R^2$ is H, F, Cl, Br, I, —CN, —OH, —CH$_3$, —CF$_3$, —CD$_3$, —OCH$_3$, —OCH$_2$CH$_3$, —OCF$_3$, or —OCH$_2$CF$_3$;

$R^3$ is H, F, Cl, Br, I, —CN, —OH, —CH$_3$, —CF$_3$, —CD$_3$, —OCH$_3$, —OCH$_2$CH$_3$, —OCF$_3$, or —OCH$_2$CF$_3$; and Ring B is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

17. The method of claim 1, wherein the compound of Formula (I) has the following structure:

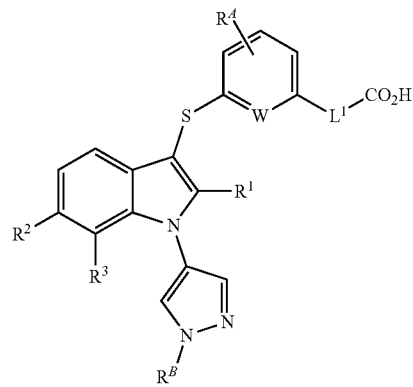

or a pharmaceutically acceptable salt, or solvate thereof, wherein:

$R^4$ is H, halogen, —CN, —OH, —$OR^9$, —$SR^9$, $C_1$-$C_6$alkyl, or $C_1$-$C_6$fluoroalkyl;

$R^B$ is H, $C_1$-$C_6$alkyl, $C_1$-$C_6$fluoroalkyl, or $C_1$-$C_6$deuteroalkyl;

or $R^B$ is hydrogen, 1-propyl, ethyl, methyl, 2-propyl, —CH$_2$CH$_2$OH, —CH$_2$CH$_2$OC(O)NH$_2$, —CH$_2$CH$_2$NH$_2$, —CH$_2$CH$_2$NHC(O)NH$_2$, —CH$_2$CH$_2$CH$_2$CO$_2$H, —CH$_2$CH$_2$CH$_2$CONH$_2$, —CH$_2$CF$_3$, —CD$_2$CD$_3$, —(CH$_2$)$_6$NH$_2$, —(CH$_2$)$_4$CCH, —CH$_2$C(CH$_3$)$_2$CH$_2$OH, —(CH$_2$)$_6$NHC(O)N-fluorescein, —CH$_2$CH$_2$CH$_2$C(O)NHCH$_3$, —CH$_2$CH$_2$CH$_2$C(O)NH(CH$_3$)$_2$, —CH$_2$CH$_2$C(CH$_3$)$_2$C(O)NH$_2$, —CH$_2$CH$_2$CH$_2$C(O)NH$_2$, —CH$_2$CH$_2$CH$_2$C(O)NHCH$_3$, —CH$_2$CH$_2$CH$_2$C(O)NH(CH$_3$)$_2$, or —CH$_2$CH$_2$C(CH$_3$)$_2$C(O)NH$_2$;

R$^1$ is —Cl, —Br, —CN, or cyclopropyl;

R$^2$ is H, halogen, —CN, —OH, C$_1$-C$_4$alkyl, C$_1$-C$_4$fluoroalkyl, C$_1$-C$_4$deuteroalkyl, C$_1$-C$_4$alkoxy, or C$_1$-C$_4$fluoroalkoxy; and R$^3$ is H, halogen, —CN, —OH, C$_1$-C$_4$alkyl, C$_1$-C$_4$fluoroalkyl, C$_1$-C$_4$deuteroalkyl, C$_1$-C$_4$alkoxy, or C$_1$-C$_4$fluoroalkoxy.

18. The method of claim 1, wherein the compound of Formula (I) is selected from:

3-((2,6-dichloro-1-(1-propyl-1H-pyrazol-4-yl)-1H-indol-3-yl)thio)benzoic acid (compound no. 1-1);

3-((2-bromo-6-chloro-1-(1-propyl-1H-pyrazol-4-yl)-1H-indol-3-yl)thio)benzoic acid (compound no. 1-2);

3-((6-chloro-2-cyano-1-(1-propyl-1H-pyrazol-4-yl)-1H-indol-3-yl)thio)benzoic acid (compound no. 1-3);

3-((6-chloro-2-cyclopropyl-1-(1-propyl-1H-pyrazol-4-yl)-1H-indol-3-yl)thio)benzoic acid (compound no. 1-4);

3-((2-amino-6-chloro-1-(1-propyl-1H-pyrazol-4-yl)-1H-indol-3-yl)thio)benzoic acid (compound no. 1-5);

3-((6-chloro-2-methoxy-1-(1-propyl-1H-pyrazol-4-yl)-1H-indol-3-yl)thio)benzoic acid (compound no. 1-6);

3-((2,6-dichloro-7-fluoro-1-(1-propyl-1H-pyrazol-4-yl)-1H-indol-3-yl)thio)benzoic acid (compound no. 1-7);

3-((2-bromo-6-chloro-7-fluoro-1-(1-propyl-1H-pyrazol-4-yl)-1H-indol-3-yl)thio)benzoic acid (compound no. 1-8);

3-((6-chloro-2-cyano-7-fluoro-1-(1-propyl-1H-pyrazol-4-yl)-1H-indol-3-yl)thio)benzoic acid (compound no. 1-9);

3-((6-chloro-2-cyclopropyl-7-fluoro-1-(1-propyl-1H-pyrazol-4-yl)-1H-indol-3-yl)thio)benzoic acid (compound no. 1-10);

3-((2-amino-6-chloro-7-fluoro-1-(1-propyl-1H-pyrazol-4-yl)-1H-indol-3-yl)thio)benzoic acid (compound no. 1-11);

3-((6-chloro-7-fluoro-2-methoxy-1-(1-propyl-1H-pyrazol-4-yl)-1H-indol-3-yl)thio)benzoic acid (compound no. 1-12);

3-((2,6-dichloro-7-fluoro-1-(1-propyl-1H-pyrazol-4-yl)-1H-indol-3-yl)thio)-2-fluorobenzoic acid (compound no. 1-13);

3-((2-bromo-6-chloro-7-fluoro-1-(1-propyl-1H-pyrazol-4-yl)-1H-indol-3-yl)thio)-2-fluoro benzoic acid (compound no. 1-14);

3-((6-chloro-2-cyano-7-fluoro-1-(1-propyl-1H-pyrazol-4-yl)-1H-indol-3-yl)thio)-2-fluorobenzoic acid (compound no. 1-15);

3-((6-chloro-2-cyclopropyl-7-fluoro-1-(1-propyl-1H-pyrazol-4-yl)-1H-indol-3-yl)thio)-2-fluorobenzoic acid (compound no. 1-16);

3-((2-amino-6-chloro-7-fluoro-1-(1-propyl-1H-pyrazol-4-yl)-1H-indol-3-yl)thio)-2-fluoro benzoic acid (compound no. 1-17);

3-((6-chloro-7-fluoro-2-methoxy-1-(1-propyl-1H-pyrazol-4-yl)-1H-indol-3-yl)thio)-2-fluorobenzoic acid (compound no. 1-18);

3-((2,6-dichloro-1-(1-ethyl-1H-pyrazol-4-yl)-1H-indol-3-yl)thio)benzoic acid (compound no. 1-19);

3-((2-bromo-6-chloro-1-(1-ethyl-1H-pyrazol-4-yl)-1H-indol-3-yl)thio)benzoic acid (compound no. 1-20);

3-((6-chloro-2-cyano-1-(1-ethyl-1H-pyrazol-4-yl)-1H-indol-3-yl)thio)benzoic acid (compound no. 1-21);

3-((6-chloro-2-cyclopropyl-1-(1-ethyl-1H-pyrazol-4-yl)-1H-indol-3-yl)thio)benzoic acid (compound no. 1-22);

3-((2-amino-6-chloro-1-(1-ethyl-1H-pyrazol-4-yl)-1H-indol-3-yl)thio)benzoic acid (compound no. 1-23);

3-((6-chloro-2-methoxy-1-(1-ethyl-1H-pyrazol-4-yl)-1H-indol-3-yl)thio)benzoic acid (compound no. 1-24);

3-((2,6-dichloro-1-(1-ethyl-1H-pyrazol-4-yl)-7-fluoro-1H-indol-3-yl)thio)benzoic acid (compound no. 1-25);

3-((2-bromo-6-chloro-1-(1-ethyl-1H-pyrazol-4-yl)-7-fluoro-1H-indol-3-yl)thio)benzoic acid (compound no. 1-26);

3-((6-chloro-2-cyano-1-(1-ethyl-1H-pyrazol-4-yl)-7-fluoro-1H-indol-3-yl)thio)benzoic acid (compound no. 1-27);

3-((6-chloro-2-cyclopropyl-1-(1-ethyl-1H-pyrazol-4-yl)-7-fluoro-1H-indol-3-yl)thio)benzoic acid (compound no. 1-28);

3-((2-amino-6-chloro-1-(1-ethyl-1H-pyrazol-4-yl)-7-fluoro-1H-indol-3-yl)thio)benzoic acid (compound no. 1-29);

3-((6-chloro-1-(1-ethyl-1H-pyrazol-4-yl)-7-fluoro-2-methoxy-1H-indol-3-yl)thio)benzoic acid (compound no. 1-30);

3-((2,6-dichloro-1-(1-ethyl-1H-pyrazol-4-yl)-7-fluoro-1H-indol-3-yl)thio)-2-fluorobenzoic acid (compound no. 1-31);

3-((2-bromo-6-chloro-1-(1-ethyl-1H-pyrazol-4-yl)-7-fluoro-1H-indol-3-yl)thio)-2-fluorobenzoic acid (compound no. 1-32);

3-((6-chloro-2-cyano-1-(1-ethyl-1H-pyrazol-4-yl)-7-fluoro-1H-indol-3-yl)thio)-2-fluorobenzoic acid (compound no. 1-33);

3-((6-chloro-2-cyclopropyl-1-(1-ethyl-1H-pyrazol-4-yl)-7-fluoro-1H-indol-3-yl)thio)-2-fluorobenzoic acid (compound no. 1-34);

3-((2-amino-6-chloro-1-(1-ethyl-1H-pyrazol-4-yl)-7-fluoro-1H-indol-3-yl)thio)-2-fluorobenzoic acid (compound no. 1-35);

3-((6-chloro-2-methoxy-1-(1-ethyl-1H-pyrazol-4-yl)-7-fluoro-1H-indol-3-yl)thio)-2-fluoro benzoic acid (compound no. 1-36);

3-((2,6-dichloro-1-(1-methyl-1H-pyrazol-4-yl)-1H-indol-3-yl)thio)benzoic acid (compound no. 1-37);

3-((2-bromo-6-chloro-1-(1-methyl-1H-pyrazol-4-yl)-1H-indol-3-yl)thio)benzoic acid (compound no. 1-38);

3-((6-chloro-2-cyano-1-(1-methyl-1H-pyrazol-4-yl)-1H-indol-3-yl)thio)benzoic acid (compound no. 1-39);

3-((6-chloro-2-cyclopropyl-1-(1-methyl-1H-pyrazol-4-yl)-1H-indol-3-yl)thio)benzoic acid (compound no. 1-40);

3-((2-amino-6-chloro-1-(1-methyl-1H-pyrazol-4-yl)-1H-indol-3-yl)thio)benzoic acid (compound no. 1-41);

3-((6-chloro-2-methoxy-1-(1-methyl-1H-pyrazol-4-yl)-1H-indol-3-yl)thio)benzoic acid (compound no. 1-42);

3-((2,6-dichloro-7-fluoro-1-(1-methyl-1H-pyrazol-4-yl)-1H-indol-3-yl)thio)benzoic acid (compound no. 1-43);

3-((2-bromo-6-chloro-7-fluoro-1-(1-methyl-1H-pyrazol-4-yl)-1H-indol-3-yl)thio)benzoic acid (compound no. 1-44);

3-((6-chloro-2-cyano-7-fluoro-1-(1-methyl-1H-pyrazol-4-yl)-1H-indol-3-yl)thio)benzoic acid (compound no. 1-45);
3-((6-chloro-2-cyclopropyl-7-fluoro-1-(1-methyl-1H-pyrazol-4-yl)-1H-indol-3-yl)thio)benzoic acid (compound no. 1-46);
3-((2-amino-6-chloro-7-fluoro-1-(1-methyl-1H-pyrazol-4-yl)-1H-indol-3-yl)thio)benzoic acid (compound no. 1-47);
3-((6-chloro-7-fluoro-1-(1-methyl-1H-pyrazol-4-yl)-2-methoxy-1H-indol-3-yl)thio)benzoic acid (compound no. 1-48);
3-((2,6-dichloro-7-fluoro-1-(1-methyl-1H-pyrazol-4-yl)-1H-indol-3-yl)thio)-2-fluorobenzoic acid (compound no. 1-49);
3-((2-bromo-6-chloro-7-fluoro-1-(1-methyl-1H-pyrazol-4-yl)-1H-indol-3-yl)thio)-2-fluoro benzoic acid (compound no. 1-50);
3-((6-chloro-2-cyano-7-fluoro-1-(1-methyl-1H-pyrazol-4-yl)-1H-indol-3-yl)thio)-2-fluoro benzoic acid (compound no. 1-51);
3-((6-chloro-2-cyclopropyl-7-fluoro-1-(1-methyl-1H-pyrazol-4-yl)-1H-indol-3-yl)thio)-2-fluorobenzoic acid (compound no. 1-52);
3-((2-amino-6-chloro-7-fluoro-1-(1-methyl-1H-pyrazol-4-yl)-1H-indol-3-yl)thio)-2-fluoro benzoic acid (compound no. 1-53);
3-((2,6-dichloro-1-(1-isopropyl-1H-pyrazol-4-yl)-1H-indol-3-yl)thio)benzoic acid (compound no. 1-54);
3-((2-bromo-6-chloro-1-(1-isopropyl-1H-pyrazol-4-yl)-1H-indol-3-yl)thio)benzoic acid (compound no. 1-55);
3-((6-chloro-2-cyano-1-(1-isopropyl-1H-pyrazol-4-yl)-1H-indol-3-yl)thio)benzoic acid (compound no. 1-56);
3-((6-chloro-2-cyclopropyl-1-(1-isopropyl-1H-pyrazol-4-yl)-1H-indol-3-yl)thio)benzoic acid (compound no. 1-57);
3-((2-amino-6-chloro-1-(1-isopropyl-1H-pyrazol-4-yl)-1H-indol-3-yl)thio)benzoic acid (compound no. 1-58);
3-((6-chloro-2-methoxy-1-(1-isopropyl-1H-pyrazol-4-yl)-1H-indol-3-yl)thio)benzoic acid (compound no. 1-59);
3-((2,6-dichloro-7-fluoro-1-(1-isopropyl-1H-pyrazol-4-yl)-1H-indol-3-yl)thio)benzoic acid (compound no. 1-60);
3-((2-bromo-6-chloro-7-fluoro-1-(1-isopropyl-1H-pyrazol-4-yl)-1H-indol-3-yl)thio)benzoic acid (compound no. 1-61);
3-((6-chloro-2-cyano-7-fluoro-1-(1-isopropyl-1H-pyrazol-4-yl)-1H-indol-3-yl)thio)benzoic acid (compound no. 1-62);
3-((6-chloro-2-cyclopropyl-7-fluoro-1-(1-isopropyl-1H-pyrazol-4-yl)-1H-indol-3-yl)thio)benzoic acid (compound no. 1-63);
3-((2-amino-6-chloro-7-fluoro-1-(1-isopropyl-1H-pyrazol-4-yl)-1H-indol-3-yl)thio)benzoic acid (compound no. 1-64);
3-((6-chloro-7-fluoro-1-(1-isopropyl-1H-pyrazol-4-yl)-2-methoxy-1H-indol-3-yl)thio)benzoic acid (compound no. 1-65);
3-((2,6-dichloro-7-fluoro-1-(1-isopropyl-1H-pyrazol-4-yl)-1H-indol-3-yl)thio)-2-fluorobenzoic acid (compound no. 1-66);
3-((2-bromo-6-chloro-7-fluoro-1-(1-isopropyl-1H-pyrazol-4-yl)-1H-indol-3-yl)thio)-2-fluorobenzoic acid (compound no. 1-67);
3-((6-chloro-2-cyano-7-fluoro-1-(1-isopropyl-1H-pyrazol-4-yl)-1H-indol-3-yl)thio)-2-fluorobenzoic acid (compound no. 1-68);
3-((6-chloro-2-cyclopropyl-7-fluoro-1-(1-isopropyl-1H-pyrazol-4-yl)-1H-indol-3-yl)thio)-2-fluorobenzoic acid (compound no. 1-69);
3-((2-amino-6-chloro-7-fluoro-1-(1-isopropyl-1H-pyrazol-4-yl)-1H-indol-3-yl)thio)-2-fluorobenzoic acid (compound no. 1-70);
6-((2,6-dichloro-1-(1-propyl-1H-pyrazol-4-yl)-1H-indol-3-yl)thio)picolinic acid (compound no. 1-71);
6-((2-bromo-6-chloro-1-(1-propyl-1H-pyrazol-4-yl)-1H-indol-3-yl)thio)picolinic acid (compound no. 1-72);
6-((6-chloro-2-cyano-1-(1-propyl-1H-pyrazol-4-yl)-1H-indol-3-yl)thio)picolinic acid (compound no. 1-73);
6-((6-chloro-2-cyclopropyl-1-(1-propyl-1H-pyrazol-4-yl)-1H-indol-3-yl)thio)picolinic acid (compound no. 1-74);
6-((2-amino-6-chloro-1-(1-propyl-1H-pyrazol-4-yl)-1H-indol-3-yl)thio)picolinic acid (compound no. 1-75);
6-((6-chloro-2-methoxy-1-(1-propyl-1H-pyrazol-4-yl)-1H-indol-3-yl)thio)picolinic acid (compound no. 1-76);
6-((2,6-dichloro-7-fluoro-1-(1-propyl-1H-pyrazol-4-yl)-1H-indol-3-yl)thio)picolinic acid (compound no. 1-77);
6-((2-bromo-6-chloro-7-fluoro-1-(1-propyl-1H-pyrazol-4-yl)-1H-indol-3-yl)thio)picolinic acid (compound no. 1-78);
6-((6-chloro-2-cyano-7-fluoro-1-(1-propyl-1H-pyrazol-4-yl)-1H-indol-3-yl)thio)picolinic acid (compound no. 1-79);
6-((6-chloro-2-cyclopropyl-7-fluoro-1-(1-propyl-1H-pyrazol-4-yl)-1H-indol-3-yl)thio)picolinic acid (compound no. 1-80);
6-((2-amino-6-chloro-7-fluoro-1-(1-propyl-1H-pyrazol-4-yl)-1H-indol-3-yl)thio)picolinic acid (compound no. 1-81);
6-((6-chloro-7-fluoro-2-methoxy-1-(1-propyl-1H-pyrazol-4-yl)-1H-indol-3-yl)thio)picolinic acid (compound no. 1-82);
6-((2,6-dichloro-1-(1-ethyl-1H-pyrazol-4-yl)-1H-indol-3-yl)thio)picolinic acid (compound no. 1-83);
6-((2-bromo-6-chloro-1-(1-ethyl-1H-pyrazol-4-yl)-1H-indol-3-yl)thio)picolinic acid (compound no. 1-84);
6-((6-chloro-2-cyano-1-(1-ethyl-1H-pyrazol-4-yl)-1H-indol-3-yl)thio)picolinic acid (compound no. 1-85);
6-((6-chloro-2-cyclopropyl-1-(1-ethyl-1H-pyrazol-4-yl)-1H-indol-3-yl)thio)picolinic acid (compound no. 1-86);
6-((2-amino-6-chloro-1-(1-ethyl-1H-pyrazol-4-yl)-1H-indol-3-yl)thio)picolinic acid (compound no. 1-87);
6-((6-chloro-1-(1-ethyl-1H-pyrazol-4-yl)-2-methoxy-1H-indol-3-yl)thio)picolinic acid (compound no. 1-88);
6-((2,6-dichloro-1-(1-ethyl-1H-pyrazol-4-yl)-7-fluoro-1H-indol-3-yl)thio)picolinic acid (compound no. 1-89);
6-((2-bromo-6-chloro-1-(1-ethyl-1H-pyrazol-4-yl)-7-fluoro-1H-indol-3-yl)thio)picolinic acid (compound no. 1-90);
6-((6-chloro-2-cyano-1-(1-ethyl-1H-pyrazol-4-yl)-7-fluoro-1H-indol-3-yl)thio)picolinic acid (compound no. 1-91);
6-((6-chloro-2-cyclopropyl-1-(1-ethyl-1H-pyrazol-4-yl)-7-fluoro-1H-indol-3-yl)thio)picolinic acid (compound no. 1-92);
6-((2-amino-6-chloro-1-(1-ethyl-1H-pyrazol-4-yl)-7-fluoro-1H-indol-3-yl)thio)picolinic acid (compound no. 1-93);

6-((6-chloro-1-(1-ethyl-1H-pyrazol-4-yl)-7-fluoro-2-methoxy-1H-indol-3-yl)thio)picolinic acid (compound no. 1-94);

6-((2,6-dichloro-1-(1-methyl-1H-pyrazol-4-yl)-1H-indol-3-yl)thio)picolinic acid (compound no. 1-95);

6-((2-bromo-6-chloro-1-(1-methyl-1H-pyrazol-4-yl)-1H-indol-3-yl)thio)picolinic acid (compound no. 1-96);

6-((6-chloro-2-cyano-1-(1-methyl-1H-pyrazol-4-yl)-1H-indol-3-yl)thio)picolinic acid (compound no. 1-97);

6-((6-chloro-2-cyclopropyl-1-(1-methyl-1H-pyrazol-4-yl)-1H-indol-3-yl)thio)picolinic acid (compound no. 1-98);

6-((2-amino-6-chloro-1-(1-methyl-1H-pyrazol-4-yl)-1H-indol-3-yl)thio)picolinic acid (compound no. 1-99);

6-((6-chloro-2-methoxy-1-(1-methyl-1H-pyrazol-4-yl)-1H-indol-3-yl)thio)picolinic acid (compound no. 1-100);

6-((2,6-dichloro-7-fluoro-1-(1-methyl-1H-pyrazol-4-yl)-1H-indol-3-yl)thio)picolinic acid (compound no. 1-101);

6-((2-bromo-6-chloro-7-fluoro-1-(1-methyl-1H-pyrazol-4-yl)-1H-indol-3-yl)thio)picolinic acid (compound no. 1-102);

6-((6-chloro-2-cyano-7-fluoro-1-(1-methyl-1H-pyrazol-4-yl)-1H-indol-3-yl)thio)picolinic acid (compound no. 1-103);

6-((6-chloro-2-cyclopropyl-7-fluoro-1-(1-methyl-1H-pyrazol-4-yl)-1H-indol-3-yl)thio)pic olinic acid (compound no. 1-104);

6-((2-amino-6-chloro-7-fluoro-1-(1-methyl-1H-pyrazol-4-yl)-1H-indol-3-yl)thio)picolinic acid (compound no. 1-105);

6-((6-chloro-7-fluoro-2-methoxy-1-(1-methyl-1H-pyrazol-4-yl)-1H-indol-3-yl)thio)picolinic acid (compound no. 1-106);

6-((2,6-dichloro-1-(1-isopropyl-1H-pyrazol-4-yl)-1H-indol-3-yl)thio)picolinic acid (compound no. 1-107);

6-((2-bromo-6-chloro-1-(1-isopropyl-1H-pyrazol-4-yl)-1H-indol-3-yl)thio)picolinic acid (compound no. 1-108);

6-((6-chloro-2-cyano-1-(1-isopropyl-1H-pyrazol-4-yl)-1H-indol-3-yl)thio)picolinic acid (compound no. 1-109);

6-((6-chloro-2-cyclopropyl-1-(1-isopropyl-1H-pyrazol-4-yl)-1H-indol-3-yl)thio)picolinic acid (compound no. 1-110);

6-((2-amino-6-chloro-1-(1-isopropyl-1H-pyrazol-4-yl)-1H-indol-3-yl)thio)picolinic acid (compound no. 1-111);

6-((6-chloro-1-(1-isopropyl-1H-pyrazol-4-yl)-2-methoxy-1H-indol-3-yl)thio)picolinic acid (compound no. 1-112);

6-((2,6-dichloro-7-fluoro-1-(1-isopropyl-1H-pyrazol-4-yl)-1H-indol-3-yl)thio)picolinic acid (compound no. 1-113);

6-((2-bromo-6-chloro-7-fluoro-1-(1-isopropyl-1H-pyrazol-4-yl)-1H-indol-3-yl)thio)picolinic acid (compound no. 1-114);

6-((6-chloro-2-cyano-7-fluoro-1-(1-isopropyl-1H-pyrazol-4-yl)-1H-indol-3-yl)thio)picolinic acid (compound no. 1-115);

6-((6-chloro-2-cyclopropyl-7-fluoro-1-(1-isopropyl-1H-pyrazol-4-yl)-1H-indol-3-yl)thio)picolinic acid (compound no. 1-116);

6-((2-amino-6-chloro-7-fluoro-1-(1-isopropyl-1H-pyrazol-4-yl)-1H-indol-3-yl)thio)picolinic acid (compound no. 1-117);

6-((6-chloro-7-fluoro-1-(1-isopropyl-1H-pyrazol-4-yl)-2-methoxy-1H-indol-3-yl)thio)picolinic acid (compound no. 1-118);

3-((6-chloro-2-cyclopropyl-7-fluoro-1-(1H-pyrazol-4-yl)-1H-indol-3-yl)thio)-2-fluorobenzoic acid (compound no. 1-119);

3-((6-chloro-2-cyclopropyl-7-fluoro-1-(1-(2-hydroxyethyl)-1H-pyrazol-4-yl)-1H-indol-3-yl)thio)-2-fluorobenzoic acid (compound no. 1-120);

3-(1-(1-(2-(carbamoyloxy)ethyl)-1H-pyrazol-4-yl)-(6-chloro-2-cyclopropyl-7-fluoro-1Hindol-3-yl)thio)-2-fluorobenzoic acid (compound no. 1-121);

3-(1-(1-(2-aminoethyl)-1H-pyrazol-4-yl)-(6-chloro-2-cyclopropyl-7-fluoro-1H-indol-3-yl)thio)-2-fluorobenzoic acid (compound no. 1-122);

3-((6-chloro-2-cyclopropyl-7-fluoro-1-(1-(2-ureidoethyl)-1H-pyrazol-4-yl)-1H-indol-3-yl) thio)-2-fluorobenzoic acid (compound no. 1-123);

3-(1-(1-(3-carboxypropyl)-1H-pyrazol-4-yl)-(6-chloro-2-cyclopropyl-7-fluoro-1H-indol-3-yl)thio)-2-fluorobenzoic acid (compound no. 1-124);

3-(1-(1-(4-amino-4-oxobutyl)-1H-pyrazol-4-yl)-(6-chloro-2-cyclopropyl-7-fluoro-1Hindol-3-yl)thio)-2-fluorobenzoic acid (compound no. 1-125);

3-((6-chloro-2-cyclopropyl-7-fluoro-1-(1-(2,2,2-trifluoroethyl)-1H-pyrazol-4-yl)-1Hindol-3-yl)thio)-2-fluorobenzoic acid (compound no. 1-126);

3-((6-chloro-2-cyclopropyl-1-(1-(2H5)ethyl-1H-pyrazol-4-yl)-7-fluoro-1H-indol-3-yl)thio)-2-fluorobenzoic acid; (compound no. 1-127);

3-(1-(1-(6-aminohexyl)-1H-pyrazol-4-yl)-(6-chloro-2-cyclopropyl-7-fluoro-1H-indol-3-yl) thio)-2-fluorobenzoic acid (compound no. 1-128);

3-((6-chloro-2-cyclopropyl-7-fluoro-1-(1-(hex-5-ynyl)-1H-pyrazol-4-yl)-1H-indol-3-yl)thio)-2-fluorobenzoic acid (compound no. 1-129);

3-((6-chloro-2-cyclopropyl-7-fluoro-1-(1-(3-hydroxy-2,2-dimethylpropyl)-1H-pyrazol-4-yl)-1H-indol-3-yl) thio)-2-fluorobenzoic acid (compound no. 1-130);

3-((6-chloro-2-cyclopropyl-1-(1-(6-(3-(3',6'-dihydroxy-3-oxo-3H-spiro[isobenzofuranl,9'-xanthen]-5-yl)ureido)hexyl)-1H-pyrazol-4-yl)-7-fluoro-1H-indol-3-yl)thio)-2-fluorobenzoic acid (compound no. 1-131);

3-((6-chloro-2-cyclopropyl-7-fluoro-1-(1-(4-(methylamino)-4-oxobutyl)-1H-pyrazol-4-yl)-1H-indol-3-yl) thio)-2-fluorobenzoic acid (compound no. 1-132);

3-(6-chloro-2-cyclopropyl-1-(1-(4-(dimethylamino)-4-oxobutyl)-1H-pyrazol-4-yl)-7-fluoro-1H-indol-3-yl-thio)-2-fluorobenzoic acid (compound no. 1-133);

3-(1-(1-(4-amino-3,3-dimethyl-4-oxobutyl)-1H-pyrazol-4-yl)-6-chloro-2-cyclopropyl-7-fluoro-1H-indol-3-yl-thio)-2-fluorobenzoic acid (compound no. 1-134);

6-(1-(1-(4-amino-4-oxobutyl)-1H-pyrazol-4-yl)-(6-chloro-2-cyclopropyl-7-fluoro-1Hindol-3-yl)thio)picolinic acid (compound no. 1-135);

6-((6-chloro-2-cyclopropyl-7-fluoro-1-(1-(4-(methylamino)-4-oxobutyl)-1H-pyrazol-4-yl)-1H-indol-3-yl) thio)picolinic acid (compound no. 1-136);

6-((6-chloro-2-cyclopropyl-1-(1-(4-(dimethylamino)-4-oxobutyl)-1H-pyrazol-4-yl)-7-fluoro-1H-indol-3-yl) thio)picolinic acid (compound no. 1-137);

6-(1-(1-(4-amino-3,3-dimethyl-4-oxobutyl)-1H-pyrazol-4-yl)-(6-chloro-2-cyclopropyl-7-fluoro-1H-indol-3-yl) thio)picolinic acid (compound no. 1-138);

3-((2,6-dichloro-7-fluoro-1-(pyridin-3-yl)-1H-indol-3-yl) thio)-2-fluorobenzoic acid (compound no. 2-1);

3-((2-bromo-6-chloro-7-fluoro-1-(pyridin-3-yl)-1H-indol-3-yl)thio)-2-fluorobenzoic acid (compound no. 2-2);

3-((6-chloro-2-cyclopropyl-7-fluoro-1-(pyridin-3-yl)-1H-indol-3-yl)thio)-2-fluorobenzoic acid (compound no. 2-3);

3-((6-chloro-2-cyano-7-fluoro-1-(pyridin-3-yl)-1H-indol-3-yl)thio)-2-fluorobenzoic acid (compound no. 2-4);

2-(3-((2,6-dichloro-1-(1-ethyl-1H-pyrazol-4-yl)-7-fluoro-1H-indol-3-yl)thio)-2-fluorophen yl)acetic acid (compound no. 2-5);

2-(3-((2-bromo-6-chloro-1-(1-ethyl-1H-pyrazol-4-yl)-7-fluoro-1H-indol-3-yl)thio)-2-fluorophenyl)acetic acid (compound no. 2-6);

2-(3-((6-chloro-2-cyclopropyl-1-(1-ethyl-1H-pyrazol-4-yl)-7-fluoro-1H-indol-3-yl)thio)-2-fluorophenyl)acetic acid (compound no. 2-7);

2-(3-((6-chloro-2-cyano-1-(1-ethyl-1H-pyrazol-4-yl)-7-fluoro-1H-indol-3-yl)thio)-2-fluoro phenyl)acetic acid (compound no. 2-8);

2-(3-((2,6-dichloro-1-(1-ethyl-1H-pyrazol-4-yl)-7-fluoro-1H-indol-3-yl)thio)-2-fluorophenyl)-2-methylpropanoic acid (compound no. 2-9);

2-(3-((2-bromo-6-chloro-1-(1-ethyl-1H-pyrazol-4-yl)-7-fluoro-1H-indol-3-yl)thio)-2-fluorophenyl)-2-methylpropanoic acid (compound no. 2-10);

2-(3-((6-chloro-2-cyclopropyl-1-(1-ethyl-1H-pyrazol-4-yl)-7-fluoro-1H-indol-3-yl)thio)-2-fluorophenyl)-2-methylpropanoic acid (compound no. 2-11);

2-(3-((6-chloro-2-cyano-1-(1-ethyl-1H-pyrazol-4-yl)-7-fluoro-1H-indol-3-yl)thio)-2-fluoro phenyl)-2-methylpropanoic acid (compound no. 2-12)

1-(3-((2,6-dichloro-1-(1-ethyl-1H-pyrazol-4-yl)-7-fluoro-1H-indol-3-yl)thio)-2-fluorophen yl)cyclopropanecarboxylic acid (compound no. 2-13);

1-(3-((2-bromo-6-chloro-1-(1-ethyl-1H-pyrazol-4-yl)-7-fluoro-1H-indol-3-yl)thio)-2-fluorophenyl)cyclopropanecarboxylic acid (compound no. 2-14);

1-(3-((6-chloro-2-cyclopropyl-1-(1-ethyl-1H-pyrazol-4-yl)-7-fluoro-1H-indol-3-yl)thio)-2-fluorophenyl)cyclopropanecarboxylic acid (compound no. 2-15);

1-(3-((6-chloro-2-cyano-1-(1-ethyl-1H-pyrazol-4-yl)-7-fluoro-1H-indol-3-yl)thio)-2-fluoro phenyl)cyclopropanecarboxylic acid (compound no. 2-16);

2-(3-((2,6-dichloro-1-(1-propyl-1H-pyrazol-4-yl)-7-fluoro-1H-indol-3-yl)thio)-2-fluoroph enyl)acetic acid (compound no. 2-17);

2-(3-((2-bromo-6-chloro-1-(1-propyl-1H-pyrazol-4-yl)-7-fluoro-1H-indol-3-yl)thio)-2-fluorophenyl)acetic acid (compound no. 2-18);

2-(3-((6-chloro-2-cyclopropyl-1-(1-propyl-1H-pyrazol-4-yl)-7-fluoro-1H-indol-3-yl)thio)-2-fluorophenyl)acetic acid (compound no. 2-19);

2-(3-((6-chloro-2-cyano-1-(1-propyl-1H-pyrazol-4-yl)-7-fluoro-1H-indol-3-yl)thio)-2-fluorophenyl)acetic acid (compound no. 2-20);

2-(3-((2,6-dichloro-1-(1-propyl-1H-pyrazol-4-yl)-7-fluoro-1H-indol-3-yl)thio)-2-fluoroph enyl)-2-methylpropanoic acid (compound no. 2-21);

2-(3-((2-bromo-6-chloro-1-(1-propyl-1H-pyrazol-4-yl)-7-fluoro-1H-indol-3-yl)thio)-2-fluorophenyl)-2-methylpropanoic acid (compound no. 2-22);

2-(3-((6-chloro-2-cyclopropyl-1-(1-propyl-1H-pyrazol-4-yl)-7-fluoro-1H-indol-3-yl)thio)-2-fluorophenyl)-2-methylpropanoic acid (compound no. 2-23);

2-(3-((6-chloro-2-cyano-1-(1-propyl-1H-pyrazol-4-yl)-7-fluoro-1H-indol-3-yl)thio)-2-fluorophenyl)-2-methylpropanoic acid (compound no. 2-24);

1-(3-((2,6-dichloro-1-(1-propyl-1H-pyrazol-4-yl)-7-fluoro-1H-indol-3-yl) thio)-2-fluoroph enyl)cyclopropanecarboxylic acid (compound no. 2-25);

1-(3-((2-bromo-6-chloro-1-(1-propyl-1H-pyrazol-4-yl)-7-fluoro-1H-indol-3-yl) thio)-2-fluorophenyl)cyclopropanecarboxylic acid (compound no. 2-26);

1-(3-((6-chloro-2-cyclopropyl-1-(1-propyl-1H-pyrazol-4-yl)-7-fluoro-1H-indol-3-yl) thio)-2-fluorophenyl)cyclopropanecarboxylic acid (compound no. 2-27);

1-(3-((6-chloro-2-cyano-1-(1-propyl-1H-pyrazol-4-yl)-7-fluoro-1H-indol-3-yl) thio)-2-fluorophenyl)cyclopropanecarboxylic acid (compound no. 2-28);

2-(6-((2,6-dichloro-1-(1-ethyl-1H-pyrazol-4-yl)-7-fluoro-1H-indol-3-yl) thio) pyridine-2-yl) acetic acid (compound no. 2-29);

2-(6-((2,6-dichloro-1-(1-ethyl-1H-pyrazol-4-yl)-7-fluoro-1H-indol-3-yl) thio) pyridine-2-yl)-2-methylpropanoic acid (compound no. 2-30);

1-(6-((2,6-dichloro-1-(1-ethyl-1H-pyrazol-4-yl)-7-fluoro-1H-indol-3-yl) thio) pyridine-2-yl) cyclopropanecarboxylic acid (compound no. 2-31);

2-(6-((2,6-dichloro-1-(1-propyl-1H-pyrazol-4-yl)-7-fluoro-1H-indol-3-yl) thio) pyridine-2-yl)acetic acid (compound no. 2-32);

2-(6-((2,6-dichloro-1-(1-propyl-1H-pyrazol-4-yl)-7-fluoro-1H-indol-3-yl) thio) pyridine-2-yl)-2-methylpropanoic acid (compound no. 2-33);

1-(6-((2,6-dichloro-1-(1-propyl-1H-pyrazol-4-yl)-7-fluoro-1H-indol-3-yl) thio) pyridine-2-yl)cyclopropanecarboxylic acid (compound no. 2-34);

or a pharmaceutically acceptable salt, or solvate thereof.

\* \* \* \* \*